(12) United States Patent
Wong et al.

(10) Patent No.: US 12,398,189 B2
(45) Date of Patent: Aug. 26, 2025

(54) METHODS OF ACTIVATING REGULATORY T CELLS

(71) Applicant: HCW Biologics, Inc., Miramar, FL (US)

(72) Inventors: Hing C. Wong, Miramar, FL (US); Niraj Shrestha, Miramar, FL (US); Varghese George, Miramar, FL (US); Michael Dee, Miramar, FL (US)

(73) Assignee: HCW Biologics, Inc., Miramar, FL (US)

( * ) Notice: Subject to any disclaimer, the term of this patent is extended or adjusted under 35 U.S.C. 154(b) by 224 days.

(21) Appl. No.: 17/173,806

(22) Filed: Feb. 11, 2021

(65) Prior Publication Data

US 2021/0268022 A1    Sep. 2, 2021

Related U.S. Application Data

(60) Provisional application No. 62/981,944, filed on Feb. 26, 2020, provisional application No. 62/975,141, filed on Feb. 11, 2020.

(51) Int. Cl.
| | | |
|---|---|---|
| *C07K 14/705* | (2006.01) | |
| *A61K 40/11* | (2025.01) | |
| *A61K 40/22* | (2025.01) | |
| *A61K 40/40* | (2025.01) | |
| *C12N 5/0783* | (2010.01) | |

(52) U.S. Cl.
CPC ............ *C07K 14/705* (2013.01); *A61K 40/11* (2025.01); *A61K 40/22* (2025.01); *A61K 40/40* (2025.01); *C12N 5/0637* (2013.01); *C12N 2501/998* (2013.01); *C12N 2501/999* (2013.01)

(58) Field of Classification Search
CPC .... A61K 35/17; C07K 14/705; C12N 5/0637; C12N 2501/998; C12N 2501/999
See application file for complete search history.

(56) References Cited

U.S. PATENT DOCUMENTS

| | | | |
|---|---|---|---|
| 5,595,756 A | 1/1997 | Bally et al. | |
| 6,117,980 A | 9/2000 | Gonzalez et al. | |
| 7,452,537 B2 | 11/2008 | Bauer et al. | |
| 7,482,436 B2 | 1/2009 | Sugimura et al. | |
| 7,488,802 B2 | 2/2009 | Collins et al. | |
| 7,521,051 B2 | 4/2009 | Collins et al. | |
| 7,612,181 B2 | 11/2009 | Wu et al. | |
| 7,691,380 B2 * | 4/2010 | Thorpe ............... | C07K 16/3015 424/155.1 |
| 7,723,482 B2 | 5/2010 | Soulillou et al. | |
| 7,968,094 B2 | 6/2011 | Jiao et al. | |
| 8,007,795 B2 | 8/2011 | Jiao et al. | |
| 8,133,485 B2 | 3/2012 | Levi-Schaffer et al. | |
| 8,217,149 B2 | 7/2012 | Irving et al. | |
| 8,258,268 B2 | 9/2012 | Wu et al. | |
| 8,475,792 B2 | 7/2013 | Dall'Acqua et al. | |
| 8,552,156 B2 | 10/2013 | Takayanagi et al. | |
| 8,586,714 B2 | 11/2013 | Ghayur et al. | |
| 8,716,450 B2 | 5/2014 | Ghayur et al. | |
| 8,722,855 B2 | 5/2014 | Ghayur et al. | |
| 8,735,546 B2 | 5/2014 | Ghayur et al. | |
| 8,741,604 B2 | 6/2014 | Campbell et al. | |
| 8,753,640 B2 | 6/2014 | Wu et al. | |
| 8,759,494 B2 | 6/2014 | Bachmann et al. | |
| 8,822,645 B2 | 9/2014 | Ghayur et al. | |
| 9,035,026 B2 | 5/2015 | Hoffmann et al. | |
| 9,067,997 B2 | 6/2015 | Romagne et al. | |
| 9,085,623 B2 | 7/2015 | Rother et al. | |
| 9,090,684 B2 | 7/2015 | Borras et al. | |
| 9,226,962 B2 | 1/2016 | Le Gall et al. | |
| 9,238,084 B2 | 1/2016 | Liu et al. | |
| 9,273,136 B2 | 3/2016 | Rader et al. | |
| 9,371,395 B2 | 6/2016 | Takahashi et al. | |
| 9,441,034 B2 | 9/2016 | Sivakumar et al. | |
| 9,505,843 B2 | 11/2016 | Kim et al. | |
| 9,617,345 B2 | 4/2017 | Berne et al. | |
| 9,701,758 B2 | 7/2017 | Cooper et al. | |
| 11,518,792 B2 | 12/2022 | Wong | |
| 11,672,826 B2 | 6/2023 | Wong | |
| 11,730,762 B2 | 8/2023 | Wong | |
| 11,738,052 B2 | 8/2023 | Wong | |
| 2001/0044427 A1 | 11/2001 | Mazel et al. | |

(Continued)

FOREIGN PATENT DOCUMENTS

| | | |
|---|---|---|
| CN | 1844150 A | * 10/2006 |
| CN | 101653603 | 2/2010 |

(Continued)

OTHER PUBLICATIONS

Putnam, A. L., et al., "Clinical grade manufacturing of human alloantigen-reactive regulatory T cells for use in transplantation," American Journal of Transplantation 13(11): 3010-3020. doi: 10.1111/ajt.12433. Epub Sep. 18, 2013. (Year: 2013).*

Shen, Z., et al., "Engineering peptide linkers for scFv immunosensors," Anal Chem 80(6): 1910-1917. doi: 10.1021/ac7018624. (Year: 2008).*

Clark, R. A., and Kupper, T. S., "IL-15 and dermal fibroblasts induce proliferation of natural regulatory T cells isolated from human skin," Blood 109(1):194-202. doi: 10.1182/blood-2006-02-002873. (Year: 2006).*

(Continued)

*Primary Examiner* — Tracy Vivlemore
*Assistant Examiner* — Eric J Rogers
(74) *Attorney, Agent, or Firm* — Fish & Richardson P.C.

(57) ABSTRACT

Provided herein are methods of stimulating or increasing the proliferation of a $T_{reg}$ cell, compositions including a population of $T_{reg}$ cells generated by these methods, and methods of treating a subject using these compositions.

14 Claims, 14 Drawing Sheets

Specification includes a Sequence Listing.

(56) References Cited

U.S. PATENT DOCUMENTS

| | | | |
|---|---|---|---|
| 2003/0124678 A1* | 7/2003 | Epstein | A61P 37/00 435/325 |
| 2003/0219441 A1 | 11/2003 | Thorpe et al. | |
| 2005/0014224 A1 | 1/2005 | Collins et al. | |
| 2006/0159655 A1 | 7/2006 | Collins et al. | |
| 2007/0160579 A1 | 7/2007 | Schmitz et al. | |
| 2008/0025979 A1* | 1/2008 | Honjo | A61P 37/00 435/69.6 |
| 2009/0148942 A1 | 6/2009 | McDonagh et al. | |
| 2012/0171197 A1 | 7/2012 | Eriksson et al. | |
| 2012/0264920 A1 | 10/2012 | Wang et al. | |
| 2013/0274446 A1 | 10/2013 | Kumagai et al. | |
| 2014/0242077 A1 | 8/2014 | Choi | |
| 2015/0218274 A1 | 8/2015 | Sabatos-Peyton et al. | |
| 2015/0259429 A1 | 9/2015 | Benaroch et al. | |
| 2016/0175397 A1 | 6/2016 | Umana et al. | |
| 2016/0340413 A1 | 11/2016 | Duerner et al. | |
| 2016/0367664 A1 | 12/2016 | Wang et al. | |
| 2017/0051063 A1 | 2/2017 | Baum et al. | |
| 2017/0080104 A1* | 3/2017 | Irvine | C07K 14/5443 |
| 2017/0198042 A1 | 7/2017 | Williams et al. | |
| 2017/0283499 A1 | 10/2017 | Delhem et al. | |
| 2018/0200366 A1 | 7/2018 | Wong | |
| 2019/0078082 A1 | 3/2019 | Amorese et al. | |
| 2019/0092846 A1 | 3/2019 | Ibebunjo et al. | |
| 2019/0177406 A1 | 6/2019 | Ledbetter et al. | |
| 2019/0315850 A1 | 10/2019 | Bedinger et al. | |
| 2020/0071374 A1 | 3/2020 | Wong | |
| 2020/0123607 A1 | 4/2020 | Serrano Marugan et al. | |
| 2020/0190174 A1 | 6/2020 | Wong | |
| 2020/0392221 A1 | 12/2020 | Van Snick et al. | |
| 2020/0399358 A1 | 12/2020 | Shapiro et al. | |
| 2021/0060064 A1 | 3/2021 | Wong | |
| 2021/0061897 A1 | 3/2021 | Ledbetter et al. | |
| 2021/0070825 A1 | 3/2021 | Wong | |
| 2021/0070826 A1 | 3/2021 | Wong | |
| 2021/0100840 A1 | 4/2021 | Wong et al. | |
| 2021/0137981 A1 | 5/2021 | Wong | |
| 2021/0277054 A1 | 9/2021 | Wong et al. | |
| 2021/0338724 A1 | 11/2021 | Wong | |
| 2021/0355204 A1 | 11/2021 | Bedinger et al. | |
| 2021/0403545 A1 | 12/2021 | Van Snick et al. | |
| 2022/0073578 A1 | 3/2022 | Wong et al. | |
| 2023/0023389 A1 | 1/2023 | Wong | |
| 2023/0039157 A1 | 2/2023 | Wong | |
| 2023/0128292 A1 | 4/2023 | Wong | |
| 2023/0174666 A1 | 6/2023 | Wong et al. | |
| 2023/0272027 A1 | 8/2023 | Wong | |
| 2023/0372399 A1 | 11/2023 | Wong | |
| 2023/0372444 A1 | 11/2023 | Wong et al. | |
| 2023/0381238 A1 | 11/2023 | Wong | |
| 2023/0398151 A1 | 12/2023 | Wong | |

FOREIGN PATENT DOCUMENTS

| | | |
|---|---|---|
| CN | 101965364 | 2/2011 |
| CN | 102153653 | 8/2011 |
| CN | 104789527 A | 7/2015 |
| CN | 106255703 | 12/2016 |
| CN | 109513003 | 3/2019 |
| EP | 1245676 | 10/2002 |
| EP | 1719528 | 11/2006 |
| EP | 2537933 | 12/2012 |
| EP | 3029069 | 6/2016 |
| EP | 3348276 | 7/2018 |
| JP | 2005-124568 | 5/2005 |
| JP | 2008-536487 | 9/2008 |
| JP | 2009-512433 | 3/2009 |
| JP | 4361133 | 8/2009 |
| KR | 2016/0127688 | 11/2016 |
| KR | 101778439 | 9/2017 |
| WO | WO 1995/015341 | 6/1995 |
| WO | WO1996001653 | * 1/1996 |
| WO | WO 2001/083755 | 11/2001 |
| WO | WO 2002/083152 | 10/2002 |
| WO | WO 2003/037911 | 5/2003 |
| WO | WO 2003/104425 | 12/2003 |
| WO | WO 2004/076488 | 9/2004 |
| WO | WO 2006/096828 | 9/2006 |
| WO | WO 2006/097743 | 9/2006 |
| WO | WO 2006/119897 | 11/2006 |
| WO | WO 2008/096158 | 8/2008 |
| WO | WO 2011/127324 | 10/2011 |
| WO | WO 2012/040323 | 3/2012 |
| WO | WO 2012/120125 | 9/2012 |
| WO | WO 2012/170470 | 12/2012 |
| WO | WO 2012/175222 | 12/2012 |
| WO | WO 2012/175692 | 12/2012 |
| WO | WO 2013/068946 | 5/2013 |
| WO | WO 2014/007513 | 1/2014 |
| WO | WO 2014/026054 | 2/2014 |
| WO | WO 2014/095808 | 6/2014 |
| WO | WO 2014/130635 | 8/2014 |
| WO | WO 2014/159531 | 10/2014 |
| WO | WO 2015/089881 | 6/2015 |
| WO | WO 2016/106221 | 6/2016 |
| WO | WO 2016/154585 | 9/2016 |
| WO | WO 2016/166348 | 10/2016 |
| WO | WO 2017/053748 | 3/2017 |
| WO | WO 2017/083612 | 5/2017 |
| WO | WO 2017/149538 | 9/2017 |
| WO | WO 2017/189526 | 11/2017 |
| WO | WO 2018/067825 | 4/2018 |
| WO | WO 2018/075989 | 4/2018 |
| WO | WO 2018/129007 | 7/2018 |
| WO | WO 2018/158350 | 9/2018 |
| WO | WO 2018/183169 | 10/2018 |
| WO | WO 2018/165208 | 12/2018 |
| WO | WO 2019/046313 | 3/2019 |
| WO | WO 2020/047299 | 3/2020 |
| WO | WO 2020/047333 | 3/2020 |
| WO | WO 2020/047462 | 3/2020 |
| WO | WO 2020/047473 | 3/2020 |
| WO | WO 2021/163369 | 8/2021 |

OTHER PUBLICATIONS

Bork, "Powers and Pitfalls in Sequence Analysis: The 70% Hurdle," Genome Research, 2000, 10:398-400.

Bowie et al., "Deciphering the Message in Protein Sequences: Tolerance to Amino Acid Substitutions," Science, 1990, 247:1306-1310.

Burgess et al., "Possible Dissociation of the Heparin-binding and Mitogenic Activities of Heparin-binding (Acidic Fibroblast) GrowthFactor-1 from its Receptor-binding Activities by Site-directed Mutagenesis of a Single Lysine Residue," J. Cell Biol., 1990, 111:2129-2138.

Greenspan et al., "Defining epitopes: Its not as easy as it seems," Nature Biotechnology, 1999, 17:936-937.

Lazar et al., "Transforming Growth Factor Alpha: Mutation of Aspartic Acid 47 and Leucine 48 Results in Different Biological Activities," Mol. Cell. Biol., 1988, 8:1247-1252.

PCT International Search Report and Written Opinion in International Appln. No. PCT/US2021/029920, dated Oct. 6, 2021, 21 pages.

PCT International Search Report and Written Opinion in International Appln. No. PCT/US2021/035285, dated Oct. 18, 2021, 14 pages.

Chandrudu et al., "Chemical methods for peptide and protein production," Molecules, 2013, 18(4):4373-4388.

Tam et al., "Methods and strategies of peptide ligation," Peptide Science: Original Research on Biomolecules, 2001, 60(3):194-205.

Mikayama et al., "Molecular cloning and functional expression of a cDNA encoding glycosylation-inhibiting factor," Proc. Natl. Acad. Sci. USA, Nov. 1, 1993, 90(21):10056-10060.

Voet et al., Biochemistry, John Wiley & Sons, Inc., 1990, pp. 126-128 and 228-234, 12 pages.

Li et al., "Transforming Growth Factor-β Regulation of Immune Responses," Annu. Rev. Immunol., 2006, 24:99-146.

McCarron et al., "TGF-β prevents T follicular helper cell accumulation and B cell autoreactivity," J Clin Invest., 2014, 124(10):4375-4386.

(56) References Cited

OTHER PUBLICATIONS

Voelker et al., "Anti-TGF-β1 Antibody Therapy in Patients with Diabetic Nephropathy," J Am Soc Nephrol., 2017, 28:953-962.
Wallace et al., "B lymphocytes confer immune tolerance via cell surface GARP-TGF-β complex," JCI Insight., 2018, 3(7):e99863, 19 pages.
PCT International Preliminary Report on Patentability in International Appln. No. PCT/US2020/038717, dated Dec. 30, 2021, 9 pages.
PCT International Preliminary Report on Patentability in International Appln. No. PCT/US2021/017620, dated Aug. 25, 2022, 12 pages.
PCT International Preliminary Report on Patentability in International Appln. No. PCT/US2021/017621, dated Aug. 25, 2022, 8 pages.
PCT International Preliminary Report on Patentability in International Appln. No. PCT/US2021/017714, dated Aug. 25, 2022, 12 pages.
International Preliminary Report on Patentability in International Appln. No. PCT/US2020/035598, mailed Dec. 6, 2022, 7 pages.
International Preliminary Report on Patentability in International Appln. No. PCT/US2021/035285, mailed Dec. 15, 2022, 7 pages.
Chan et al., "Molecular mechanisms of natural killer cell activation in response to cellular stress," Cell Death & Differentiation, Jan. 2014, 21(1):5-14.
Chang et al., "The dock and lock method: a novel platform technology for building multivalent, multifunctional structures of defined composition with retained bioactivity," Clinical cancer research, Sep. 15, 2007, 13(18):5586s-5591s.
Hui et al., "Butyrate inhibit collagen-induced arthritis via Treg/IL-10/Th17 axis," International immunopharmacology, Mar. 1, 2019, 68: Abstract 1 page.
Li et al., "Lipid metabolism fuels cancer's spread," Cell metabolism, Feb. 7, 2017, 25(2):228-230.
Wilchek et al., "Essentials of biorecognition: The (strept) avidin-biotin system as a model for protein-protein and protein-ligand interaction," Immunology letters, Feb. 28, 2006, 103(1): Abstract 2 pages.
Zhang et al., "Depletion of NK cells improves cognitive function in the Alzheimer disease mouse model," The Journal of Immunology, Jul. 15, 2020, 205(2): 10pages.
Abbott et al., "Genomic organization, exact localization, and tissue expression of the human CD26 (dipeptidyl peptidase IV) gene," Immunogentics, Sep. 1994, 40(5):331-338.
Abdul-Aziz et al., "Acute myeloid leukemia induces protumoral p16INK4a-driven senescence in the bone marrow microenvironment," Blood, Jan. 31, 2019, 133(5):446-456.
Aertgeerts et al., "Crystal structure of human dipeptidyl peptidase IV in complex with a decapeptide reveals details on substrate specificity and tetrahedral intermediate formation," Protein Science, Feb. 2004, 13(2):412-421.
Ait-Oufella el al., "Natural regulatory T cells control the development of atherosclerosis in mice," Nature Medicine, Feb. 5, 2006, 12:178-180.
Akbari, et al., "Design, expression and evaluation of a novel humanized single chain antibody against epidermal growth factor receptor (EGFR)," Protein Expr. Purif., 2016, 127:8-15.
Ali et al., "Regulatory T cells in skin," Immunology, Jul. 12, 2017, 152(3):372-381.
Angevin et al., "First-in-human phase 1 of YS110, a monoclonal antibody directed against CD26 in advanced CD26-expressing cancers," British Journal of Cancer, Mar. 14, 2017, 116(9):1126-1134.
Bachelet et al., "Mast Cell Costimulation by CD226/CD112 (DNAM-1/Nectin-2) A Novel Interface in the Allergic Process," Journal of Biological Chemistry, Sep. 15, 2006, 281(37):27190-6.
Baker, et al., "Clearance of p16Ink4a-positive senescent cells delays ageing-associated disorders," Nature, 2011, 479(7372): 232-236.
Bennett et al., "Erratum: Killing the old: cell senescence in atherosclerosis," Nature Reviews Cardiology, Jan. 12, 2017, 14(3):132.
Bennett et al., "Killing the old: cell senescence in atherosclerosis," Nature Reviews Cardiology, Dec. 12, 2016, 14(1):8-9, 2 pages.
Bentebibel et al., "A First-in-Human Study and Biomarker Analysis of NKTR-214, a Novel IL2Raf Biased Cytokine, in Patients with Advanced or Metastatic Solid Tumors," Cancer Discovery, Jun. 2019, 9(6):711-721.
Bhat et al., "Astrocyte Senescence as a Component of Alzheimer's Disease," PLoS One, Sep. 12, 2012, 7(9):e45069, 10 pages.
Biran et al., "Senescent cells communicate via intercellular protein transfer," Genes & Development, Apr. 8, 2015, 29(8):791-802, 13 pages.
Borea et al., "Pharmacology of Adenosine Receptors: The State of the Art," Physiological Reviews, May 31, 2918, 98(3):1591-1625.
Borgerding et al., "B-lymphoma cells escape rituximab-triggered elimination by NK cells through increased HLA class I expression," Experimental Hematology, Mar. 1, 2010, 38(3):213-21.
Bourgeois et al., "Regulation of cellular senescence via the FOXO4-p53 axis," FEBS Lett., 2018, 592(12): 2083-2097.
Boyman et al., "IL-7/Anti-IL-7 mAb Complexes Restore T Cell Development and Induce Homeostatic T Cell Expansion without Lymphopenia," The Journal of Immunology, Jun. 1, 2008, 180:7265-7275.
Boyman et al., "Selective Stimulation of T Cell Subsets with Antibody-Cytokine Immune Complexes," Science, Mar. 31, 2006, 311(5769):1924-1927.
Brennan et al., "Structural determination of lipid antigens captured at the CD1d-T-cell receptor interface," PNAS, 2017, 114(31):8348-8353.
Brighton et al., "Clearance of senescent decidual cells by uterine natural killer cells in cycling human endometrium," Elife, Dec. 11, 2017, 6:e31274, 23 pages.
Brooks et al., "Combined inhibition of PD1 and CD96 checkpoints improves survival in a resectable murine model of pancreatic cancer," European Journal of Cancer, Jul. 1, 2016, 61:S189, 1 page.
Broxmeyer et al., "Modulation of Hematopoietic Chemokine Effects In Vitro and In Vivo by DPP-4/CD26," Stem Cells and Development, Mar. 4, 2016, 25(8):575-585.
Brunstein et al., "Infusion of Ex Vivo Expanded T Regulatory Cells in Adults Transplanted with Umbilical Cord Blood: Safety Profile and Detection Kinetics," Blood, Jan. 20, 2011, 117(3):1061-1070.
Brunstein et al., "Umbilical cord blood-derived T regulatory cells to prevent GVHD:kinetics, toxicity profile, and clinical effect," Blood, Feb. 25, 2016, 127(8):1044-1051.
Buhling et al., "Functional role of CD26 on human B lymphocytes," Immunology Letters, Feb. 1995, 45(1-2):47-51.
Bussian et al., "Clearance of senescent glial cells prevents tau-dependent pathology and cognitive decline," Nature, Sep. 19, 2018, 562(7728):578-582, 21 pages.
Cai et al., "Chibby suppresses aerobic glycolysis and proliferation of nasopharyngeal carcinoma via the Wnt/β-catenin-Lin28/let7-PDK1 cascade," Journal of Experimental & Clinical Cancer Research, Dec. 1, 2018, 37(1):104.
Cao et al., "Expression and characterization of recombinant humanized anti-HER2 single-chain antibody in Pichia pastoris for targeted cancer therapy," Biotechnology Letters, Jul. 1, 2015, 37(7):1347-54.
Cao, "Self-regulation and cross-regulation of pattern-recognition receptor signaling in health and disease," Nature Reviews Immunology, Dec. 29, 2015, 16(1):35-50.
Carr et al., "NK Cell-Mediated Lysis of Autologous HCMV-Infected Skin Fibroblasts Is Highly Variable among NK Cell Clones and Polyclonal NK Cell Lines," Clinical Immunology, Nov. 2002, 105(2):126-140.
Catania et al., "The tumor-targeting immunocytokine F16-IL2 in combination with doxorubicin: dose escalation in patients with advanced solid tumors and expansion into patients with metastatic breast cancer," Cell Adhesion and Migration, Jan.-Apr. 2015, 9(1-2):14-21.
Cavinato et al., "Molecular mechanisms of UVB-induced senescence of dermal fibroblasts and its relevance for photoaging of the human skin," Experimental Gerontology. Aug. 2017, 94:78-82.
Chalan et al., "Expression of Lectin-Like Transcript 1, the Ligand for CD161, in Rheumatoid Arthritis," PLoS ONE, 2015, 10(7):e0132436.

(56) References Cited

OTHER PUBLICATIONS

Chambers et al., "Can blocking inflammation enhance immunity during aging?," Journal of Allergy and Clinical Immunology, May 2020, 145(5):1323-1331.
Chance et al., "A simple and rapid assay of oxidative phosphorylation," Nature, Jun. 1955, 175(4469):1120-1121.
Chattopadyhay et al., "Structural Basis of Inducible Costimulator Ligand Costimulatory Function: Determination of the Cell Surface Oligomeric State and Functional Mapping of the Receptor Binding Site of the Protein1," J Immunol., 2006, 3920-3929.
Chen et al., "Sterile inflammation: sensing and reacting to damage," Nature Reviews Immunology, Nov. 19, 2010, 10(12):826-837.
Chichili et al., "Linkers in the structural biology of protein-protein interactions," Protein Science, Feb. 2013, 22(2):153-67.
Childs et al., "Senescent cells: an emerging target for diseases of ageing," Nature Reviews Drug Discovery, Jul. 21, 2017, 16(10):718-735, 18 pages.
Childs et al., "Senescent intimal foam cells are deleterious at all stages of atherosclerosis," Science, Oct. 28, 2016, 354(6311):472-477.
Chinta, et al., "Cellular senescence is induced by the environmental neurotoxin paraquat and bontributes to neuropathology linked to Parkinson's Disease," Cell Rep., 2018, 22(4): 930-940.
Chong et al., "CD36 initiates the secretory phenotype during the establishment of cellular senescence," EMBO Rep., May 18, 2018, 19(6):e45274, 13 pages.
Ciaglia, et al., "Recognition by natural killer cells of N6-isopentenyladensoine-treated human glioma cell lines," Int. J. Cancer, 2018 142(1): 176-190.
Cichocki et al., "GSK3 inhibition drives maturation of NK cells and enhances their antitumor activity," Cancer Research, Oct. 15, 2017, 77(20):5664-75.
Cifaldi et al., "Boosting Natural Killer Cell-Based Immunotherapy with Anticancer Drugs: a Perspective," Trends Molecular Medicine, Dec. 2017, 23(12):1156-1175, 20 pages.
Cipriani et al., "Hippocampal Radial Glial Subtypes and Their Neurogenic Potential in Human Fetuses and Healthy and Alzheimer's Disease Adults," Cerebral Cortex, May 2, 2018, 28(7):2458-2478, 21 pages.
Clayton et al., "Soluble T Cell Immunoglobulin Mucin Domain 3 is Shed from CD8 T Cells by the Sheddase ADAM10, Is Increased in Plasma during Untreated HIV Infection, and Correlates with HIV Disease Progression," J Viral., 2015, 89(7):3723-3736.
Collado et al., "Senescence in tumours: evidence from mice and humans," Nature Reviews Cancer, Jan. 2010, 10(1):51-57.
Conarello et al., "Mice lacking dipeptidyl peptidase IV are protected against obesity and insulin resistance," Proc. Natl. Acad. Sci. U.S.A., May 27, 2003, 100(11):6825-6830.
Conlon et al., "Abstract CT082: Phase (Ph) I/Ib study of NIZ985 with and without spartalizumab (PDR001) in patients (pts) with metastatic/unresectable solid tumors," Cancer Res. 79(13 Suppl.):CT082, Jul. 1, 2019, 2 pages.
Coppe et al., "Tumor Suppressor and Aging Biomarker p16INK4a Induces Cellular Senescence without the Associated Inflammatory Secretory Phenotype," Journal of Biological Chemistry, Oct. 21, 2011, 286(42): 36396-36403.
Cosman et al., "ULBPs, novel MHC class I-related molecules, bind to CMV glycoprotein UL 16 and stimulate NK cytotoxicity through the NKG2D receptor," Immunity, Feb. 1, 2001, 14(2):123-33.
Costa et al., "Targeting the epidermal growth factor receptor can counteract the inhibition of natural killer cell function exerted by colorectal tumor-associated fibroblasts," Frontiers in Immunology, May 29, 2018, 9:1150, 14 pages.
Crews et al., "Molecular mechanisms of neurodegeneration in Alzheimer's disease," Human Molecular Genetics, Apr. 22, 2010, 19(R1):R12-R20, 9 pages.
Cromie et al., "Nanobodies and their use in GPCR drug discovery," Current Topics in Medicinal Chemistry, Dec. 1, 2015, 15(24):2543-57.
Czaja et al., "A comprehensive analysis of the binding of anti-KIR antibodies to activating KIRs," Genes and Immunity, Jan. 2014, 15(1), 15 pages.
Da Silva et al., "Dipeptidylpeptidase 4 inhibition enhances lymphocyte trafficking, improving both naturally occurring tumor immunity and immunotherapy," Nature Immunology, Jun. 15, 2015, 16(8):850-858, 11 pages.
Dall'Era et al., "Adoptive Regulatory T Cell Therapy in a Patient with Systemic Lupus Erythematosus, " Arthritis Rheumatology, Mar. 2019, 71(3):431-440.
De Crescenzo et al., "Engineering TGF-β Traps: Artificially Dimerized Receptor Ectodomains as High-affinity Blockers of TGF-62 Action," Transforming Growth Factor-β in Cancer Therapy, vol. II, 2008, Humana Press, 671-84.
De Genst et al., "Antibody repertoire development in camelids," Developmental & Comparative Immunology, Jan. 1, 2006, 30(1-2):187-98.
De Meyer et al., "Nanobody-based products as research and diagnostic tools," Trends in Biotechnology, May 1, 2014, 32(5):263-70.
De Stefano et al., "Establishing pathological cut-offs of brain atrophy rates in multiple sclerosis," Journal of Neurology, Neurosurgery, and Psychiatry, Jan. 2016, 87(1):93-99.
Deacon, "Physiology and Pharmacology of DPP-4 in Glucose Homeostasis and the Treatment of Type 2 Diabetes," Frontiers in Endocrinology, Feb. 2019, 10:80, 14 pages.
Deaglio et al., "Adenosine generation catalyzed by CD39 and CD73 expressed on regulatory T cells mediates immune suppression," Journal of Experimental Medicine, May 14, 2007, 204(6):1257-1265.
Demaria et al., "An Essential Role for Senescent Cellsin Optimal Wound Healingthrough Secretion of PDGF-AA," Developmental Cell, Dec. 22, 2014, 31(6):722-733.
Deyev et al., "Design of multivalent complexes using the barnase·barstar module," Nature Biotechnology, Dec. 2003, 21(12):1486-92.
Di Ianni et al., "Tregs prevent GVHD and promote immune reconstitution inHLA-haploidentical transplantation," Blood, Apr. 7, 2011, 117(14):3921-3928.
Dietel et al., "Decreased numbers of regulatory T cells are associated with human atherosclerotic lesion vulnerability and inversely correlate with infiltrated mature dendritic cells," Atherosclerosis, Sep. 2013, 230:92-99.
DiGiammarino et al., "Design and generation of DVD-IgTM molecules for dual-specific targeting," Therapeutic Proteins: Methods and Protocols, Methods in Molecular Biology, 2012, Humana Press, Totowa, NJ., 899:145-516.
Dikov et al., "New fluorescent method for the histochemical detection of tripeptidyl peptidase I using glycyl-1-proly1-1-met-2-anthraquinonyl hydrazide as substrate," Cellular and Molecular Biology, Jan. 1, 2004, 50 Online Pub: OL565-568, 1 page (Abstract Only).
Dimri et al., "A biomarker that identifies senescent human cells in culture and in aging skin in vivo," Proceedings of the National Academy of Sciences, Sep. 29, 1995, 92(20):9363-9367.
Dinarello, "Interleukin 1 and interleukin 18 as mediators of inflammation and the aging process," The American Journal of Clinical Nutrition, Feb. 1, 2006, 83(2):447S-455S.
Docagne et al., "A soluble transforming growth factor-β (TGF-β) type I receptor mimics TGF-β responses," Journal of Biological Chemistry, Dec. 7, 2001, 276(49):46243-50.
Dong et al., "Characterization of adenosine deaminase binding to human CD26 on T cells and its biologic role in immune response, " Journal of Immunology, Feb. 15, 1996, 156(4):1349-1355.
Dong et al., "Determination of adenosine deaminase binding domain on CD26 and its immunoregulatory effect on T cell activation," Journal of Immunology, Dec. 15, 1997, 159(12):6070-6076.
Dong et al., "Loss of methylation at theIFNGpromoter and CNS-1 is associated with the development of functional IFN-γ memory in human CD4+T lymphocytes," European Journal of Immunology, 2013, 43(3), 793-804.

(56) References Cited

OTHER PUBLICATIONS

Dou et al., "Cytoplasmic chromatin triggers inflammation in senescence and cancer," Nature, Oct. 4, 2017, 550(7676):402-406, 21 pages.
Drees, et al., "Soluble production of a biologically active single-chain antibody against murine PD-L1 in *Escherichia coli*," Protein Express. Purif., 2014, 94:60-66.
Dubois et al., "Preassociation of IL-15 with IL-15Rα-IgG1-Fc Enhances its Activity on Proliferation of NK and CD8+/CD44high T Cells and its Antitumor Action," The Journal of Immunology, Feb. 15, 2008, 180:2099-2106.
Edwardraja et al., "Redesigning of anti-c-met single chain Fv antibody for the cytoplasmic folding and its structural analysis," Biotechnology and Bioengineering, Jun. 15, 2010, 106(3):367-75.
Eisenhut et al., "Ion Channels in Inflammation," Pflugers Archive, Jan. 29, 2011, 461(4):401-421.
Elgueta et al., "Molecular mechanism and function of CD40/CD40L engagement in the immune system," Immunological Reviews, 2009, 229(1):152-172 doi.org/10.1111/j.1600-065X.2009.00782.x.
Elpek et al., "Mature natural killer cells with phenotypic and functional alterations accumulate upon sustained stimulation with IL-15/IL-15Rβ complexes," Proceedings of the National Academy of Science, Dec. 14, 2010, 107: 21647-21652.
Engel et al., "The crystal structure of dipeptidyl peptidase IV (CD26) reveals its functional regulation and enzymatic mechanism," Proc. Natl. Acad. Sci. U.S.A., Apr. 29, 2003, 100(9):5063-5068.
Epardaud et al., "Interleukin-15/Interleukin-15RA Complexes Promote Destruction of Established Tumors by Reviving Tumor-Resident CD8+ T Cells," Cancer Research 68: Apr. 15, 2008, 2972-2983.
Esensten et al., "Regulatory T-cell therapy for autoimmune and autoinflammatory diseases: The next frontier," The Journal of Allergy and Clinical Immunology, Dec. 1, 2018, 142(6):1710-1718.
Farr, et al., "Targeting cellular senescence prevents age-related bone loss in mice," Nat. Med., 2017, 23(9): 1072-1079.
Fehniger et al., "A Phase 1 Trial of CNDO-109-Activated Natural Killer Cells in Patients with High-Risk Acute Myeloid Leukemia," Biology of Blood and Marrow Transplantation, Aug. 2018, 24(8):1581-1589.
Feng et al., "The yin and yang functions of extracellular ATP and adenosine in tumor immunity," Cancer Cell International, Apr. 7, 2020, 20:110, 11 pages.
Ferreira et al., "Next-generation regulatory T cell therapy," Nature Reviews Drug Discovery, Sep. 20, 2019, 18(10):749-769, 21 pages.
Ferrucci et al., "The origins of age-related proinflammatory state," Blood, Mar. 15, 2005, 105(6):2294-2299.
Finkelman et al., "Anti-cytokine antibodies as carrier proteins. Prolongation of in vivo effects of exogenous cytokines by injection of cytokine-anti-cytokine antibody complexes," The Journal of Immunology, Aug. 1, 1993, 151:1235-1244.
Finkelstein et al., "Obesity and Severe Obesity Forecasts Through 2030," American Journal of Preventative Medicine, Jun. 2012, 42(6):563-570.
Ford et al., "TREM and TREM-like receptors in inflammation and disease," Current Opinion in Immunology, Feb. 21, 2009, 21(1):38-46.
Franceschi et al., "Inflamm-aging. An evolutionary perspective on immunosenescence," Annals of the New York Academy of Sciences, Jun. 2000, 908:244-254.
Frutoso et al., "Emergence of NK Cell Hyporesponsiveness after Two IL-15 Stimulation Cycles," Journal of Immunology, May 30, 2018, 201: 493-506.
Ganesh et al., "TGF-β Inhibition and Immunotherapy: Checkmate," Immunity, Apr. 17, 2018, 48(4):626-628.
Garber, "Bispecific antibodies rise again," Nat. Rev. Drug Discov., 2014, 13:799-801.
Gaulton et al., "Characterization of a monoclonal rat anti-mouse interleukin 2 (IL-2) receptor antibody and its use in the biochemical characterization of the murine IL-2 receptor," Clinical Immunology and Immunopathology, Jul. 1, 1985, 36(1):18-29.
Gejima et al., "Human single-chain Fv (scFv) antibody specific to human IL-6 with the inhibitory activity on IL-6-signaling," Human Antibodies, Jan. 1, 2002, 11(4):121-9.
Geng et al., "A novel anti-TNF scFv constructed with human antibody frameworks and antagonistic peptides," Immunol. Res. 62(3):377-385, 2015.
Georgilis et al., "PTBP1-Mediated Alternative Splicing Regulates the Inflammatory Secretome and the Pro-tumorigenic Effects of Senescent Cells," Cancer Cell, Jul. 9, 2018, 34(1):85-102.
Ghosh et al., "The Senescence-Associated Secretory Phenotype: Critical Effector in SkinCancer and Aging," Journal of Investigative Dermatology, Nov. 2016, 136(11):2133-2139.
Gibbs et al., "Identification of the factor VIIa binding site on tissue factor by homologous loop swap and alanine scanning mutagenesis, " Biochemistry, Nov. 1, 1994, 33(47):14003-10.
Gong et al., "DAMP-sensing receptors in sterile inflammation and inflammatory diseases," Nature Reviews Immunology, Sep. 26, 2019, 20(2):95-112.
Gorrell et al., "Expression of the rat CD26 Antigen (dipeptidyl peptidase IV) on subpopulations of rat lymphocytes," Cellular Immunology, Apr. 15, 1991, 134(1):205-215.
Grupp et al., "Chimeric Antigen Receptor-Modified T Cells for Acute Lymphoid Leukemia," The New England Journal of Medicine, Apr. 18, 2013, 368(16):1509-1518.
Gu et al., "Human CD39hi regulatory T cells present stronger stability and function under inflammatory conditions," Cellular and Molecular Immunology, Jul. 4, 2016, 14(6):521-528.
Guo et al., "Immunobiology of the IL-15-IL-15R complex as an antitumor and antiviral agent," 2017, Cytokine & Growth Factor Reviews, 38:10-21.
Gutschmidt et al., "A quantitative histochemical study of dipeptidyl peptidase IV (DPP IV)," Histochemistry, 1981, 73(2):285-304.
Haile et al., "Soluble CD80 Restores T Cell Activation and Overcomes Tumor Cell Programmed Death Ligand 1—Mediated Immune Suppression," J. Immunol., 2013, 191(5):2829-2836.
Hayflick et al., "The serial cultivation of human diploid cell strains," Experimental Cell Research, Dec. 1961, 25:585-621.
He et al., "Senescence in Health and Disease," Cell, Jun. 1, 2017, 169(6):1000-1011.
Hebbar et al., "Detection of circulating soluble CD28 in patients with systemic lupus erythematosus, primary Sjögren's syndrome and systemic sclerosis," Clinical & Experimental Immunology, May 2004, 136(2):388-92.
Helfrich et al., "A rapid and versatile method for harnessing scFv antibody fragments with varous biological effector functions," Journal of Immunological methods, 2000, 237(1-2):131-145 DOI:10.1016/S0022-1759(99)O0220-3.
Heneka et al., "Inflammasome signaling in brain function and neurodegenerative disease," Nature Reviews Neuroscience, Sep. 11, 2018, 19(10):610-621.
Heneka et al., "NLRP3 is activated in Alzheimer's disease and contributes to pathology in APP/PS1 mice, " Nature, Jan. 31, 2013, 493(7434):674-678, 8 pages.
Heng et al., "G Protein-Coupled Receptors Revisited: Therapeutic Applications Inspired by Synthetic Biology," Annual Review of Pharmacology and Toxicology, Jan. 2014, 54:227-249.
Heng et al., Sophea, et al. "Multiple soluble TGF-β receptors in addition to soluble endoglin are elevated in preeclamptic serum and they synergistically inhibit TGF-β signalling." Placenta, 2017 57:320 (1 page).
Highfill et al., "Overcoming Challenges in Process Development of Cellular Therapies," Current Hematologic Malignancy Reports, Jul. 6, 2019, 14(4):269-277, 9 pages.
Hoare et al., "The Power Behind the Throne: Senescence and the Hallmarks of Cancer," Annual Review of Cancer Biology, 2018, 2:175-194.
Hoffmann et al., "Large-scale in vitro expansion of polyclonal human CD4+CD25high regulatory T Cells," Blood, Aug. 2004, 104(3):895-903.

(56) References Cited

OTHER PUBLICATIONS

Hollande et al., "Inhibition of the dipeptidyl peptidase DPP4 (CD26) reveals IL-33-dependent eosinophil-mediated control of tumor growth," Nature Immunology, Feb. 18, 2019, 20(3):257-264.
Hombach et al., "Generation of the single chain antibody fragment conserves the idiotypic profile of the anti-CD30 monoclonal antibody HRS3," Scandinavian Journal of Immunology, Nov. 1998, 48(5):497-501.
Hu et al., "Discovery of a novel IL-15 based protein with improved developability and efficacy for cancer immunotherapy," Scientific Reports, 2018, 8:7675, 11 pages.
Huang et al., "Substrate recognition by tissue factor-factor VIIa Evidence for interaction of residues Lys165 and Lys166 of tissue factor with the 4-carboxyglutamate-rich domain of factor X," Journal of Biological Chemistry, Sep. 6, 1996, 271(36):21752-7.
Hudak et al., "Glycocalyx engineering reveals a Siglec-based mechanism for NK cell immunoevasion," Nature Chemical Biology, Jan. 2014, 10(1), 20 pages.
Hudson et al., "Targeting RAGE Signaling in Inflammatory Disease," Annual Review of Medicine, Jan. 2018, 69:349-364, 16 pages.
Huell et al., "Interleukin-6 is present in early stages of plaque formation and is restricted to the brains of Alzheimer's disease patients," Acta Neuropathologica, Nov. 1995, 89(6):544-551.
Hughes, et al., "Transfer of a TCR gene derived from a patient with a marked antitumor response conveys highly active T-cell effector functions," Hum. Gene Ther., 2005, 16:457-72.
Hynes et al., "In vitro analysis of cell metabolism using a long-decay pH-sensitive lanthanide probe and extracellular acidification assay," Analytical biochemistry, Jul. 1, 2009, 390(1):21-28.
Iannello et al., "p53-dependent chemokine production by senescent tumor cells supports NKG2D- dependent tumor elimination by natural killer cells," Journal of Experimental Medicine, Sep. 23, 2013, 210(10):2057-69.
Iihoshi et al., "Aclarubicin, an anthracycline anti-cancer drug, fluorescently contrasts mitochondria and reduces the oxygen consumption rate in living human cells," Toxicology Letters, Aug. 5, 2017, 277:109-114, 22 pages.
Inzucchi et al., "New Drugs for the Treatment of Diabetes, Part II: Incretin-Based Therapy and Beyond, " Circulation, Jan. 29, 2008, 117(4):574-584, 21 pages.
Jain et al., "Mitochondrial Reactive Oxygen Species Regulate Transforming Growth Factor-β Signaling," Journal of Biological Chemistry, Jan. 11, 2013, 288(2):770-777.
Jakob et al., "Structure reveals function of the dual variable domain immunoglobulin (DVD-Ig™) molecule, " Mabs, May 1, 2013, Taylor & Francis, 5(3):358-63.
Janeway, "Approaching the Asymptote? Evolution and Revolution in Immunology," Cold Spring Harbor Symposia on Quantitative Biology, 1989, 54 Pt 1:1-13.
Jeannin et al., "Soluble CD86 is a Costimulatory Moleculefor Human T Lymphocytes," Immunity, 2000, 13(3):303-312.
Jin et al., "Novel Insights Into the NLRP3 Inflammasome in Atherosclerosis," Journal of the American Heart Association, Jun. 11, 2019, 8(12):e012219, 12 pages.
Justice et al., "Senolytics in idiopathic pulmonary fibrosis: Results from a first-in-human, open-label, pilot study," EBioMedicine, Feb. 2019, 40:554-563.
Kain et al., "The identification of the endogenous ligands of natural killer T cells reveals the presence of mammalian a-linked glycosylceramides," Immunity, Oct. 16, 2014, 41(4):543-54.
Karin et al., "Senescent cell turnover slows with age providing an explanation for the Gompertz law," Nature Communications, 10:5495, 9 pages.
Karkera et al., "The anti-interleukin-6 antibody siltuximab down-regulates genes implicated in tumorigenesis in prostate cancer patients from a phase I study," The Prostate, Feb. 14, 2011, 71(13):1455-1465.
Katsuumi et al., "Vascular Senescence in Cardiovascular and Metabolic Diseases," Frontiers in Cardiovascular Medicine, 5:18, 13 pages.
Kellner et al., "Enhancing natural killer cell-mediated lysis of lymphoma cells by combining therapeutic antibodies with CD20-specific immunoligands engaging NKG2D or NKp30," Oncoimmunology, Jan. 2, 2016, 5(1):e1058459, 12 pages.
Kijanka et al., "Nanobody-based cancer therapy of solid tumors," Nanomedicine, Jan. 2015, 10(1):161-74.
Kim et al., "Experimental malaria infection triggers early expansion of natural killer cells," Infection and Immunity, Dec. 1, 2008, 76(12):5873-82.
Kim et al., "Identification of senescent cell surface targetable protein DPP4," Genes & Development, 2017, 31(15):1529-1534.
Kim et al., "SCAMP4 enhances the senescent cell secretome," Genes & Development, 2018, 32(13-14):909-914.
Kirchhofer et al., "The tissue factor region that interacts with substrates factor IX and factor X," Biochemistry, Jun. 27, 2000, 39(25):7380-7.
Kirkland et al., "Cellular Senescence: A Translational Perspective," EBioMedicine, Jul. 2017, 21:21-28.
Klein et al., "Cergutuzumab amunaleukin (CEA-IL2v), a CEA-targeted IL-2 variant-based immunocytokine for combination cancer immunotherapy: Overcoming limitations of aldesleukin and conventional IL-2-based immunocytokines," Oncoimmunology, 2017 6(3):e1277306, 15 pages.
Klein et al., "Design and characterization of structured protein linkers with differing flexibilities," Protein Engineering, Design & Selection, 2014, 27(10):325-30.
Klemann et al., "Cut to the chase: a review of CD26/dipeptidyl peptidase-4's (DPP4) entanglement in the immune system," Clinical and Experimental Immunology, Feb. 25, 2016, 185(1):1-21.
Klingenberg et al., "Depletion of FOXP3+ regulatory T cells promotes hypercholesterolemia and atherosclerosis," The Journal of Clinical Investigation, Feb. 15, 2013, 123:1323-1334.
Kondo et al., "Requirements for the functional expression of OX40 ligand on human activated CD4+ and CD8+ T cells, " Human Immunology, 2007, 68(7):563-571.
Kovaleva et al., "Shark variable new antigen receptor biologics—a novel technology platform for therapeutic drug development," Expert Opinion on Biological Therapy, Oct. 1, 2014, 14(10):1527-39.
Krah et al., "Single-domain antibodies for biomedical applications," Immunopharmacology and Immunotoxicology, Jan. 2, 2016, 38(1):21-8.
Kritsilis et al., "Ageing, Cellular Senescence and Neurodegenerative Disease," International Journal of Molecular Sciences, Sep. 27, 2018, 19(10):2937, 37 pages.
Krizhanovsky et al., "Senescence of activated stellate cells limits liver fibrosis," Cell, Aug. 22, 2008, 134(4):657-67.
Kumagai et al., "Monitoring of glutamate-induced excitotoxicity by mitochondrial oxygen consumption, " Synapse, Jan. 2019, 73(1):e22067, 24 Pages.
Lambeir et al., "Dipeptidyl-Peptidase IV from Bench to Bedside: An Update on Structural Properties, Functions, and Clinical Aspects of the Enzyme DPP IV," Critical Reviews in Clinical Laboratory Sciences, Sep. 29, 2003, 40(3):209-294.
Lamkanfi et al., "Mechanisms and Functions of Inflammasomes," Cell, May 22, 2014, 157(5):1013-1022.
Lansigan et al., "DI-Leu16-IL2, an Anti-CD20-Interleukin-2 Immunocytokine, is Safe and Active in Patients with Relapsed and Refractory B-Cell Lymphoma: A Report of Maximum Tolerated Dose, Optimal Biologic Dose, and Recommended Phase 2 Dose," Blood, Dec. 2, 2016, 128(22):620, 3 pages (Abstract Only).
Latz et al., "Activation and regulation of the inflammasomes," Nature Reviews Immunology, May 24, 2013, 13(6):397-411.
Latz et al., "NLRP3 inflammasome activation in inflammaging," Seminars in Immunology, Dec. 2018, 40:61-73, 13 pages.
Lau et al., "RNA-associated autoantigens activate B cells by combined B cell antigen receptor/Toll-like receptor 7 engagement," The Journal of Experimental Medicine, Oct. 31, 2005, 202(9):1171-1177.

(56) References Cited

OTHER PUBLICATIONS

Li et al., "A Novel I L2-based Irrmunotherapeutic Protein Prevents the Development of Atherosclerosis in ApoE-/mice and LDLR-/-mice," Journal of Immunology, May 1, 2020, 204(1):Supplement (Abstract Only), 2 pages.

Li et al., "Adoptive transfer of natural killer cells in combination with chemotherapy improves outcomes of patients with locally advanced colon carcinoma," Cytotherapy, Jan. 2018, 20(1):134-148, 15 pages.

Li et al., "The cGAS-cGAMP-STING pathway connects DNA damage to inflammation, senescence, and cancer," Journal of Experimental Medicine, Apr. 5, 2018, 215(5):1287-1299.

Liton et al., "Cellular senescence in the glaucomatous outflow pathway," Experimental Gerontology, Aug.-Sep. 2005, 40(8-9):745-748.

Liu et al., "A Novel Fusion of ALT-803 (IL-15 Superagonist) with an Antibody Demonstrates Antigen-specific Antitumor Responses," Journal of Biological Chemistry, 2016, 291(46):23869-23881.

Liu et al., "Evaluation of the biological activities of the IL-15 superagonist complex, ALT-803, following intravenous versus subcutaneous administration in murine models," Cytokine, Jul. 2018, 107: 105-112, 8 pages.

Loster et al., "The Cysteine-Rich Region of Dipeptidyl Peptidase IV (CD 26) is the Collagen Binding Site," Biochemical and Biophysical Research Communications, Dec. 5, 1995, 217(1):341-348.

Lu et al., "Molecular basis of binding between novel human coronavirus MERS-CoV and its receptor CD26," Nature, Jul. 7, 2013, 500(7461):227-231.

Lujambio et al., "Non-Cell-Autonomous Tumor Suppression by p53," Cell, Apr. 11, 2013, 153(2):449-460.

Maeda et al., "Original Ligand for LTβR is LIGHT: Insight into Evolution of the LT/LTBR System," J Immunol., 2018, 201(1):202-214.

Maganto-García et al., "Dynamic Changes in Regulatory T Cells Are Linked to Levels of Diet-Induced Hypercholesterolemia," Circulation, Jun. 20, 2011, 124:185-195.

Mandelboim et al., "Recognition of haemagglutinins on virus-infected cells by NKp46 activates lysis by human NK cells, " Nature, Feb. 2001, 409(6823):1055.

Marguet et al., "Enhanced insulin secretion and improved glucose tolerance in mice lacking CD26," Proc. Natl. Acad. Sci. U.S.A., Jun. 6, 2000, 97(12):6874-6879.

Martelli et al., "HLA-haploidentical transplantation with regulatory and conventionalT-cell adoptive immunotherapy prevents acute leukemia relapse," Blood, Jul. 24, 2014, 124(4):638-644.

Masoumi et al., "The role of hypoxia as the driving force for non-erythroid production of globin chains in preeclamptic placentas," Placenta. 2017;57:320.

McHugh et al., "Senescence and aging: Causes, consequences, and therapeutic avenues," Journal of Cellular Biology, Nov. 7, 2017, 217(1):65-77.

Mehta et al., "Why do trials for Alzheimer's disease drugs keep failing? A discontinued drug perspective for 2010-2015," Expert Opinion on Investigational Drugs, May 2017, 26(6):735-739.

Menshawy et al., "CD58; leucocyte function adhesion-3 (LFA-3) could be used as a differentiating marker between immune and non-immune thyroid disorders," Comparative Clinical Pathology, 2018, 27(3), 721-727, doi.org/10.1007/s00580-018-2657-x.

Mentlein et al., "Dipeptidyl-peptidase IV (CD26)-role in the inactivation of regulatory peptides," Regulatory Peptides, Nov. 30, 1999, 85(1):9-24.

Miah et al., "KIR2DL4 differentially signals downstream functions in human NK cells through distinct structural modules," The Journal of Immunology, Mar. 1, 2008, 180(5):2922-32.

Michelet et al., "Metabolic reprogramming of natural killer cells in obesity limits antitumor responses," Nature Immunology, Nov. 12, 2018, 19(12):1330-1340.

Milanovic et al., "Senescence-associated reprogramming promotes cancer stemness," Nature, Dec. 20, 2017, 553(7686):96-100.

Milanovic et al., "The Senescence-Stemness Alliance—A Cancer-Hijacked Regeneration Principle," Trends in Cellular Biology, Dec. 2018, 28(12):1049-1061, 13 pages.

Miller et al., "Soluble CD70: a novel immunotherapeutic agent for experimental glioblastoma," J Neurosurg., 2010, 113(2):280-285.

Miller et al., "Successful adoptive transfer and in vivo expansion of human haploidentical NK cells in patients with cancer," Blood, Apr. 15, 2005, 105(8):3051-3057.

Minamino et al., "A crucial role for adipose tissue p53 in the regulation of insulin resistance," Nature Medicine, Aug. 30, 2009, 15(9):1082-1087.

Mitterberger et al., "Adipogenic Differentiation is Impaired in Replicative Senescent Human Subcutaneous Adipose-Derived Stromal/Progenitor Cells," The Journals of Gerontology: Series A, Biological Sciences and Medical Sciences, Jan. 2014, 69(1):13-24.

Miyazaki et al., "Abstract 3265: NKTR-255, a polymer-conjugated IL-15 enhances anti-tumor NK cell responses and synergizes with monoclonal antibodies to provide long-term survival in human lymphoma model," Proceedings: AACR Annual Meeting 2019, Atlanta, GA, Mar. 29-Apr. 3, 2019, 1 page.

Moesta et al., "Targeting CD39 in cancer," Nature Reviews Immunology, Jul. 29, 2020, 20(12):739- 755, 17 pages.

Moiseeva et al., "Metformin inhibits the senescence-associated secretory phenotype by interfering with IKK/NF-κb activation," Aging Cell, Mar. 23, 2013, 12(3):489-498.

Molema et al., "The use of bispecific antibodies in tumor cell and tumor vasculature directed immunotherapy, " Journal of Controlled Release, 2000, 64(1-3):229-239.

Molgora et al., "Regulatory role of IL-1R8 in immunity and disease," Frontiers in Immunology, Apr. 20, 2016, 7:149.

Mookerjee et al., "Measurement and Analysis of Extracellular Acid Production to Determine Glycolytic Rate," Journal of Visualized Experiments : Jove, Dec. 2015, (106):e53464, 9 Pages.

Moore et al., "Macrophages in atherosclerosis: a dynamic balance," Nature Reviews Immunology, Sep. 2, 2013, 13:709-721, 13 pages.

Moreno et al., "Molecular Evidence of Adenosine Deaminase Linking Adenosine A2A Receptor and CD26 Proteins," Frontiers in Pharmacology, Feb. 15, 2018, 9:106, 18 pages.

Moretta et al., "CD69-mediated pathway of lymphocyte activation: anti-CD69 monoclonal antibodies trigger the cytolytic activity of different lymphoid effector cells with the exception of cytolytic T lymphocytes expressing T cell receptor alpha/beta," Journal of Experimental Medicine, Dec. 1, 1991, 174(6):1393-8.

Mujić-Delić et al., "GPCR-targeting nanobodies: attractive research tools, diagnostics, and therapeutics," Trends in Pharmacological Sciences, May 1, 2014, 35(5):247-55.

Muller et al., "Antibody fusions with immunomodulatory proteins for cancer therapy," Pharmacology and Therapeutics, 2015, 154:57-66.

Mulvihill et al., "Pharmacology, Physiology, and Mechanisms of Action of Dipeptidyl Peptidase-4 Inhibitors," Endocrine Reviews, Dec. 1, 2014, 35(6):992-1019.

Munoz-Espin et al., "Cellular senescence: from physiology to pathology," Nature Reviews Molecular Cellular Biology, Jun. 23, 2014, 15(7):482-496.

Munoz-Espin et al., "Programmed Cell Senescence during Mammalian Embryonic Development," Cell, Nov. 21, 2013, 155(5):1104-1118.

Musi et al., "Tau protein aggregation is associated with cellular senescence in the brain," Aging Cell, Aug. 20, 2018, 17(6):e12840, 13 pages.

Must et al., "The Disease Burden Associated with Overweight and Obesity," Endotext, Feingold et al. (eds.), South Dartmouth, MA, 2000, 35 pages.

Muyldermans et al., "Recognition of antigens by single-domain antibody fragments: the superfluous luxury of paired domains," Trends in Biochemical Sciences, Apr. 1, 2001, 26(4):230-5.

Muyldermans, "Nanobodies: natural single-domain antibodies," Annual Review of Biochemistry, Jun. 2, 2013, 82:775-97.

Muyldermans, "Single domain camel antibodies: current status," Reviews in Molecular Biotechnology, Jun. 1, 2001, 74(4):277-302.

(56) References Cited

OTHER PUBLICATIONS

Myung et al., "Evidence of DNA damage in Alzheimer disease: phosphorylation of histone H2AX in astrocytes," Age, Apr. 23, 2008, 30(4):209-215.
Nag et al., "Soluble MHC II-peptide complexes induce antigen-specific apoptosis in T cells," Cellular Immunology, May 25, 1996, 170(1):25-33.
Nayyar et al., "Overcoming Resistance to Natural Killer Cell Based Immunotherapies for Solid Tumors," Frontiers in Oncology, 2019, 9: DOI:10.3389/fonc.2019.00051.
Nelson et al., "A senescent cell bystander effect: senescence-induced senescence," Aging Cell, Feb. 9, 2012, 11(2):345-349.
Nilsson et al., "Targeted delivery of tissue factor to the ED-B domain of fibronectin, a marker of angiogenesis, mediates the infarction of solid tumors in mice, " Cancer Research, American Association for Cancer Researc, Proceddings: AACR 107th Annual Meeting, 2016, Apr. 16-20, 2016, New Orleans, LA 61(2):711-716.
Nishida et al., "CD26 is a potential therapeutic target by humanized monoclonal antibody for the treatment of multiple myeloma," Blood Cancer Journal, Oct. 22, 2018, 8(11):99, 17 pages.
O'Sullivan et al., "Natural Killer Cell Memory," Immunity, Oct. 20, 2015, 43(4):634-645.
Oberle et al., "Rapid Suppression of Cytokine Transcription in Human CD4+CD25-T Cells by CD4+Foxp3+ Regulatory T Cells: Independence of IL-2 Consumption, TGF-β, and Various Inhibitors of TCR Signaling," The Journal of Immunology, Sep. 15, 2007, 179(6):3578-3587.
Ogrodnik et al., "Cellular senescence drives age-dependent hepatic steatosis," Nat Commun. Jun. 13, 2017;8:15691, 12 pages.
Ogrodnik et al., "Obesity-Induced Cellular Senescence Drives Anxiety and Impairs Neurogenesis," Cell Metabolism, May 2019, 29(5):1061-1077, 25 pages.
Ohnuma et al., "Blockade of CD26-mediated T cell costimulation with soluble caveolin-1-Ig fusion protein induces anergy in CD4+T cells," Biochemical and Biophysics Research Communications, Aug. 21, 2009, 386(2):327-332.
Ohnuma et al., "CD26 Mediates Dissociation of Tollip and IRAK-1 from Caveolin-1 and Induces Upregulation of CD86 on Antigen-Presenting Cells," Molecular and Cellular Biology, Sep. 1, 2005, 25(17):7743-7757.
Ohnuma et al., "CD26 up-regulates expression of CD86 on antigen-presenting cells by means of caveolin-1," Proc. Natl. Acad. Sci. U.S.A., Sep. 28, 2004, 101(39):14186-14191.
Ohnuma et al., "Role of CD26/dipeptidyl peptidase IV in human T cell activation and function," Frontiers in Bioscience, Jan. 1, 2008, 13:2299-2310.
Ohnuma et al., "Soluble CD26/Dipeptidyl Peptidase IV Induces T Cell Proliferation Through CD86 Up-Regulation on APCs," Journal of Immunology, Dec. 15, 2001, 167(12):6745-6755.
Ovadya et al., "Strategies targeting cellular senescence," The Journal of Clinical Investigation, Apr. 2, 2018, 128(4):1247-54.
Owicki et al., "Biosensors based on the energy metabolism of living cells: the physical chemistry and cell biology of extracellular acidification," Biosensors and Bioelectronics, Jan. 1, 1992, 7(4):255-272.
Padutsch et al., "Superior Treg-Expanding Properties of a Novel Dual-Acting Cytokine Fusion Protein," Frontiers in Pharmacology, Dec. 18, 2019, 10:1490, 10 pages.
Palmer et al., "Cellular Senescence in Type 2 Diabetes: A Therapeutic Opportunity," Diabetes, Jul. 2015, 64(7):2289-2298.
Parker et al., "Design, production, and characterization of a single-chain variable fragment (ScFv) derived from the prostate specific membrane antigen (PSMA) monoclonal antibody J591," Protein Expression and Purification, Jun. 1, 2013, 89(2):136-45.
PCT International Preliminary Report on Patentability in International Appln. No. PCT/US2019/048881, dated Mar. 11, 2021, 7 pages.
PCT International Preliminary Report on Patentability in International Appln. No. PCT/US2019/048930, dated Mar. 11, 2021, 9 pages.
PCT International Preliminary Report on Patentability in International Appln. No. PCT/US2019/049142, dated Mar. 11, 2021, 11 pages.
PCT International Preliminary Report on Patentability in International Appln. No. PCT/US2019/049158, dated Mar. 11, 2021, 8 pages.
PCT International Search Report and Written Opinion in International Appln. No. PCT/US2019/048881, dated Nov. 9, 2019, 16 pages.
PCT International Search Report and Written Opinion in International Appln. No. PCT/US2019/048930, dated Nov. 20, 2019, 18 pages.
PCT International Search Report and Written Opinion in International Appln. No. PCT/US2019/04912, dated Jun. 23, 2020, 20 pages.
PCT International Search Report and Written Opinion in International Appln. No. PCT/US2019/049158, dated Jan. 20, 2020, 18 pages.
PCT International Search Report and Written Opinion in International Appln. No. PCT/US2020/035598, dated Feb. 18, 2021, 12 pages.
PCT International Search Report and Written Opinion in International Appln. No. PCT/US2021/017620, dated Aug. 6, 2021, 22 pages.
PCT International Search Report and Written Opinion in International Appln. No. PCT/US2021/017621, dated Jun. 9, 2021, 15 pages.
PCT International Search Report and Written Opinion in International Appln. No. PCT/US2021/017714, dated Aug. 27, 2021, 22 pages.
PCT International Search Report and Written Opinion in International Appln. No. PCTUS2020/038717, dated Oct. 16, 2020, 17 pages.
Peipp et al., "HER2-specific immunoligands engaging NKp30 or NKp80 trigger NK-cell-mediated lysis of tumor cells and enhance antibody-dependent cell-mediated cytotoxicity," Oncotarget, Oct. 13, 2015, 6(31):32075.
Pittayapruek et al., "Role of Matrix Metalloproteinases in Photoaging and Photocarcinogenesis," International Journal of Molecular Sciences, 2016, 17(6):868, 20 pages.
Priyanka et al., "Linkers in the structural biology of protein-protein interactions, " Protein Sci., 2013, 22(2):153-167.
Purohit et al., "Smad3-dependent regulation of type I collagen in human dermal fibroblasts: Impact on human skin connective tissue aging," Journal of Dermatological Science, Jul. 2016, 83(1):80-83, 4 pages.
Qin et al., "Critical Role of P2Y12 Receptor in Regulation of Th17 Differentiation and Experimental Autoimmune Encephalomyelitis Pathogenesis," The Journal of Immunology, Jul. 1, 2017, 199(1):72-81.
Rafei et al., "Off-the-shelf virus specific T-cells for therapy of adenovirus disease in immunosuppressed patients," Journal of Clinical Oncology, May 26, 2019, 37(15 Suppl.):7008, 2 pages.
Rahbarizadeh et al., "Nanobody; an old concept and new vehicle for immunotargeting," Immunological Investigations, Jan. 1, 2011, 40(3):299-338.
Raj et al., "Adenosine Deaminase Acts as a Natural Antagonist for Dipeptidyl Peptidase 4-Mediated Entry of the Middle East Respiratory Syndrome Coronavirus," Journal of Virology, Feb. 2014, 88(3):1834-1838, 7 pages.
Ranganathan et al., "Pinpointing the putative heparin/sialic acid-binding residues in the 'sushi' domain 7 of factor H: a molecular modeling study," Biocomputing 2000, 1999, 155-67.
Rao et al., "Purification and characterization of rabbit tissue factor," Thrombosis Research, Oct. 1, 1989, 56(1):109-118.
Rasmussen et al., "Crystal structure of human dipeptidyl peptidase IV/CD26 in complex with a substrate analog," Nature Structural and Molecular Biology, 2003, 10(1):19-25.
Raz et al., "Efficacy and safety of the dipeptidyl peptidase-4 inhibitor sitagliptin as monotherapy in patients with type 2 diabetes mellitus, " Diabetologia, Sep. 26, 2006, 49(11):2564-2571.
Resta et al., "Ecto-enzyme and signaling functions of lymphocyte CD 7 3," Immunological Reviews, 1998, 161:95-109.

(56) References Cited

OTHER PUBLICATIONS

Rhein et al., "Characterization of Human and Murine T-Cell Immunoglobulin Mucin Domain 4 (TIM-4) IgV Domain Residues Critical for Ebola Virus Entry," J Viral., 2016, 90(13):6097-6111.

Rippmann et al., "Fusion of the Tissue Factor Extracellular Domain to a Tumor Stromaspecific Single-Chain Fragment Variable Antibody Results in an Antigen-Specific Coagulation-Promoting Molecule," Biochemical Journal, 2000, 349(3):805-812.

Rittie et al., "Natural and Sun-Induced Aging of Human Skin," Cold Spring Harbor Perspective in Medicine, 2015, 5(1):a015370, 15 pages.

Rocha et al., "A novel immunofluorescent assay to investigate oxidative phosphorylation deficiency in mitochondrial myopathy: understanding mechanisms and improving diagnosis," Scientific reports, Oct. 15, 2015, 5:15037, 17 Pages.

Rodier et al., "Persistent DNA damage signaling triggers senescence-associated inflammatory cytokine secretion," Nature Cell Biology, Jul. 13, 2009, 11(8): 973-979, 15 pages.

Rogge et al., "Antibodies to the IL-12 receptor β2 chain mark human Th1 but not Th2 cells in vitro and in vivo," The Journal of Immunology, Apr. 1, 1999, 162(7):3926-32.

Roh et al., "Damage-Associated Molecular Patterns in Inflammatory Diseases," Immune Network, Aug. 2018, 18(4):e27, 14 pages.

Romano et al., "Past, Present, and Future of Regulatory T Cell Therapy in Transplantation and Autoimmunity," Frontiers in Immunology, Jan. 1, 2019, 10:43, 14 pages.

Romee et al., "Cytokine activation induces human memory-like NK cells," Blood, Dec. 6, 2012, 120(24):4751-4760.

Rossi et al., "Complex and defined biostructures with the dock-and-lock method, " Trends in Pharmacological Sciences, Sep. 1, 2012, 33(9):474-81.

Rossi et al., "Stably tethered multifunctional structures of defined composition made by the dock and lock method for use in cancer targeting, " Proceedings of the National Academy of Sciences, May 2, 2006, 103(18):6841-6.

Rubinstein et al., "Converting IL-15 to a superagonist by binding to soluble IL-15Rα," Proceedings of the National Academy of Sciences U.S.A., Jun. 13, 2006, 103(24):9166-9171.

Ruf et al., "Cofactor residues lysine 165 and 166 are critical for protein substrate recognition by the tissue factor-factor VIIa protease complex," Journal of Biological Chemistry, Mar. 25, 1992, 267(9):6375-81.

Ruf et al., "Tissue factor residues 157-167 are required for efficient proteolytic activation of factor X and factor VII," Journal of Biological Chemistry, Nov. 5, 1992, 267(31):22206-10.

Ruscetti et al., "NK cell-mediated cytotoxicity contributes to tumor control by a cytostatic drug combination, " Science, Dec. 21, 2018, 362(6421):1416-1422, 8 pages.

Sagiv et al., "Granule exocytosis mediates immune surveillance of senescent cells," Oncogene, 2013, 32(15):1971-1977.

Sakaguchi et al., "Regulatory T Cells and Human Disease," Annual Review of Immunology, Apr. 26, 2020, 38:541-566.

Sakaguchi et al., "Regulatory T Cells and Immune Tolerance," Cell, May 30, 2008, 133(5):775-787.

Sakaguchi et al., "Regulatory T cells: how do they suppress immune responses?" International Immunology, Sep. 7, 2009, 21(10):1105-1111.

Sakamoto et al., "Phase I clinical trial of autologous NK cell therapy using novel expansion method in patients with advanced digestive cancer," Journal of Translational Medicine, Aug. 25, 2015, 13:277, 13 pages.

Sakamuri et al., "Measurement of respiratory function in isolated cardiac mitochondria using Seahorse XFe24 Analyzer: applications for aging research," Geroscience, Jun. 1, 2018, 40(3):347-356.

Salminen et al., "Emerging role of NF-κB signaling in the induction of senescence-associated secretory phenotype (SASP), " Cellular Signaling, Apr. 2012, 24(4):835-845.

Sandusky et al., "Regulation of 2B4 (CD244)-mediated NK cell activation by ligand-induced receptor modulation," European Journal of Immunology, Dec. 2006, 36(12):3268-76.

Sato et al., "Recombinant soluble murine IL-4 receptor can inhibit or enhance IgE responses in vivo," The Journal of Immunology, Apr. 1, 1993, 150:2717-2723.

Schafer et al., "Cellular senescence mediates fibrotic pulmonary disease," Nat Commun., Feb. 2017, 8:14532, 11 pages.

Schullek et al., "Key ligand interface residues in tissue factor contribute independently to factor VIIa binding, " Journal of Biological Chemistry, Jul. 29, 1994, 269(30):19399-403.

Schwoppe et al., "Tissue-factor fusion proteins induce occlusion of tumor vessels," Thrombosis Research, Apr. 1, 2010, 125:S143-S150.

Seo et al., "Positive Feedback Loop between Plasminogen Activator Inhibitor-1 and Transforming Growth Factor-Beta1 during Renal Fibrosis in Diabetes," American Journal of Nephrology, Sep. 25, 2009, 30:481-490.

Sharkey et al., "Improved Therapeutic Results by Pretargeted Radioimmunotherapy of Non-Hodgkin's Lymphoma with a New Recombinant, Trivalent, Anti-CD20, Bispecific Antibody," Cancer Research, Jul. 1, 2008, 68(13):5282-90.

Sharma et al., "Regulatory T Cells License Macrophage Pro Resolving Functions During Atherosclerosis Regression," Circulation Research, Apr. 27, 2020, 127:335-353.

Smith et al., "Antigen Nature and Complexity Influence Human Antibody Light Chain Usage and Specificity," Vaccine, 2016, 34(25): 2813-2820.

Smith et al., "Development and evaluation of an optimal human single-chain variable fragment-derived BCMA-targeted Car T cell vector," Molecular Therapy, Jun. 6, 2018, 26(6):1447-56.

Soerensen et al., "Safety, PK/PD, and anti-tumor activity of RO6874281, an engineered variant of interleukin-2 (IL-2v) targeted to tumor-associated fibroblasts via binding to fibroblast activation protein (FAP), " Journal of Clinical Oncology, Jun. 1, 2018, 36(No. 15 Suppl.):e15155, 2 pages.

Sondel et al., "Combination Therapy with Interleukin-2 and Anti-tumor Monoclonal Antibodies," Cancer Journal from Scientific American, Jan. 1, 1997, 3(Suppl. 1):S121-S127.

Sone et al., "Pancreatic beta cell senescence contributes to the pathogenesis of type 2 diabetes in high-fat diet-induced diabetic mice," Diabetologia, 2005, 48(1):58-67.

Song et al., "IL-12/IL-18-preactivated donor NK cells enhance GVL effects and mitigate GvHD after allogeneic hematopoietic stem cell transplantation," European Journal of Immunology, Apr. 2018, 48(4):670-682.

Soriani et al., "ATM-ATR-dependent up-regulation of DNAM-1 and NKG2D ligands on multiple myeloma cells by therapeutic agents results in enhanced NK-cell susceptibility and is associated with a senescent phenotype," Blood, Apr. 9, 2009, 113(15):3503-11.

Spiess et al., "Alternative molecular formats and therapeutic applications for bispecific antibodies," Molecular Immunology, Oct. 1, 2015, 67(2):95-106.

Stoklasek et al., "Combined IL-15/IL-15Rα Immunotherapy Maximizes IL-15 Activity In Vivo," The Journal of Immunology, Nov. 1, 2006, 177(9):6072-6080.

Storer et al., "Senescence is a Developmental Mechanism that Contributes to Embryonic Growth and Patterning, " Cell, Nov. 21, 2013, 155(5):1119-1130.

Stryer, Biochemistry Fourth Edition, W. H. Freeman and Company, New York, 1995, pp. 18-23, 8 pages.

Swanson et al., "The NLRP3 inflammasome: molecular activation and regulation to therapeutics," Nature Reviews Immunology, Apr. 29, 2019, 19(8):477-489, 13 pages.

Szalay et al., "Cutting edge: anti-CD1 monoclonal antibody treatment reverses the production patterns of TGF-β2 and Th1 cytokines and ameliorates listeriosis in mice," The Journal of Immunology, Jun. 15, 1999, 162(12):6955-8.

Tahara-Hanaoka et al., "Functional characterization of DNAM-1 (CD226) interaction with its ligands PVR (CD155) and nectin-2 (PRR-2/CD112)," International Immunology, Apr. 1, 2004, 16(4):533-8.

Takahashi et al., "Downregulation of cytoplasmic DNases is implicated in cytoplasmic DNA accumulation and SASP in senescent cells," Nature Communications, Mar. 28, 2018, 9:1249, 12 pages.

(56) References Cited

OTHER PUBLICATIONS

Takahashi et al., "Simple and inexpensive technique for measuring oxygen consumption rate in adherent cultured cells," The Journal of Physiological Sciences, Nov. 2017, 67(6):731-737.

Takeda et al., "Phase I study of YS110, a recombinant humanized monoclonal antibody to CD26, in Japanese patients with advanced malignant pleural mesothelioma," Lung Cancer, Nov. 2019, 137:64-70.

Tanaka et al., "Cloning and functional expression of the T cell activation antigen CD26," Journal of Immunology, Jul. 15, 1992, 149(2):481-486.

Tang et al., "The Foxp3+ regulatory T cell: a jack of all trades, master of regulation," Nature Immunology, Feb. 19, 2008, 9(3):239-244.

Teissier et al., "The receptor for advanced glycation end-products (RAGE) is an important pattern recognition receptor (PRR) for inflammaging," Biogerontology, Apr. 9, 2019, 20(3):279-301, 23 pages.

Teng et al., "Structural assessment of the effects of amino acid substitutions on protein stability and protein proteininteraction," International journal of computational biology and drug design, Feb. 7, 2011, 3(4):334-349.

Theil et al., "Adoptive transfer of allogeneic regulatory T cells into patients with chronic graft-versus-host disease, " Cytotherapy, Apr. 2015, 17(4):473-486, 14 pages.

Thonhoff et al., "Expanded autologous regulatory T-lymphocyte infusions in ALS," Neurology Neuroimmunology Neuroinflammation, May 18, 2018, 5(4):e465, 8 pages.

Tobin et al., "NK cells in childhood obesity are activated, metabolically stressed, and functionally deficient," JCI Insight, Dec. 21, 2017, 2(24):e94939, 9 pages.

Tomala et al., "In Vivo Expansion of Activated Naive CD8+ T Cells and NK Cells Driven by Complexes of IL-2 and Anti-IL-2 Monoclonal Antibody As Novel Approach of Cancer Immunotherapy, " The Journal of Immunology, Oct. 15, 2009, 183:4904-4912.

Tominaga et al., "TGF-β Signaling in Cellular Senescence and Aging-Related Pathology," International Journal of Molecular Sciences, Oct. 10, 2019, 20(20):5002, 18 pages.

Trevani et al., "Extracellular acidification induces human neutrophil activation," The Journal of Immunology, Apr. 15, 1999, 162(8):4849-4857.

Tse et al., "ABT-263: A Potent and Orally Bioavailable Bcl-2 Family Inhibitor," Cancer Research, May 2008, 68(9):3421-3428.

Uryga et al., "Ageing induced vascular smooth muscle cell senescence in atherosclerosis," Journal of Physiology, Apr. 15, 2016, 594(8):2115-2124.

Vaishampayan et al., "A phase I trial of ALKS 4230, an engineered cytokine activator of NK and effector T cells, in patients with advanced solid tumors," Journal of Clinical Oncology, 2017, 35(15 Suppl.):TPS3111, 4 pages (Abstract Only).

Van Audenhove et al., "Nanobodies as versatile tools to understand, diagnose, visualize and treat cancer," EBioMedicine, Jun. 1, 2016, 8:40-8.

Van den Bergh et al., "IL-15 receptor alpha as the magic wand to boost the success of IL-15 antitumor therapies: The upswing of IL-15 transpresentation, " Pharmacology and Therapeutics, 2017, 170:73-79.

Van Deursen, "The role of senescent cells in ageing, " Nature, May 21, 2014, 509(7501):439-446.

Vankadari et al., "Emerging COVID-19 coronavirus: glycan shield and structure prediction of spike glycoprotein and its interaction with human CD26," Emerging Microbes and Infection, Mar. 17, 2020, 9(1):601-604.

Vidarsson et al., "IgG subclasses and allotypes: from structure to effector functions," Frontiers in immunology, Oct. 20, 2014, 5:520, 17 Pages.

Vincke et al., "Introduction to heavy chain antibodies and derived Nanobodies," Single Domain Antibodies, Humana Press, Totowa, NJ, 2012, pp. 15-26.

Von Kobbe, "Cellular senescence: a view throughout organismal life," Cellular and Molecular Life Sciences, Jul. 20, 2018, 75:3553-3567, 15 pages.

Waaijer et al., "Do senescence markers correlate in vitro and in situ within individual human donors?," Aging Feb. 2018, 10(2):278-289.

Walsh et al., "Inflammasomes in the CNS," Nature Reviews Neuroscience, Jan. 8, 2014, 15(2):84-97, 14 pages.

Wang et al., A New Recombinant Single Chain Trispecific Antibody Recruits T Lymphocytes to Kill CEA (Carcinoma Embryonic Antigen) Positive Tumor Cells In Vitro Efficiently, Journal of Biochemisty, 2004, 135(4):555-565 DOI: 10.1093/jb/mvh065.

Wang et al., "Biomarkers of Cellular Senescence and Skin Aging," Frontiers in Genetics, Aug. 23, 2018, 9:247, 14 pages.

Wang et al., "Loss of lamin B1 is a biomarker to quantify cellular senescence in photoaged skin," Scientific Reports, Nov. 15, 2017, 7(1):15678, 8 pages.

Wang et al., "Recombinant human CD137L for cancer immunotherapy: effects of different fusions and linkers on its activity, " Cancer Immunol Immunother., 2012, 61(4):489-495.

Washburn et al., "A potential role for shed soluble major histocompatibility class I molecules as modulators of neurite outgrowth, " PLoS One, Mar. 31, 2011, 6(3):e18439.

Weber et al., "Specific low-affinity recognition of major histocompatibility complex plus peptide by soluble T-cell receptor," Nature, Apr. 1992, 356(6372):793.

Weihermann et al., "Elastin structure and its involvement in skin photoageing," International Journal of Cosmetic Science, Jun. 2017, 39(3):241-247.

Weihofen et al., "Crystal Structure of CD26/Dipeptidyl-peptidase IV in Complex with Adenosine Deaminase Reveals a Highly Amphiphilic Interface," Journal of Biological Chemistry, Oct. 2004, 279(41):43330-43335.

Weiner et al., "Antibody-based immunotherapy of cancer," Cell, Mar. 16, 2012, 148(6):1081-4.

Weiss et al., "Formyl-Peptide Receptors in Infection, Inflammation, and Cancer," Trends in Immunology, Oct. 2018, 39(10):815-829, 15 pages.

Wesolowski et al., "Single domain antibodies: promising experimental and therapeutic tools in infection and immunity," Medical Microbiology and Immunology. Aug. 1, 2009, 198(3):157-74.

Wiemann et al., "Hepatocyte telomere shortening and senescence are general markers of human liver cirrhosis," The FASEB Journal, Jul. 2002, 16(9):935-942.

Wiley et al., "Mitochondrial Dysfunction Induces Senescence with a Distinct Secretory Phenotype," Cell Metabolism, Feb. 9, 2016, 23(2):303-314.

Witkowsa et al., "Soluble intercellular adhesion molecule-1 (sICAM-1): an overview," Eur Cytokine Netw. 2004, 15(2):91-98.

Xiong et al., "Maternal uterine NK cell-activating receptor KIR2DS1 enhances placentation, " The Journal of Clinical Investigation, Oct. 1, 2013, 123(10):4264-72.

Xu et al., "JAK inhibition alleviates the cellular senescence-associated secretory phenotype and frailty in old age," Proceedings of the National Academy of Sciences U.S.A., Nov. 17, 2015, 112(46):E6301-6310, 10 pages.

Xu et al., "Senolytics improve physical function and increase lifespan in old age," Nature Medicine, Aug. 2018, 24(8):1246, 15 pages.

Xu et al., "Transplanted senescent cells induce an osteoarthritis-like condition in mice, " The Journals of Gerontology: Series A, Jun. 1, 2017, 72(6):780-5.

Yamamoto et al., "Measurement of glucose uptake in cultured cells," Curr Protoc Pharmacol, Dec. 2011, Chapter 12:12.14.1-12.14.22.

Yamazaki et al., "Vascular Cell Senescence Contributes to Blood-Brain Barrier Breakdown," Stroke, Feb. 16, 2016, 47(4):1068-1077, 15 pages.

Yan et al., "Obesity- and aging-induced excess of central transforming growth factor-β potentiates diabetic development via an RNA stress response," Nature Medicine, Aug. 3, 2014, 20:1001-1008, 9 pages.

(56) References Cited

OTHER PUBLICATIONS

Yanai et al., "Cellular senescence-like features of lung fibroblasts derived from idiopathic pulmonary fibrosis patients," Aging (Albany NY), Sep. 2015, 7(9):664-672.
Yigit et al., "A combination of an anti-SLAMF6 antibody and ibrutinib efficiently abrogates expansion of chronic lymphocytic leukemia cells, " Oncotarget, May 3, 2016, 7(18):26346.
Yousefzadeh et al., "An aged immune system drives senescence and ageing of solid organs," Nature, May 12, 2021, 594:100-105, 34 pages.
Yu et al., "Targeting the Senescence-Overriding Cooperative Activity of Structurally Unrelated H3K9 Demethylases in Melanoma," Cancer Cell, Feb. 12, 2018, 33(2):322-336, 23 pages.
Yu et al., "The dipeptidyl peptidase IV family in cancer and cell biology," FEBS Journal, Feb. 5, 2010, 277(5):1126-1144.
Yun et al., "Recurrent turnover of senescent cells during regeneration of a complex structure," Elife, May 5, 2015, 4:e05505, 16 pages.
Yung et al., "A selective transforming growth factor-β ligand trap attenuates pulmonary hypertension," American Journal of Respiratory and Critical Care Medicine, Nov. 1, 2016, 194(9):1140-51.
Zhang et al., "AAED1 modulates proliferation and glycolysis in gastric cancer," Oncology Reports, Aug. 1, 2018, 40(2):1156-1164.
Zhang et al., "The bone anabolic effects of irisin are through preferential stimulation of aerobic glycolysis," Bone, Sep. 1, 2018, 114:150-160.
Zhao et al., "Histone Deacetylase-3 Modification of MicroRNA-31 Promotes Cell Proliferation and Aerobic Glycolysis in Breast Cancer and is Predictive of Poor Prognosis," Journal of breast cancer, Jun. 1, 2018, 21(2):112-123.
Zheng et al., "Acquisition of Suppressive Function by Activated Human CD4+CD25-T Cells is Associated with the Expression of CTLA-4 Not FoxP3," The Journal of Immunology, Aug. 1, 2008, 181(3):1683-1691.
Zhong et al., "A Potential Role for Dendritic Cell/Macrophage-Expressing DPP4 in Obesity-Induced Visceral Inflammation," Diabetes, Jan. 2013, 62(1):149-157.
Zhou et al., "A novel chimeric antigen receptor redirecting T-cell specificity towards CD26cancer cells," Leukemia, Apr. 2020, 35(1):119-129, 11 pages.
Zhu et al., "New agents that target senescent cells: the flavone, fisetin, and the BCL-XL inhibitors, A1331852 and A1155463," Aging (Albany NY), Mar. 2017, 9(3):955-963.
Zhu et al., "Novel Human Interleukin-15 Agonists," The Journal of Immunology, Sep. 15, 2009, 183(6):3598-3607.
Zou et al., "2-NBDG as a fluorescent indicator for direct glucose uptake measurement," Journal of biochemical and biophysical methods, Sep. 30, 2005, 64(3):207-215.
Zwaagstra et al., "Engineering and therapeutic application of single-chain bivalent TGF-β family traps," Molecular Cancer Therapeutics, Jul. 1, 2012, 11(7):1477-87.
Baker et al., "Chronic treatment with the beta(2)-adrenoceptor agonist prodrug BRL-47672 impairs rat skeletal muscle function by inducing a comprehensive shift to a faster muscle phenotype," J Pharmacol Exp Ther., Oct. 2006, 319(1):439-446.
Baker et al., "Effects of conjugated linoleic acid (CLA) on tissue composition parameters in a murine cachexia model," The FASEB Journal, Mar. 2006, 20(4), 2 pages (Abstract Only).
Berry et al., "Cancer Anorexia and Cachexia: Screening in an Ambulatory Infusion Service and Nutrition Consultation," Clin J Oncol Nurs., 2018, 22(1):63-68.
Chang et al., "Association Between Sarcopenia and Cognitive Impairment: A Systematic Review and Meta-Analysis," J Am Med Dir Assoc., Dec. 1, 2016, 17(12):1164e7-1164e15, 9 pages.
Chen et al., "Circulating levels of resistin and risk of type 2 diabetes in men and women: results from two prospective cohorts," Diabetes Care, Feb. 2009, 32(2):329-334.
Cosgrove et al., "Usher protein functions in hair cells and photoreceptors," Int J Biochem Cell Biol., Jan. 2014, 46:80-89.

Helman et al., "Effects of ageing and senescence on pancreatic β-cell function," Diabetes Obes Metab., Sep. 2016, 18(Suppl. 1):58-62.
Jeon et al., "Local clearance of senescent cells attenuates the development of post-traumatic osteoarthritis and creates a pro-regenerative environment," Nat Med., Jun. 2017, 23(6):775-781.
Kim et al., "Insulin resistance, inflammation, and nonalcoholic fatty liver disease in non-obese adults without metabolic syndrome components," Hepatol Int., Jun. 2013, 7(2):586-591.
Kuyinu et al., "Animal models of osteoarthritis: classification, update, and measurement of outcomes," J Orthop Surg Res., Feb. 2, 2016, 11:19, 27 pages.
Melk et al., "Expression of p16INK4a and other cell cycle regulator and senescence associated genes in aging human kidney," Kidney Int., Feb. 2004, 65(2):510-520.
Melk et al., "Senescence of renal cells: molecular basis and clinical implications," Nephrology Dialysis Transplantation, Dec. 2003, 18(12):2474-2478.
Price et al., "Comparison of collagenase-cleaved articular cartilage collagen in mice in the naturally occurring STR/ort model of osteoarthritis and in collagen-induced arthritis," Osteoarthritis Cartilage, Mar. 2002, 10(3):172-179.
Sousa-Victor et al., "Geroconversion of aged muscle stem cells under regenerative pressure," Cell Cycle, Oct. 15, 2014, 13(20):3183-3190.
Xu et al., "Celecoxib attenuates cachectic events in mice by modulating the expression of vascular endothelial growth factor," Mol Med Rep., Jan. 2015, 11(1):289-294.
Huang et al., "Targeting the vasculature of colorectal carcinoma with a fused protein of (RGD) 3-tTF" The Scientific World Journal, 2013(637086):1-11, 2013.
PCT International Preliminary Report on Patentability in International Appln. No. PCT/US2021/029920, dated Nov. 10, 2022, 11 pages.
[No Author Listed], "CN Br-activated Sepharose 4 Fast Flow," 1999, Affinity Chromatography, 4 pages.
Bartscht et al., "Dasatinib blocks transcriptional and promigratory responses to transforming growth factor-beta in pancreatic adenocarcinoma cells through inhibition of Smad signaling: implications for in vivo mode of action," Molecular Cancer, Dec. 2015, 14(199):1-12.
Bird et al., "TGFβ inhibition restores a regenerative response in acute liver injury by suppressing paracrine senescence," Science translational medicine, Aug. 15, 2018, 10(454):eaan 1230, 15 pages.
Brämer et al., "Membrane adsorber for the fast purification of a monoclonal antibody using protein a chromatography," Membranes, Nov. 27, 2019, 9(12):159, 15 pages.
Cai et al., "Quercetin inhibits transforming growth factor β1-induced epithelial-mesenchymal transition in human retinal pigment epithelial cells via the Smad pathway," Drug design, development and therapy, Dec. 6, 2018, 12:4149-4161.
Chabannon et al., "Manufacturing natural killer cells as medicinal products," Frontiers in Immunology, Nov. 15, 2016, 7(504): 1-9.
Chen et al., "A novel idea for establishing Parkinson's disease mouse model by intranasal administration of paraquat" Neurological Research, 43(4):267-277, 2021.
Fernando et al., "Targeting tumor endothelial marker 8 in the tumor vasculature of colorectal carcinomas in mice," Cancer research, Jun. 15, 2009, 69(12):5126-5132.
Guha et al., "Affinity purification of human tissue factor: interaction of factor VII and tissue factor in detergent micelles," Proceedings of the National Academy of Sciences, Jan. 1986, 83(2):299-302.
Hélie et al., "Application of the Protein Maker as a platform purification system for therapeutic antibody research and development," Computational and Structural Biotechnology Journal, Jan. 1, 2016, 14:238-244.
Igarashi et al., "VEGF-C and TGF-β reciprocally regulate mesenchymal stem cell commitment to differentiation into lymphatic endothelial or osteoblastic phenotypes," International journal of molecular medicine, Apr. 1, 2016, 37(4):1005-1013.
Infante-Duarte et al., "New developments in understanding and treating neuroinflammation" Journal of Molecular Medicine, 86:975-985, Sep. 2008.

(56) References Cited

OTHER PUBLICATIONS info.gbiosciences.com [Online], "G-Biosciences, The Basics of Affinity Purification/Affinity Chromatography," Jul. 31, 2018, retrieved on Apr. 18, 2023, retrieved from URL<https://info.gbiosciences.com/blog/the-basics-of-affinity-purification/affinity-chromatography?utm_campaign=G-Bio+Search+Ads&utm_term=&utm_source=adwords&utm_medium=ppc&hsa_src=g&hsa_ver=3&hsa_cam=737902488&hsa_kw=&hsa_ad=621736020174&hsa_tgt-dsa-460355902483&hsa_mt=&hsa_acc-6752996364&hsa_grp-92226101427&hsa_net=adwords&gclid=CjwKCAjw_ihBhADEiwAXEazJvXifVFgeRGVW99XbY72eRROhWnHtdd695ydPgyh8qdvTwd9ikGIRoCdecQAvD_BWE>, 5 pages.

International Search Report and Written Opinion in International Appln. No. PCT/US2023/065745, mailed on Jun. 26, 2023, 14 pages.

Janeway et al., "The interaction of the antibody molecule with specific antigen" In Immunobiology: The Immune System in Health and Disease, 5th edition, 5 pages, 2001.

Klingemann et al., "Natural killer cells for immunotherapy-advantages of the NK-92 cell line over blood NK cells," Frontiers in immunology, Mar. 14, 2016, 7(91): 1-7.

Kozlowska et al., "Adoptive transfer of osteoclast-expanded natural killer cells for immunotherapy targeting cancer stem-like cells in humanized mice," Cancer Immunology, Immunotherapy, Jul. 2016, 65:835-845.

Matsuura et al., "Pole test is a useful method for evaluating the mouse movement disorder caused by striatal dopamine depletion" Journal of neuroscience methods, 73(1):45-48, 1997.

Mortier et al., "Soluble interleukin-15 receptor α (IL-15Rα)-sushi as a selective and potent agonist of IL-15 action through IL-15Rβ/γ: hyperagonist IL-15. IL-15Rα fusion proteins," Journal of Biological Chemistry, Jan. 20, 2006, 281(3):1612-1619.

Reddy et al., "Linkers in the structural biology of protein-protein interactions" Protein science, 22(2):153-167, 2013.

Ross et al., "Signaling and function of interleukin-2 in T lymphocytes" Annual review of immunology, 36:411-433, 201.

ThermoFisher.com [Online], "Covalent Immobilization of Affinity Ligands," 2018, retrieved on Apr. 18, 2023, retrieved from <URLhttps://www.thermofisher.com/US/en/home/life-science/protein-biology/protein-biology-learning-center/protein-biology-resource-library/pierce-protein-methods/covalent-immobilization-affinity-ligands.html>, 13 pages.

Uppendahl et al., "Natural killer cell-based immunotherapy in gynecologic malignancy: a review," Frontiers in immunology, Jan. 5, 2018, 8(1825): 1-15.

Urh et al., "Affinity chromatography: general methods," Methods in enzymology, Jan. 1, 2009, 463: 23 pages.

Van Bockstaele et al., "The development of nanobodies for therapeutic applications" Current opinion in investigational drugs, 10(11):1212-1224, 2009.

Veluchamy et al., "The rise of allogeneic natural killer cells as a platform for cancer immunotherapy: recent innovations and future developments," Frontiers in immunology, May 31, 2017, 8(631): 1-20.

Wong et al., "Interleukin-15: Interleukin-15 receptor α scaffold for creation of multivalent targeted immune molecules," Protein Engineering, Design & Selection, Apr. 1, 2011, 24(4):373-383.

Zhou, "Emerging mechanisms and applications of low-dose IL-2 therapy in autoimmunity," Cytokine & Growth Factor Reviews, Jun. 30, 2022, 67: 80-88.

Auerbach et al., "Angiogenesis assays: Problems and pitfalls," Cancer and Metastasis Reviews, 2000, 19(1-2):167-172.

Beans, "Targeting Metastasis to halt cancer's spread," PNAS, Dec. 2011, 11(50):12539-12543.

Gravanis et al., "The changing world of cancer drug development: the regulatory bodies' perspective," Chinese Clinical Oncology, 2014, 3(2):22 pp. 1-5.

Gura, "Systems for Identifying New Drugs are Often Faulty," Science., Nov. 1997, 278(5340):1041-2.

Hait, "Anticancer drug development: the grand challenges," Nature Reviews, Apr. 2010, 9(4):253-254.

Heppner et al., "Tumor heterogeneity: biological implications and therapeutic consequences," Cancer Metastasis Reviews, 1983, 2(1):5-23.

Jain et al., "Barriers to Drug Delivery in Solid Tumors," Scientific American, Jul. 1994, 271(1):58-65.

Ng et al., "Stimulation of natural killer cell-mediated tumor immunity by an IL-15/TGF-β neutralizing fusion protein," Cancer Research, Oct. 2016, 76(19):5683-5695.

Quatromoni et al., "The timing of TGF-β inhibition affects the generation of antigen-specific CD8+ T Cells," BMC Immunology, 2013, 14(30):1-16.

Search Report in Singapore Appln. No. 11202113136T, mailed on Oct. 17, 2024, 8 pages.

Sporn et al., "Chemoprevention of cancer," Carcinogens, 2000, 21(3):525-530.

* cited by examiner

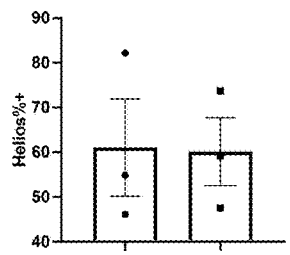
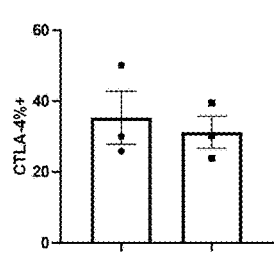
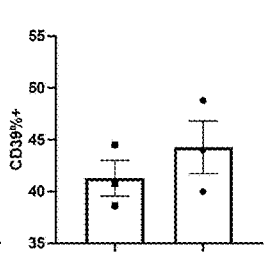
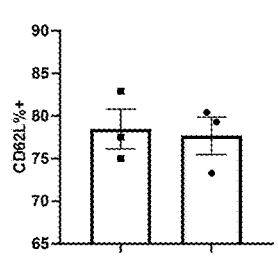
FIG. 2A    FIG. 2B    FIG. 2C    FIG. 2D
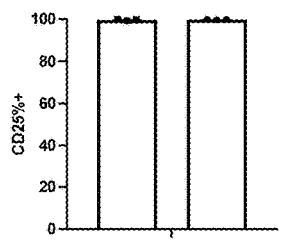
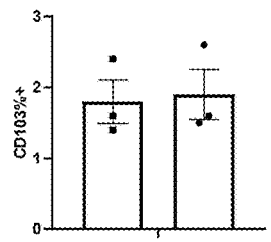
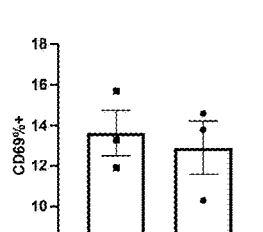
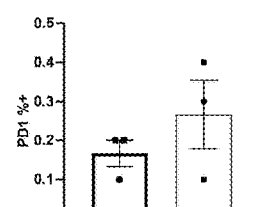
FIG. 2E    FIG. 2F    FIG. 2G    FIG. 2H
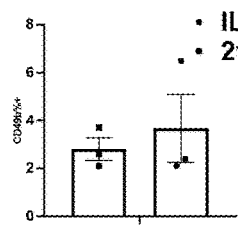
FIG. 2I

METHODS OF ACTIVATING REGULATORY T CELLS

CROSS-REFERENCE TO RELATED APPLICATION

This application claims priority to U.S. Provisional Patent Application Ser. No. 62/981,944, filed on Feb. 26, 2020, and U.S. Provisional Patent Application Ser. No. 62/975,141, filed on Feb. 11, 2020, which is incorporated herein by reference in its entirety.

SEQUENCE LISTING

This application contains a Sequence Listing that has been submitted electronically as an ASCII text file named 47039-0019001 ST25.txt. The ASCII text file, created on Jul. 10, 2023, is 147,000 bytes in size. The material in the ASCII text file is hereby incorporated by reference in its entirety.

TECHNICAL FIELD

The present disclosure relates to the fields of biotechnology and immunology, and more specifically, to methods of stimulating or increasing the proliferation of a $T_{reg}$ cell.

BACKGROUND

Tissue factor (TF), a 263 amino acid integral membrane glycoprotein with a molecular weight of ~46 kDa and the trigger protein of the extrinsic blood coagulation pathway, is the primary initiator of coagulation in vivo. Tissue factor, normally not in contact with circulating blood, initiates the coagulation cascade upon exposure to the circulating coagulation serine protease factors. Vascular damage exposes sub-endothelial cells expressing tissue factor, resulting in the formation of a calcium-dependent, high-affinity complex with pre-existing plasma factor VIIa (FVIIa). Binding of the serine protease FVIIa to tissue factor promotes rapid cleavage of FX to FXa and FIX to FIXa. The proteolytic activity of the resulting FXa and an active membrane surface then inefficiently converts a small amount of prothrombin to thrombin. The thrombin generated by FXa initiates platelet activation and activates minute amounts of the pro-cofactors factor V (FV) and factor VIII (FVIII) to become active cofactors, factor Va (FVa) and factor VIIIa (FVIIIa). FIXa complexes with FVIIIa on the platelet surface forming the intrinsic tenase complex, which results in rapid generation of FXa. FXa complexes with FVa to form the pro-thrombinase complex on the activated platelet surface which results in rapid cleavage of prothrombin to thrombin.

In addition to the tissue factor-FVIIa complex, a recent study showed that the tissue factor-FVIIa-FXa complex can activate FVIII, which would provide additional levels of FVIIIa during the initiation phase. The extrinsic pathway is paramount in initiating coagulation via the activation of limited amounts of thrombin, whereas the intrinsic pathway maintains coagulation by dramatic amplification of the initial signal.

Much of the tissue factor expressed on a cell surface is "encrypted," which must be "decrypted" for full participation in coagulation. The mechanism of "decryption" of cell-surface tissue factor is still unclear at this time, however, exposure of anionic phospholipids plays a major role in this process. Healthy cells actively sequester anionic phospholipids such as phosphatidyl serine (PS) to the inner leaflet of the plasma membrane. Following cellular damage, activation, or increased levels of cytosolic $Ca^{2+}$, this bilayer asymmetry is lost, resulting in increased PS exposure on the outer leaflet, which increases the specific activity of cell-surface tissue factor-FVIIa complexes. PS exposure is known to decrease the apparent Km for activation of FIX and FX by tissue factor-FVIIa complexes, but additional mechanisms could include conformational rearrangement of tissue factor or tissue factor-FVIIa and subsequent exposure of substrate binding sites.

Adoptive immunotherapy or cellular therapy requires the culture of immune cells obtained from a subject in vivo (and optionally genetic manipulation of the immune cells to express a chimeric antigen receptor or a T-cell receptor) before administration back into the subject. A sufficient number of immune cells is necessary in order to provide a therapeutic effect in the subject. In many examples, immune cells obtained from a subject need to be cultured for three or more weeks before a therapeutically effective number of immune cells can be obtained. In addition, many methods of culturing immune cells obtained from a subject in vitro require a layer of feeder cells, which requires subsequent purification or isolation of the immune cells before administration back to the subject.

SUMMARY

Excellent safety profiles have been shown in patients receiving Treg cells (Esensten et al., *J Allergy Clin Immunol* 142(6): 1710-1718, 2018). Early clinical studies showed encouraging results in using Treg cells to prevent and treat acute and chronic Graft versus Host Diseases (Brunstein et al., *Blood* 117(3): 1061-1070, 2011; Di Ianni et al., *Blood* 117(14): 3921-3928, 2011; Martelli et al., *Blood* 124(4): 638-644, 2014; Theil et al., *Cytotherapy* 17(4): 473-486, 2015; Brunstein et al., *Blood* 127(8): 1044-1051, 2016), autoimmune and neurodegenerative diseases (Thonhoff et al., *Neurol Neuroimmunol Neuroinflamm* 5(4): e465, 2018; Dall'Era et al., *Arthritis Rheumatol* 71(3): 431-440, 2019).

To use T cell-based adoptive therapies, including Treg cells, ex-vivo cell stimulation step is required for GMP manufacturing setting. Anti-CD3/anti-CD28 antibody-coated magnetic beads (Dynabeads, Thermo Fisher) is most commonly used for cell stimulation and expansion in combination with IL-2 (Highfill et al., *Curr Hematol Malig Rep* 14(4): 269-277, 2019). If using this approach, methods must be developed to ensure T cells are "bead free" at the culture harvest and prior to infusion into patients. In this study, we describe a method of employing 2t2 and 3t15*-28s to effectively substitute IL-2 and anti-CD3/antiCD28-coated magnetic beads, respectively, for T cell stimulation and expansion without using rapamycin. 3t15*-28s is soluble fusion protein complex that can be easily removed from the culture with simple wash steps which eliminates the need for bead removal, saving time and processing cost, and enhancing cell recovery. In addition, we also demonstrated that the inclusion of a separation step using an anti-CD39 antibody in the isolation or the purification of Treg cells before or after cell stimulation and expansion could enrich the $CD4^+$ $CD25^{hi}$ $CD127^{lo}$ and $CD39^{hi}$ Tregs, resulting in $T_{reg}$ cells with increased the purity, consistency, and the effector functions.

Aging in humans is associated with elevated systemic inflammation (Ferrucci et al., *Blood* 105(6): 2294-2299, 2005; Dinarello, *Am J Clin Nutr* 83(2): 447S-455S, 2006). The process that connects inflammation with aging has been termed inflamm-aging (Franceschi et al., *Ann N Y Acad Sci* 908:244-254, 2000). The process of aging is connected with major changes that affect the immune system and results in a variety aging-associated pathologies.

The function of the immune system is to detect and respond to damage to tissues or to the invasion of pathogenic microorganisms. The innate immune cells, the first line of defense against infection, express distinct germ-line encoded pattern recognition receptors (PRRs) that recognize conserved pathogen-associated molecular patterns (PAMPs) unique to microbes (Janeway, *Cold Spring Harb Symp Quant Biol* 54 Pt 1:1-13, 1989; Gong et al., *Nat Rev Immunol* 20(2): 95-112, 2020). Danger signals released by distressed or damaged cells are also recognized by the receptors of damage-associated molecular patterns (DAMPs) (Gong et al., *Nat Rev Immunol* 20(2): 95-112, 2020). Both PAMPs and DAMPs can initiate innate immune responses through the activation of classical PRRs, such as Toll-like receptors (TLRs), and multiple germ-line-encoded receptors, such as NOD-like receptors (NLRs), retinoic acid-inducible gene I (RIG-I)-like receptors (RLRs), C-type lectin receptors (CLRs) and intracellular DNA sensors (Cao, *Nat Rev Immunol* 16(1): 35-50, 2016). DAMPs can also be sensed by several other receptors. These include receptor for advanced glycation end products (RAGE) (Hudson et al., *Annu Rev Med* 69: 349-364, 2018; Teissier et al., *Biogerontology* 20(3): 279-301, 2019), triggering receptors expressed on myeloid cells (TREMs) (Ford et al., *Curr Opin Immunol* 21(1): 38-46, 2009), several G-protein-coupled receptors (GPCRs) (Heng et al., *Annu Rev Pharmacol Toxicol* 54: 227-249, 2014; Weiss et al., *Trends Immunol* 39(10): 815-829, 2018) and ion channels (Eisenhut et al., *Pflugers Arch* 461(4): 401-421, 2011).

DAMPs-initiated inflammatory responses are referred as sterile inflammation because they are independent of pathogen infection (Chen et al., *Nat Rev Immunol* 10(12): 826-837, 2010). DAMPs can activate both non-immune cells and innate immune cells (Chen et al., *Nat Rev Immunol* 10(12): 826-837, 2010). Activation of these cells leads to the production of cytokines and chemokines, which in turn recruit inflammatory cells and activate adaptive immune responses (Chen et al., *Nat Rev Immunol* 10(12): 826-837, 2010). Some DAMPs are also known to directly activate adaptive immune cells (Lau et al., *J Exp Med* 202(9): 1171-1177, 2005; Qin et al., *J Immunol* 199(1): 72-81, 2017). Although sterile inflammation plays an essential role in tissue repair and regeneration to reestablish the tissue hemostasis after injurious insults, unresolved chronic inflammation due to repeated tissue damage or in response to an overabundance of innate-immune triggers present in tissue is detrimental to the host and may lead to sterile inflammatory diseases, including cancer, metabolic disorders (e.g., diabetes), neurodegenerative diseases (e.g., Alzheimer's disease, Parkinson's disease), and autoimmune diseases (e.g., multiple sclerosis) (Roh et al., *Immune Netw* 18(4): e27, 2018).

Inflammasomes are large, multimeric protein complexes comprising a cytosolic pattern-recognition receptor, the adaptor protein apoptosis-associated Speck-like protein containing a caspase recruitment domain (ASC), and a caspase-1 (Lamkanfi et al., *Cell* 157(5): 1013-1022, 2014). Their assembly in innate immune cells and other cells is triggered by a variety of stimuli and culminates in the activation of caspase-1 which then cleaves pro-IL-1β to IL-1β (Latz et al., *Nat Rev Immunol* 13(6): 397-411, 2013; Walsh et al., *Nat Rev Neurosci* 15(2): 84-97, 2014). To date, diverse inflammasomes have been discovered. Among the various inflammasomes identified, the nucleotide-binding oligomerization domain, leucine-rich repeat-containing receptor (NLR) family pyrin domain-containing 3 (NLRP3) inflammasome is best characterized (Swanson et al., *Nat Rev Immunol* 19(8): 477-489, 2019). The NLRs are recognized as the key sensors of pathogens and danger signals. The NLRP3 inflammasome has a two-step activation mechanism: "priming", which entails induction of Pro-IL-1β and NLRP3, and "activation", wherein a functional inflammasome complex is assembled following uptake of PAMPs or DAMPs. The pathology of various diseases, including Alzheimer's disease (Heneka et al., *Nature* 493(7434): 674-678, 2013), Parkinson's disease (Heneka et al., *Nat Rev Neurosci* 19(10): 610-621, 2018), and atherosclerosis (Jin et al., *J Am Heart Assoc* 8(12): e012219, 2019) has been linked to hyperactivation of the NLRP3 inflammasome.

Sterile inflammation can also result from the accumulation of senescent cells. Cellular senescence is defined as an irreversible cell cycle arrest that occurs in responses to cellular stress and prevents transmission of defects to the next generation (Collado et al., *Nat Rev Cancer* 10(1): 51-57, 2010; McHugh et al., *J Cell Biol* 217(1): 65-77, 2018). Cellular senescence plays a major protective role in the process of development, tissue hemostasis, and wound healing (Munoz-Espin et al., *Cell* 155(5): 1104-1118, 2013; Storer et al., *Cell* 155(5): 1119-1130, 2013; Demaria et al., *Dev Cell* 31(6): 722-733, 2014; Yun et al., *Elife* 4, 2015). Cellular senescent is accompanied by a pro-inflammatory phenotype. The phenotype is referred to the senescence-associated secretory phenotype (SASP) (McHugh et al., *J Cell Biol* 217(1): 65-77, 2018). The SASP is characterized by the release of inflammatory cytokines, chemokines, growth factors and proteases. This reinforces cellular senescence through autocrine and paracrine signaling, and recruits and instructs immune cells to clear senescence cells. Thus, cellular senescence and SASP are a vital physiological response that maintains homeostasis at the cellular level, tissue level and organ level. However, upon persistent damage or during aging, senescent cell clearance is compromised, and dysfunctional cells accumulate. The SASP from these uncleared and accumulated senescent cells is a protracted and chronic source of inflammatory factors that create an inflammatory microenvironment that results in a diverse range of pathological manifestations (Munoz-Espin et al., *Nat Rev Mol Cell Biol* 15(7): 482-496, 2014; van Deursen, *Nature* 509(7501): 439-446, 2014; McHugh et al., *J Cell Biol* 217(1): 65-77, 2018). In addition, some of the SASP factors prime the inflammasome-containing cells which increases the risk of fueling chronic inflammasome activation to induce sterile inflammation.

Regulatory T (Treg) cells are essential mediators of peripheral tolerance and the global immunoregulatory potential in hosts to self and non-self-antigens (Sakaguchi et al., *Cell* 133(5): 775-787, 2008; Sakaguchi et al., *Annu Rev Immunol* 38:541-566, 2020). Treg cells achieve this immunoregulatory control through multiple suppressive mechanisms. These include IL-2 deprivation, the secretion of inhibitory cytokines (i.e., IL-10 and TGF-β) and the acquisition of co-stimulatory molecules from antigen-presenting cells via high-affinity binding to CTLA-4 (Oberle et al., *J Immunol* 179(6): 3578-3587, 2007; Tang et al., *Nat Immunol* 9(3): 239-244, 2008; Zheng et al., *J Immunol* 181(3): 1683-1691, 2008) The adenosine triphosphate (ATP)-adenosine pathway is also utilized by regulatory Treg as a key modulator of innate and adaptive immunity. CD39 is the dominant ecto-nucleotidase broadly expressed on immune cells (e.g., Tregs), endothelial cells and tumor cell, that hydrolyses ATP and adenosine diphosphate (ADP) to adenosine monophosphate (AMP) (Moesta et al., *Nat Rev Immunol* 20(12): 739-755, 2020). AMP is then hydrolyzed by CD73 to adenosine. Adenosine binds to its receptors A1, A2A, A2B, and A3 displayed on immune cells. A2A and A2B receptors (A2AR and A2BR) are Gs-coupled receptors that increase intracellular cAMP and PKA levels, playing dominant roles in adenosine-induced immunosuppression in a cAMP-dependent manner. A1 and A3 receptors (AIR and A3R) are Gi/o-coupled receptors that decrease intracellular cAMP favoring cell activation, and therefore are generally viewed as immune-promoting adenosine receptors. In humans, AIR, A2AR and A3R display high affinity for adenosine whereas A2BR has a significantly lower affinity. A2A and A2BR are expressed on immune cells (Feng et al., *Cancer Cell Int* 20: 110, 2020). Recently, it has been shown that human $CD39^{hi}$ regulatory T cells exhibits stronger stability, higher Foxp3 expression, and suppressive ability under inflammatory conditions (Gu et al., *Cell Mol Immunol* 14(6): 521-528, 2017). Alternations in Treg cell development, homeostasis or function can predispose these cells to a variety of disease conditions including allergy, autoimmunity, graft rejection, cancer, and response to immunotherapies (Sakaguchi et al., *Annu Rev Immunol* 38: 541-566, 2020). Current research is focused on developing novel therapies to enhance Treg cell functions in vivo through use of cytokines and small molecular weight drugs to support endogenous Treg cell proliferation or activation, ex-vivo manipulated Treg cells in autologous adoptive cell therapy (ACT) to promote immunoregulation in settings of autoimmunity, or antigen-specific Treg cells, including chimeric antigen receptor Treg (CAR-Treg) cells, to strengthen tolerance in allergic inflammation (Ferreira et al., *Nat Rev Drug Discov* 18(10): 749-769, 2019). The present invention is a method that uses Treg cells to deactivate the inflammasome and then subsequently uses immune cells activated by one or more immunotherapeutics to reduce the accumulated senescent cells in an individual to treat inflamm-aging and/or any aging-associated pathologies. Provided is a method of inhibiting inflammasome related diseases and inhibiting senescent related diseases. The Treg cells can be in-vivo enhanced endogenous Treg cells or ex-vivo manipulated Treg cells used in an ACT setting. The immune cells for senescent-cell clearance could be activated by immunotherapeutics in vivo or generated by ex-vivo stimulation and expansion methods to support an ACT administration. The present invention is based on the discovery that single-chain chimeric polypeptides that include a soluble tissue factor domain or multi-chain chimeric polypeptides that include a soluble tissue factor domain, in combination with CD3/CD28-binding agents or IL-2 receptor-activating agents are effective in stimulating or increasing the proliferation of a $T_{reg}$ cell. Based on this discovery provided herein are methods of stimulating or increasing the proliferation of a $T_{reg}$ cell that include culturing a $T_{reg}$ cell in a liquid culture medium over a period of time, where at the beginning of the period of time, the liquid culture medium includes: a CD3/CD28-binding agent; and a single-chain chimeric polypeptide including a first target-binding domain, a soluble tissue factor domain, and a second target-binding domain, where the first target-binding domain and the second target-binding domain bind to a receptor for IL-2.

In some embodiments of any of the methods of stimulating or increasing the proliferation of a $T_{reg}$ cell described herein, the liquid culture medium further includes an IgG1 antibody construct that comprises at least one antigen-binding domain that binds specifically to the soluble tissue factor domain of the single-chain chimeric polypeptide. In some embodiments of any of the methods of stimulating or increasing the proliferation of a $T_{reg}$ cell described herein, the IgG1 antibody construct comprises a heavy chain variable domain comprising CDRs of SEQ ID NOs: 66, 67 or 74, and 68, and a light chain variable domain comprising CDRs of SEQ ID NOs: 69, 70, and 71. In some embodiments of any of the methods of stimulating or increasing the proliferation of a $T_{reg}$ cell described herein, the heavy chain variable domain comprises a sequence that is at least 90% identical to SEQ ID NO: 72, and the light chain variable domain comprises a sequence that is at least 90% identical to SEQ ID NO: 73. In some embodiments of any of the methods of stimulating or increasing the proliferation of a $T_{reg}$ cell described herein, the heavy chain variable domain comprises SEQ ID NO: 72, and the light chain variable domain comprises SEQ ID NO: 73. In some embodiments of any of the methods of stimulating or increasing the proliferation of a $T_{reg}$ cell described herein, the first target-binding domain and the soluble tissue factor domain directly abut each other. In some embodiments of any of the methods of stimulating or increasing the proliferation of a $T_{reg}$ cell described herein, the single-chain chimeric polypeptide further comprises a linker sequence between the first target-binding domain and the soluble tissue factor domain. In some embodiments of any of the methods of stimulating or increasing the proliferation of a $T_{reg}$ cell described herein, the soluble tissue factor domain and the second target-binding domain directly abut each other. In some embodiments of any of the methods of stimulating or increasing the proliferation of a $T_{reg}$ cell described herein, the single-chain chimeric polypeptide further comprises a linker sequence between the soluble tissue factor domain and the second target-binding domain. In some embodiments of any of the methods of stimulating or increasing the proliferation of a $T_{reg}$ cell described herein, the first target-binding domain and the second target-binding domain comprise the same amino acid sequence. In some embodiments of any of the methods of stimulating or increasing the proliferation of a $T_{reg}$ cell described herein, the first target-binding domain and the second target-binding domain comprise a soluble IL-2. In some embodiments of any of the methods of stimulating or increasing the proliferation of a $T_{reg}$ cell described herein, the soluble IL-2 is a human soluble IL-2. In some embodiments of any of the methods of stimulating or increasing the proliferation of a $T_{reg}$ cell described herein, the first target-binding domain and the second target-binding domain each comprise a sequence that is at least 80% identical to SEQ ID NO: 1. In some embodiments of any of the methods of stimulating or increasing the proliferation of a $T_{reg}$ cell described herein, the first target-binding domain and the second target-binding domain each comprise a sequence that is at least 90% identical to SEQ ID NO: 1. In some embodiments of any of the methods of stimulating or increasing the proliferation of a $T_{reg}$ cell described herein, the first target-binding domain and the second target-binding domain each comprise a sequence of SEQ ID NO: 1. In some embodiments of any of the methods of stimulating or increasing the proliferation of a $T_{reg}$ cell described herein, the soluble tissue factor domain is a soluble human tissue factor domain. In some embodiments of any of the methods of stimulating or increasing the proliferation of a $T_{reg}$ cell described herein, the soluble human tissue factor domain comprises a sequence that is at least 80% identical to SEQ ID NO: 2. In some embodiments of any of the methods of stimulating or increasing the proliferation of a $T_{reg}$ cell described herein, the soluble human tissue factor domain comprises a sequence that is at least 90% identical to SEQ ID NO: 2. In some embodiments of any of the methods of stimulating or increasing the proliferation of a $T_{reg}$ cell described herein, the soluble human tissue factor domain comprises a sequence of SEQ ID NO: 2. In some embodiments of any of the methods of stimulating or increasing the proliferation of a $T_{reg}$ cell described herein, the soluble tissue factor domain comprises or consists of a sequence from a wildtype soluble human tissue factor. In some embodiments of any of the methods of stimulating or increasing the proliferation of a $T_{reg}$ cell described herein, the soluble tissue factor domain does not comprise any of: a lysine at an amino acid position that corresponds to amino acid position 20 of mature wildtype human tissue factor protein; an isoleucine at an amino acid position that corresponds to amino acid position 22 of mature wildtype human tissue factor protein; a tryptophan at an amino acid position that corresponds to amino acid position 45 of mature wildtype human tissue factor protein; an aspartic acid at an amino acid position that corresponds to amino acid position 58 of mature wildtype human tissue factor protein; a tyrosine at an amino acid position that corresponds to amino acid position 94 of mature wildtype human tissue factor protein; an arginine at an amino acid position that corresponds to amino acid position 135 of mature wildtype human tissue factor protein; and a phenylalanine at an amino acid position that corresponds to amino acid position 140 of mature wildtype human tissue factor protein. In some embodiments of any of the methods of stimulating or increasing the proliferation of a $T_{reg}$ cell described herein, the soluble tissue factor domain comprises one or more of: a lysine at an amino acid position that corresponds to amino acid position 20 of mature wildtype human tissue factor protein; an isoleucine at an amino acid position that corresponds to amino acid position 22 of mature wildtype human tissue factor protein; a tryptophan at an amino acid position that corresponds to amino acid position 45 of mature wildtype human tissue factor protein; an aspartic acid at an amino acid position that corresponds to amino acid position 58 of mature wildtype human tissue factor protein; a tyrosine at an amino acid position that corresponds to amino acid position 94 of mature wildtype human tissue factor protein; an arginine at an amino acid position that corresponds to amino acid position 135 of mature wildtype human tissue factor protein; and a phenylalanine at an amino acid position that corresponds to amino acid position 140 of mature wildtype human tissue factor protein. In some embodiments of any of the methods of stimulating or increasing the proliferation of a $T_{reg}$ cell described herein, the soluble tissue factor domain does not initiate blood coagulation. In some embodiments of any of the methods of stimulating or increasing the proliferation of a $T_{reg}$ cell described herein, the single-chain chimeric polypeptide does not initiate blood coagulation. In some embodiments of any of the methods of stimulating or increasing the proliferation of a $T_{reg}$ cell described herein, the single-chain chimeric polypeptide comprises a sequence that is at least 80% identical to SEQ ID NO: 3. In some embodiments of any of the methods of stimulating or increasing the proliferation of a $T_{reg}$ cell described herein, the single-chain chimeric polypeptide comprises a sequence that is at least 90% identical to SEQ ID NO: 3. In some embodiments of any of the methods of stimulating or increasing the proliferation of a $T_{reg}$ cell described herein, the single-chain chimeric polypeptide comprises a sequence of SEQ ID NO: 3. In some embodiments of any of the methods of stimulating or increasing the proliferation of a $T_{reg}$ cell described herein, the single-chain chimeric polypeptide comprises a sequence that is at least 80% identical to SEQ ID NO: 4. In some embodiments of any of the methods of stimulating or increasing the proliferation of a $T_{reg}$ cell described herein, the single-chain chimeric polypeptide comprises a sequence that is at least 90% identical to SEQ ID NO: 4. In some embodiments of any of the methods of stimulating or increasing the proliferation of a $T_{reg}$ cell described herein, the single-chain chimeric polypeptide comprises a sequence of SEQ ID NO: 4. In some embodiments of any of the methods of stimulating or increasing the proliferation of a $T_{reg}$ cell described herein, the liquid culture medium comprises about 10 nM to about 500 nM of the single-chain chimeric polypeptide. In some embodiments of any of the methods of stimulating or increasing the proliferation of a $T_{reg}$ cell described herein, the liquid culture medium comprises about 50 nM to about 150 nM of the single-chain chimeric polypeptide. In some embodiments of any of the methods of stimulating or increasing the proliferation of a $T_{reg}$ cell described herein, the CD3/CD28-binding agent is an anti-CD3/anti-CD28 bead. In some embodiments of any of the methods of stimulating or increasing the proliferation of a $T_{reg}$ cell described herein, the liquid culture medium comprises the anti-CD3/anti-CD28 bead at a ratio of about 1:1 to about 6:1 beads/cell. In some embodiments of any of the methods of stimulating or increasing the proliferation of a $T_{reg}$ cell described herein, the liquid culture medium comprises the anti-CD3/anti-CD28 bead at a ratio of about 3:1 to about 5:1 beads/cell. In some embodiments of any of the methods of stimulating or increasing the proliferation of a $T_{reg}$ cell described herein, the CD3/CD28-binding agent is an additional single-chain chimeric polypeptide comprising a first target-binding domain, a soluble tissue factor domain, and a second target-binding domain, wherein: the first target-binding domain of the additional single-chain chimeric polypeptide binds to CD3 and the second target-binding domain of the additional single-chain chimeric polypeptide binds to CD28. In some embodiments of any of the methods of stimulating or increasing the proliferation of a $T_{reg}$ cell described herein, the liquid culture medium further includes an IgG1 antibody construct that comprises at least one antigen-binding domain that binds specifically to the soluble tissue factor domain of the additional single-chain chimeric polypeptide. In some embodiments of any of the methods of stimulating or increasing the proliferation of a $T_{reg}$ cell described herein, the IgG1 antibody construct comprises a heavy chain variable domain comprising CDRs of SEQ ID NOs: 66, 67 or 74, and 68, and a light chain variable domain comprising CDRs of SEQ ID NOs: 69, 70, and 71. In some embodiments of any of the methods of stimulating or increasing the proliferation of a $T_{reg}$ cell described herein, the heavy chain variable domain comprises a sequence that is at least 90% identical to SEQ ID NO: 72, and the light chain variable domain comprises a sequence that is at least 90% identical to SEQ ID NO: 73. In some embodiments of any of the methods of stimulating or increasing the proliferation of a $T_{reg}$ cell described herein, the heavy chain variable domain comprises SEQ ID NO: 72, and the light chain variable domain comprises SEQ ID NO: 73. In some embodiments of any of the methods of stimulating or increasing the proliferation of a $T_{reg}$ cell described herein, the first target-binding domain of the additional single-chain chimeric polypeptide and the soluble tissue factor domain directly abut each other. In some embodiments of any of the methods of stimulating or increasing the proliferation of a $T_{reg}$ cell described herein, the additional single-chain chimeric polypeptide further comprises a linker sequence between the first target-binding domain and the soluble tissue factor domain. In some embodiments of any of the methods of stimulating or increasing the proliferation of a $T_{reg}$ cell described herein, the soluble tissue factor domain and the second target-binding domain of the additional single-chain chimeric polypeptide directly abut each other. In some embodiments of any of the methods of stimulating or increasing the proliferation of a $T_{reg}$ cell described herein, the additional single-chain chimeric polypeptide further comprises a linker sequence between the soluble tissue factor domain and the second target-binding domain. In some embodiments of any of the methods of stimulating or increasing the proliferation of a $T_{reg}$ cell described herein, the CD3 is human CD3. In some embodiments of any of the methods of stimulating or increasing the proliferation of a $T_{reg}$ cell described herein, the first target-binding domain of the additional single-chain chimeric polypeptide comprises a sequence that is at least 80% identical to SEQ ID NO: 5. In some embodiments of any of the methods of stimulating or increasing the proliferation of a $T_{reg}$ cell described herein, the first target-binding domain of the additional single-chain chimeric polypeptide comprises a sequence that is at least 90% identical to SEQ ID NO: 5. In some embodiments of any of the methods of stimulating or increasing the proliferation of a $T_{reg}$ cell described herein, the first target-binding domain of the additional single-chain chimeric polypeptide comprises a sequence of SEQ ID NO: 5. In some embodiments of any of the methods of stimulating or increasing the proliferation of a $T_{reg}$ cell described herein, the CD28 is human CD28. In some embodiments of any of the methods of stimulating or increasing the proliferation of a $T_{reg}$ cell described herein, the second target-binding domain of the additional single-chain chimeric polypeptide comprises a sequence that is at least 80% identical to SEQ ID NO: 6. In some embodiments of any of the methods of stimulating or increasing the proliferation of a $T_{reg}$ cell described herein, the second target-binding domain of the additional single-chain chimeric polypeptide comprises a sequence that is at least 90% identical to SEQ ID NO: 6. In some embodiments of any of the methods of stimulating or increasing the proliferation of a $T_{reg}$ cell described herein, the second target-binding domain of the additional single-chain chimeric polypeptide comprises a sequence of SEQ ID NO: 6. In some embodiments of any of the methods of stimulating or increasing the proliferation of a $T_{reg}$ cell described herein, the soluble tissue factor domain of the additional single-chain chimeric polypeptide is a soluble human tissue factor domain. In some embodiments of any of the methods of stimulating or increasing the proliferation of a $T_{reg}$ cell described herein, the soluble human tissue factor domain of the additional single-chain chimeric polypeptide comprises a sequence that is at least 80% identical to SEQ ID NO: 2. In some embodiments of any of the methods of stimulating or increasing the proliferation of a $T_{reg}$ cell described herein, the soluble human tissue factor domain of the additional single-chain chimeric polypeptide comprises a sequence that is at least 90% identical to SEQ ID NO: 2. In some embodiments of any of the methods of stimulating or increasing the proliferation of a $T_{reg}$ cell described herein, the soluble human tissue factor domain of the additional single-chain chimeric polypeptide comprises a sequence of SEQ ID NO: 2. In some embodiments of any of the methods of stimulating or increasing the proliferation of a $T_{reg}$ cell described herein, the soluble tissue factor domain of the single-chain chimeric polypeptide comprises or consists of a sequence from a wildtype soluble human tissue factor. In some embodiments of any of the methods of stimulating or increasing the proliferation of a $T_{reg}$ cell described herein, the soluble tissue factor domain does not comprise any of: a lysine at an amino acid position that corresponds to amino acid position 20 of mature wildtype human tissue factor protein; an isoleucine at an amino acid position that corresponds to amino acid position 22 of mature wildtype human tissue factor protein; a tryptophan at an amino acid position that corresponds to amino acid position 45 of mature wildtype human tissue factor protein; an aspartic acid at an amino acid position that corresponds to amino acid position 58 of mature wildtype human tissue factor protein; a tyrosine at an amino acid position that corresponds to amino acid position 94 of mature wildtype human tissue factor protein; an arginine at an amino acid position that corresponds to amino acid position 135 of mature wildtype human tissue factor protein; and a phenylalanine at an amino acid position that corresponds to amino acid position 140 of mature wildtype human tissue factor protein. In some embodiments of any of the methods of stimulating or increasing the proliferation of a $T_{reg}$ cell described herein, the soluble tissue factor domain comprises one or more of: a lysine at an amino acid position that corresponds to amino acid position 20 of mature wildtype human tissue factor protein; an isoleucine at an amino acid position that corresponds to amino acid position 22 of mature wildtype human tissue factor protein; a tryptophan at an amino acid position that corresponds to amino acid position 45 of mature wildtype human tissue factor protein; an aspartic acid at an amino acid position that corresponds to amino acid position 58 of mature wildtype human tissue factor protein; a tyrosine at an amino acid position that corresponds to amino acid position 94 of mature wildtype human tissue factor protein; an arginine at an amino acid position that corresponds to amino acid position 135 of mature wildtype human tissue factor protein; and a phenylalanine at an amino acid position that corresponds to amino acid position 140 of mature wildtype human tissue factor protein. In some embodiments of any of the methods of stimulating or increasing the proliferation of a $T_{reg}$ cell described herein, the soluble tissue factor domain of the additional single-chain chimeric polypeptide does not initiate blood coagulation. In some embodiments of any of the methods of stimulating or increasing the proliferation of a $T_{reg}$ cell described herein, the additional single-chain chimeric polypeptide does not initiate blood coagulation. In some embodiments of any of the methods of stimulating or increasing the proliferation of a $T_{reg}$ cell described herein, the additional single-chain chimeric polypeptide comprises a sequence that is at least 80% identical to SEQ ID NO: 7. In some embodiments of any of the methods of stimulating or increasing the proliferation of a $T_{reg}$ cell described herein, the additional single-chain chimeric polypeptide comprises a sequence that is at least 90% identical to SEQ ID NO: 7. In some embodiments of any of the methods of stimulating or increasing the proliferation of a $T_{reg}$ cell described herein, the additional single-chain chimeric polypeptide comprises a sequence of SEQ ID NO: 7. In some embodiments of any of the methods of stimulating or increasing the proliferation of a $T_{reg}$ cell described herein, the additional single-chain chimeric polypeptide comprises a sequence that is at least 80% identical to SEQ ID NO: 8. In some embodiments of any of the methods of stimulating or increasing the proliferation of a $T_{reg}$ cell described herein, the additional single-chain chimeric polypeptide comprises a sequence that is at least 90% identical to SEQ ID NO: 8. In some embodiments of any of the methods of stimulating or increasing the proliferation of a $T_{reg}$ cell described herein, the additional single-chain chimeric polypeptide comprises a sequence of SEQ ID NO: 8. In some embodiments of any of the methods of stimulating or increasing the proliferation of a $T_{reg}$ cell described herein, the liquid culture medium comprises about 10 nM to about 1000 nM of the additional single-chain chimeric polypeptide. In some embodiments of any of the methods of stimulating or increasing the proliferation of a $T_{reg}$ cell described herein, the liquid culture medium comprises about 50 nM to about 300 nM of the additional single-chain chimeric polypeptide.

In some embodiments of any of the methods of stimulating or increasing the proliferation of a Treg cell described herein, the CD3/CD28 binding agent is a multi-chain chimeric polypeptide comprising: (a) a first chimeric polypeptide comprising: (i) a first target-binding domain; (ii) a soluble tissue factor domain; and (iii) a first domain of a pair of affinity domains; and (b) a second chimeric polypeptide comprising: (i) a second domain of a pair of affinity domains; and (ii) a second target-binding domain, wherein the first chimeric polypeptide and the second chimeric polypeptide associate through the binding of the first domain and the second domain of the pair of affinity domains; and wherein the first target-binding domain binds to CD3 and the second target-binding domain binds to CD28, or the first target-binding domain binds to CD28 and the second target-binding domain to CD3.

In some embodiments of any of the methods of stimulating or increasing the proliferation of a Treg cell described herein, the liquid culture medium further includes an IgG1 antibody construct that comprises at least one antigen-binding domain that binds specifically to the soluble tissue factor domain of the multi-chain chimeric polypeptide. In some embodiments of any of the methods of stimulating or increasing the proliferation of a Treg cell described herein, the IgG1 antibody construct comprises a heavy chain variable domain comprising CDRs of SEQ ID NOs: 66, 67 or 74, and 68, and a light chain variable domain comprising CDRs of SEQ ID NOs: 69, 70, and 71. In some embodiments of any of the methods of stimulating or increasing the proliferation of a Treg cell described herein, the heavy chain variable domain comprises a sequence that is at least 90% identical to SEQ ID NO: 72, and the light chain variable domain comprises a sequence that is at least 90% identical to SEQ ID NO: 73. In some embodiments of any of the methods of stimulating or increasing the proliferation of a Treg cell described herein, the heavy chain variable domain comprises SEQ ID NO: 72, and the light chain variable domain comprises SEQ ID NO: 73.

In some embodiments of any of the methods of stimulating or increasing the proliferation of a Treg cell described herein, the first target-binding domain of the first chimeric polypeptide and the soluble tissue factor domain directly abut each other. In some embodiments of any of the methods of stimulating or increasing the proliferation of a Treg cell described herein, the first chimeric polypeptide further comprises a linker sequence between the first target-binding domain and the soluble tissue factor domain. In some embodiments of any of the methods of stimulating or increasing the proliferation of a Treg cell described herein, the soluble tissue factor domain and the second target-binding domain of the second chimeric polypeptide directly abut each other. In some embodiments of any of the methods of stimulating or increasing the proliferation of a Treg cell described herein, the second chimeric polypeptide further comprises a linker sequence between the soluble tissue factor domain and the second target-binding domain.

In some embodiments of any of the methods of stimulating or increasing the proliferation of a Treg cell described herein, the CD3 is human CD3. In some embodiments of any of the methods of stimulating or increasing the proliferation of a Treg cell described herein, the first target-binding domain of the first chimeric polypeptide comprises a sequence that is at least 80% identical to SEQ ID NO: 5. In some embodiments of any of the methods of stimulating or increasing the proliferation of a Treg cell described herein, the first target-binding domain of the first chimeric polypeptide comprises a sequence that is at least 90% identical to SEQ ID NO: 5. In some embodiments of any of the methods of stimulating or increasing the proliferation of a Treg cell described herein, the first target-binding domain of the first chimeric polypeptide comprises a sequence of SEQ ID NO: 5.

In some embodiments of any of the methods of stimulating or increasing the proliferation of a Treg cell described herein, the soluble tissue factor domain of the first chimeric polypeptide is a soluble human tissue factor domain. In some embodiments of any of the methods of stimulating or increasing the proliferation of a Treg cell described herein, the soluble human tissue factor domain of the first chimeric polypeptide comprises a sequence that is at least 80% identical to SEQ ID NO: 2. In some embodiments of any of the methods of stimulating or increasing the proliferation of a Treg cell described herein, the soluble human tissue factor domain of the first chimeric polypeptide comprises a sequence that is at least 90% identical to SEQ ID NO: 2. In some embodiments of any of the methods of stimulating or increasing the proliferation of a Treg cell described herein, the soluble human tissue factor domain of the first chimeric polypeptide comprises a sequence of SEQ ID NO: 2. In some embodiments of any of the methods of stimulating or increasing the proliferation of a Treg cell described herein, the soluble tissue factor domain of the first chimeric polypeptide comprises or consists of a sequence from a wildtype soluble human tissue factor.

In some embodiments of any of the methods of stimulating or increasing the proliferation of a Treg cell described herein, the soluble tissue factor domain of the first chimeric polypeptide does not comprise any of: a lysine at an amino acid position that corresponds to amino acid position 20 of mature wildtype human tissue factor protein; an isoleucine at an amino acid position that corresponds to amino acid position 22 of mature wildtype human tissue factor protein; a tryptophan at an amino acid position that corresponds to amino acid position 45 of mature wildtype human tissue factor protein; an aspartic acid at an amino acid position that corresponds to amino acid position 58 of mature wildtype human tissue factor protein; a tyrosine at an amino acid position that corresponds to amino acid position 94 of mature wildtype human tissue factor protein; an arginine at an amino acid position that corresponds to amino acid position 135 of mature wildtype human tissue factor protein; and a phenylalanine at an amino acid position that corresponds to amino acid position 140 of mature wildtype human tissue factor protein.

In some embodiments of any of the methods of stimulating or increasing the proliferation of a Treg cell described herein, the soluble tissue factor domain of the first chimeric polypeptide comprises one or more of: a lysine at an amino acid position that corresponds to amino acid position 20 of mature wildtype human tissue factor protein; an isoleucine at an amino acid position that corresponds to amino acid position 22 of mature wildtype human tissue factor protein; a tryptophan at an amino acid position that corresponds to amino acid position 45 of mature wildtype human tissue factor protein; an aspartic acid at an amino acid position that corresponds to amino acid position 58 of mature wildtype human tissue factor protein; a tyrosine at an amino acid position that corresponds to amino acid position 94 of mature wildtype human tissue factor protein; an arginine at an amino acid position that corresponds to amino acid position 135 of mature wildtype human tissue factor protein; and a phenylalanine at an amino acid position that corresponds to amino acid position 140 of mature wildtype human tissue factor protein.

In some embodiments of any of the methods of stimulating or increasing the proliferation of a Treg cell described herein, the soluble tissue factor domain of the first chimeric polypeptide does not initiate blood coagulation. In some embodiments of any of the methods of stimulating or increasing the proliferation of a Treg cell described herein, the first chimeric polypeptide comprises a sequence that is at least 80% identical to SEQ ID NO: 102. In some embodiments of any of the methods of stimulating or increasing the proliferation of a Treg cell described herein, the first chimeric polypeptide comprises a sequence that is at least 90% identical to SEQ ID NO: 102. In some embodiments of any of the methods of stimulating or increasing the proliferation of a Treg cell described herein, the first chimeric polypeptide comprises a sequence of SEQ ID NO: 102. In some embodiments of any of the methods of stimulating or increasing the proliferation of a Treg cell described herein, the first chimeric polypeptide comprises a sequence that is at least 80% identical to SEQ ID NO: 104. In some embodiments of any of the methods of stimulating or increasing the proliferation of a Treg cell described herein, the first chimeric polypeptide comprises a sequence that is at least 90% identical to SEQ ID NO: 104. In some embodiments of any of the methods of stimulating or increasing the proliferation of a Treg cell described herein, the first chimeric polypeptide comprises a sequence of SEQ ID NO: 104.

In some embodiments of any of the methods of stimulating or increasing the proliferation of a Treg cell described herein, the CD28 is human CD28. In some embodiments of any of the methods of stimulating or increasing the proliferation of a Treg cell described herein, the second target-binding domain of the second chimeric polypeptide comprises a sequence that is at least 80% identical to SEQ ID NO: 6. In some embodiments of any of the methods of stimulating or increasing the proliferation of a Treg cell described herein, the second target-binding domain of the second chimeric polypeptide comprises a sequence that is at least 90% identical to SEQ ID NO: 6. In some embodiments of any of the methods of stimulating or increasing the proliferation of a Treg cell described herein, the second target-binding domain of the second chimeric polypeptide comprises a sequence of SEQ ID NO: 6. In some embodiments of any of the methods of stimulating or increasing the proliferation of a Treg cell described herein, the second chimeric polypeptide comprises a sequence that is at least 80% identical to SEQ ID NO: 106. In some embodiments of any of the methods of stimulating or increasing the proliferation of a Treg cell described herein, the second chimeric polypeptide comprises a sequence that is at least 90% identical to SEQ ID NO: 106. In some embodiments of any of the methods of stimulating or increasing the proliferation of a Treg cell described herein, the second chimeric polypeptide comprises a sequence of SEQ ID NO: 106. In some embodiments of any of the methods of stimulating or increasing the proliferation of a Treg cell described herein, the second chimeric polypeptide comprises a sequence that is at least 80% identical to SEQ ID NO: 108. In some embodiments of any of the methods of stimulating or increasing the proliferation of a Treg cell described herein, the second chimeric polypeptide comprises a sequence that is at least 90% identical to SEQ ID NO: 108. In some embodiments of any of the methods of stimulating or increasing the proliferation of a Treg cell described herein, the second chimeric polypeptide comprises a sequence of SEQ ID NO: 108.

In some embodiments of any of the methods of stimulating or increasing the proliferation of a Treg cell described herein, the multi-chain chimeric polypeptide does not initiate blood coagulation. In some embodiments of any of the methods of stimulating or increasing the proliferation of a Treg cell described herein, the liquid culture medium comprises about 10 nM to about 1000 nM of the multi-chain chimeric polypeptide. In some embodiments of any of the methods of stimulating or increasing the proliferation of a Treg cell described herein, the liquid culture medium comprises about 50 nM to about 300 nM of the multi-chain chimeric polypeptide.

In some embodiments of any of the methods of stimulating or increasing the proliferation of a $T_{reg}$ cell described herein, the liquid culture medium further comprises an mTOR inhibitor. In some embodiments of any of the methods of stimulating or increasing the proliferation of a $T_{reg}$ cell described herein, the mTOR inhibitor is rapamycin. In some embodiments of any of the methods of stimulating or increasing the proliferation of a $T_{reg}$ cell described herein, the liquid culture medium comprises about 10 nM to about 500 nM of the mTOR inhibitor. In some embodiments of any of the methods of stimulating or increasing the proliferation of a $T_{reg}$ cell described herein, the liquid culture medium comprises about 50 nM to about 150 nM of the mTOR inhibitor. In some embodiments of any of the methods of stimulating or increasing the proliferation of a Treg cell described herein, the liquid culture medium does not comprise an mTOR inhibitor.

In some embodiments of any of the methods of stimulating or increasing the proliferation of a $T_{reg}$ cell described herein, the methods further include: periodically adding to the liquid culture medium, after each 36 hours to about 60 hours after the start of the period of time, the single-chain chimeric polypeptide. In some embodiments of any of the methods of stimulating or increasing the proliferation of a $T_{reg}$ cell described herein, the periodic addition of the single-chain chimeric polypeptide is performed to result in a concentration of about 10 nM to about 500 nM of the single-chain chimeric polypeptide in the liquid culture medium. In some embodiments of any of the methods of stimulating or increasing the proliferation of a $T_{reg}$ cell described herein, the periodic addition of the single-chain chimeric polypeptide is performed to result in a concentration of about 50 nM to about 150 nM of the single-chain chimeric polypeptide in the liquid culture medium. In some embodiments of any of the methods of stimulating or increasing the proliferation of a $T_{reg}$ cell described herein, the methods further include: periodically adding to the liquid culture medium, after each about 6 days to about 8 days after the start of the period of time, the CD3/CD28-binding agent. In some embodiments of any of the methods of stimulating or increasing the proliferation of a $T_{reg}$ cell described herein, the period of time is about 7 days to about 56 days. In some embodiments of any of the methods of stimulating or increasing the proliferation of a $T_{reg}$ cell described herein, the period of claim is about 15 days to about 25 days. In some embodiments of any of the methods of stimulating or increasing the proliferation of a $T_{reg}$ cell described herein, the method further comprises, before the culturing step, a step of isolating the $T_{reg}$ cell from a sample obtained from a subject. In some embodiments of any of the methods of stimulating or increasing the proliferation of a Treg cell described herein, the method further comprises, after the culturing step, a step of isolating the Treg cell from a sample obtained from a subject.

In some embodiments of any of the methods of stimulating or increasing the proliferation of a $T_{reg}$ cell described herein, the isolating comprises the use of fluorescence-assorted cell sorting. In some embodiments of any of the methods of stimulating or increasing the proliferation of a $T_{reg}$ cell described herein, the $T_{reg}$ cell is an autologous $T_{reg}$ cell, a haploidentical $T_{reg}$ cell, or an allogeneic $T_{reg}$ cell isolated from peripheral blood or umbilical cord blood. In some embodiments of any of the methods of stimulating or increasing the proliferation of a $T_{reg}$ cell described herein, the $T_{reg}$ cell is a $CD4^+CD25^+Foxp3^+$ cell. In some embodiments of any of the methods of stimulating or increasing the proliferation of a $T_{reg}$ cell described herein, the $T_{reg}$ cell is a $CD4^+CD25^+CD127^{dim}$ cell. In some embodiments of any of the methods of stimulating or increasing the proliferation of a $T_{reg}$ cell described herein, the $T_{reg}$ cells comprises a chimeric antigen receptor.

In another aspect, provided herein are populations of $T_{reg}$ cells generated by any of the methods of stimulating or increasing the proliferation of a $T_{reg}$ cell described herein. Provided herein are compositions comprising any of the population of $T_{reg}$ cells generated by any of the methods of stimulating or increasing the proliferation of a $T_{reg}$ cell described herein and a pharmaceutically acceptable carrier. Also provided herein are methods of treating a subject in need thereof, the methods include administering to the subject a therapeutically effective amount of any of the compositions comprising any of the population of $T_{reg}$ cells generated by any of the methods of stimulating or increasing the proliferation of a $T_{reg}$ cell described herein and a pharmaceutically acceptable carrier. In some embodiments of any of the methods of treating a subject in need thereof, the subject has been identified or diagnosed as having an aging-related disease or an inflammatory disease. In some embodiments of any of the methods of treating a subject in need thereof, the aging-related disease is selected from the group consisting of: Alzheimer's disease, aneurysm, cystic fibrosis, fibrosis in pancreatitis, glaucoma, hypertension, idiopathic pulmonary fibrosis, inflammatory bowel disease, intervertebral disc degeneration, macular degeneration, osteoarthritis, type 2 diabetes mellitus, adipose atrophy, lipodystrophy, atherosclerosis, cataracts, COPD, idiopathic pulmonary fibrosis, kidney transplant failure, liver fibrosis, loss of bone mass, myocardial infarction, sarcopenia, wound healing, alopecia, cardiomyocyte hypertrophy, osteoarthritis, Parkinson's disease, age-associated loss of lung tissue elasticity, macular degeneration, cachexia, glomerulosclerosis, liver cirrhosis, NAFLD, osteoporosis, amyotrophic lateral sclerosis, Huntington's disease, spinocerebellar ataxia, multiple sclerosis, neurodegeneration, stroke, dementia, vascular disease, infection susceptibility, chronic inflammation, and renal dysfunction. In some embodiments of any of the methods of treating a subject in need thereof, the inflammatory disease is selected from the group consisting of: rheumatoid arthritis, inflammatory bowel disease, lupus erythematosus, lupus nephritis, diabetic nephropathy, CNS injury, Alzheimer's disease, Parkinson's disease, amyotrophic lateral sclerosis, Crohn's disease, multiple sclerosis, Guillain-Barre syndrome, psoriasis, Grave's disease, ulcerative colitis, nonalcoholic steatohepatitis, and mood disorders.

In another aspect, provided herein are kits that include: (i) a CD3/CD28-binding agent; (ii) a single-chain chimeric polypeptide comprising a first target-binding domain, a soluble tissue factor domain, and a second target-binding domain, wherein the first target-binding domain and the second target-binding domain bind to a receptor for IL-2; and (iii) an mTOR inhibitor. In some embodiments of any of the kits described herein, the kits further include an IgG1 antibody construct that comprises at least one antigen-binding domain that binds specifically to the soluble tissue factor domain of the single-chain chimeric polypeptide. In some embodiments of any of the kits described herein, the CD3/CD28-binding agent is an anti-CD3/anti-CD28 bead. In some embodiments of any of the kits described herein, the CD3/CD28-binding agent is an additional single-chain chimeric polypeptide comprising a first target-binding domain, a soluble tissue factor domain, and a second target-binding domain, wherein: the first target-binding domain of the additional single-chain chimeric polypeptide binds to CD3 and the second target-binding domain of the additional single-chain chimeric polypeptide binds to CD28. In some embodiments of any of the kits described herein, the kits further include an IgG1 antibody construct that comprises at least one antigen-binding domain that binds specifically to the soluble tissue factor domain of the additional single-chain chimeric polypeptide.

In some embodiments of any of the kits described herein, the CD3/CD28-binding agent is a multi-chain chimeric polypeptide comprising: (a) a first chimeric polypeptide comprising: (i) a first target-binding domain; (ii) a soluble tissue factor domain; and (iii) a first domain of a pair of affinity domains; and (b) a second chimeric polypeptide comprising: (i) a second domain of a pair of affinity domains; and (ii) a second target-binding domain, wherein: the first chimeric polypeptide and the second chimeric polypeptide associate through the binding of the first domain and the second domain of the pair of affinity domains; and wherein the first target-binding domain binds to CD3 and the second target-binding domain binds to CD28, or the first target-binding domain binds to CD28 and the second target-binding domain to CD3. In some embodiments of any of the kits described herein, the liquid culture medium further includes an IgG1 antibody construct that comprises at least one antigen-binding domain that binds specifically to the soluble tissue factor domain of the multi-chain chimeric polypeptide.

In another aspect, provided herein are methods of stimulating or increasing the proliferation of a $T_{reg}$ cell, the methods include: culturing a $T_{reg}$ cell in a liquid culture medium over a period of time, wherein at the beginning of the period of time, the liquid culture medium comprises: an IL-2 receptor-activating agent; and a single-chain chimeric polypeptide comprising a first target-binding domain, a soluble tissue factor domain, and a second target-binding domain, wherein: the first target-binding domain of the additional single-chain chimeric polypeptide binds to CD3 and the second target-binding domain of the additional single-chain chimeric polypeptide binds to CD28. In some embodiments of any of the methods of stimulating or increasing the proliferation of a $T_{reg}$ cell described herein, the liquid culture medium further includes an IgG1 antibody construct that comprises at least one antigen-binding domain that binds specifically to the soluble tissue factor domain of the single-chain chimeric polypeptide. In some embodiments of any of the methods of stimulating or increasing the proliferation of a $T_{reg}$ cell described herein, the IgG1 antibody construct comprises a heavy chain variable domain comprising CDRs of SEQ ID NOs: 66, 67 or 74, and 68, and a light chain variable domain comprising CDRs of SEQ ID NOs: 69, 70, and 71. In some embodiments of any of the methods of stimulating or increasing the proliferation of a $T_{reg}$ cell described herein, the heavy chain variable domain comprises a sequence that is at least 90% identical to SEQ ID NO: 72, and the light chain variable domain comprises a sequence that is at least 90% identical to SEQ ID NO: 73. In some embodiments of any of the methods of stimulating or increasing the proliferation of a $T_{reg}$ cell described herein, the heavy chain variable domain comprises SEQ ID NO: 72, and the light chain variable domain comprises SEQ ID NO: 73. In some embodiments of any of the methods of stimulating or increasing the proliferation of a $T_{reg}$ cell described herein, the first target-binding domain and the soluble tissue factor domain directly abut each other. In some embodiments of any of the methods of stimulating or increasing the proliferation of a $T_{reg}$ cell described herein, the single-chain chimeric polypeptide further comprises a linker sequence between the first target-binding domain and the soluble tissue factor domain. In some embodiments of any of the methods of stimulating or increasing the proliferation of a $T_{reg}$ cell described herein, the soluble tissue factor domain and the second target-binding domain directly abut each other. In some embodiments of any of the methods of stimulating or increasing the proliferation of a $T_{reg}$ cell described herein, the single-chain chimeric polypeptide further comprises a linker sequence between the soluble tissue factor domain and the second target-binding domain. In some embodiments of any of the methods of stimulating or increasing the proliferation of a $T_{reg}$ cell described herein, the CD3 is human CD3. In some embodiments of any of the methods of stimulating or increasing the proliferation of a $T_{reg}$ cell described herein, the first target-binding domain comprises a sequence that is at least 80% identical to SEQ ID NO: 5. In some embodiments of any of the methods of stimulating or increasing the proliferation of a $T_{reg}$ cell described herein, the first target-binding domain comprises a sequence that is at least 90% identical to SEQ ID NO: 5. In some embodiments of any of the methods of stimulating or increasing the proliferation of a $T_{reg}$ cell described herein, the first target-binding domain comprises a sequence of SEQ ID NO: 5. In some embodiments of any of the methods of stimulating or increasing the proliferation of a $T_{reg}$ cell described herein, the CD28 is human CD28. In some embodiments of any of the methods of stimulating or increasing the proliferation of a $T_{reg}$ cell described herein, the second target-binding domain comprises a sequence that is at least 80% identical to SEQ ID NO: 6. In some embodiments of any of the methods of stimulating or increasing the proliferation of a $T_{reg}$ cell described herein, the second target-binding domain comprises a sequence that is at least 90% identical to SEQ ID NO: 6. In some embodiments of any of the methods of stimulating or increasing the proliferation of a $T_{reg}$ cell described herein, the second target-binding domain comprises a sequence of SEQ ID NO: 6. In some embodiments of any of the methods of stimulating or increasing the proliferation of a $T_{reg}$ cell described herein, the soluble tissue factor domain is a soluble human tissue factor domain. In some embodiments of any of the methods of stimulating or increasing the proliferation of a $T_{reg}$ cell described herein, the soluble human tissue factor domain comprises a sequence that is at least 80% identical to SEQ ID NO: 2. In some embodiments of any of the methods of stimulating or increasing the proliferation of a $T_{reg}$ cell described herein, the soluble human tissue factor domain comprises a sequence that is at least 90% identical to SEQ ID NO: 2. In some embodiments of any of the methods of stimulating or increasing the proliferation of a $T_{reg}$ cell described herein, the soluble human tissue factor domain comprises a sequence of SEQ ID NO: 2. In some embodiments of any of the methods of stimulating or increasing the proliferation of a $T_{reg}$ cell described herein, the soluble tissue factor domain comprises or consists of a sequence from a wildtype soluble human tissue factor. In some embodiments of any of the methods of stimulating or increasing the proliferation of a $T_{reg}$ cell described herein, the soluble tissue factor domain does not comprise any of: a lysine at an amino acid position that corresponds to amino acid position 20 of mature wildtype human tissue factor protein; an isoleucine at an amino acid position that corresponds to amino acid position 22 of mature wildtype human tissue factor protein; a tryptophan at an amino acid position that corresponds to amino acid position 45 of mature wildtype human tissue factor protein; an aspartic acid at an amino acid position that corresponds to amino acid position 58 of mature wildtype human tissue factor protein; a tyrosine at an amino acid position that corresponds to amino acid position 94 of mature wildtype human tissue factor protein; an arginine at an amino acid position that corresponds to amino acid position 135 of mature wildtype human tissue factor protein; and a phenylalanine at an amino acid position that corresponds to amino acid position 140 of mature wildtype human tissue factor protein. In some embodiments of any of the methods of stimulating or increasing the proliferation of a $T_{reg}$ cell described herein, the soluble tissue factor domain comprises one or more of: a lysine at an amino acid position that corresponds to amino acid position 20 of mature wildtype human tissue factor protein; an isoleucine at an amino acid position that corresponds to amino acid position 22 of mature wildtype human tissue factor protein; a tryptophan at an amino acid position that corresponds to amino acid position 45 of mature wildtype human tissue factor protein; an aspartic acid at an amino acid position that corresponds to amino acid position 58 of mature wildtype human tissue factor protein; a tyrosine at an amino acid position that corresponds to amino acid position 94 of mature wildtype human tissue factor protein; an arginine at an amino acid position that corresponds to amino acid position 135 of mature wildtype human tissue factor protein; and a phenylalanine at an amino acid position that corresponds to amino acid position 140 of mature wildtype human tissue factor protein. In some embodiments of any of the methods of stimulating or increasing the proliferation of a $T_{reg}$ cell described herein, the soluble tissue factor domain does not initiate blood coagulation. In some embodiments of any of the methods of stimulating or increasing the proliferation of a $T_{reg}$ cell described herein, the single-chain chimeric polypeptide does not initiate blood coagulation. In some embodiments of any of the methods of stimulating or increasing the proliferation of a $T_{reg}$ cell described herein, the single-chain chimeric polypeptide comprises a sequence that is at least 80% identical to SEQ ID NO: 7. In some embodiments of any of the methods of stimulating or increasing the proliferation of a $T_{reg}$ cell described herein, the single-chain chimeric polypeptide comprises a sequence that is at least 90% identical to SEQ ID NO: 7. In some embodiments of any of the methods of stimulating or increasing the proliferation of a $T_{reg}$ cell described herein, the single-chain chimeric polypeptide comprises a sequence of SEQ ID NO: 7. In some embodiments of any of the methods of stimulating or increasing the proliferation of a $T_{reg}$ cell described herein, the single-chain chimeric polypeptide comprises a sequence that is at least 80% identical to SEQ ID NO: 8. In some embodiments of any of the methods of stimulating or increasing the proliferation of a $T_{reg}$ cell described herein, the single-chain chimeric polypeptide comprises a sequence that is at least 90% identical to SEQ ID NO: 8. In some embodiments of any of the methods of stimulating or increasing the proliferation of a $T_{reg}$ cell described herein, the single-chain chimeric polypeptide comprises a sequence of SEQ ID NO: 8. In some embodiments of any of the methods of stimulating or increasing the proliferation of a $T_{reg}$ cell described herein, the liquid culture medium comprises about 10 nM to about 1000 nM of the single-chain chimeric polypeptide. In some embodiments of any of the methods of stimulating or increasing the proliferation of a $T_{reg}$ cell described herein, the liquid culture medium comprises about 50 nM to about 300 nM of the single-chain chimeric polypeptide. In some embodiments of any of the methods of stimulating or increasing the proliferation of a $T_{reg}$ cell described herein, the IL-2 receptor-activating agent is a soluble IL-2. In some embodiments of any of the methods of stimulating or increasing the proliferation of a $T_{reg}$ cell described herein, the soluble IL-2 is a human soluble IL-2. In some embodiments of any of the methods of stimulating or increasing the proliferation of a $T_{reg}$ cell described herein, the human soluble IL-2 comprises a sequence that is at least 80% identical to SEQ ID NO: 1. In some embodiments of any of the methods of stimulating or increasing the proliferation of a $T_{reg}$ cell described herein, the human soluble IL-2 comprises a sequence that is at least 90% identical to SEQ ID NO: 1. In some embodiments of any of the methods of stimulating or increasing the proliferation of a $T_{reg}$ cell described herein, the human soluble IL-2 comprises a sequence of SEQ ID NO: 1. In some embodiments of any of the methods of stimulating or increasing the proliferation of a $T_{reg}$ cell described herein, the liquid culture medium comprises about 100 IU/mL to about 800 IU/mL of the human soluble IL-2. In some embodiments of any of the methods of stimulating or increasing the proliferation of a $T_{reg}$ cell described herein, the liquid culture medium comprises about 400 IU/mL to about 600 IU/mL of the human soluble IL-2. In some embodiments of any of the methods of stimulating or increasing the proliferation of a $T_{reg}$ cell described herein, the liquid culture medium further comprises an mTOR inhibitor. In some embodiments of any of the methods of stimulating or increasing the proliferation of a $T_{reg}$ cell described herein, the mTOR inhibitor is rapamycin. In some embodiments of any of the methods of stimulating or increasing the proliferation of a $T_{reg}$ cell described herein, the liquid culture medium comprises about 10 nM to about 500 nM of the mTOR inhibitor. In some embodiments of any of the methods of stimulating or increasing the proliferation of a $T_{reg}$ cell described herein, the liquid culture medium comprises about 50 nM to about 150 nM of the mTOR inhibitor. In some embodiments of any of the methods of stimulating or increasing the proliferation of a Treg cell described herein, the liquid culture medium does not comprise an mTOR inhibitor.

In some embodiments of any of the methods of stimulating or increasing the proliferation of a $T_{reg}$ cell described herein, the methods further include: periodically adding to the liquid culture medium, after each 36 hours to about 60 hours after the start of the period of time, the IL-2 receptor-activating agent. In some embodiments of any of the methods of stimulating or increasing the proliferation of a $T_{reg}$ cell described herein, the periodic addition of the IL-2 receptor-activating agent is performed to result in a concentration of about 10 nM to about 1000 nM of the IL-2 receptor-activating agent in the liquid culture medium. In some embodiments of any of the methods of stimulating or increasing the proliferation of a $T_{reg}$ cell described herein, the periodic addition of the IL-2 receptor activating agent is performed to result in a concentration of about 50 nM to about 150 nM of the IL-2 receptor-activating agent in the liquid culture medium. In some embodiments of any of the methods of stimulating or increasing the proliferation of a $T_{reg}$ cell described herein, the methods further include: periodically adding to the liquid culture medium, after each about 6 days to about 8 days after the start of the period of time, the single-chain chimeric polypeptide. In some embodiments of any of the methods of stimulating or increasing the proliferation of a $T_{reg}$ cell described herein, the period of time is about 7 days to about 56 days. In some embodiments of any of the methods of stimulating or increasing the proliferation of a $T_{reg}$ cell described herein, the period of claim is about 15 days to about 25 days. In some embodiments of any of the methods of stimulating or increasing the proliferation of a $T_{reg}$ cell described herein, the methods further include, before the culturing step, a step of isolating the $T_{reg}$ cell from a sample obtained from a subject. In some embodiments of any of the methods of stimulating or increasing the proliferation of a Treg cell described herein, the method further comprises, after the culturing step, a step of isolating the Treg cell from a sample obtained from a subject.

In some embodiments of any of the methods of stimulating or increasing the proliferation of a $T_{reg}$ cell described herein, the isolating comprises the use of fluorescence-assorted cell sorting. In some embodiments of any of the methods of stimulating or increasing the proliferation of a $T_{reg}$ cell described herein, the $T_{reg}$ cell is an autologous $T_{reg}$ cell, a haploidentical $T_{reg}$ cell, or an allogeneic $T_{reg}$ cell isolated from peripheral blood or umbilical cord blood. In some embodiments of any of the methods of stimulating or increasing the proliferation of a $T_{reg}$ cell described herein, the $T_{reg}$ cell is a CD4$^+$CD25$^+$Foxp3$^+$ cell. In some embodiments of any of the methods of stimulating or increasing the proliferation of a $T_{reg}$ cell described herein, the $T_{reg}$ cell is a CD4$^+$CD25$^+$CD127$^{dim}$ cell. In some embodiments of any of the methods of stimulating or increasing the proliferation of a $T_{reg}$ cell described herein, the $T_{reg}$ cells comprises a chimeric antigen receptor.

Provided herein are populations of $T_{reg}$ cells generated by any of the methods of stimulating or increasing the proliferation of a $T_{reg}$ cell described herein. Provided herein are compositions comprising any populations of $T_{reg}$ cells generated by any of the methods of stimulating or increasing the proliferation of a $T_{reg}$ cell described herein and a pharmaceutically acceptable carrier. Also provided herein are methods of treating a subject in need thereof, the methods include administering to the subject a therapeutically effective amount of any of the compositions comprising any populations of $T_{reg}$ cells generated by any of the methods of stimulating or increasing the proliferation of a $T_{reg}$ cell described herein and a pharmaceutically acceptable carrier. In some embodiments of any of the methods of treating a subject in need thereof described herein, the subject has been identified or diagnosed as having an aging-related disease or an inflammatory disease. In some embodiments of any of the methods of treating a subject in need thereof described herein, the aging-related disease is selected from the group consisting of: Alzheimer's disease, aneurysm, cystic fibrosis, fibrosis in pancreatitis, glaucoma, hypertension, idiopathic pulmonary fibrosis, inflammatory bowel disease, intervertebral disc degeneration, macular degeneration, osteoarthritis, type 2 diabetes mellitus, adipose atrophy, lipodystrophy, atherosclerosis, cataracts, COPD, idiopathic pulmonary fibrosis, kidney transplant failure, liver fibrosis, loss of bone mass, myocardial infarction, sarcopenia, wound healing, alopecia, cardiomyocyte hypertrophy, osteoarthritis, Parkinson's disease, age-associated loss of lung tissue elasticity, macular degeneration, cachexia, glomerulosclerosis, liver cirrhosis, NAFLD, osteoporosis, amyotrophic lateral sclerosis, Huntington's disease, spinocerebellar ataxia, multiple sclerosis, neurodegeneration, stroke, dementia, vascular disease, infection susceptibility, chronic inflammation, and renal dysfunction. In some embodiments of any of the methods of treating a subject in need thereof described herein, the inflammatory disease is selected from the group consisting of: rheumatoid arthritis, inflammatory bowel disease, lupus erythematosus, lupus nephritis, diabetic nephropathy, CNS injury, Alzheimer's disease, Parkinson's disease, amyotrophic lateral sclerosis, Crohn's disease, multiple sclerosis, Guillain-Barre syndrome, psoriasis, Grave's disease, ulcerative colitis, nonalcoholic steatohepatitis, and mood disorders.

In another aspect, provided herein are kits that include: (i) an interleukin-2 receptor-activating agent; (ii) a single-chain chimeric polypeptide comprising a first target-binding domain, a soluble tissue factor domain, and a second target-binding domain, wherein: the first target-binding domain binds to CD3 and the second target-binding domain binds to CD28; and (iii) an mTOR inhibitor. In some embodiments of any of the kits described herein, the kits further include an IgG1 antibody construct that comprises at least one antigen-binding domain that binds specifically to the soluble tissue factor domain of the single-chain chimeric polypeptide.

In another aspect, provided herein are methods of stimulating or increasing the proliferation of a $T_{reg}$ cell, the methods include: culturing a $T_{reg}$ cell in a liquid culture medium over a period of time, wherein at the beginning of the period of time, the liquid culture medium comprises: a CD3/CD28-binding agent; and a multi-chain chimeric polypeptide comprising: (a) a first chimeric polypeptide comprising: (i) a first target-binding domain; (ii) a soluble tissue factor domain; and (iii) a first domain of a pair of affinity domains; and (b) a second chimeric polypeptide comprising: (i) a second domain of a pair of affinity domains; and (ii) a second target-binding domain, wherein the first chimeric polypeptide and the second chimeric polypeptide associate through the binding of the first domain and the second domain of the pair of affinity domains. In some embodiments of any of the methods of stimulating or increasing the proliferation of a $T_{reg}$ cell described herein, the liquid culture medium further includes an IgG1 antibody construct that comprises at least one antigen-binding domain that binds specifically to the soluble tissue factor domain of the multi-chain chimeric polypeptide. In some embodiments of any of the methods of stimulating or increasing the proliferation of a $T_{reg}$ cell described herein, the IgG1 antibody construct comprises a heavy chain variable domain comprising CDRs of SEQ ID NOs: 66, 67 or 74, and 68, and a light chain variable domain comprising CDRs of SEQ ID NOs: 69, 70, and 71. In some embodiments of any of the methods of stimulating or increasing the proliferation of a $T_{reg}$ cell described herein, the heavy chain variable domain comprises a sequence that is at least 90% identical to SEQ ID NO: 72, and the light chain variable domain comprises a sequence that is at least 90% identical to SEQ ID NO: 73. In some embodiments of any of the methods of stimulating or increasing the proliferation of a $T_{reg}$ cell described herein, the heavy chain variable domain comprises SEQ ID NO: 72, and the light chain variable domain comprises SEQ ID NO: 73. In some embodiments of any of the methods of stimulating or increasing the proliferation of a $T_{reg}$ cell described herein, the first target-binding domain and the soluble tissue factor domain directly abut each other in the first chimeric polypeptide. In some embodiments of any of the methods of stimulating or increasing the proliferation of a $T_{reg}$ cell described herein, the first chimeric polypeptide further comprises a linker sequence between the first target-binding domain and the soluble tissue factor domain in the first chimeric polypeptide. In some embodiments of any of the methods of stimulating or increasing the proliferation of a $T_{reg}$ cell described herein, the soluble tissue factor domain and the first domain of the pair of affinity domains directly abut each other in the first chimeric polypeptide. In some embodiments of any of the methods of stimulating or increasing the proliferation of a $T_{reg}$ cell described herein, the first chimeric polypeptide further comprises a linker sequence between the soluble tissue factor domain and the first domain of the pair of affinity domains in the first chimeric polypeptide. In some embodiments of any of the methods of stimulating or increasing the proliferation of a $T_{reg}$ cell described herein, the second domain of the pair of affinity domains and the second target-binding domain directly abut each other in the second chimeric polypeptide. In some embodiments of any of the methods of stimulating or increasing the proliferation of a $T_{reg}$ cell described herein, second chimeric polypeptide further comprises a linker sequence between the second domain of the pair of affinity domains and the second target-binding domain in the second chimeric polypeptide. In some embodiments of any of the methods of stimulating or increasing the proliferation of a $T_{reg}$ cell described herein, the first target-binding domain and the second target-binding domain bind specifically to the same antigen. In some embodiments of any of the methods of stimulating or increasing the proliferation of a $T_{reg}$ cell described herein, the first target-binding domain and the second target-binding domain bind specifically to different antigens. In some embodiments of any of the methods of stimulating or increasing the proliferation of a $T_{reg}$ cell described herein, one or both of the first target-binding domain and the second target-binding domain is an antigen-binding domain. In some embodiments of any of the methods of stimulating or increasing the proliferation of a $T_{reg}$ cell described herein, one or both of the first target-binding domain and the second target-binding domain bind specifically to a target selected from the group consisting of: CD16a, CD28, CD3, CD33, CD20, CD19, CD22, CD123, IL-1R, IL-1, VEGF, IL-6R, IL-4, IL-10, PDL-1, TIGIT, PD-1, TIM3, CTLA4, MICA, MICB, IL-6, IL-8, TNFα, CD26, CD36, ULBP2, CD30, CD200, IGF-1R, MUC4AC, MUC5AC, Trop-2, CMET, EGFR, HER1, HER2, HER3, PSMA, CEA, B7H3, EPCAM, BCMA, P-cadherin, CEACAM5, a UL16-binding protein, HLA-DR, DLL4, TYRO3, AXL, MER, CD122, CD155, PDGF-DD, a ligand of TGF-β receptor II (TGF-βRII), a ligand of TGF-βRIII, a ligand of DNAM-1, a ligand of NKp46, a ligand of NKp44, a ligand of NKG2D, a ligand of NKp30, a ligand for a scMHCI, a ligand for a scMHCII, a ligand for a scTCR, a receptor for IL-1, a receptor for IL-2, a receptor for IL-3, a receptor for IL-7, a receptor for IL-8, a receptor for IL-10, a receptor for IL-12, a receptor for IL-15, a receptor for IL-17, a receptor for IL-18, a receptor for IL-21, a receptor for PDGF-DD, a receptor for stem cell factor (SCF), a receptor for stem cell-like tyrosine kinase 3 ligand (FLT3L), a receptor for MICA, a receptor for MICB, a receptor for a ULP16-binding protein, a receptor for CD155, a receptor for CD122, and a receptor for CD28. In some embodiments of any of the methods of stimulating or increasing the proliferation of a T$_{reg}$ cell described herein, one or both of the first target-binding domain and the second target-binding domain is a soluble interleukin or cytokine protein. In some embodiments of any of the methods of stimulating or increasing the proliferation of a T$_{reg}$ cell described herein, the soluble interleukin, cytokine, or ligand protein is selected from the group consisting of: IL-1, IL-2, IL-3, IL-7, IL-8, IL-10, IL-12, IL-15, IL-17, IL-18, IL-21, PDGF-DD, SCF, and FLT3L. In some embodiments of any of the methods of stimulating or increasing the proliferation of a T$_{reg}$ cell described herein, one or both of the first target-binding domain and the second target-binding domain is a soluble interleukin or cytokine receptor. In some embodiments of any of the methods of stimulating or increasing the proliferation of a T$_{reg}$ cell described herein, the soluble receptor is a soluble TGF-β receptor II (TGF-βRII), a soluble TGF-βRIII, a soluble NKG2D, a soluble NKp30, a soluble NKp44, a soluble NKp46, a soluble DNAM-1, a scMHCI, a scMHCII, a scTCR, a soluble CD155, or a soluble CD28. In some embodiments of any of the methods of stimulating or increasing the proliferation of a T$_{reg}$ cell described herein, the first chimeric polypeptide further comprises one or more additional target-binding domain(s). In some embodiments of any of the methods of stimulating or increasing the proliferation of a T$_{reg}$ cell described herein, the second chimeric polypeptide further comprises one or more additional target-binding domains. In some embodiments of any of the methods of stimulating or increasing the proliferation of a T$_{reg}$ cell described herein, the pair of affinity domains is a sushi domain from an alpha chain of human IL-15 receptor (IL15Ra) and a soluble IL-15. In some embodiments of any of the methods of stimulating or increasing the proliferation of a T$_{reg}$ cell described herein, the soluble IL-15 has a D8N or D8A amino acid substitution. In some embodiments of any of the methods of stimulating or increasing the proliferation of a T$_{reg}$ cell described herein, the pair of affinity domains is selected from the group consisting of: barnase and barnstar, a PKA and an AKAP, adapter/docking tag modules based on mutated RNase I fragments, and SNARE modules based on interactions of the proteins syntaxin, synaptotagmin, synaptobrevin, and SNAP25. In some embodiments of any of the methods of stimulating or increasing the proliferation of a T$_{reg}$ cell described herein, the soluble tissue factor domain is a soluble human tissue factor domain. In some embodiments of any of the methods of stimulating or increasing the proliferation of a T$_{reg}$ cell described herein, the soluble human tissue factor domain comprises a sequence that is at least 80% identical to SEQ ID NO: 2. In some embodiments of any of the methods of stimulating or increasing the proliferation of a T$_{reg}$ cell described herein, the soluble human tissue factor domain comprises a sequence that is at least 90% identical to SEQ ID NO: 2. In some embodiments of any of the methods of stimulating or increasing the proliferation of a T$_{reg}$ cell described herein, the soluble human tissue factor domain comprises a sequence of SEQ ID NO: 2. In some embodiments of any of the methods of stimulating or increasing the proliferation of a T$_{reg}$ cell described herein, the soluble tissue factor domain comprises or consists of a sequence from a wildtype soluble human tissue factor. In some embodiments of any of the methods of stimulating or increasing the proliferation of a T$_{reg}$ cell described herein, the soluble tissue factor domain does not comprise any of: a lysine at an amino acid position that corresponds to amino acid position 20 of mature wildtype human tissue factor protein; an isoleucine at an amino acid position that corresponds to amino acid position 22 of mature wildtype human tissue factor protein; a tryptophan at an amino acid position that corresponds to amino acid position 45 of mature wildtype human tissue factor protein; an aspartic acid at an amino acid position that corresponds to amino acid position 58 of mature wildtype human tissue factor protein; a tyrosine at an amino acid position that corresponds to amino acid position 94 of mature wildtype human tissue factor protein; an arginine at an amino acid position that corresponds to amino acid position 135 of mature wildtype human tissue factor protein; and a phenylalanine at an amino acid position that corresponds to amino acid position 140 of mature wildtype human tissue factor protein. In some embodiments of any of the methods of stimulating or increasing the proliferation of a T$_{reg}$ cell described herein, the soluble tissue factor domain comprises one or more of: a lysine at an amino acid position that corresponds to amino acid position 20 of mature wildtype human tissue factor protein; an isoleucine at an amino acid position that corresponds to amino acid position 22 of mature wildtype human tissue factor protein; a tryptophan at an amino acid position that corresponds to amino acid position 45 of mature wildtype human tissue factor protein; an aspartic acid at an amino acid position that corresponds to amino acid position 58 of mature wildtype human tissue factor protein; a tyrosine at an amino acid position that corresponds to amino acid position 94 of mature wildtype human tissue factor protein; an arginine at an amino acid position that corresponds to amino acid position 135 of mature wildtype human tissue factor protein; and a phenylalanine at an amino acid position that corresponds to amino acid position 140 of mature wildtype human tissue factor protein. In some embodiments of any of the methods of stimulating or increasing the proliferation of a T$_{reg}$ cell described herein, the soluble tissue factor domain does not initiate blood coagulation. In some embodiments of any of the methods of stimulating or increasing the proliferation of a T$_{reg}$ cell described herein, the multi-chain chimeric polypeptide does not initiate blood coagulation. In some embodiments of any of the methods of stimulating or increasing the proliferation of a T$_{reg}$ cell described herein, the CD3/CD28-binding agent is an anti-CD3/anti-CD28 bead. In some embodiments of any of the methods of stimulating or increasing the proliferation of a T$_{reg}$ cell described herein, the liquid culture medium comprises the anti-CD3/anti-CD28 bead at a ratio of about 1:1 to about 6:1 beads/cell. In some embodiments of any of the methods of stimulating or increasing the proliferation of a T$_{reg}$ cell described herein, the liquid culture medium comprises the anti-CD3/anti-CD28 bead at a ratio of about 3:1 to about 5:1 beads/cell. In some embodiments of any of the methods of stimulating or increasing the proliferation of a T$_{reg}$ cell described herein, the CD3/CD28-binding agent is an single-chain chimeric polypeptide comprising a first target-binding domain, a soluble tissue factor domain, and a second target-binding domain, wherein: the first target-binding domain of the single-chain chimeric polypeptide binds to CD3 and the second target-binding domain of the single-chain chimeric polypeptide binds to CD28. In some embodiments of any of the methods of stimulating or increasing the proliferation of a T$_{reg}$ cell described herein, the liquid culture medium further includes an IgG1 antibody construct that comprises at least one antigen-binding domain that binds specifically to the soluble tissue factor domain of the single-chain chimeric polypeptide. In some embodiments of any of the methods of stimulating or increasing the proliferation of a T$_{reg}$ cell described herein, the IgG1 antibody construct comprises a heavy chain variable domain comprising CDRs of SEQ ID NOs: 66, 67 or 74, and 68, and a light chain variable domain comprising CDRs of SEQ ID NOs: 69, 70, and 71. In some embodiments of any of the methods of stimulating or increasing the proliferation of a $T_{reg}$ cell described herein, the heavy chain variable domain comprises a sequence that is at least 90% identical to SEQ ID NO: 72, and the light chain variable domain comprises a sequence that is at least 90% identical to SEQ ID NO: 73. In some embodiments of any of the methods of stimulating or increasing the proliferation of a $T_{reg}$ cell described herein, the heavy chain variable domain comprises SEQ ID NO: 72, and the light chain variable domain comprises SEQ ID NO: 73. In some embodiments of any of the methods of stimulating or increasing the proliferation of a $T_{reg}$ cell described herein, the first target-binding domain of the single-chain chimeric polypeptide and the soluble tissue factor domain directly abut each other. In some embodiments of any of the methods of stimulating or increasing the proliferation of a $T_{reg}$ cell described herein, the single-chain chimeric polypeptide further comprises a linker sequence between the first target-binding domain and the soluble tissue factor domain. In some embodiments of any of the methods of stimulating or increasing the proliferation of a $T_{reg}$ cell described herein, the soluble tissue factor domain and the second target-binding domain of the single-chain chimeric polypeptide directly abut each other. In some embodiments of any of the methods of stimulating or increasing the proliferation of a $T_{reg}$ cell described herein, the single-chain chimeric polypeptide further comprises a linker sequence between the soluble tissue factor domain and the second target-binding domain. In some embodiments of any of the methods of stimulating or increasing the proliferation of a $T_{reg}$ cell described herein, the CD3 is human CD3. In some embodiments of any of the methods of stimulating or increasing the proliferation of a $T_{reg}$ cell described herein, the first target-binding domain of the single-chain chimeric polypeptide comprises a sequence that is at least 80% identical to SEQ ID NO: 5. In some embodiments of any of the methods of stimulating or increasing the proliferation of a $T_{reg}$ cell described herein, the first target-binding domain of the single-chain chimeric polypeptide comprises a sequence that is at least 90% identical to SEQ ID NO: 5. In some embodiments of any of the methods of stimulating or increasing the proliferation of a $T_{reg}$ cell described herein, the first target-binding domain of the single-chain chimeric polypeptide comprises a sequence of SEQ ID NO: 5. In some embodiments of any of the methods of stimulating or increasing the proliferation of a $T_{reg}$ cell described herein, the CD28 is human CD28. In some embodiments of any of the methods of stimulating or increasing the proliferation of a $T_{reg}$ cell described herein, the second target-binding domain of the single-chain chimeric polypeptide comprises a sequence that is at least 80% identical to SEQ ID NO: 6. In some embodiments of any of the methods of stimulating or increasing the proliferation of a $T_{reg}$ cell described herein, the second target-binding domain of the single-chain chimeric polypeptide comprises a sequence that is at least 90% identical to SEQ ID NO: 6. In some embodiments of any of the methods of stimulating or increasing the proliferation of a $T_{reg}$ cell described herein, the second target-binding domain of the single-chain chimeric polypeptide comprises a sequence of SEQ ID NO: 6. In some embodiments of any of the methods of stimulating or increasing the proliferation of a $T_{reg}$ cell described herein, the soluble tissue factor domain of the single-chain chimeric polypeptide is a soluble human tissue factor domain. In some embodiments of any of the methods of stimulating or increasing the proliferation of a $T_{reg}$ cell described herein, the soluble human tissue factor domain of the single-chain chimeric polypeptide comprises a sequence that is at least 80% identical to SEQ ID NO: 2. In some embodiments of any of the methods of stimulating or increasing the proliferation of a $T_{reg}$ cell described herein, the soluble human tissue factor domain of the single-chain chimeric polypeptide comprises a sequence that is at least 90% identical to SEQ ID NO: 2. In some embodiments of any of the methods of stimulating or increasing the proliferation of a $T_{reg}$ cell described herein, the soluble human tissue factor domain of the single-chain chimeric polypeptide comprises a sequence of SEQ ID NO: 2. In some embodiments of any of the methods of stimulating or increasing the proliferation of a $T_{reg}$ cell described herein, the soluble tissue factor domain of the single-chain chimeric polypeptide comprises or consists of a sequence from a wildtype soluble human tissue factor. In some embodiments of any of the methods of stimulating or increasing the proliferation of a $T_{reg}$ cell described herein, the soluble tissue factor domain does not comprise any of: a lysine at an amino acid position that corresponds to amino acid position 20 of mature wildtype human tissue factor protein; an isoleucine at an amino acid position that corresponds to amino acid position 22 of mature wildtype human tissue factor protein; a tryptophan at an amino acid position that corresponds to amino acid position 45 of mature wildtype human tissue factor protein; an aspartic acid at an amino acid position that corresponds to amino acid position 58 of mature wildtype human tissue factor protein; a tyrosine at an amino acid position that corresponds to amino acid position 94 of mature wildtype human tissue factor protein; an arginine at an amino acid position that corresponds to amino acid position 135 of mature wildtype human tissue factor protein; and a phenylalanine at an amino acid position that corresponds to amino acid position 140 of mature wildtype human tissue factor protein. In some embodiments of any of the methods of stimulating or increasing the proliferation of a $T_{reg}$ cell described herein, the soluble tissue factor domain comprises one or more of: a lysine at an amino acid position that corresponds to amino acid position 20 of mature wildtype human tissue factor protein; an isoleucine at an amino acid position that corresponds to amino acid position 22 of mature wildtype human tissue factor protein; a tryptophan at an amino acid position that corresponds to amino acid position 45 of mature wildtype human tissue factor protein; an aspartic acid at an amino acid position that corresponds to amino acid position 58 of mature wildtype human tissue factor protein; a tyrosine at an amino acid position that corresponds to amino acid position 94 of mature wildtype human tissue factor protein; an arginine at an amino acid position that corresponds to amino acid position 135 of mature wildtype human tissue factor protein; and a phenylalanine at an amino acid position that corresponds to amino acid position 140 of mature wildtype human tissue factor protein. In some embodiments of any of the methods of stimulating or increasing the proliferation of a $T_{reg}$ cell described herein, the soluble tissue factor domain of the single-chain chimeric polypeptide does not initiate blood coagulation. In some embodiments of any of the methods of stimulating or increasing the proliferation of a $T_{reg}$ cell described herein, the single-chain chimeric polypeptide does not initiate blood coagulation. In some embodiments of any of the methods of stimulating or increasing the proliferation of a $T_{reg}$ cell described herein, the single-chain chimeric polypeptide comprises a sequence that is at least 80% identical to SEQ ID NO: 7. In some embodiments of any of the methods of stimulating or increasing the proliferation of a $T_{reg}$ cell described herein, the single-chain chimeric polypeptide comprises a sequence that is at least 90% identical to SEQ ID NO: 7. In some embodiments of any of the methods of stimulating or increasing the proliferation of a $T_{reg}$ cell described herein, the single-chain chimeric polypeptide comprises a sequence of SEQ ID NO: 7. In some embodiments of any of the methods of stimulating or increasing the proliferation of a $T_{reg}$ cell described herein, the single-chain chimeric polypeptide comprises a sequence that is at least 80% identical to SEQ ID NO: 8. In some embodiments of any of the methods of stimulating or increasing the proliferation of a $T_{reg}$ cell described herein, the single-chain chimeric polypeptide comprises a sequence that is at least 90% identical to SEQ ID NO: 8. In some embodiments of any of the methods of stimulating or increasing the proliferation of a $T_{reg}$ cell described herein, the single-chain chimeric polypeptide comprises a sequence of SEQ ID NO: 8. In some embodiments of any of the methods of stimulating or increasing the proliferation of a $T_{reg}$ cell described herein, the liquid culture medium comprises about 10 nM to about 1000 nM of the single-chain chimeric polypeptide. In some embodiments of any of the methods of stimulating or increasing the proliferation of a $T_{reg}$ cell described herein, the liquid culture medium comprises about 50 nM to about 300 nM of the single-chain chimeric polypeptide.

In some embodiments of any of the methods of stimulating or increasing the proliferation of a Treg cell described herein, the CD3/CD28 binding agent is an additional multi-chain chimeric polypeptide comprising: (a) a first chimeric polypeptide comprising: (i) a first target-binding domain; (ii) a soluble tissue factor domain; and (iii) a first domain of a pair of affinity domains; and (b) a second chimeric polypeptide comprising: (i) a second domain of a pair of affinity domains; and (ii) a second target-binding domain, wherein the first chimeric polypeptide and the second chimeric polypeptide associate through the binding of the first domain and the second domain of the pair of affinity domains; and wherein the first target-binding domain binds to CD3 and the second target-binding domain binds to CD28, or the first target-binding domain binds to CD28 and the second target-binding domain to CD3.

In some embodiments of any of the methods of stimulating or increasing the proliferation of a Treg cell described herein, the liquid culture medium further includes an IgG1 antibody construct that comprises at least one antigen-binding domain that binds specifically to the soluble tissue factor domain of the additional multi-chain chimeric polypeptide. In some embodiments of any of the methods of stimulating or increasing the proliferation of a Treg cell described herein, the IgG1 antibody construct comprises a heavy chain variable domain comprising CDRs of SEQ ID NOs: 66, 67 or 74, and 68, and a light chain variable domain comprising CDRs of SEQ ID NOs: 69, 70, and 71. In some embodiments of any of the methods of stimulating or increasing the proliferation of a Treg cell described herein, the heavy chain variable domain comprises a sequence that is at least 90% identical to SEQ ID NO: 72, and the light chain variable domain comprises a sequence that is at least 90% identical to SEQ ID NO: 73. In some embodiments of any of the methods of stimulating or increasing the proliferation of a Treg cell described herein, the heavy chain variable domain comprises SEQ ID NO: 72, and the light chain variable domain comprises SEQ ID NO: 73.

In some embodiments of any of the methods of stimulating or increasing the proliferation of a Treg cell described herein, the first target-binding domain of the first chimeric polypeptide and the soluble tissue factor domain of the additional multi-chain chimeric polypeptide directly abut each other. In some embodiments of any of the methods of stimulating or increasing the proliferation of a Treg cell described herein, the first chimeric polypeptide of the additional multi-chain chimeric polypeptide further comprises a linker sequence between the first target-binding domain and the soluble tissue factor domain. In some embodiments of any of the methods of stimulating or increasing the proliferation of a Treg cell described herein, the soluble tissue factor domain and the second target-binding domain of the second chimeric polypeptide of the additional multi-chain chimeric polypeptide directly abut each other. In some embodiments of any of the methods of stimulating or increasing the proliferation of a Treg cell described herein, the second chimeric polypeptide of the additional multi-chain chimeric polypeptide further comprises a linker sequence between the soluble tissue factor domain and the second target-binding domain.

In some embodiments of any of the methods of stimulating or increasing the proliferation of a Treg cell described herein, the CD3 is human CD3. In some embodiments of any of the methods of stimulating or increasing the proliferation of a Treg cell described herein, the first target-binding domain of the first chimeric polypeptide comprises a sequence that is at least 80% identical to SEQ ID NO: 5. In some embodiments of any of the methods of stimulating or increasing the proliferation of a Treg cell described herein, the first target-binding domain of the additional single-chain chimeric polypeptide comprises a sequence that is at least 90% identical to SEQ ID NO: 5. In some embodiments of any of the methods of stimulating or increasing the proliferation of a Treg cell described herein, the first target-binding domain of the additional single-chain chimeric polypeptide comprises a sequence of SEQ ID NO: 5.

In some embodiments of any of the methods of stimulating or increasing the proliferation of a Treg cell described herein, the soluble tissue factor domain of the first chimeric polypeptide of the additional multi-chain chimeric polypeptide is a soluble human tissue factor domain. In some embodiments of any of the methods of stimulating or increasing the proliferation of a Treg cell described herein, the soluble human tissue factor domain of the first chimeric polypeptide of the additional multi-chain chimeric polypeptide comprises a sequence that is at least 80% identical to SEQ ID NO: 2. In some embodiments of any of the methods of stimulating or increasing the proliferation of a Treg cell described herein, the soluble human tissue factor domain of the first chimeric polypeptide of the additional multi-chain chimeric polypeptide comprises a sequence that is at least 90% identical to SEQ ID NO: 2. In some embodiments of any of the methods of stimulating or increasing the proliferation of a Treg cell described herein, the soluble human tissue factor domain of the first chimeric polypeptide of the additional multi-chain chimeric polypeptide comprises a sequence of SEQ ID NO: 2. In some embodiments of any of the methods of stimulating or increasing the proliferation of a Treg cell described herein, the soluble tissue factor domain of the first chimeric polypeptide of the additional multi-chain chimeric polypeptide comprises or consists of a sequence from a wildtype soluble human tissue factor.

In some embodiments of any of the methods of stimulating or increasing the proliferation of a Treg cell described herein, the soluble tissue factor domain of the first chimeric polypeptide of the additional multi-chain chimeric polypeptide does not comprise any of: a lysine at an amino acid position that corresponds to amino acid position 20 of mature wildtype human tissue factor protein; an isoleucine at an amino acid position that corresponds to amino acid position 22 of mature wildtype human tissue factor protein; a tryptophan at an amino acid position that corresponds to amino acid position 45 of mature wildtype human tissue factor protein; an aspartic acid at an amino acid position that corresponds to amino acid position 58 of mature wildtype human tissue factor protein; a tyrosine at an amino acid position that corresponds to amino acid position 94 of mature wildtype human tissue factor protein; an arginine at an amino acid position that corresponds to amino acid position 135 of mature wildtype human tissue factor protein; and a phenylalanine at an amino acid position that corresponds to amino acid position 140 of mature wildtype human tissue factor protein.

In some embodiments of any of the methods of stimulating or increasing the proliferation of a Treg cell described herein, the soluble tissue factor domain of the first chimeric polypeptide of the additional multi-chain chimeric polypeptide comprises one or more of: a lysine at an amino acid position that corresponds to amino acid position 20 of mature wildtype human tissue factor protein; an isoleucine at an amino acid position that corresponds to amino acid position 22 of mature wildtype human tissue factor protein; a tryptophan at an amino acid position that corresponds to amino acid position 45 of mature wildtype human tissue factor protein; an aspartic acid at an amino acid position that corresponds to amino acid position 58 of mature wildtype human tissue factor protein; a tyrosine at an amino acid position that corresponds to amino acid position 94 of mature wildtype human tissue factor protein; an arginine at an amino acid position that corresponds to amino acid position 135 of mature wildtype human tissue factor protein; and a phenylalanine at an amino acid position that corresponds to amino acid position 140 of mature wildtype human tissue factor protein.

In some embodiments of any of the methods of stimulating or increasing the proliferation of a Treg cell described herein, the soluble tissue factor domain of the first chimeric polypeptide of the additional multi-chain chimeric polypeptide does not initiate blood coagulation.

In some embodiments of any of the methods of stimulating or increasing the proliferation of a Treg cell described herein, the first chimeric polypeptide of the additional multi-chain chimeric polypeptide comprises a sequence that is at least 80% identical to SEQ ID NO: 102. In some embodiments of any of the methods of stimulating or increasing the proliferation of a Treg cell described herein, the first chimeric polypeptide of the additional multi-chain chimeric polypeptide comprises a sequence that is at least 90% identical to SEQ ID NO: 102. In some embodiments of any of the methods of stimulating or increasing the proliferation of a Treg cell described herein, the first chimeric polypeptide of the additional multi-chain chimeric polypeptide comprises a sequence of SEQ ID NO: 102. In some embodiments of any of the methods of stimulating or increasing the proliferation of a Treg cell described herein, the first chimeric polypeptide of the additional multi-chain chimeric polypeptide comprises a sequence that is at least 80% identical to SEQ ID NO: 104. In some embodiments of any of the methods of stimulating or increasing the proliferation of a Treg cell described herein, the first chimeric polypeptide of the additional multi-chimeric polypeptide comprises a sequence that is at least 90% identical to SEQ ID NO: 104. In some embodiments of any of the methods of stimulating or increasing the proliferation of a Treg cell described herein, the first chimeric polypeptide of the additional multi-chain chimeric polypeptide comprises a sequence of SEQ ID NO: 104.

In some embodiments of any of the methods of stimulating or increasing the proliferation of a Treg cell described herein, the CD28 is human CD28. In some embodiments of any of the methods of stimulating or increasing the proliferation of a Treg cell described herein, the second target-binding domain of the second chimeric polypeptide of the additional multi-chain chimeric polypeptide comprises a sequence that is at least 80% identical to SEQ ID NO: 6. In some embodiments of any of the methods of stimulating or increasing the proliferation of a Treg cell described herein, the second target-binding domain of the second chimeric polypeptide of the additional multi-chain chimeric polypeptide comprises a sequence that is at least 90% identical to SEQ ID NO: 6. In some embodiments of any of the methods of stimulating or increasing the proliferation of a Treg cell described herein, the second target-binding domain of the second chimeric polypeptide of the additional multi-chain chimeric polypeptide comprises a sequence of SEQ ID NO: 6.

In some embodiments of any of the methods of stimulating or increasing the proliferation of a Treg cell described herein, the second chimeric polypeptide of the additional multi-chain chimeric polypeptide comprises a sequence that is at least 80% identical to SEQ ID NO: 106. In some embodiments of any of the methods of stimulating or increasing the proliferation of a Treg cell described herein, the second chimeric polypeptide of the additional multi-chain chimeric polypeptide comprises a sequence that is at least 90% identical to SEQ ID NO: 106. In some embodiments of any of the methods of stimulating or increasing the proliferation of a Treg cell described herein, the second chimeric polypeptide of the additional multi-chain chimeric polypeptide comprises a sequence of SEQ ID NO: 106. In some embodiments of any of the methods of stimulating or increasing the proliferation of a Treg cell described herein, the second chimeric polypeptide of the additional multi-chain chimeric polypeptide comprises a sequence that is at least 80% identical to SEQ ID NO: 108. In some embodiments of any of the methods of stimulating or increasing the proliferation of a Treg cell described herein, the second chimeric polypeptide of the additional multi-chain chimeric polypeptide comprises a sequence that is at least 90% identical to SEQ ID NO: 108. In some embodiments of any of the methods of stimulating or increasing the proliferation of a Treg cell described herein, the second chimeric polypeptide of the additional multi-chain chimeric polypeptide comprises a sequence of SEQ ID NO: 108.

In some embodiments of any of the methods of stimulating or increasing the proliferation of a Treg cell described herein, the additional multi-chain chimeric polypeptide does not initiate blood coagulation. In some embodiments of any of the methods of stimulating or increasing the proliferation of a Treg cell described herein, the liquid culture medium comprises about 10 nM to about 1000 nM of the additional multi-chain chimeric polypeptide. In some embodiments of any of the methods of stimulating or increasing the proliferation of a Treg cell described herein, the liquid culture medium comprises about 50 nM to about 300 nM of the additional multi-chain chimeric polypeptide.

In some embodiments of any of the methods of stimulating or increasing the proliferation of a $T_{reg}$ cell described herein, the liquid culture medium further comprises an mTOR inhibitor. In some embodiments of any of the methods of stimulating or increasing the proliferation of a $T_{reg}$ cell described herein, the mTOR inhibitor is rapamycin. In some embodiments of any of the methods of stimulating or increasing the proliferation of a $T_{reg}$ cell described herein, the liquid culture medium comprises about 10 nM to about 500 nM of the mTOR inhibitor. In some embodiments of any of the methods of stimulating or increasing the proliferation of a $T_{reg}$ cell described herein, the liquid culture medium comprises about 50 nM to about 150 nM of the mTOR inhibitor. In some embodiments of any of the methods of stimulating or increasing the proliferation of a $T_{reg}$ cell described herein, the methods further include: periodically adding to the liquid culture medium, after each 36 hours to about 60 hours after the start of the period of time, the multi-chain chimeric polypeptide. In some embodiments of any of the methods of stimulating or increasing the proliferation of a $T_{reg}$ cell described herein, the periodic addition of the multi-chain chimeric polypeptide is performed to result in a concentration of about 10 nM to about 500 nM of the multi-chain chimeric polypeptide in the liquid culture medium. In some embodiments of any of the methods of stimulating or increasing the proliferation of a $T_{reg}$ cell described herein, the periodic addition of the multi-chain chimeric polypeptide is performed to result in a concentration of about 50 nM to about 150 nM of the multi-chain chimeric polypeptide in the liquid culture medium. In some embodiments of any of the methods of stimulating or increasing the proliferation of a $T_{reg}$ cell described herein, the methods further include: periodically adding to the liquid culture medium, after each about 6 days to about 8 days after the start of the period of time, the CD3/CD28-binding agent. In some embodiments of any of the methods of stimulating or increasing the proliferation of a $T_{reg}$ cell described herein, the period of time is about 7 days to about 56 days. In some embodiments of any of the methods of stimulating or increasing the proliferation of a $T_{reg}$ cell described herein, the period of claim is about 15 days to about 25 days. In some embodiments of any of the methods of stimulating or increasing the proliferation of a $T_{reg}$ cell described herein, the method further comprises, before the culturing step, a step of isolating the $T_{reg}$ cell from a sample obtained from a subject. In some embodiments of any of the methods of stimulating or increasing the proliferation of a Treg cell described herein, the method further comprises, after the culturing step, a step of isolating the Treg cell from a sample obtained from a subject.

In some embodiments of any of the methods of stimulating or increasing the proliferation of a $T_{reg}$ cell described herein, the isolating comprises the use of fluorescence-assorted cell sorting. In some embodiments of any of the methods of stimulating or increasing the proliferation of a $T_{reg}$ cell described herein, the $T_{reg}$ cell is an autologous $T_{reg}$ cell, a haploidentical $T_{reg}$ cell, or an allogeneic $T_{reg}$ cell isolated from peripheral blood or umbilical cord blood. In some embodiments of any of the methods of stimulating or increasing the proliferation of a $T_{reg}$ cell described herein, the $T_{reg}$ cell is a $CD4^+CD25^+Foxp3^+$ cell. In some embodiments of any of the methods of stimulating or increasing the proliferation of a $T_{reg}$ cell described herein, the $T_{reg}$ cell is a $CD4^+CD25^+CD127^{dim}$ cell. In some embodiments of any of the methods of stimulating or increasing the proliferation of a $T_{reg}$ cell described herein, the $T_{reg}$ cells comprises a chimeric antigen receptor.

Provided herein are populations of $T_{reg}$ cells generated by any of the methods of stimulating or increasing the proliferation of a $T_{reg}$ cell described herein. Also provided herein are compositions comprising any of the populations of $T_{reg}$ cells generated by any of the methods of stimulating or increasing the proliferation of a $T_{reg}$ cell described herein and a pharmaceutically acceptable carrier. Provided herein are methods of treating a subject in need thereof, the methods include administering to the subject a therapeutically effective amount of any of the compositions comprising any of the populations of $T_{reg}$ cells generated by any of the methods of stimulating or increasing the proliferation of a $T_{reg}$ cell described herein and a pharmaceutically acceptable carrier. In some embodiments of any of the methods of treating a subject in need thereof described herein, the subject has been identified or diagnosed as having an aging-related disease or an inflammatory disease. In some embodiments of any of the methods of treating a subject in need thereof described herein, the aging-related disease is selected from the group consisting of: Alzheimer's disease, aneurysm, cystic fibrosis, fibrosis in pancreatitis, glaucoma, hypertension, idiopathic pulmonary fibrosis, inflammatory bowel disease, intervertebral disc degeneration, macular degeneration, osteoarthritis, type 2 diabetes mellitus, adipose atrophy, lipodystrophy, atherosclerosis, cataracts, COPD, idiopathic pulmonary fibrosis, kidney transplant failure, liver fibrosis, loss of bone mass, myocardial infarction, sarcopenia, wound healing, alopecia, cardiomyocyte hypertrophy, osteoarthritis, Parkinson's disease, age-associated loss of lung tissue elasticity, macular degeneration, cachexia, glomerulosclerosis, liver cirrhosis, NAFLD, osteoporosis, amyotrophic lateral sclerosis, Huntington's disease, spinocerebellar ataxia, multiple sclerosis, neurodegeneration, stroke, dementia, vascular disease, infection susceptibility, chronic inflammation, and renal dysfunction. In some embodiments of any of the methods of treating a subject in need thereof described herein, the inflammatory disease is selected from the group consisting of: rheumatoid arthritis, inflammatory bowel disease, lupus erythematosus, lupus nephritis, diabetic nephropathy, CNS injury, Alzheimer's disease, Parkinson's disease, amyotrophic lateral sclerosis, Crohn's disease, multiple sclerosis, Guillain-Barre syndrome, psoriasis, Grave's disease, ulcerative colitis, non-alcoholic steatohepatitis, and mood disorders.

In another aspect, provided herein are kits that include: a CD3/CD28-binding agent; a multi-chain chimeric polypeptide comprising: (a) a first chimeric polypeptide comprising: (i) a first target-binding domain; (ii) a soluble tissue factor domain; and (iii) a first domain of a pair of affinity domains; (b) a second chimeric polypeptide comprising: (i) a second domain of a pair of affinity domains; and (ii) a second target-binding domain, wherein the first chimeric polypeptide and the second chimeric polypeptide associate through the binding of the first domain and the second domain of the pair of affinity domains; and an mTOR inhibitor. In some embodiments of any of the kits described herein, the kits further include an IgG1 antibody construct that comprises at least one antigen-binding domain that binds specifically to the soluble tissue factor domain of the multi-chain chimeric polypeptide. In some embodiments of any of the kits described herein, the CD3/CD28-binding agent is an anti-CD3/anti-CD28 bead. In some embodiments of any of the kits described herein, the CD3/CD28-binding agent is an single-chain chimeric polypeptide comprising a first target-binding domain, a soluble tissue factor domain, and a second target-binding domain, wherein the first target-binding domain of the additional single-chain chimeric polypeptide binds to CD3 and the second target-binding domain of the additional single-chain chimeric polypeptide binds to CD28. In some embodiments of any of the kits described herein, the kits further include an IgG1 antibody construct that comprises at least one antigen-binding domain that binds specifically to the soluble tissue factor domain of the single-chain chimeric polypeptide.

In some embodiments of any of the kits described herein, the CD3/CD28-binding agent is an additional multi-chain chimeric polypeptide comprising: (a) a first chimeric polypeptide comprising: (i) a first target-binding domain; (ii) a soluble tissue factor domain; and (iii) a first domain of a pair of affinity domains; and (b) a second chimeric polypeptide comprising: (i) a second domain of a pair of affinity domains; and (ii) a second target-binding domain, wherein the first chimeric polypeptide and the second chimeric polypeptide associate through the binding of the first domain and the second domain of the pair of affinity domains; and wherein the first target-binding domain binds to CD3 and the second target-binding domain binds to CD28, or the first target-binding domain binds to CD28 and the second target-binding domain to CD3.

In some embodiments of any of the kits described herein, the liquid culture medium further includes an IgG1 antibody construct that comprises at least one antigen-binding domain that binds specifically to the soluble tissue factor domain of the additional multi-chain chimeric polypeptide.

In another aspect, provided herein are methods of isolating a Treg cell from a sample obtained from a subject, wherein the method comprises separating the Treg cell from the sample based on its expression of CD39, thereby isolating the Treg cell.

In some embodiments of any of the methods of isolating a Treg cell described herein, the method comprises: mixing the sample with an antibody or ligand capable of binding CD39 under conditions that allow binding of the antibody or ligand to Treg cells expressing CD39; separating the Treg cell bound to the antibody or ligand from other components in the sample, thereby isolating the Treg cell.

In some embodiments of any of the methods of isolating a Treg cell described herein, the antibody is a mouse, a humanized, or a human antibody or antigen-binding fragment thereof; and/or the antibody or the ligand is labeled with at least one of biotin, avidin, streptavidin, or a fluorochrome, or is bound to a particle, bead, resin, or solid support. In some embodiments of any of the methods of isolating a Treg cell described herein, separating comprises the use of flow cytometry, fluorescence-activated cell sorting (FACS), centrifugation, or column, plate, particle, or bead-based methods.

In some embodiments of any of the methods of isolating a Treg cell described herein, the method further comprises: mixing the sample with a biotinylated antibody or ligand capable of binding CD39 under conditions that allow binding of the antibody or the ligand to the Treg cell; capturing the Treg cell bound to the biotinylated antibody or the ligand using streptavidin-coated magnetic particles; separating the magnetic particle-bound Treg cell using a magnet; washing the magnet particle-bound Treg cell to remove other components in the sample; and releasing the magnetic particle-bound Treg cell from the magnet into a solution, thereby isolating the Treg cell.

In some embodiments of any of the methods of isolating a Treg cell described herein, the Treg cell is an autologous Treg cell, a haploidentical Treg cell, or an allogeneic Treg cell isolated from a sample comprising fresh or frozen peripheral blood, umbilical cord blood, peripheral blood mononuclear cells, lymphocytes, CD4$^+$ T cells or Treg cells. In some embodiments of any of the methods of isolating a Treg cell described herein, the Treg cell is a CD4$^+$CD25$^+$ Foxp3$^+$ cell. In some embodiments of any of the methods of isolating a Treg cell described herein, the Treg cell is a CD4$^+$CD25$^+$CD127$^{dim}$ cell. In some embodiments of any of the methods of isolating a Treg cell described herein, the Treg cells comprises a chimeric antigen receptor. In some embodiments of any of the methods of isolating a Treg cell described herein, the Treg cells are immunosuppressive in vitro and in vivo.

In another aspect, provided herein are populations of isolated Treg cells generated by any one of the methods described herein. In some embodiments of any of the populations of isolated Treg cells described herein, the isolated population of Treg cells are greater than 70% CD39$^+$ cells. Also provided are method of expanding any of the populations of isolated Treg cells described herein that include culturing the population of isolated Treg cells under conditions that allow for proliferation of the isolated Treg cells.

Also provided herein are compositions comprising any of the populations of isolated Treg cells described herein and a pharmaceutically acceptable carrier.

Also provided herein are methods of treating a subject in need thereof, comprising administering to the subject a therapeutically effective amount of any of the compositions described herein. In some embodiments of any of the methods of treating a subject in need described herein, the subject has been identified or diagnosed as having an aging-related disease or an inflammatory disease. In some embodiments of any of the methods of treating a subject in need described herein, the aging-related disease is selected from the group consisting of: Alzheimer's disease, aneurysm, cystic fibrosis, fibrosis in pancreatitis, glaucoma, hypertension, idiopathic pulmonary fibrosis, inflammatory bowel disease, intervertebral disc degeneration, macular degeneration, osteoarthritis, type 2 diabetes mellitus, adipose atrophy, lipodystrophy, atherosclerosis, cataracts, COPD, idiopathic pulmonary fibrosis, kidney transplant failure, liver fibrosis, loss of bone mass, myocardial infarction, sarcopenia, wound healing, alopecia, cardiomyocyte hypertrophy, osteoarthritis, Parkinson's disease, age-associated loss of lung tissue elasticity, macular degeneration, cachexia, glomerulosclerosis, liver cirrhosis, NAFLD, osteoporosis, amyotrophic lateral sclerosis, Huntington's disease, spinocerebellar ataxia, multiple sclerosis, neurodegeneration, stroke, dementia, vascular disease, infection susceptibility, chronic inflammation, and renal dysfunction. In some embodiments of any of the methods of treating a subject in need described herein, the inflammatory disease is selected from the group consisting of: rheumatoid arthritis, inflammatory bowel disease, lupus erythematosus, lupus nephritis, diabetic nephropathy, CNS injury, Alzheimer's disease, Parkinson's disease, amyotrophic lateral sclerosis, Crohn's disease, multiple sclerosis, Guillain-Barre syndrome, psoriasis, Grave's disease, ulcerative colitis, nonalcoholic steatohepatitis, and mood disorders.

As used herein, the term "chimeric" refers to a polypeptide that includes amino acid sequences (e.g., domains) originally derived from two different sources (e.g., two different naturally-occurring proteins, e.g., from the same or different species). For example, a chimeric polypeptide can include domains from at least two different naturally occurring human proteins. In some examples, a chimeric polypeptide can include a domain that is a synthetic sequence (e.g., a scFv) and a domain that is derived from a naturally-occurring protein (e.g., a naturally-occurring human protein). In some embodiments, a chimeric polypeptide can include at least two different domains that are synthetic sequences (e.g., two different scFvs).

An "antigen-binding domain" is one or more protein domain(s) (e.g., formed from amino acids from a single polypeptide or formed from amino acids from two or more polypeptides (e.g., the same or different polypeptides) that is capable of specifically binding to one or more different antigen(s). In some examples, an antigen-binding domain can bind to an antigen or epitope with specificity and affinity similar to that of naturally-occurring antibodies. In some embodiments, the antigen-binding domain can be an antibody or a fragment thereof. In some embodiments, an antigen-binding domain can include an alternative scaffold. Non-limiting examples of antigen-binding domains are described herein. Additional examples of antigen-binding domains are known in the art.

A "soluble tissue factor domain" refers to a polypeptide having at least 70% identity (e.g., at least 75% identity, at least 80% identity, at least 85% identity, at least 90% identity, at least 95% identity, at least 99% identity, or 100% identical) to a segment of a wildtype mammalian tissue factor protein (e.g., a wildtype human tissue factor protein) that lacks the transmembrane domain and the intracellular domain. Non-limiting examples of soluble tissue factor domains are described herein.

The term "antibody" is used herein in its broadest sense and includes certain types of immunoglobulin molecules that include one or more antigen-binding domains that specifically bind to an antigen or epitope. An antibody specifically includes, e.g., intact antibodies (e.g., intact immunoglobulins), antibody fragments, and multi-specific antibodies. One example of an antigen-binding domain is an antigen-binding domain formed by a VH-VL dimer. Additional examples of an antibody are described herein. Additional examples of an antibody are known in the art.

"Affinity" refers to the strength of the sum total of non-covalent interactions between an antigen-binding site and its binding partner (e.g., an antigen or epitope). Unless indicated otherwise, as used herein, "affinity" refers to intrinsic binding affinity, which reflects a 1:1 interaction between members of an antigen-binding domain and an antigen or epitope. The affinity of a molecule X for its partner Y can be represented by the dissociation equilibrium constant ($K_D$). The kinetic components that contribute to the dissociation equilibrium constant are described in more detail below. Affinity can be measured by common methods known in the art, including those described herein. Affinity can be determined, for example, using surface plasmon resonance (SPR) technology (e.g., BIACORE®) or biolayer interferometry (e.g., FORTEBIO®). Additional methods for determining the affinity for an antigen-binding domain and its corresponding antigen or epitope are known in the art.

A "single-chain polypeptide" as used herein refers to a single protein chain.

A "multi-chain polypeptide" as used herein to refers to a polypeptide comprising two or more (e.g., three, four, five, six, seven, eight, nine, or ten) protein chains (e.g., at least a first chimeric polypeptide and a second polypeptide), where the two or more proteins chains associate through non-covalent bonds to form a quaternary structure.

The term "epitope" means a portion of an antigen that specifically binds to an antigen-binding domain. Epitopes can, e.g., consist of surface-accessible amino acid residues and/or sugar side chains and may have specific three-dimensional structural characteristics, as well as specific charge characteristics. Conformational and non-conformational epitopes are distinguished in that the binding to the former but not the latter may be lost in the presence of denaturing solvents. An epitope may comprise amino acid residues that are directly involved in the binding, and other amino acid residues, which are not directly involved in the binding. Methods for identifying an epitope to which an antigen-binding domain binds are known in the art.

The term "treatment" means to ameliorate at least one symptom of a disorder. In some examples, the disorder being treated is cancer and to ameliorate at least one symptom of cancer includes reducing aberrant proliferation, gene expression, signaling, translation, and/or secretion of factors. Generally, the methods of treatment include administering a therapeutically effective amount of composition that reduces at least one symptom of a disorder to a subject who is in need of, or who has been determined to be in need of such treatment.

The term "CD3/CD28-binding agent" means an agent that binds specifically to both CD3 and CD28 on the surface of a mammalian cell (e.g., a T cell, such as a $T_{reg}$ cell) and induces downstream signaling in the mammalian cell. Non-limiting examples of CD3/CD28-binding agents are described herein.

The term "IL-2 receptor activating agent" means an agent that binds specifically to an IL-2 receptor present on a surface of a mammalian cell (e.g., a T cell, such as a $T_{reg}$ cell) and induces downstream signaling in the mammalian cell. Non-limiting examples of IL-2 receptor activating agents are described herein.

The term "IgG1 antibody construct" means a single chain polypeptide or a multi-chain polypeptide that includes at least one antigen-binding domain that binds to a soluble tissue factor domain (e.g., any of the exemplary soluble tissue factor domains described herein) and at least one IgG1 Fc domain. Non-limiting examples of IgG1 antibody constructs are described herein.

Unless otherwise defined, all technical and scientific terms used herein have the same meaning as commonly understood by one of ordinary skill in the art to which this invention belongs. Methods and materials are described herein for use in the present invention; other, suitable methods and materials known in the art can also be used. The materials, methods, and examples are illustrative only and not intended to be limiting. All publications, patent applications, patents, sequences, database entries, and other references mentioned herein are incorporated by reference in their entirety. In case of conflict, the present specification, including definitions, will control.

Other features and advantages of the invention will be apparent from the following detailed description and figures, and from the claims.

BRIEF DESCRIPTION OF DRAWINGS

FIGS. 2A-2I are diagrams showing an increase in Helios$^+$, CTLA-4$^+$, CD39$^+$, CD62L$^+$, CD25$^+$, CD103$^+$, CD69$^+$, PD1$^+$, and CD49b$^+$ markers after stimulation of $T_{reg}$ cells with (1) 2t2, CD3/CD28 beads, and rapamycin or (2) recombinant human IL-2, CD3/CD28 beads, and rapamycin.

FIG. 3A shows levels of glycolysis of $T_{reg}$ cells. FIG. 3B shows levels of glycolytic capacity of $T_{reg}$ cells. FIG. 3C shows levels of glycolytic reserve of $T_{reg}$ cells. FIG. 3D shows levels of non-glycolytic acidification of $T_{reg}$ cells.

DETAILED DESCRIPTION

Figure 1:
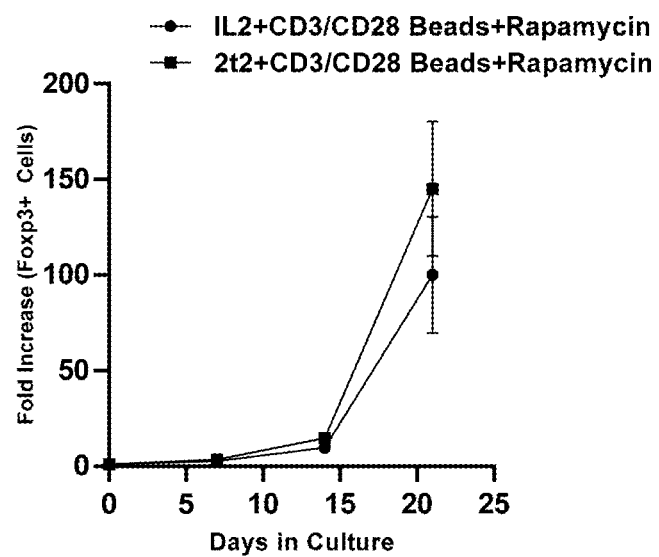
FIG. 1 is a diagram showing expansion of Foxp3$^+$ $T_{reg}$ cells using either (1) 2t2, CD3/CD28 beads, and rapamycin or (2) recombinant human IL-2, CD3/CD28 beads, and rapamycin.
Figure 3A:
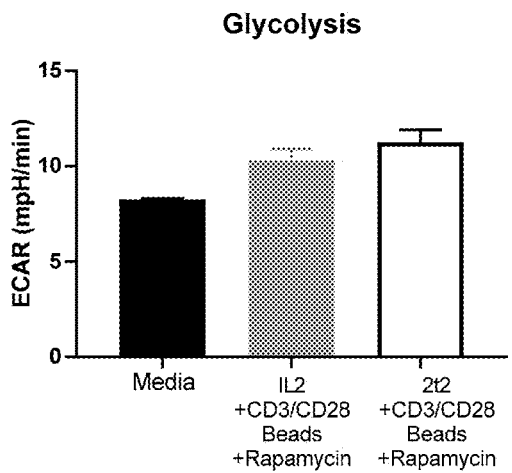
FIGS. 3A-3D are diagrams showing glucose metabolism levels upon activation of human $T_{reg}$ cells with (1) 2t2, CD3/CD28 beads, and rapamycin, or (2) recombinant human IL-2, CD3/CD28 beads, and rapamycin.
Figure 3B:
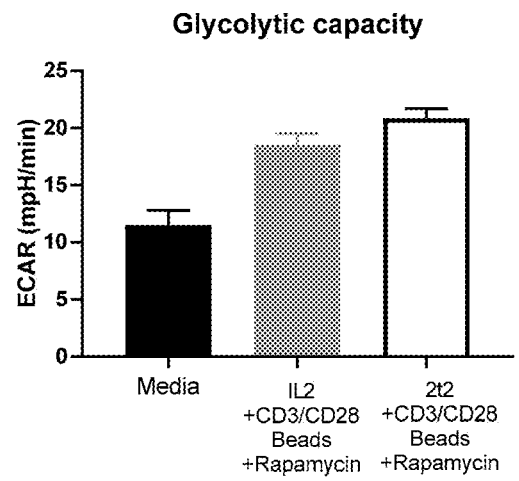
Figure 3C:
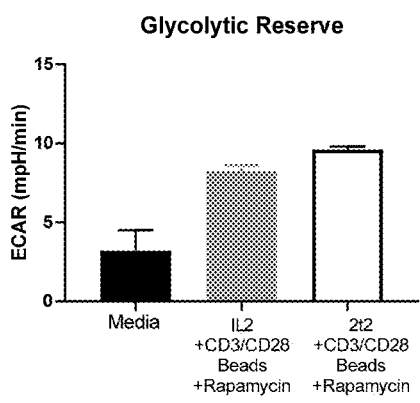
Figure 3D:
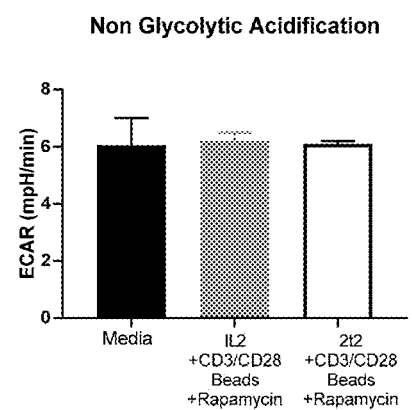

Provided herein are methods of stimulating or increasing the proliferation of a $T_{reg}$ cell (e.g., any of the $T_{reg}$ cells described herein), a population of $T_{reg}$ cells produced using any of the methods described herein, a composition including any of these populations of $T_{reg}$ cells, and methods of treating a subject that include administering any of these populations of $T_{reg}$ cells or compositions.

Tissue Factor

Human tissue factor is a 263 amino-acid transmembrane protein containing three domains: (1) a 219-amino acid N-terminal extracellular domain (residues 1-219); (2) a 22-amino acid transmembrane domain (residues 220-242); and (3) a 21-amino acid cytoplasmic C-terminal tail (residues 242-263) ((UniProtKB Identifier Number: P13726). The cytoplasmic tail contains two phosphorylation sites at Ser253 and Ser258, and one S-palmitoylation site at Cys245. Deletion or mutation of the cytoplasmic domain was not found to affect tissue factor coagulation activity. Tissue factor has one S-palmitoylation site in the intracellular domain of the protein at Cys245. The Cys245 is located at the amino acid terminus of the intracellular domain and close to the membrane surface. The tissue factor transmembrane domain is composed of a single-spanning α-helix.

The extracellular domain of tissue factor, composed of two fibronectin type III domains, is connected to the transmembrane domain through a six-amino acid linker. This linker provides conformational flexibility to decouple the tissue factor extracellular domain from its transmembrane and cytoplasmic domains. Each tissue factor fibronectin type III module is composed of two overlapping β sheets with the top sheet domain containing three antiparallel β-strands and the bottom sheet containing four β-strands. The β-strands are connected by β-loops between strand βA and βB, βC and βD, and βE and βF, all of which are conserved in conformation in the two modules. There are three short α-helix segments connecting the β-strands. A unique feature of tissue factor is a 17-amino acid β-hairpin between strand β10 and strand β11, which is not a common element of the fibronectin superfamily. The N-terminal domain also contains a 12 amino acid loop between β6F and β7G that is not present in the C-terminal domain and is unique to tissue factor. Such a fibronectin type III domain structure is a feature of the immunoglobulin-like family of protein folds and is conserved among a wide variety of extracellular proteins.

The zymogen FVII is rapidly converted to FVIIa by limited proteolysis once it binds to tissue to form the active tissue factor-FVIIa complex. The FVIIa, which circulates as an enzyme at a concentration of approximately 0.1 nM (1% of plasma FVII), can also bind directly to tissue factor. The allosteric interaction between tissue factor and FVIIa on the tissue factor-FVIIa complex greatly increases the enzymatic activity of FVIIa: an approximate 20- to 100-fold increase in the rate of hydrolysis of small, chromogenic peptidyl substrates, and nearly a million-fold increase in the rate of activation of the natural macromolecular substrates FIX and FX. In concert with allosteric activation of the active site of FVIIa upon binding to tissue factor, the formation of tissue factor-FVIIa complex on phospholipid bilayer (i.e., upon exposure of phosphatidyl-L-serine on membrane surfaces) increases the rate of FIX or FX activation, in a $Ca^{2+}$-dependent manner, an additional 1,000-fold. The roughly million-fold overall increase in FX activation by tissue factor-FVIIa-phospholipid complex relative to free FVIIa is a critical regulatory point for the coagulation cascade.

FVII is a ~50 kDa, single-chain polypeptide consisting of 406 amino acid residues, with an N-terminal γ-carboxyglutamate-rich (GLA) domain, two epidermal growth factor-like domains (EGF1 and EFG2), and a C-terminal serine protease domain. FVII is activated to FVIIa by a specific proteolytic cleavage of the Ile-$^{154}$-Arg$^{152}$ bond in the short linker region between the EGF2 and the protease domain. This cleavage results in the light and heavy chains being held together by a single disulfide bond of Cys$^{135}$ and Cys$^{262}$. FVIIa binds phospholipid membrane in a $Ca^{2+}$-dependent manner through its N-terminal GLA-domain. Immediately C-terminal to the GLA domain is an aromatic stack and two EGF domains. The aromatic stack connects the GLA to EGF1 domain which binds a single $Ca^{2+}$ ion. Occupancy of this $Ca^{2+}$-binding site increases FVIIa amidolytic activity and tissue factor association. The catalytic triad consist of His$^{193}$, Asp$^{242}$, and Ser$^{344}$, and binding of a single $Ca^{2+}$ ion within the FVIIa protease domain is critical for its catalytic activity. Proteolytic activation of FVII to FVIIa frees the newly formed amino terminus at Ile$^{153}$ to fold back and be inserted into the activation pocket forming a salt bridge with the carboxylate of Asp$^{343}$ to generate the oxyanion hole. Formation of this salt bridge is critical for FVIIa activity. However, oxyanion hole formation does not occur in free FVIIa upon proteolytic activation. As a result, FVIIa circulates in a zymogen-like state that is poorly recognized by plasma protease inhibitors, allowing it to circulate with a half-life of approximately 90 minutes.

Tissue factor-mediated positioning of the FVIIa active site above the membrane surface is important for FVIIa towards cognate substrates. Free FVIIa adopts a stable, extended structure when bound to the membrane with its active site positioned ~80 Å above the membrane surface. Upon FVIIa binding to tissue factor, the FVa active site is repositioned ~6 Å closer to the membrane. This modulation may aid in a proper alignment of the FVIIa catalytic triad with the target substrate cleavage site. Using GLA-domainless FVIIa, it has been shown that the active site was still positioned a similar distance above the membrane, demonstrating that tissue factor is able to fully support FVIIa active site positioning even in the absence of FVIIa-membrane interaction. Additional data showed that tissue factor supported full FVIIa proteolytic activity as long as the tissue factor extracellular domain was tethered in some way to the membrane surface. However, raising the active site of FVIIa greater than 80 Å above the membrane surface greatly reduced the ability of the tissue factor-FVIIa complex to activate FX but did not diminish tissue factor-FVIIa amidolytic activity.

Alanine scanning mutagenesis has been used to assess the role of specific amino acid side chains in the tissue factor extracellular domain for interaction with FVIIa (Gibbs et al., *Biochemistry* 33(47): 14003-14010, 1994; Schullek et al., *J Biol Chem* 269(30): 19399-19403, 1994). Alanine substitution identified a limited number of residue positions at which alanine replacements cause 5- to 10-fold lower affinity for FVIIa binding. Most of these residue side chains were found to be well-exposed to solvent in the crystal structure, concordant with macromolecular ligand interaction. The FVIIa ligand-binding site is located over an extensive region at the boundary between the two modules. In the C-module, residues Arg$^{135}$ and Phe$^{140}$ located on the protruding B-C loop provide an independent contact with FVIIa. Leu$^{133}$ is located at the base of the fingerlike structure and packed into the cleft between the two modules. This provides continuity to a major cluster of important binding residues consisting of Lys$^{20}$, Thr$^{60}$, Asp$^{58}$, and Ile$^{22}$. Thr$^{60}$ is only partially solvent-exposed and may play a local structural role rather than making a significant contact with ligand. The binding site extends onto the concave side of the intermodule angle involving Glu$^{24}$ and Gln$^{110}$, and potentially the more distant residue Val$^{207}$. The binding region extends from Asp$^{58}$ onto a convex surface area formed by Lys$^{48}$, Lys$^{46}$, Gln$^{37}$, Asp$^{44}$, and Trp$^{45}$. Trp$^{45}$ and Asp$^{44}$ do not interact independently with FVIIa, indicating that the mutational effect at the Trp$^{45}$ position may reflect a structural importance of this side chain for the local packing of the adjacent Asp$^{44}$ and Gln$^{37}$ side chain. The interactive area further includes two surface-exposed aromatic residues, Phe$^{76}$ and Tyr$^{78}$, which form part of the hydrophobic cluster in the N-module.

The known physiologic substrates of tissue factor-FVIIa are FVII, FIX, and FX and certain proteinase-activated receptors. Mutational analysis has identified a number of residues that, when mutated, support full FVIIa amidolytic activity towards small peptidyl substrates but are deficient in their ability to support macromolecular substrate (i.e., FVII, FIX, and FX) activation (Ruf et al., *J Biol Chem* 267(31): 22206-22210, 1992; Ruf et al., *J Biol Chem* 267(9): 6375-6381, 1992; Huang et al., *J Biol Chem* 271(36): 21752-21757, 1996; Kirchhofer et al., *Biochemistry* 39(25): 7380-7387, 2000). The tissue factor loop region at residues 159-165, and residues in or adjacent to this flexible loop have been shown to be critical for the proteolytic activity of the tissue factor-FVIIa complex. This defines the proposed substrate-binding exosite region of tissue factor that is quite distant from the FVIIa active site. A substitution of the glycine residue by a marginally bulkier residue alanine, significantly impairs tissue factor-FVIIa proteolytic activity. This suggests that the flexibility afforded by glycine is critical for the loop of residues 159-165 for tissue factor macromolecular substrate recognition.

The residues Lys$^{165}$ and Lys$^{166}$ have also been demonstrated to be important for substrate recognition and binding. Mutation of either of these residues to alanine results in a significant decrease in the tissue factor co-factor function. Lys$^{165}$ and Lys$^{166}$ face away from each other, with Lys$^{165}$ pointing towards FVIIa in most tissue factor-FVIIa structures, and Lys$^{166}$ pointing into the substrate binding exosite region in the crystal structure. Putative salt bridge formation between Lys$^{165}$ of and Gla$^{35}$ of FVIIa would support the notion that tissue factor interaction with the GLA domain of FVIIa modulates substrate recognition. These results suggest that the C-terminal portion of the tissue factor ectodomain directly interacts with the GLA-domain, the possible adjacent EGF1 domains, of FIX and FX, and that the presence of the FVIIa GLA-domain may modulate these interactions either directly or indirectly.

Multi-Chain Chimeric Polypeptides

Non-limiting examples of cell activating agents are multi-chain chimeric polypeptides that include: (a) a first chimeric polypeptide including: (i) a first target-binding domain; (ii) a soluble tissue factor domain; and (iii) a first domain of a pair of affinity domains; and (b) a second chimeric polypeptide including: (i) a second domain of a pair of affinity domains; and (ii) a second target-binding domain, where the first chimeric polypeptide and the second chimeric polypeptide associate through the binding of the first domain and the second domain of the pair of affinity domains.

In some embodiments of any of the multi-chain chimeric polypeptides described herein, the first target-binding domain (e.g., any of the first target-binding domains described herein) and the soluble tissue factor domain (e.g., any of the exemplary soluble tissue factor domains described herein) directly abut each other in the first chimeric polypeptide. In some embodiments of any of the multi-chain chimeric polypeptides described herein, the first chimeric polypeptide further comprises a linker sequence (e.g., any of the exemplary linker sequences described herein or known in the art) between the first target-binding domain (e.g., any of the exemplary first target-binding domains described herein) and the soluble tissue factor domain (e.g., any of the exemplary soluble tissue factor domains described herein) in the first chimeric polypeptide.

In some embodiments of any of the multi-chain chimeric polypeptides described herein, the soluble tissue factor domain (e.g., any of the exemplary soluble tissue factor domains described herein) and the first domain of the pair of affinity domains (e.g., any of the exemplary first domains of any of the exemplary pairs of affinity domains described herein) directly abut each other in the first chimeric polypeptide. In some embodiments of any of the multi-chain chimeric polypeptides described herein, the first chimeric polypeptide further comprises a linker sequence (e.g., any of the exemplary linker sequences described herein or known in the art) between the soluble tissue factor domain (e.g., any of the exemplary soluble tissue factor domains described herein) and the first domain of the pair of affinity domains (e.g., any of the exemplary first domains of any of the exemplary pairs of affinity domains described herein) in the first chimeric polypeptide.

In some embodiments of any of the multi-chain chimeric polypeptides described herein, the second domain of the pair of affinity domains (e.g., any of the exemplary second domains of any of the exemplary pairs of affinity domains described herein) and the second target-binding domain (e.g., any of the exemplary second target-binding domains described herein) directly abut each other in the second chimeric polypeptide. In some embodiments of any of the multi-chain chimeric polypeptides described herein, the second chimeric polypeptide further comprises a linker sequence (e.g., any of the exemplary linker sequences described herein or known in the art) between the second domain of the pair of affinity domains (e.g., any of the exemplary second domains of any of the exemplary pairs of affinity domains described herein) and the second target-binding domain (e.g., any of the exemplary second target-binding domains described herein) in the second chimeric polypeptide.

In some embodiments of any of the multi-chain chimeric polypeptides described herein, one or both of the first target-binding domain (e.g., any of the exemplary target-binding domains described herein or known in the art) and the second target-binding domain (e.g., any of the exemplary target-binding domains described herein or known in the art) bind specifically to a target selected from the group consisting of: CD16a, CD28, CD3, CD33, CD20, CD19, CD22, CD123, IL-1R, IL-1, VEGF, IL-6R, IL-4, IL-10, PDL-1, TIGIT, PD-1, TIM3, CTLA4, MICA, MICB, IL-6, IL-8, TNFα, CD26, CD36, ULBP2, CD30, CD200, IGF-1R, MUC4AC, MUC5AC, Trop-2, CMET, EGFR, HER1, HER2, HER3, PSMA, CEA, B7H3, EPCAM, BCMA, P-cadherin, CEACAM5, a UL16-binding protein, HLA-DR, DLL4, TYRO3, AXL, MER, CD122, CD155, PDGF-DD, a ligand of TGF-β receptor II (TGF-βRII), a ligand of TGF-βRIII, a ligand of DNAM1, a ligand of NKp46, a ligand of NKp44, a ligand of NKG2D, a ligand of NKp30, a ligand for a scMHCI, a ligand for a scMHCII, a ligand for a scTCR, a receptor for IL-1, a receptor for IL-2, a receptor for IL-3, a receptor for IL-7, a receptor for IL-8, a receptor for IL-10, a receptor for IL-12, a receptor for IL-15, a receptor for IL-17, a receptor for IL-18, a receptor for IL-21, a receptor for PDGF-DD, a receptor for stem cell factor (SCF), a receptor for stem cell-like tyrosine kinase 3 ligand (FLT3L), a receptor for MICA, a receptor for MICB, a receptor for a ULP16-binding protein, a receptor for CD155, a receptor for CD122, and a receptor for CD28.

In some embodiments of any of the multi-chain chimeric polypeptides described herein, one or both of the first target-binding domain (e.g., any of the exemplary target-binding domains described herein or known in the art) and the second target-binding domain (e.g., any of the exemplary target-binding domains described herein or known in the art) is a soluble interleukin or cytokine protein. Non-limiting examples of soluble interleukin proteins and soluble cytokine proteins include: IL-1, IL-2, IL-3, IL-7, IL-8, IL-10, IL-12, IL-15, IL-17, IL-18, IL-21, PDGF-DD, and SCF.

In some embodiments of any of the multi-chain chimeric polypeptides described herein, one or both of the first target-binding domain and the second target-binding domain (e.g., any of the exemplary target-binding domains described herein or known in the art) is a soluble interleukin or cytokine receptor. Non-limiting examples of soluble interleukin receptors and soluble cytokine receptors include: a soluble TGF-β receptor II (TGF-βRII), a soluble TGF-βRIII, a soluble NKG2D, a soluble NKp30, a soluble NKp44, a soluble NKp46, a soluble DNAM-1, a scMHCI, a scMHCII, a scTCR, a soluble CD155, a soluble CD122, a soluble CD3, or a soluble CD28.

In some embodiments of any of the multi-chain chimeric polypeptides described herein, one or both of the first target-binding domain and the second target-binding domain is a soluble interleukin or cytokine receptor. In some embodiments of any of the multi-chain chimeric polypeptides described herein, the soluble receptor is a soluble TGF-β receptor II (TGF-βRII) a soluble TGF-βRIII, a soluble receptor for TNFα, a soluble receptor for IL-4, or a soluble receptor for IL-10.

Soluble Tissue Factor Domains

In some embodiments, the soluble tissue factor domain can be a wildtype tissue factor polypeptide lacking the signal sequence, the transmembrane domain, and the intracellular domain. In some examples, the soluble tissue factor domain can be a tissue factor mutant, wherein a wildtype tissue factor polypeptide lacking the signal sequence, the transmembrane domain, and the intracellular domain, and has been further modified at selected amino acids. In some examples, the soluble tissue factor domain can be a soluble human tissue factor domain. In some examples, the soluble tissue factor domain can be a soluble mouse tissue factor domain. In some examples, the soluble tissue factor domain can be a soluble rat tissue factor domain. Non-limiting examples of soluble human tissue factor domains, a mouse soluble tissue factor domain, a rat soluble tissue factor domain, and mutant soluble tissue factor domains are shown below.

```
Exemplary Soluble Human Tissue Factor Domain
                                                 (SEQ ID NO: 2)
SGTTNTVAAYNLTWKSTNFKTILEWEPKPVNQVYTVQISTKSGDWKSKCFYTTD
TECDLTDEIVKDVKQTYLARVFSYPAGNVESTGSAGEPLYENSPEFTPYLETNLGQ
PTIQSFEQVGTKVNVTVEDERTLVRRNNTFLSLRDVFGKDLIYTLYYWKSSSSGK
KTAKTNTNEFLIDVDKGENYCFSVQAVIPSRTVNRKSTDSPVECMGQEKGEFRE
Exemplary Nucleic Acid Encoding Soluble Human Tissue
Factor Domain
                                                 (SEQ ID NO: 13)
AGCGGCACAACCAACACAGTCGCTGCCTATAACCTCACTTGGAAGAGCACCA
ACTTCAAAACCATCCTCGAATGGGAACCCAAACCCGTTAACCAAGTTTACACC
GTGCAGATCAGCACCAAGTCCGGCGACTGGAAGTCCAAATGTTTCTATACCAC
CGACACCGAGTGCGATCTCACCGATGAGATCGTGAAAGATGTGAAACAGACC
TACCTCGCCCGGGTGTTTAGCTACCCCGCCGGCAATGTGGAGAGCACTGGTTC
CGCTGGCGAGCCTTTATACGAGAACAGCCCCGAATTTACCCCTTACCTCGAGA
CCAATTTAGGACAGCCCACCATCCAAAGCTTTGAGCAAGTTGGCACAAAGGT
GAATGTGACAGTGGAGGACGAGCGGACTTTAGTGCGGCGGAACAACACCTTT
CTCAGCCTCCGGGATGTGTTCGGCAAAGATTTAATCTACACACTGTATTACTGG
```

```
                              -continued
AAGTCCTCTTCCTCCGGCAAGAAGACAGCTAAAACCAACACAAACGAGTTTT
TAATCGACGTGGATAAAGGCGAAAACTACTGTTTCAGCGTGCAAGCTGTGATC
CCCTCCCGGACCGTGAATAGGAAAAGCACCGATAGCCCCGTTGAGTGCATGG
GCCAAGAAAAGGGCGAGTTCCGGGAG Exemplary Soluble Mouse Tissue Factor Domain
                                              (SEQ ID NO: 14)
agipekafnltwistdfktilewqpkptnytytvqisdrsrnwknkcfstt
dtecdltdeivkdvtwayeakvlsvprrnsvhgdgdqlvihgeeppftnap
kflpyrdtnlgqpviqqfeqdgrklnvvvkdsltlvrkngtfltlrqvfgk
dlgyiityrkgsstgkktnitntnefsidveegvsycffvqamifsrktnq
nspgsstvcteqwksflge Exemplary Soluble Rat Tissue Factor Domain
                                              (SEQ ID NO: 15)
Agtppgkafnltwistdfktilewqpkptnytytvqisdrsrnwkykctgt
tdtecdltdeivkdvnwtyearvlsvpwinsthgketlfgthgeeppftna
rkflpyrdtkigqpviqkyeqggtklkvtvkdsftlvrkngtfltlrqvfg
ndlgyiltyrkdsstgrktntthtneflidvekgvsycffaqavifsrktn
hkspesitkcteqwksvlge Exemplary Mutant Soluble Human Tissue Factor Domain
                                              (SEQ ID NO: 16)
SGTTNTVAAYNLTWKSTNFATALEWEPKPVNQVYTVQISTKSGDWKSKCFYTT
DTECALTDEIVKDVKQTYLARVFSYPAGNVESTGSAGEPLYENSPEFTPYLETNL
GQPTIQSFEQVGTKVNVTVEDERTLVARNNTALSLRDVFGKDLIYTLYYWKSSSS
GKKTAKTNTNEFLIDVDKGENYCFSVQAVIPSRTVNRKSTDSPVECMGQEKGEF
RE Exemplary Mutant Soluble Human Tissue Factor Domain
                                              (SEQ ID NO: 17)
SGTTNTVAAYNLTWKSTNFATALEWEPKPVNQVYTVQISTKSGDAKSKCFYTTD
TECALTDEIVKDVKQTYLARVFSYPAGNVESTGSAGEPLAENSPEFTPYLETNLG
QPTIQSFEQVGTKVNVTVEDERTLVARNNTALSLRDVFGKDLIYTLYYWKSSSSG
KKTAKTNTNEFLIDVDKGENYCFSVQAVIPSRTVNRKSTDSPVECMGQEKGEFR
E
```

In some embodiments, a soluble tissue factor domain can include a sequence that is at least 70% identical, at least 72% identical, at least 74% identical, at least 76% identical, at least 78% identical, at least 80% identical, at least 82% identical, at least 84% identical, at least 86% identical, at least 88% identical, at least 90% identical, at least 92% identical, at least 94% identical, at least 96% identical, at least 98% identical, at least 99% identical, or 100% identical to SEQ ID NO: 2, 14, 15, 16, or 17. In some embodiments, a soluble tissue factor domain can include a sequence of SEQ ID NO: 2, 14, 15, 16, or 17 with one to twenty amino acids (e.g., 2, 3, 4, 5, 6, 7, 8, 9, 10, 11, 12, 13, 14, 15, 16, 17, 18, 19, or 20) amino acids removed from its N-terminus and/or one to twenty amino acids (e.g., 2, 3, 4, 5, 6, 7, 8, 9, 10, 11, 12, 13, 14, 15, 16, 17, 18, 19, or 20) amino acids removed from its C-terminus.

As can be appreciated in the art, one skilled in the art would understand that mutation of amino acids that are conserved between different mammalian species is more likely to decrease the activity and/or structural stability of the protein, while mutation of amino acids that are not conserved between different mammalian species is less likely to decrease the activity and/or structural stability of the protein.

In some examples, the soluble tissue factor domain is not capable of binding to Factor VIIa. In some examples, the soluble tissue factor domain does not convert inactive Factor X into Factor Xa. In some embodiments, any of the single-chain chimeric polypeptides or multi-chain chimeric polypeptides described herein does not stimulate blood coagulation in a mammal.

In some examples, the soluble tissue factor domain can be a soluble human tissue factor domain. In some embodiments, the soluble tissue factor domain can be a soluble mouse tissue factor domain. In some embodiments, the soluble tissue factor domain can be a soluble rat tissue factor domain.

In some examples, the soluble tissue factor domain does not include one or more (e.g., two, three, four, five, six or seven) of: a lysine at an amino acid position that corresponds to amino acid position 20 of mature wildtype human tissue factor protein; an isoleucine at an amino acid position that corresponds to amino acid position 22 of mature wildtype human tissue factor protein; a tryptophan at an amino acid position that corresponds to amino acid position 45 of mature wildtype human tissue factor protein; an aspartic acid at an amino acid position that corresponds to amino acid position 58 of mature wildtype human tissue factor protein; a tyrosine at an amino acid position that corresponds to amino acid position 94 of mature wildtype human tissue factor protein; an arginine at an amino acid position that corresponds to amino acid position 135 of mature wildtype human tissue factor protein; and a phenylalanine at an amino acid position that corresponds to amino acid position 140 of mature wildtype human tissue factor protein.

In some examples, the soluble tissue factor domain does not include any of: a lysine at an amino acid position that corresponds to amino acid position 20 of mature wildtype human tissue factor protein; an isoleucine at an amino acid position that corresponds to amino acid position 22 of mature wildtype human tissue factor protein; a tryptophan at an amino acid position that corresponds to amino acid position 45 of mature wildtype human tissue factor protein; an aspartic acid at an amino acid position that corresponds to amino acid position 58 of mature wildtype human tissue factor protein; a tyrosine at an amino acid position that corresponds to amino acid position 94 of mature wildtype human tissue factor protein; an arginine at an amino acid position that corresponds to amino acid position 135 of mature wildtype human tissue factor protein; and a phenylalanine at an amino acid position that corresponds to amino acid position 140 of mature wildtype human tissue factor protein.

In some examples, the soluble tissue factor domain includes one or more of: a lysine at an amino acid position that corresponds to amino acid position 20 of mature wildtype human tissue factor protein; an isoleucine at an amino acid position that corresponds to amino acid position 22 of mature wildtype human tissue factor protein; a tryptophan at an amino acid position that corresponds to amino acid position 45 of mature wildtype human tissue factor protein; an aspartic acid at an amino acid position that corresponds to amino acid position 58 of mature wildtype human tissue factor protein; a tyrosine at an amino acid position that corresponds to amino acid position 94 of mature wildtype human tissue factor protein; an arginine at an amino acid position that corresponds to amino acid position 135 of mature wildtype human tissue factor protein; and a phenylalanine at an amino acid position that corresponds to amino acid position 140 of mature wildtype human tissue factor protein.

In some embodiments, the mutant soluble tissue factor possesses the amino acid sequence of SEQ ID NO: 16 or SEQ ID NO: 17.

In some examples, the soluble tissue factor domain can be encoded by a nucleic acid including a sequence that is at least 70% identical, at least 72% identical, at least 74% identical, at least 76% identical, at least 78% identical, at least 80% identical, at least 82% identical, at least 84% identical, at least 86% identical, at least 88% identical, at least 90% identical, at least 92% identical, at least 94% identical, at least 96% identical, at least 98% identical, at least 99% identical, or 100% identical to SEQ ID NO: 13.

In some embodiments, the soluble tissue factor domain can have a total length of about 20 amino acids to about 220 amino acids, about 20 amino acids to about 215 amino acids, about 20 amino acids to about 210 amino acids, about 20 amino acids to about 205 amino acids, about 20 amino acids to about 200 amino acids, about 20 amino acids to about 195 amino acids, about 20 amino acids to about 190 amino acids, about 20 amino acids to about 185 amino acids, about 20 amino acids to about 180 amino acids, about 20 amino acids to about 175 amino acids, about 20 amino acids to about 170 amino acids, about 20 amino acids to about 165 amino acids, about 20 amino acids to about 160 amino acids, about 20 amino acids to about 155 amino acids, about 20 amino acids to about 150 amino acids, about 20 amino acids to about 145 amino acids, about 20 amino acids to about 140 amino acids, about 20 amino acids to about 135 amino acids, about 20 amino acids to about 130 amino acids, about 20 amino acids to about 125 amino acids, about 20 amino acids to about 120 amino acids, about 20 amino acids to about 115 amino acids, about 20 amino acids to about 110 amino acids, about 20 amino acids to about 105 amino acids, about 20 amino acids to about 100 amino acids, about 20 amino acids to about 95 amino acids, about 20 amino acids to about 90 amino acids, about 20 amino acids to about 85 amino acids, about 20 amino acids to about 80 amino acids, about 20 amino acids to about 75 amino acids, about 20 amino acids to about 70 amino acids, about 20 amino acids to about 60 amino acids, about 20 amino acids to about 50 amino acids, about 20 amino acids to about 40 amino acids, about 20 amino acids to about 30 amino acids, about 30 amino acids to about 220 amino acids, about 30 amino acids to about 215 amino acids, about 30 amino acids to about 210 amino acids, about 30 amino acids to about 205 amino acids, about 30 amino acids to about 200 amino acids, about 30 amino acids to about 195 amino acids, about 30 amino acids to about 190 amino acids, about 30 amino acids to about 185 amino acids, about 30 amino acids to about 180 amino acids, about 30 amino acids to about 175 amino acids, about 30 amino acids to about 170 amino acids, about 30 amino acids to about 165 amino acids, about 30 amino acids to about 160 amino acids, about 30 amino acids to about 155 amino acids, about 30 amino acids to about 150 amino acids, about 30 amino acids to about 145 amino acids, about 30 amino acids to about 140 amino acids, about 30 amino acids to about 135 amino acids, about 30 amino acids to about 130 amino acids, about 30 amino acids to about 125 amino acids, about 30 amino acids to about 120 amino acids, about 30 amino acids to about 115 amino acids, about 30 amino acids to about 110 amino acids, about 30 amino acids to about 105 amino acids, about 30 amino acids to about 100 amino acids, about 30 amino acids to about 95 amino acids, about 30 amino acids to about 90 amino acids, about 30 amino acids to about 85 amino acids, about 30 amino acids to about 80 amino acids, about 30 amino acids to about 75 amino acids, about 30 amino acids to about 70 amino acids, about 30 amino acids to about 60 amino acids, about 30 amino acids to about 50 amino acids, about 30 amino acids to about 40 amino acids, about 40 amino acids to about 220 amino acids, about 40 amino acids to about 215 amino acids, about 40 amino acids to about 210 amino acids, about 40 amino acids to about 205 amino acids, about 40 amino acids to about 200 amino acids, about 40 amino acids to about 195 amino acids, about 40 amino acids to about 190 amino acids, about 40 amino acids to about 185 amino acids, about 40 amino acids to about 180 amino acids, about 40 amino acids to about 175 amino acids, about 40 amino acids to about 170 amino acids, about 40 amino acids to about 165 amino acids, about 40 amino acids to about 160 amino acids, about 40 amino acids to about 155 amino acids, about 40 amino acids to about 150 amino acids, about 40 amino acids to about 145 amino acids, about 40 amino acids to about 140 amino acids, about 40 amino acids to about 135 amino acids, about 40 amino acids to about 130 amino acids, about 40 amino acids to about 125 amino acids, about 40 amino acids to about 120 amino acids, about 40 amino acids to about 115 amino acids, about 40 amino acids to about 110 amino acids, about 40 amino acids to about 105 amino acids, about 40 amino acids to about 100 amino acids, about 40 amino acids to about 95 amino acids, about 40 amino acids to about 90 amino acids, about 40 amino acids to about 85 amino acids, about 40 amino acids to about 80 amino acids, about 40 amino acids to about 75 amino acids, about 40 amino acids to about 70 amino acids, about 40 amino acids to about 60 amino acids, about 40 amino acids to about 50 amino acids, about 50 amino acids to about 220 amino acids, about 50 amino acids to about 215 amino acids, about 50 amino acids to about 210 amino acids, about 50 amino acids to about 205 amino acids, about 50 amino acids to about 200 amino acids, about 50 amino acids to about 195 amino acids, about 50 amino acids to about 190 amino acids, about 50 amino acids to about 185 amino acids, about 50 amino acids to about 180 amino acids, about 50 amino acids to about 175 amino acids, about 50 amino acids to about 170 amino acids, about 50 amino acids to about 165 amino acids, about 50 amino acids to about 160 amino acids, about 50 amino acids to about 155 amino acids, about 50 amino acids to about 150 amino acids, about 50 amino acids to about 145 amino acids, about 50 amino acids to about 140 amino acids, about 50 amino acids to about 135 amino acids, about 50 amino acids to about 130 amino acids, about 50 amino acids to about 125 amino acids, about 50 amino acids to about 120 amino acids, about 50 amino acids to about 115 amino acids, about 50 amino acids to about 110 amino acids, about 50 amino acids to about 105 amino acids, about 50 amino acids to about 100 amino acids, about 50 amino acids to about 95 amino acids, about 50 amino acids to about 90 amino acids, about 50 amino acids to about 85 amino acids, about 50 amino acids to about 80 amino acids, about 50 amino acids to about 75 amino acids, about 50 amino acids to about 70 amino acids, about 50 amino acids to about 60 amino acids, about 60 amino acids to about 220 amino acids, about 60 amino acids to about 215 amino acids, about 60 amino acids to about 210 amino acids, about 60 amino acids to about 205 amino acids, about 60 amino acids to about 200 amino acids, about 60 amino acids to about 195 amino acids, about 60 amino acids to about 190 amino acids, about 60 amino acids to about 185 amino acids, about 60 amino acids to about 180 amino acids, about 60 amino acids to about 175 amino acids, about 60 amino acids to about 170 amino acids, about 60 amino acids to about 165 amino acids, about 60 amino acids to about 160 amino acids, about 60 amino acids to about 155 amino acids, about 60 amino acids to about 150 amino acids, about 60 amino acids to about 145 amino acids, about 60 amino acids to about 140 amino acids, about 60 amino acids to about 135 amino acids, about 60 amino acids to about 130 amino acids, about 60 amino acids to about 125 amino acids, about 60 amino acids to about 120 amino acids, about 60 amino acids to about 115 amino acids, about 60 amino acids to about 110 amino acids, about 60 amino acids to about 105 amino acids, about 60 amino acids to about 100 amino acids, about 60 amino acids to about 95 amino acids, about 60 amino acids to about 90 amino acids, about 60 amino acids to about 85 amino acids, about 60 amino acids to about 80 amino acids, about 60 amino acids to about 75 amino acids, about 60 amino acids to about 70 amino acids, about 70 amino acids to about 220 amino acids, about 70 amino acids to about 215 amino acids, about 70 amino acids to about 210 amino acids, about 70 amino acids to about 205 amino acids, about 70 amino acids to about 200 amino acids, about 70 amino acids to about 195 amino acids, about 70 amino acids to about 190 amino acids, about 70 amino acids to about 185 amino acids, about 70 amino acids to about 180 amino acids, about 70 amino acids to about 175 amino acids, about 70 amino acids to about 170 amino acids, about 70 amino acids to about 165 amino acids, about 70 amino acids to about 160 amino acids, about 70 amino acids to about 155 amino acids, about 70 amino acids to about 150 amino acids, about 70 amino acids to about 145 amino acids, about 70 amino acids to about 140 amino acids, about 70 amino acids to about 135 amino acids, about 70 amino acids to about 130 amino acids, about 70 amino acids to about 125 amino acids, about 70 amino acids to about 120 amino acids, about 70 amino acids to about 115 amino acids, about 70 amino acids to about 110 amino acids, about 70 amino acids to about 105 amino acids, about 70 amino acids to about 100 amino acids, about 70 amino acids to about 95 amino acids, about 70 amino acids to about 90 amino acids, about 70 amino acids to about 85 amino acids, about 70 amino acids to about 80 amino acids, about 80 amino acids to about 220 amino acids, about 80 amino acids to about 215 amino acids, about 80 amino acids to about 210 amino acids, about 80 amino acids to about 205 amino acids, about 80 amino acids to about 200 amino acids, about 80 amino acids to about 195 amino acids, about 80 amino acids to about 190 amino acids, about 80 amino acids to about 185 amino acids, about 80 amino acids to about 180 amino acids, about 80 amino acids to about 175 amino acids, about 80 amino acids to about 170 amino acids, about 80 amino acids to about 165 amino acids, about 80 amino acids to about 160 amino acids, about 80 amino acids to about 155 amino acids, about 80 amino acids to about 150 amino acids, about 80 amino acids to about 145 amino acids, about 80 amino acids to about 140 amino acids, about 80 amino acids to about 135 amino acids, about 80 amino acids to about 130 amino acids, about 80 amino acids to about 125 amino acids, about 80 amino acids to about 120 amino acids, about 80 amino acids to about 115 amino acids, about 80 amino acids to about 110 amino acids, about 80 amino acids to about 105 amino acids, about 80 amino acids to about 100 amino acids, about 80 amino acids to about 95 amino acids, about 80 amino acids to about 90 amino acids, about 90 amino acids to about 220 amino acids, about 90 amino acids to about 215 amino acids, about 90 amino acids to about 210 amino acids, about 90 amino acids to about 205 amino acids, about 90 amino acids to about 200 amino acids, about 90 amino acids to about 195 amino acids, about 90 amino acids to about 190 amino acids, about 90 amino acids to about 185 amino acids, about 90 amino acids to about 180 amino acids, about 90 amino acids to about 175 amino acids, about 90 amino acids to about 170 amino acids, about 90 amino acids to about 165 amino acids, about 90 amino acids to about 160 amino acids, about 90 amino acids to about 155 amino acids, about 90 amino acids to about 150 amino acids, about 90 amino acids to about 145 amino acids, about 90 amino acids to about 140 amino acids, about 90 amino acids to about 135 amino acids, about 90 amino acids to about 130 amino acids, about 90 amino acids to about 125 amino acids, about 90 amino acids to about 120 amino acids, about 90 amino acids to about 115 amino acids, about 90 amino acids to about 110 amino acids, about 90 amino acids to about 105 amino acids, about 90 amino acids to about 100 amino acids, about 100 amino acids to about 220 amino acids, about 100 amino acids to about 215 amino acids, about 100 amino acids to about 210 amino acids, about 100 amino acids to about 205 amino acids, about 100 amino acids to about 200 amino acids, about 100 amino acids to about 195 amino acids, about 100 amino acids to about 190 amino acids, about 100 amino acids to about 185 amino acids, about 100 amino acids to about 180 amino acids, about 100 amino acids to about 175 amino acids, about 100 amino acids to about 170 amino acids, about 100 amino acids to about 165 amino acids, about 100 amino acids to about 160 amino acids, about 100 amino acids to about 155 amino acids, about 100 amino acids to about 150 amino acids, about 100 amino acids to about 145 amino acids, about 100 amino acids to about 140 amino acids, about 100 amino acids to about 135 amino acids, about 100 amino acids to about 130 amino acids, about 100 amino acids to about 125 amino acids, about 100 amino acids to about 120 amino acids, about 100 amino acids to about 115 amino acids, about 100 amino acids to about 110 amino acids, about 110 amino acids to about 220 amino acids, about 110 amino acids to about 215 amino acids, about 110 amino acids to about 210 amino acids, about 110 amino acids to about 205 amino acids, about 110 amino acids to about 200 amino acids, about 110 amino acids to about 195 amino acids, about 110 amino acids to about 190 amino acids, about 110 amino acids to about 185 amino acids, about 110 amino acids to about 180 amino acids, about 110 amino acids to about 175 amino acids, about 110 amino acids to about 170 amino acids, about 110 amino acids to about 165 amino acids, about 110 amino acids to about 160 amino acids, about 110 amino acids to about 155 amino acids, about 110 amino acids to about 150 amino acids, about 110 amino acids to about 145 amino acids, about 110 amino acids to about 140 amino acids, about 110 amino acids to about 135 amino acids, about 110 amino acids to about 130 amino acids, about 110 amino acids to about 125 amino acids, about 110 amino acids to about 120 amino acids, about 110 amino acids to about 115 amino acids, about 115 amino acids to about 220 amino acids, about 115 amino acids to about 215 amino acids, about 115 amino acids to about 210 amino acids, about 115 amino acids to about 205 amino acids, about 115 amino acids to about 200 amino acids, about 115 amino acids to about 195 amino acids, about 115 amino acids to about 190 amino acids, about 115 amino acids to about 185 amino acids, about 115 amino acids to about 180 amino acids, about 115 amino acids to about 175 amino acids, about 115 amino acids to about 170 amino acids, about 115 amino acids to about 165 amino acids, about 115 amino acids to about 160 amino acids, about 115 amino acids to about 155 amino acids, about 115 amino acids to about 150 amino acids, about 115 amino acids to about 145 amino acids, about 115 amino acids to about 140 amino acids, about 115 amino acids to about 135 amino acids, about 115 amino acids to about 130 amino acids, about 115 amino acids to about 125 amino acids, about 115 amino acids to about 120 amino acids, about 120 amino acids to about 220 amino acids, about 120 amino acids to about 215 amino acids, about 120 amino acids to about 210 amino acids, about 120 amino acids to about 205 amino acids, about 120 amino acids to about 200 amino acids, about 120 amino acids to about 195 amino acids, about 120 amino acids to about 190 amino acids, about 120 amino acids to about 185 amino acids, about 120 amino acids to about 180 amino acids, about 120 amino acids to about 175 amino acids, about 120 amino acids to about 170 amino acids, about 120 amino acids to about 165 amino acids, about 120 amino acids to about 160 amino acids, about 120 amino acids to about 155 amino acids, about 120 amino acids to about 150 amino acids, about 120 amino acids to about 145 amino acids, about 120 amino acids to about 140 amino acids, about 120 amino acids to about 135 amino acids, about 120 amino acids to about 130 amino acids, about 120 amino acids to about 125 amino acids, about 125 amino acids to about 220 amino acids, about 125 amino acids to about 215 amino acids, about 125 amino acids to about 210 amino acids, about 125 amino acids to about 205 amino acids, about 125 amino acids to about 200 amino acids, about 125 amino acids to about 195 amino acids, about 125 amino acids to about 190 amino acids, about 125 amino acids to about 185 amino acids, about 125 amino acids to about 180 amino acids, about 125 amino acids to about 175 amino acids, about 125 amino acids to about 170 amino acids, about 125 amino acids to about 165 amino acids, about 125 amino acids to about 160 amino acids, about 125 amino acids to about 155 amino acids, about 125 amino acids to about 150 amino acids, about 125 amino acids to about 145 amino acids, about 125 amino acids to about 140 amino acids, about 125 amino acids to about 135 amino acids, about 125 amino acids to about 130 amino acids, about 130 amino acids to about 220 amino acids, about 130 amino acids to about 215 amino acids, about 130 amino acids to about 210 amino acids, about 130 amino acids to about 205 amino acids, about 130 amino acids to about 200 amino acids, about 130 amino acids to about 195 amino acids, about 130 amino acids to about 190 amino acids, about 130 amino acids to about 185 amino acids, about 130 amino acids to about 180 amino acids, about 130 amino acids to about 175 amino acids, about 130 amino acids to about 170 amino acids, about 130 amino acids to about 165 amino acids, about 130 amino acids to about 160 amino acids, about 130 amino acids to about 155 amino acids, about 130 amino acids to about 150 amino acids, about 130 amino acids to about 145 amino acids, about 130 amino acids to about 140 amino acids, about 130 amino acids to about 135 amino acids, about 135 amino acids to about 220 amino acids, about 135 amino acids to about 215 amino acids, about 135 amino acids to about 210 amino acids, about 135 amino acids to about 205 amino acids, about 135 amino acids to about 200 amino acids, about 135 amino acids to about 195 amino acids, about 135 amino acids to about 190 amino acids, about 135 amino acids to about 185 amino acids, about 135 amino acids to about 180 amino acids, about 135 amino acids to about 175 amino acids, about 135 amino acids to about 170 amino acids, about 135 amino acids to about 165 amino acids, about 135 amino acids to about 160 amino acids, about 135 amino acids to about 155 amino acids, about 135 amino acids to about 150 amino acids, about 135 amino acids to about 145 amino acids, about 135 amino acids to about 140 amino acids, about 140 amino acids to about 220 amino acids, about 140 amino acids to about 215 amino acids, about 140 amino acids to about 210 amino acids, about 140 amino acids to about 205 amino acids, about 140 amino acids to about 200 amino acids, about 140 amino acids to about 195 amino acids, about 140 amino acids to about 190 amino acids, about 140 amino acids to about 185 amino acids, about 140 amino acids to about 180 amino acids, about 140 amino acids to about 175 amino acids, about 140 amino acids to about 170 amino acids, about 140 amino acids to about 165 amino acids, about 140 amino acids to about 160 amino acids, about 140 amino acids to about 155 amino acids, about 140 amino acids to about 150 amino acids, about 140 amino acids to about 145 amino acids, about 145 amino acids to about 220 amino acids, about 145 amino acids to about 215 amino acids, about 145 amino acids to about 210 amino acids, about 145 amino acids to about 205 amino acids, about 145 amino acids to about 200 amino acids, about 145 amino acids to about 195 amino acids, about 145 amino acids to about 190 amino acids, about 145 amino acids to about 185 amino acids, about 145 amino acids to about 180 amino acids, about 145 amino acids to about 175 amino acids, about 145 amino acids to about 170 amino acids, about 145 amino acids to about 165 amino acids, about 145 amino acids to about 160 amino acids, about 145 amino acids to about 155 amino acids, about 145 amino acids to about 150 amino acids, about 150 amino acids to about 220 amino acids, about 150 amino acids to about 215 amino acids, about 150 amino acids to about 210 amino acids, about 150 amino acids to about 205 amino acids, about 150 amino acids to about 200 amino acids, about 150 amino acids to about 195 amino acids, about 150 amino acids to about 190 amino acids, about 150 amino acids to about 185 amino acids, about 150 amino acids to about 180 amino acids, about 150 amino acids to about 175 amino acids, about 150 amino acids to about 170 amino acids, about 150 amino acids to about 165 amino acids, about 150 amino acids to about 160 amino acids, about 150 amino acids to about 155 amino acids, about 155 amino acids to about 220 amino acids, about 155 amino acids to about 215 amino acids, about 155 amino acids to about 210 amino acids, about 155 amino acids to about 205 amino acids, about 155 amino acids to about 200 amino acids, about 155 amino acids to about 195 amino acids, about 155 amino acids to about 190 amino acids, about 155 amino acids to about 185 amino acids, about 155 amino acids to about 180 amino acids, about 155 amino acids to about 175 amino acids, about 155 amino acids to about 170 amino acids, about 155 amino acids to about 165 amino acids, about 155 amino acids to about 160 amino acids, about 160 amino acids to about 220 amino acids, about 160 amino acids to about 215 amino acids, about 160 amino acids to about 210 amino acids, about 160 amino acids to about 205 amino acids, about 160 amino acids to about 200 amino acids, about 160 amino acids to about 195 amino acids, about 160 amino acids to about 190 amino acids, about 160 amino acids to about 185 amino acids, about 160 amino acids to about 180 amino acids, about 160 amino acids to about 175 amino acids, about 160 amino acids to about 170 amino acids, about 160 amino acids to about 165 amino acids, about 165 amino acids to about 220 amino acids, about 165 amino acids to about 215 amino acids, about 165 amino acids to about 210 amino acids, about 165 amino acids to about 205 amino acids, about 165 amino acids to about 200 amino acids, about 165 amino acids to about 195 amino acids, about 165 amino acids to about 190 amino acids, about 165 amino acids to about 185 amino acids, about 165 amino acids to about 180 amino acids, about 165 amino acids to about 175 amino acids, about 165 amino acids to about 170 amino acids, about 170 amino acids to about 220 amino acids, about 170 amino acids to about 215 amino acids, about 170 amino acids to about 210 amino acids, about 170 amino acids to about 205 amino acids, about 170 amino acids to about 200 amino acids, about 170 amino acids to about 195 amino acids, about 170 amino acids to about 190 amino acids, about 170 amino acids to about 185 amino acids, about 170 amino acids to about 180 amino acids, about 170 amino acids to about 175 amino acids, about 175 amino acids to about 220 amino acids, about 175 amino acids to about 215 amino acids, about 175 amino acids to about 210 amino acids, about 175 amino acids to about 205 amino acids, about 175 amino acids to about 200 amino acids, about 175 amino acids to about 195 amino acids, about 175 amino acids to about 190 amino acids, about 175 amino acids to about 185 amino acids, about 175 amino acids to about 180 amino acids, about 180 amino acids to about 220 amino acids, about 180 amino acids to about 215 amino acids, about 180 amino acids to about 210 amino acids, about 180 amino acids to about 205 amino acids, about 180 amino acids to about 200 amino acids, about 180 amino acids to about 195 amino acids, about 180 amino acids to about 190 amino acids, about 180 amino acids to about 185 amino acids, about 185 amino acids to about 220 amino acids, about 185 amino acids to about 215 amino acids, about 185 amino acids to about 210 amino acids, about 185 amino acids to about 205 amino acids, about 185 amino acids to about 200 amino acids, about 185 amino acids to about 195 amino acids, about 185 amino acids to about 190 amino acids, about 190 amino acids to about 220 amino acids, about 190 amino acids to about 215 amino acids, about 190 amino acids to about 210 amino acids, about 190 amino acids to about 205 amino acids, about 190 amino acids to about 200 amino acids, about 190 amino acids to about 195 amino acids, about 195 amino acids to about 220 amino acids, about 195 amino acids to about 215 amino acids, about 195 amino acids to about 210 amino acids, about 195 amino acids to about 205 amino acids, about 195 amino acids to about 200 amino acids, about 200 amino acids to about 220 amino acids, about 200 amino acids to about 215 amino acids, about 200 amino acids to about 210 amino acids, about 200 amino acids to about 205 amino acids, about 205 amino acids to about 220 amino acids, about 205 amino acids to about 215 amino acids, about 205 amino acids to about 210 amino acids, about 210 amino acids to about 220 amino acids, about 210 amino acids to about 215 amino acids, or about 215 amino acids to about 220 amino acids.

In some embodiments, the soluble tissue factor domain can comprise or consist of a soluble wildtype human tissue factor (or any sequence therefrom).

Linker Sequences

In some embodiments, the linker sequence can be a flexible linker sequence. Non-limiting examples of linker sequences that can be used are described in Klein et al., Protein Engineering, Design & Selection Vol. 27, No. 10, pp. 325-330, 2014; Priyanka et al., Protein Sci., 2013 February; 22(2): 153-167. In some examples, the linker sequence is a synthetic linker sequence.

In some embodiments of any of the single-chain chimeric polypeptides described herein can include one, two, three, four, five, six, seven, eight, nine, or ten linker sequence(s) (e.g., the same or different linker sequences, e.g., any of the exemplary linker sequences described herein or known in the art). In some embodiments of any of the single-chain chimeric polypeptides described herein can include one, two, three, four, five, six, seven, eight, nine, or ten linker sequence(s) (e.g., the same or different linker sequences, e.g., any of the exemplary linker sequences described herein or known in the art).

In some embodiments of any of the first chimeric polypeptides and/or the second chimeric polypeptides described herein can include one, two, three, four, five, six, seven, eight, nine, or ten linker sequence(s) (e.g., the same or different linker sequences, e.g., any of the exemplary linker sequences described herein or known in the art). In some embodiments of any of the first chimeric polypeptides and/or the second chimeric polypeptides described herein can include one, two, three, four, five, six, seven, eight, nine, or ten linker sequence(s) (e.g., the same or different linker sequences, e.g., any of the exemplary linker sequences described herein or known in the art).

In some embodiments, a linker sequence can have a total length of 1 amino acid to about 100 amino acids, 1 amino acid to about 90 amino acids, 1 amino acid to about 80 amino acids, 1 amino acid to about 70 amino acids, 1 amino acid to about 60 amino acids, 1 amino acid to about 50 amino acids, 1 amino acid to about 45 amino acids, 1 amino acid to about 40 amino acids, 1 amino acid to about 35 amino acids, 1 amino acid to about 30 amino acids, 1 amino acid to about 25 amino acids, 1 amino acid to about 24 amino acids, 1 amino acid to about 22 amino acids, 1 amino acid to about 20 amino acids, 1 amino acid to about 18 amino acids, 1 amino acid to about 16 amino acids, 1 amino acid to about 14 amino acids, 1 amino acid to about 12 amino acids, 1 amino acid to about 10 amino acids, 1 amino acid to about 8 amino acids, 1 amino acid to about 6 amino acids, 1 amino acid to about 4 amino acids, about 2 amino acids to about 100 amino acids, about 2 amino acids to about 90 amino acids, about 2 amino acids to about 80 amino acids, about 2 amino acids to about 70 amino acids, about 2 amino acids to about 60 amino acids, about 2 amino acids to about 50 amino acids, about 2 amino acids to about 45 amino acids, about 2 amino acids to about 40 amino acids, about 2 amino acids to about 35 amino acids, about 2 amino acids to about 30 amino acids, about 2 amino acids to about 25 amino acids, about 2 amino acids to about 24 amino acids, about 2 amino acids to about 22 amino acids, about 2 amino acids to about 20 amino acids, about 2 amino acids to about 18 amino acids, about 2 amino acids to about 16 amino acids, about 2 amino acids to about 14 amino acids, about 2 amino acids to about 12 amino acids, about 2 amino acids to about 10 amino acids, about 2 amino acids to about 8 amino acids, about 2 amino acids to about 6 amino acids, about 2 amino acids to about 4 amino acids, about 4 amino acids to about 100 amino acids, about 4 amino acids to about 90 amino acids, about 4 amino acids to about 80 amino acids, about 4 amino acids to about 70 amino acids, about 4 amino acids to about 60 amino acids, about 4 amino acids to about 50 amino acids, about 4 amino acids to about 45 amino acids, about 4 amino acids to about 40 amino acids, about 4 amino acids to about 35 amino acids, about 4 amino acids to about 30 amino acids, about 4 amino acids to about 25 amino acids, about 4 amino acids to about 24 amino acids, about 4 amino acids to about 22 amino acids, about 4 amino acids to about 20 amino acids, about 4 amino acids to about 18 amino acids, about 4 amino acids to about 16 amino acids, about 4 amino acids to about 14 amino acids, about 4 amino acids to about 12 amino acids, about 4 amino acids to about 10 amino acids, about 4 amino acids to about 8 amino acids, about 4 amino acids to about 6 amino acids, about 6 amino acids to about 100 amino acids, about 6 amino acids to about 90 amino acids, about 6 amino acids to about 80 amino acids, about 6 amino acids to about 70 amino acids, about 6 amino acids to about 60 amino acids, about 6 amino acids to about 50 amino acids, about 6 amino acids to about 45 amino acids, about 6 amino acids to about 40 amino acids, about 6 amino acids to about 35 amino acids, about 6 amino acids to about 30 amino acids, about 6 amino acids to about 25 amino acids, about 6 amino acids to about 24 amino acids, about 6 amino acids to about 22 amino acids, about 6 amino acids to about 20 amino acids, about 6 amino acids to about 18 amino acids, about 6 amino acids to about 16 amino acids, about 6 amino acids to about 14 amino acids, about 6 amino acids to about 12 amino acids, about 6 amino acids to about 10 amino acids, about 6 amino acids to about 8 amino acids, about 8 amino acids to about 100 amino acids, about 8 amino acids to about 90 amino acids, about 8 amino acids to about 80 amino acids, about 8 amino acids to about 70 amino acids, about 8 amino acids to about 60 amino acids, about 8 amino acids to about 50 amino acids, about 8 amino acids to about 45 amino acids, about 8 amino acids to about 40 amino acids, about 8 amino acids to about 35 amino acids, about 8 amino acids to about 30 amino acids, about 8 amino acids to about 25 amino acids, about 8 amino acids to about 24 amino acids, about 8 amino acids to about 22 amino acids, about 8 amino acids to about 20 amino acids, about 8 amino acids to about 18 amino acids, about 8 amino acids to about 16 amino acids, about 8 amino acids to about 14 amino acids, about 8 amino acids to about 12 amino acids, about 8 amino acids to about 10 amino acids, about 10 amino acids to about 100 amino acids, about 10 amino acids to about 90 amino acids, about 10 amino acids to about 80 amino acids, about 10 amino acids to about 70 amino acids, about 10 amino acids to about 60 amino acids, about 10 amino acids to about 50 amino acids, about 10 amino acids to about 45 amino acids, about 10 amino acids to about 40 amino acids, about 10 amino acids to about 35 amino acids, about 10 amino acids to about 30 amino acids, about 10 amino acids to about 25 amino acids, about 10 amino acids to about 24 amino acids, about 10 amino acids to about 22 amino acids, about 10 amino acids to about 20 amino acids, about 10 amino acids to about 18 amino acids, about 10 amino acids to about 16 amino acids, about 10 amino acids to about 14 amino acids, about 10 amino acids to about 12 amino acids, about 12 amino acids to about 100 amino acids, about 12 amino acids to about 90 amino acids, about 12 amino acids to about 80 amino acids, about 12 amino acids to about 70 amino acids, about 12 amino acids to about 60 amino acids, about 12 amino acids to about 50 amino acids, about 12 amino acids to about 45 amino acids, about 12 amino acids to about 40 amino acids, about 12 amino acids to about 35 amino acids, about 12 amino acids to about 30 amino acids, about 12 amino acids to about 25 amino acids, about 12 amino acids to about 24 amino acids, about 12 amino acids to about 22 amino acids, about 12 amino acids to about 20 amino acids, about 12 amino acids to about 18 amino acids, about 12 amino acids to about 16 amino acids, about 12 amino acids to about 14 amino acids, about 14 amino acids to about 100 amino acids, about 14 amino acids to about 90 amino acids, about 14 amino acids to about 80 amino acids, about 14 amino acids to about 70 amino acids, about 14 amino acids to about 60 amino acids, about 14 amino acids to about 50 amino acids, about 14 amino acids to about 45 amino acids, about 14 amino acids to about 40 amino acids, about 14 amino acids to about 35 amino acids, about 14 amino acids to about 30 amino acids, about 14 amino acids to about 25 amino acids, about 14 amino acids to about 24 amino acids, about 14 amino acids to about 22 amino acids, about 14 amino acids to about 20 amino acids, about 14 amino acids to about 18 amino acids, about 14 amino acids to about 16 amino acids, about 16 amino acids to about 100 amino acids, about 16 amino acids to about 90 amino acids, about 16 amino acids to about 80 amino acids, about 16 amino acids to about 70 amino acids, about 16 amino acids to about 60 amino acids, about 16 amino acids to about 50 amino acids, about 16 amino acids to about 45 amino acids, about 16 amino acids to about 40 amino acids, about 16 amino acids to about 35 amino acids, about 16 amino acids to about 30 amino acids, about 16 amino acids to about 25 amino acids, about 16 amino acids to about 24 amino acids, about 16 amino acids to about 22 amino acids, about 16 amino acids to about 20 amino acids, about 16 amino acids to about 18 amino acids, about 18 amino acids to about 100 amino acids, about 18 amino acids to about 90 amino acids, about 18 amino acids to about 80 amino acids, about 18 amino acids to about 70 amino acids, about 18 amino acids to about 60 amino acids, about 18 amino acids to about 50 amino acids, about 18 amino acids to about 45 amino acids, about 18 amino acids to about 40 amino acids, about 18 amino acids to about 35 amino acids, about 18 amino acids to about 30 amino acids, about 18 amino acids to about 25 amino acids, about 18 amino acids to about 24 amino acids, about 18 amino acids to about 22 amino acids, about 18 amino acids to about 20 amino acids, about 20 amino acids to about 100 amino acids, about 20 amino acids to about 90 amino acids, about 20 amino acids to about 80 amino acids, about 20 amino acids to about 70 amino acids, about 20 amino acids to about 60 amino acids, about 20 amino acids to about 50 amino acids, about 20 amino acids to about 45 amino acids, about 20 amino acids to about 40 amino acids, about 20 amino acids to about 35 amino acids, about 20 amino acids to about 30 amino acids, about 20 amino acids to about 25 amino acids, about 20 amino acids to about 24 amino acids, about 20 amino acids to about 22 amino acids, about 22 amino acids to about 100 amino acids, about 22 amino acids to about 90 amino acids, about 22 amino acids to about 80 amino acids, about 22 amino acids to about 70 amino acids, about 22 amino acids to about 60 amino acids, about 22 amino acids to about 50 amino acids, about 22 amino acids to about 45 amino acids, about 22 amino acids to about 40 amino acids, about 22 amino acids to about 35 amino acids, about 22 amino acids to about 30 amino acids, about 22 amino acids to about 25 amino acids, about 22 amino acids to about 24 amino acids, about 25 amino acids to about 100 amino acids, about 25 amino acids to about 90 amino acids, about 25 amino acids to about 80 amino acids, about 25 amino acids to about 70 amino acids, about 25 amino acids to about 60 amino acids, about 25 amino acids to about 50 amino acids, about 25 amino acids to about 45 amino acids, about 25 amino acids to about 40 amino acids, about 25 amino acids to about 35 amino acids, about 25 amino acids to about 30 amino acids, about 30 amino acids to about 100 amino acids, about 30 amino acids to about 90 amino acids, about 30 amino acids to about 80 amino acids, about 30 amino acids to about 70 amino acids, about 30 amino acids to about 60 amino acids, about 30 amino acids to about 50 amino acids, about 30 amino acids to about 45 amino acids, about 30 amino acids to about 40 amino acids, about 30 amino acids to about 35 amino acids, about 35 amino acids to about 100 amino acids, about 35 amino acids to about 90 amino acids, about 35 amino acids to about 80 amino acids, about 35 amino acids to about 70 amino acids, about 35 amino acids to about 60 amino acids, about 35 amino acids to about 50 amino acids, about 35 amino acids to about 45 amino acids, about 35 amino acids to about 40 amino acids, about 40 amino acids to about 100 amino acids, about 40 amino acids to about 90 amino acids, about 40 amino acids to about 80 amino acids, about 40 amino acids to about 70 amino acids, about 40 amino acids to about 60 amino acids, about 40 amino acids to about 50 amino acids, about 40 amino acids to about 45 amino acids, about 45 amino acids to about 100 amino acids, about 45 amino acids to about 90 amino acids, about 45 amino acids to about 80 amino acids, about 45 amino acids to about 70 amino acids, about 45 amino acids to about 60 amino acids, about 45 amino acids to about 50 amino acids, about 50 amino acids to about 100 amino acids, about 50 amino acids to about 90 amino acids, about 50 amino acids to about 80 amino acids, about 50 amino acids to about 70 amino acids, about 50 amino acids to about 60 amino acids, about 60 amino acids to about 100 amino acids, about 60 amino acids to about 90 amino acids, about 60 amino acids to about 80 amino acids, about 60 amino acids to about 70 amino acids, about 70 amino acids to about 100 amino acids, about 70 amino acids to about 90 amino acids, about 70 amino acids to about 80 amino acids, about 80 amino acids to about 100 amino acids, about 80 amino acids to about 90 amino acids, or about 90 amino acids to about 100 amino acids.

In some embodiments, the linker is rich in glycine (Gly or G) residues. In some embodiments, the linker is rich in serine (Ser or S) residues. In some embodiments, the linker is rich in glycine and serine residues. In some embodiments, the linker has one or more glycine-serine residue pairs (GS), e.g., 1, 2, 3, 4, 5, 6, 7, 8, 9, or 10 or more GS pairs. In some embodiments, the linker has one or more Gly-Gly-Gly-Ser (GGGS) (SEQ ID NO: 111) sequences, e.g., 1, 2, 3, 4, 5, 6, 7, 8, 9, or 10 or more GGGS (SEQ ID NO: 111) sequences. In some embodiments, the linker has one or more Gly-Gly-Gly-Gly-Ser (GGGGS) (SEQ ID NO: 110) sequences, e.g., 1, 2, 3, 4, 5, 6, 7, 8, 9, or 10 or more GGGGS (SEQ ID NO: 110) sequences. In some embodiments, the linker has one or more Gly-Gly-Ser-Gly (GGSG) (SEQ ID NO: 112) sequences, e.g., 1, 2, 3, 4, 5, 6, 7, 8, 9, or 10 or more GGSG (SEQ ID NO: 112) sequences.

In some embodiments, the linker sequence can comprise or consist of GGGGSGGGGSGGGGS (SEQ ID NO: 18). In some embodiments, the linker sequence can be encoded by a nucleic acid comprising or consisting of: GGCGGTGGAGGATCCGGAGGAGGTGGCTCCGGCGGCGGAGGATCT (SEQ ID NO: 19). In some embodiments, the linker sequence can comprise or consist of: GGGSGGGS (SEQ ID NO: 20).

Target-Binding Domains

In some embodiments of any of the single- or multi-chain chimeric polypeptides described herein, the first target-binding domain, the second target-binding domain, and/or the additional one or more target-binding domains can be an antigen-binding domain (e.g., any of the exemplary antigen-binding domains described herein or known in the art), a soluble interleukin or cytokine protein (e.g., any of the exemplary soluble interleukin proteins or soluble cytokine proteins described herein), and a soluble interleukin or cytokine receptor (e.g., any of the exemplary soluble interleukin receptors or soluble cytokine receptors described herein).

In some embodiments of any of the single- or multi-chain chimeric polypeptides described herein, the first target-binding domain, the second target-binding domain, and/or the one or more additional target-binding domains can each independent have a total number of amino acids of about 5 amino acids to about 1000 amino acids, about 5 amino acids to about 950 amino acids, about 5 amino acids to about 900 amino acids, about 5 amino acids to about 850 amino acids, about 5 amino acids to about 800 amino acids, about 5 amino acids to about 750 amino acids, about 5 amino acids to about 700 amino acids, about 5 amino acids to about 650 amino acids, about 5 amino acids to about 600 amino acids, about 5 amino acids to about 550 amino acids, about 5 amino acids to about 500 amino acids, about 5 amino acids to about 450 amino acids, about 5 amino acids to about 400 amino acids, about 5 amino acids to about 350 amino acids, about 5 amino acids to about 300 amino acids, about 5 amino acids to about 280 amino acids, about 5 amino acids to about 260 amino acids, about 5 amino acids to about 240 amino acids, about 5 amino acids to about 220 amino acids, about 5 amino acids to about 200 amino acids, about 5 amino acids to about 195 amino acids, about 5 amino acids to about 190 amino acids, about 5 amino acids to about 185 amino acids, about 5 amino acids to about 180 amino acids, about 5 amino acids to about 175 amino acids, about 5 amino acids to about 170 amino acids, about 5 amino acids to about 165 amino acids, about 5 amino acids to about 160 amino acids, about 5 amino acids to about 155 amino acids, about 5 amino acids to about 150 amino acids, about 5 amino acids to about 145 amino acids, about 5 amino acids to about 140 amino acids, about 5 amino acids to about 135 amino acids, about 5 amino acids to about 130 amino acids, about 5 amino acids to about 125 amino acids, about 5 amino acids to about 120 amino acids, about 5 amino acids to about 115 amino acids, about 5 amino acids to about 110 amino acids, about 5 amino acids to about 105 amino acids, about 5 amino acids to about 100 amino acids, about 5 amino acids to about 95 amino acids, about 5 amino acids to about 90 amino acids, about 5 amino acids to about 85 amino acids, about 5 amino acids to about 80 amino acids, about 5 amino acids to about 75 amino acids, about 5 amino acids to about 70 amino acids, about 5 amino acids to about 65 amino acids, about 5 amino acids to about 60 amino acids, about 5 amino acids to about 55 amino acids, about 5 amino acids to about 50 amino acids, about 5 amino acids to about 45 amino acids, about 5 amino acids to about 40 amino acids, about 5 amino acids to about 35 amino acids, about 5 amino acids to about 30 amino acids, about 5 amino acids to about 25 amino acids, about 5 amino acids to about 20 amino acids, about 5 amino acids to about 15 amino acids, about 5 amino acids to about 10 amino acids, Any of the target-binding domains described herein can bind to its target with a dissociation equilibrium constant ($K_D$) of less than $1 \times 10^{-7}$ M, less than $1 \times 10^{-8}$ M, less than $1 \times 10^{-9}$ M, less than $1 \times 10^{-10}$ M, less than $1 \times 10^{-11}$ M, less than $1 \times 10^{-12}$ M, or less than $1 \times 10^{-13}$ M. In some embodiments, the antigen-binding protein construct provided herein can bind to an identifying antigen with a $K_D$ of about $1 \times 10^{-3}$ M to about $1 \times 10^{-5}$ M, about $1 \times 10^{-4}$ M to about $1 \times 10^{-6}$ M, about $1\times10^{-5}$ M to about $1\times10^{-7}$ M, about $1\times10^{-6}$ M to about $1\times10^{-8}$ M, about $1\times10^{-7}$ M to about $1\times10^{-9}$ M, about $1\times10^{-8}$ M to about $1\times10^{-10}$ M, or about $1\times10^{-9}$ M to about $1\times10^{-11}$ M (inclusive).

Any of the target-binding domains described herein can bind to its target with a $K_D$ of between about 1 pM to about 30 nM (e.g., about 1 pM to about 25 nM, about 1 pM to about 20 nM, about 1 pM to about 15 nM, about 1 pM to about 10 nM, about 1 pM to about 5 nM, about 1 pM to about 2 nM, about 1 pM to about 1 nM, about 1 pM to about 950 pM, about 1 pM to about 900 pM, about 1 pM to about 850 pM, about 1 pM to about 800 pM, about 1 pM to about 750 pM, about 1 pM to about 700 pM, about 1 pM to about 650 pM, about 1 pM to about 600 pM, about 1 pM to about 550 pM, about 1 pM to about 500 pM, about 1 pM to about 450 pM, about 1 pM to about 400 pM, about 1 pM to about 350 pM, about 1 pM to about 300 pM, about 1 pM to about 250 pM, about 1 pM to about 200 pM, about 1 pM to about 150 pM, about 1 pM to about 100 pM, about 1 pM to about 90 pM, about 1 pM to about 80 pM, about 1 pM to about 70 pM, about 1 pM to about 60 pM, about 1 pM to about 50 pM, about 1 pM to about 40 pM, about 1 pM to about 30 pM, about 1 pM to about 20 pM, about 1 pM to about 10 pM, about 1 pM to about 5 pM, about 1 pM to about 4 pM, about 1 pM to about 3 pM, about 1 pM to about 2 pM).

Any of the target-binding domains described herein can bind to its target with a $K_D$ of between about 1 nM to about 10 nM (e.g., about 1 nM to about 9 nM, about 1 nM to about 8 nM, about 1 nM to about 7 nM, about 1 nM to about 6 nM, about 1 nM to about 5 nM, about 1 nM to about 4 nM, about 1 nM to about 3 nM, about 1 nM to about 2 nM, about 2 nM to about 10 nM, about 2 nM to about 9 nM, about 2 nM to about 8 nM, about 2 nM to about 7 nM, about 2 nM to about 6 nM, about 2 nM to about 5 nM, about 2 nM to about 4 nM, about 2 nM to about 3 nM, about 3 nM to about 10 nM, about 3 nM to about 9 nM, about 3 nM to about 8 nM, about 3 nM to about 7 nM, about 3 nM to about 6 nM, about 3 nM to about 5 nM, about 3 nM to about 4 nM, about 4 nM to about 10 nM, about 4 nM to about 9 nM, about 4 nM to about 8 nM, about 4 nM to about 7 nM, about 4 nM to about 6 nM, about 4 nM to about 5 nM, about 5 nM to about 10 nM, about 5 nM to about 9 nM, about 5 nM to about 8 nM, about 5 nM to about 7 nM, about 5 nM to about 6 nM, about 6 nM to about 10 nM, about 6 nM to about 9 nM, about 6 nM to about 8 nM, about 6 nM to about 7 nM, about 7 nM to about 10 nM, about 7 nM to about 9 nM, about 7 nM to about 8 nM, about 8 nM to about 10 nM, about 8 nM to about 9 nM, and about 9 nM to about 10 nM).

A variety of different methods known in the art can be used to determine the $K_D$ values of any of the antigen-binding protein constructs described herein (e.g., an electrophoretic mobility shift assay, a filter binding assay, surface plasmon resonance, and a biomolecular binding kinetics assay, etc.).

Antigen-Binding Domains

In some embodiments of any of the single-chain or multi-chain chimeric polypeptides described herein, the first target-binding domain and the second target-binding domain bind specifically to the same antigen. In some embodiments of these single-chain or multi-chain chimeric polypeptides, the first target-binding domain and the second target-binding domain bind specifically to the same epitope. In some embodiments of these single-chain or multi-chain chimeric polypeptides, the first target-binding domain and the second target-binding domain include the same amino acid sequence.

In some embodiments of any of the single-chain or multi-chain chimeric polypeptides described herein, the first target-binding domain and the second target-binding domain bind specifically to different antigens.

In some embodiments of any of the single-chain or multi-chain chimeric polypeptides described herein, one or both of the first target-binding domain and the second target-binding domain is an antigen-binding domain. In some embodiments of any of the single-chain or multi-chain chimeric polypeptides described herein, the first target-binding domain and the second target-binding domain are each antigen-binding domains. In some embodiments of any of the single-chain or multi-chain chimeric polypeptides described herein, the antigen-binding domain includes or is a scFv or a single domain antibody (e.g., a $Va_HH$ or a $V_{NAR}$ domain).

In some examples, an antigen-binding domain (e.g., any of the antigen-binding domains described herein) can bind specifically to any one of CD16a (see, e.g., those described in U.S. Pat. No. 9,035,026), CD28 (see, e.g., those described in U.S. Pat. No. 7,723,482), CD3 (see, e.g., those described in U.S. Pat. No. 9,226,962), CD33 (see, e.g., those described in U.S. Pat. No. 8,759,494), CD20 (see, e.g., those described in WO 2014/026054), CD19 (see, e.g., those described in U.S. Pat. No. 9,701,758), CD22 (see, e.g., those described in WO 2003/104425), CD123 (see, e.g., those described in WO 2014/130635), IL-1R (see, e.g., those described in U.S. Pat. No. 8,741,604), IL-1 (see, e.g., those described in WO 2014/095808), VEGF (see, e.g., those described in U.S. Pat. No. 9,090,684), IL-6R (see, e.g., those described in U.S. Pat. No. 7,482,436), IL-4 (see, e.g., those described in U.S. Patent Application Publication No. 2012/0171197), IL-10 (see, e.g., those described in U.S. Patent Application Publication No. 2016/0340413), PDL-1 (see, e.g., those described in Drees et al., *Protein Express. Purif.* 94:60-66, 2014), TIGIT (see, e.g., those described in U.S. Patent Application Publication No. 2017/0198042), PD-1 (see, e.g., those described in U.S. Pat. No. 7,488,802), TIM3 (see, e.g., those described in U.S. Pat. No. 8,552,156), CTLA4 (see, e.g., those described in WO 2012/120125), MICA (see, e.g., those described in WO 2016/154585), MICB (see, e.g., those described in U.S. Pat. No. 8,753,640), IL-6 (see, e.g., those described in Gejima et al., *Human Antibodies* 11(4): 121-129, 2002), IL-8 (see, e.g., those described in U.S. Pat. No. 6,117,980), TNFα (see, e.g., those described in Geng et al., *Immunol. Res.* 62(3): 377-385, 2015), CD26 (see, e.g., those described in WO 2017/189526), CD36 (see, e.g., those described in U.S. Patent Application Publication No. 2015/0259429), ULBP2 (see, e.g., those described in U.S. Pat. No. 9,273,136), CD30 (see, e.g., those described in Homach et al., *Scand. J. Immunol.* 48(5): 497-501, 1998), CD200 (see, e.g., those described in U.S. Pat. No. 9,085,623), IGF-1R (see, e.g., those described in U.S. Patent Application Publication No. 2017/0051063), MUC4AC (see, e.g., those described in WO 2012/170470), MUC5AC (see, e.g., those described in U.S. Pat. No. 9,238,084), Trop-2 (see, e.g., those described in WO 2013/068946), CMET (see, e.g., those described in Edwardraja et al., *Biotechnol. Bioeng.* 106(3): 367-375, 2010), EGFR (see, e.g., those described in Akbari et al., *Protein Expr. Purif.* 127:8-15, 2016), HER1 (see, e.g., those described in U.S. Patent Application Publication No. 2013/0274446), HER2 (see, e.g., those described in Cao et al., *Biotechnol. Lett.* 37(7): 1347-1354, 2015), HER3 (see, e.g., those described in U.S. Pat. No. 9,505,843), PSMA (see, e.g., those described in Parker et al., *Protein Expr. Purif.* 89(2): 136-145, 2013), CEA (see, e.g., those described in WO 1995/015341), B7H3 (see, e.g., those described in U.S. Pat. No. 9,371,395), EPCAM (see, e.g., those described in WO 2014/159531), BCMA (see, e.g., those described in Smith et al., *Mol. Ther.* 26(6): 1447-1456, 2018), P-cadherin (see, e.g., those described in U.S. Pat. No. 7,452,537), CEACAM5 (see, e.g., those described in U.S. Pat. No. 9,617,345), a UL16-binding protein (see, e.g., those described in WO 2017/083612), HLA-DR (see, e.g., Pistillo et al., *Exp. Clin. Immunogenet.* 14(2): 123-130, 1997), DLL4 (see, e.g., those described in WO 2014/007513), TYRO3 (see, e.g., those described in WO 2016/166348), AXL (see, e.g., those described in WO 2012/175692), MER (see, e.g., those described in WO 2016/106221), CD122 (see, e.g., those described in U.S. Patent Application Publication No. 2016/0367664), CD155 (see, e.g., those described in WO 2017/149538), or PDGF-DD (see, e.g., those described in U.S. Pat. No. 9,441,034).

The antigen-binding domains present in any of the single-chain or multi-chain chimeric polypeptides described herein are each independently selected from the group consisting of: a VHH domain, a VNAR domain, and a scFv. In some embodiments, any of the antigen-binding domains described herein is a BiTe, a (scFv) 2, a nanobody, a nanobody-HSA, a DART, a TandAb, a scDiabody, a scDiabody-CH3, scFv-CH-CL-scFv, a HSAbody, scDiabody-HAS, or a tandem-scFv. Additional examples of antigen-binding domains that can be used in any of the single-chain or multi-chain chimeric polypeptide are known in the art.

A VHH domain is a single monomeric variable antibody domain that can be found in camelids. A VNAR domain is a single monomeric variable antibody domain that can be found in cartilaginous fish. Non-limiting aspects of VHH domains and VNAR domains are described in, e.g., Cromie et al., *Curr. Top. Med. Chem.* 15:2543-2557, 2016; De Genst et al., *Dev. Comp. Immunol.* 30:187-198, 2006; De Meyer et al., *Trends Biotechnol.* 32:263-270, 2014; Kijanka et al., Nanomedicine 10:161-174, 2015; Kovaleva et al., *Expert. Opin. Biol. Ther.* 14:1527-1539, 2014; Krah et al., *Immunopharmacol. Immunotoxicol.* 38:21-28, 2016; Mujic-Delic et al., *Trends Pharmacol. Sci.* 35:247-255, 2014; Muyldermans, *J. Biotechnol.* 74:277-302, 2001; Muyldermans et al., *Trends Biochem. Sci.* 26:230-235, 2001; Muyldermans, *Ann. Rev. Biochem.* 82:775-797, 2013; Rahbarizadeh et al., *Immunol. Invest.* 40:299-338, 2011; Van Audenhove et al., *EBioMedicine* 8:40-48, 2016; Van Bockstaele et al., *Curr. Opin. Investig. Drugs* 10:1212-1224, 2009; Vincke et al., *Methods Mol. Biol.* 911:15-26, 2012; and Wesolowski et al., *Med. Microbiol. Immunol.* 198:157-174, 2009.

In some embodiments, each of the antigen-binding domains in the single-chain or multi-chain chimeric polypeptides described herein are both VHH domains, or at least one antigen-binding domain is a VHH domain. In some embodiments, each of the antigen-binding domains in the single-chain or multi-chain chimeric polypeptides described herein are both VNAR domains, or at least one antigen-binding domain is a VNAR domain. In some embodiments, each of the antigen-binding domains in the single-chain or multi-chain chimeric polypeptides described herein are both scFv domains, or at least one antigen-binding domain is a scFv domain.

In some embodiments, two or more of polypeptides present in the single-chain or multi-chain chimeric polypeptide can assemble (e.g., non-covalently assemble) to form any of the antigen-binding domains described herein, e.g., an antigen-binding fragment of an antibody (e.g., any of the antigen-binding fragments of an antibody described herein), a VHH-scAb, a VHH-Fab, a Dual scFab, a F(ab')$_2$, a diabody, a crossMab, a DAF (two-in-one), a DAF (four-in-one), a DutaMab, a DT-IgG, a knobs-in-holes common light chain, a knobs-in-holes assembly, a charge pair, a Fab-arm exchange, a SEEDbody, a LUZ-Y, a Fcab, a κλ-body, an orthogonal Fab, a DVD-IgG, a IgG(H)-scFv, a scFv-(H)IgG, IgG(L)-scFv, scFv-(L)IgG, IgG(L,H)-Fv, IgG(H)-V, V(H)-IgG, IgG (L)-V, V(L)-IgG, KIH IgG-scFab, 2scFv-IgG, IgG-2scFv, scFv4-Ig, Zybody, DVI-IgG, Diabody-CH3, a triple body, a miniantibody, a minibody, a TriBi minibody, scFv-CH3 KIH, Fab-scFv, a F(ab')$_2$-scFv$_2$, a scFv-KIH, a Fab-scFv-Fc, a tetravalent HCAb, a scDiabody-Fc, a Diabody-Fc, a tandem scFv-Fc, an Intrabody, a dock and lock, a 1 mm TAC, an IgG-IgG conjugate, a Cov-X-Body, and a scFv1-PEG-scFv2. See, e.g., Spiess et al., *Mol. Immunol.* 67:95-106, 2015, incorporated in its entirety herewith, for a description of these elements. Non-limiting examples of an antigen-binding fragment of an antibody include an Fv fragment, a Fab fragment, a F(ab')$_2$ fragment, and a Fab' fragment. Additional examples of an antigen-binding fragment of an antibody is an antigen-binding fragment of an IgG (e.g., an antigen-binding fragment of IgG1, IgG2, IgG3, or IgG4) (e.g., an antigen-binding fragment of a human or humanized IgG, e.g., human or humanized IgG1, IgG2, IgG3, or IgG4); an antigen-binding fragment of an IgA (e.g., an antigen-binding fragment of IgA1 or IgA2) (e.g., an antigen-binding fragment of a human or humanized IgA, e.g., a human or humanized IgA1 or IgA2); an antigen-binding fragment of an IgD (e.g., an antigen-binding fragment of a human or humanized IgD); an antigen-binding fragment of an IgE (e.g., an antigen-binding fragment of a human or humanized IgE); or an antigen-binding fragment of an IgM (e.g., an antigen-binding fragment of a human or humanized IgM).

An "Fv" fragment includes a non-covalently-linked dimer of one heavy chain variable domain and one light chain variable domain.

A "Fab" fragment includes, the constant domain of the light chain and the first constant domain ($C_{H1}$) of the heavy chain, in addition to the heavy and light chain variable domains of the Fv fragment.

A "F(ab')$_2$" fragment includes two Fab fragments joined, near the hinge region, by disulfide bonds.

A "dual variable domain immunoglobulin" or "DVD-Ig" refers to multivalent and multispecific binding proteins as described, e.g., in DiGiammarino et al., *Methods Mol. Biol.* 899:145-156, 2012; Jakob et al., *MABs* 5:358-363, 2013; and U.S. Pat. Nos. 7,612,181; 8,258,268; 8,586,714; 8,716,450; 8,722,855; 8,735,546; and 8,822,645, each of which is incorporated by reference in its entirety.

DARTs are described in, e.g., Garber, Nature Reviews Drug Discovery 13:799-801, 2014.

In some embodiments of any of the antigen-binding domains described herein can bind to an antigen selected from the group consisting of: a protein, a carbohydrate, a lipid, and a combination thereof.

Additional examples and aspects of antigen-binding domains are known in the art.

Soluble Interleukin or Cytokine Protein

In some embodiments of any of the single-chain or multi-chain chimeric polypeptides described herein, one or both of the first target-binding domain and the second target-binding domain can be a soluble interleukin protein or soluble cytokine protein. In some embodiments, the soluble interleukin or soluble cytokine protein is selected from the group of: IL-2, IL-3, IL-7, IL-8, IL-10, IL-12, IL-15, IL-17, IL-18, IL-21, PDGF-DD, SCF, and FLT3L. Non-limiting examples of soluble IL-2, IL-3, IL-7, IL-8, IL-10, IL-15, IL-17, IL-18, IL-21, PDGF-DD, SCF, and FLT3L are provided below.

Human Soluble IL-2
(SEQ ID NO: 75)
aptssstkkt qlqlehllld lqmilnginn yknpkltrml tfkfympkka
telkhlqcle eelkpleevl nlaqsknfhl rprdlisnin vivlelkgse
ttfmceyade tativeflnr witfcqsiis tlt Human Soluble IL-3
(SEQ ID NO: 76)
apmtqttplkt swvncsnmid eiithlkqpp lplldinnln gedqdilmen
nlrrpnleaf nravkslqna saiesilknl lpclplataa ptrhpihikd
gdwnefrrkl tfylktlena qaqqttlsla if Human Soluble IL-7
(SEQ ID NO: 77)
dcdiegkdgkqyesv lmvsidqlld smkeigsncl nnefnffkrh icdankegmf
lfraarklrq flkmnstgdf dlhllkvseg ttillnctgq vkgrkpaalg
eaqptkslee nkslkeqkkl ndlcflkrll qeiktcwnki lmgtkeh Human Soluble IL-8
(SEQ ID NO: 78)
egavlprsak elrcqcikty skpfhpkfik elrviesgph canteiivkl
sdgrelcldp kenwvqrvve kflkraens Human Soluble IL-10
(SEQ ID NO: 79)
spgqgtqsensc thfpgnlpnm lrdlrdafsr vktffqmkdq ldnlllkesl
ledfkgylgc qalsemiqfy leevmpqaen qdpdikahvn slgenlktlr
lrlrrchrfl pcenkskave qvknafnklq ekgiykamse fdifinyiea
ymtmkirn Human Soluble IL-15
(SEQ ID NO: 80)
nwvnvisdlkki edliqsmhid atlytesdvh psckvtamkc fllelqvisl
esgdasihdt venliilann slssngnvte sgckeceele eknikeflqs
fvhivqmfin ts Human Soluble IL-15 D8N Mutant
(SEQ ID NO: 99)
NWVNVISNLKKIEDLIQSMHIDATLYTESDVHPSCKVTAMKCFLLELQVISLESGDASI
HDTVENLIILANNSLSSNGNVTESGCKECEELEEKNIKEFLQSFVHIVQMFINTS Human Soluble IL-15 D8N Mutant
(SEQ ID NO: 100)
AACTGGGTGAACGTCATCAGCAATTTAAAGAAGATCGAAGATTTAATTCAGTC
CATGCATATCGACGCCACTTTATACACAGAATCCGACGTGCACCCCTCTTGTAA
GGTGACCGCCATGAAATGTTTTTTACTGGAGCTGCAAGTTATCTCTTTAGAGAG
CGGAGACGCTAGCATCCACGACACCGTGGAGAATTTAATCATTTTAGCCAATA
ACTCTTTATCCAGCAACGGCAACGTGACAGAGTCCGGCTGCAAGGAGTGCGA
AGAGCTGGAGGAGAAGAACATCAAGGAGTTTCTGCAATCCTTTGTGCACATTG
TCCAGATGTTCATCAATACCTCC Human Soluble IL-17
(SEQ ID NO: 81)
gitiprn pgcpnsedkn fprtvmvnln ihnrntntnp krssdyynrs
tspwnlhrne dperypsviw eakcrhlgci nadgnvdyhm nsvpiqqeil
vlrrepphcp nsfrlekilv svgctcvtpi vhhva Human Soluble IL-18
(SEQ ID NO: 82)
yfgklesklsvirn lndqvlfidq gnrplfedmt dsdcrdnapr tifiismykd
sqprgmavti svkcekistl scenkiisfk emnppdnikd tksdiiffqr
svpghdnkmq fesssyegyf lacekerdlf klilkkedel gdrsimftvq ned Human Soluble PDGF-DD
(SEQ ID NO: 83)
rdtsatpqsasi kalrnanlrr desnhltdly rrdetiqvkg ngyvqsprfp
nsyprnlllt wrlhsqentr iqlvfdnqfg leeaendicr ydfvevedis
etstiirgrw cghkevppri ksrtnqikit fksddyfvak pgfkiyysll
edfqpaaase tnwesvtssi sgvsynspsv tdptliadal dkkiaefdtv
edllkyfnpe swqedlenmy ldtpryrgrs yhdrkskvdl drlnddakry
sctprnysvn ireelklanv vffprcllvq rcggncgcgt vnwrsctens
gktvkkyhev lqfepghikr rgraktmalv diqldhherc dcicssrppr Human Soluble SCF
(SEQ ID NO: 84)
egicrnrvtnnvkdv tklvanlpkd ymitlkyvpg mdvlpshcwi semvvqlsds
ltdlldkfsn iseglsnysi idklvnivdd lvecvkenss kdlkksfksp
eprlftpeef frifnrsida fkdfvvaset sdcvvsstls pekdsrvsvt
kpfmlppvaa sslrndsssss nrkaknppgd sslhwaamal palfsliigf
afgalywkkr qpsltraven iqineednei smlqekeref qev -continued Human Soluble FLT3L
(SEQ ID NO: 85)
tqdcsfqhspissd favkirelsd yllqdypvtv asnlqdeelc gglwrlvlaq
rwmerlktva gskmqgller vnteihfvtk cafqpppscl rfvqtnisrl
lqetseqlva lkpwitrqnf srclelqcqp dsstlpppws prpleatapt
apqppllll llpvgllla aawclhwqrt rrrtprpgeq vppvpspqdl
llveh Non-limiting examples of soluble MICA, MICB, ULBP1,
ULBP2, ULBP3, ULBP4, ULBP5, and ULBP6 are provided below.

Human Soluble MICA
(SEQ ID NO: 86)
ephslry nltvlswdgs vqsgfltevh ldgqpflrcd rqkcrakpqg
qwaedvlgnk twdretrdlt gngkdlrmtl ahikdqkegl hslqeirvce
ihednstrss qhfyydgelf lsqnletkew tmpqssraqt lamnvrnflk
edamktkthy hamhadclqe lrrylksgvv lrrtvppmvn vtrseasegn
itvtcrasgf ypwnitlswr qdgvslshdt qqwgdvlpdg ngtyqtwvat
ricqgeeqrf tcymehsgnh sthpvpsgkv lvlqshwqtf hvsavaaaai
fviiifyvrc ckkktsaaeg pelvslqvld qhpvgtsdhr datqlgfqpl
msdlgstgst ega Human Soluble MICB
(SEQ ID NO: 87)
aephslry nlmvlsqdes vqsgflaegh ldgqpflryd rqkrrakpqg
qwaedvlgak twdtetedlt engqdlrrtl thikdqkggl hslqeirvce
ihedsstrgs rhfyydgelf lsqnletqes tvpqssraqt lamnvtnfwk
edamktkthy ramqadclqk lqrylksgva irrtvppmvn vtcsevsegn
itvtcrassf yprnitltwr qdgvslshnt qqwgdvlpdg ngtyqtwvat
rirqgeeqrf tcymehsgnh gthpvpsgkv lvlqsqrtdf pyvsaampcf
viiiilcvpc ckkktsaaeg pelvslqvld qhpvgtgdhr
daaqlgfqpl msatgstgst ega Human Soluble ULBP1
(SEQ ID NO: 88)
wvdthclcydfiit pksrpepqwc evqglvderp flhydcvnhk akafaslgkk
vnvtktweeq tetlrdvvdf lkgqlldiqv enlipieplt lqarmscehe
ahghgrgswq flfngqkfll fdsnnrkwta lhpgakkmte kweknrdvtm
ffqkislgdc kmwleeflmy weqmldptkp pslapg Human Soluble ULBP2
(SEQ ID NO: 89)
gradphslcyditvi pkfrpgprwc avqgqvdekt flhydcgnkt vtpvsplgkk
lnvttawkaq npvlrevvdi lteqlrdiql enytpkeplt lqarmsceqk
aeghssgswq fsfdgqifll fdsekrmwtt vhpgarkmke kwendkvvam
sfhyfsmgdc igwledflmg mdstlepsag aplams Human Soluble ULBP3
(SEQ ID NO: 90)
dahslwynfti ihlprhgqqw cevqsqvdqk nflsydcgsd kvlsmghlee
qlyatdawgk qlemlrevgq rlrleladte ledftpsgpl tlqvrmscec
eadgyirgsw qfsfdgrkfl lfdsnnrkwt vvhagarrmk ekwekdsglt
tffkmvsmrd ckswirdflm hrkkrlepta pptmapg Human Soluble ULBP4
(SEQ ID NO: 91)
hslcfnftik slsrpgqpwc eaqvflnknl flqynsdnnm vkplgllgkk
vyatstwgel tqtlgevgrd lrmllcdikp qiktsdpstl qvemfcqrea
erctgaswqf atngeksllf damnmtwtvi nheaskiket wkkdrgleky
frklskgdcd hwlreflghw eampeptvsp vnasdihwss sslpdrwiil
gafillvlmg ivlicvwwqn gewqaglwpl rts Human Soluble ULBP5
(SEQ ID NO: 92)
gladp hslcyditvi pkfrpgprwc avqgqvdekt flhydcgskt
vtpvsplgkk lnvttawkaq npvlrevvdi lteqlldiql enyipkeplt
lqarmsceqk aeghgsgswq lsfdgqifll fdsenrmwtt vhpgarkmke
kwendkdmtm sfhyismgdc tgwledflmg mdstlepsag apptmssg Human Soluble ULBP6
(SEQ ID NO: 93)
rrddp hslcyditvi pkfrpgprwc avqgqvdekt flhydcgnkt
vtpvsplgkk lnvtmawkaq npvlrevvdi lteqlldiql enytpkeplt
lqarmsceqk aeghssgswq fsidgqtfll fdsekrmwtt vhpgarkmke
kwendkdvam sfhyismgdc igwledflmg mdstlepsag aplamssg Additional examples of soluble interleukin proteins and soluble cytokine proteins are known in the art.

Soluble Receptor

In some embodiments of any of the single-chain or multi-chain chimeric polypeptides described herein, one or both of the first target-binding domain and the second target-binding domain is a soluble interleukin receptor or a soluble cytokine receptor. In some embodiments, the soluble receptor is a soluble TGF-β receptor II (TGF-β RII) (see, e.g., those described in Yung et al., *Am. J. Resp. Crit. Care*

*Med.* 194(9): 1140-1151, 2016), a soluble TGF-βRIII (see, e.g., those described in Heng et al., *Placenta* 57:320, 2017), a soluble NKG2D (see, e.g., Cosman et al., *Immunity* 14(2): 123-133, 2001; Costa et al., *Front. Immunol.*, Vol. 9, Article 1150 May 29, 2018; doi: 10.3389/fimmu.2018.01150), a soluble NKp30 (see, e.g., Costa et al., *Front. Immunol.*, Vol. 9, Article 1150 May 29, 2018; doi: 10.3389/fimmu.2018.01150), a soluble NKp44 (see, e.g., those described in Costa et al., *Front. Immunol.*, Vol. 9, Article 1150 May 29, 2018; doi: 10.3389/fimmu.2018.01150), a soluble NKp46 (see, e.g., Mandelboim et al., *Nature* 409: 1055-1060, 2001; Costa et al., *Front. Immunol.*, Vol. 9, Article 1150 May 29, 2018; doi: 10.3389/fimmu.2018.01150), a soluble DNAM1 (see, e.g., those described in Costa et al., *Front. Immunol.*, Vol. 9, Article 1150 May 29, 2018; doi: 10.3389/fimmu.2018.01150), a scMHCI (see, e.g., those described in Washburn et al., *PLOS One* 6(3): e18439, 2011), a scMHCII (see, e.g., those described in Bishwajit et al., *Cellular Immunol.* 170(1): 25-33, 1996), a scTCR (see, e.g., those described in Weber et al., *Nature* 356(6372): 793-796, 1992), a soluble CD155 (see, e.g., those described in Tahara-Hanaoka et al., *Int. Immunol.* 16(4): 533-538, 2004), or a soluble CD28 (see, e.g., Hebbar et al., *Clin. Exp. Immunol.* 136:388-392, 2004). Additional examples of soluble interleukin receptors and soluble cytokine receptors are known in the art.

Pairs of Affinity Domains

In some embodiments, a multi-chain chimeric polypeptide includes: 1) a first chimeric polypeptide that includes a first domain of a pair of affinity domains, and 2) a second chimeric polypeptide that includes a second domain of a pair of affinity domains such that the first chimeric polypeptide and the second chimeric polypeptide associate through the binding of the first domain and the second domain of the pair of affinity domains. In some embodiments, the pair of affinity domains is a sushi domain from an alpha chain of human IL-15 receptor (IL15Rα) and a soluble IL-15. A sushi domain, also known as a short consensus repeat or type 1 glycoprotein motif, is a common motif in protein-protein interaction. Sushi domains have been identified on a number of protein-binding molecules, including complement components C1r, C1s, factor H, and C2m, as well as the nonimmunologic molecules factor XIII and β2-glycoprotein. A typical Sushi domain has approximately 60 amino acid residues and contains four cysteines (Ranganathan, Pac. Symp Biocomput. 2000:155-67). The first cysteine can form a disulfide bond with the third cysteine, and the second cysteine can form a disulfide bridge with the fourth cysteine. In some embodiments in which one member of the pair of affinity domains is a soluble IL-15, the soluble IL15 has a D8N or D8A amino acid substitution. In some embodiments in which one member of the pair of affinity domains is an alpha chain of human IL-15 receptor (IL15Rα), the human IL15Rα is a mature full-length IL15Rα. In some embodiments, the pair of affinity domains is barnase and barnstar. In some embodiments, the pair of affinity domains is a PKA and an AKAP. In some embodiments, the pair of affinity domains is an adapter/docking tag module based on mutated RNase I fragments (Rossi, *Proc Natl Acad Sci USA.* 103: 6841-6846, 2006; Sharkey et al., *Cancer Res.* 68:5282-5290, 2008; Rossi et al., *Trends Pharmacol Sci.* 33:474-481, 2012) or SNARE modules based on interactions of the proteins syntaxin, synaptotagmin, synaptobrevin, and SNAP25 (Deyev et al., *Nat Biotechnol.* 1486-1492, 2003).

In some embodiments, a first chimeric polypeptide of a multi-chain chimeric polypeptide includes a first domain of a pair of affinity domains and a second chimeric polypeptide of the multi-chain chimeric polypeptide includes a second domain of a pair of affinity domains, wherein the first domain of the pair of affinity domains and the second domain of the pair of affinity domains bind to each other with a dissociation equilibrium constant ($K_D$) of less than $1 \times 10^{-7}$ M, less than $1 \times 10^{-8}$ M, less than $1 \times 10^{-9}$ M, less than $1 \times 10^{-10}$ M, less than $1 \times 10^{-11}$ M, less than $1 \times 10^{-12}$ M, or less than $1 \times 10^{-13}$ M. In some embodiments, the first domain of the pair of affinity domains and the second domain of the pair of affinity domains bind to each other with a $K_D$ of about $1 \times 10^{-4}$ M to about $1 \times 10^{-6}$ M, about $1 \times 10^{-5}$ M to about $1 \times 10^{-7}$ M, about $1 \times 10^{-6}$ M to about $1 \times 10^{-8}$ M, about $1 \times 10^{-7}$ M to about $1 \times 10^{-9}$ M, about $1 \times 10^{-8}$ M to about $1 \times 10^{-10}$ M, about $1 \times 10^{-9}$ M to about $1 \times 10^{-11}$ M, about $1 \times 10^{-10}$ M to about $1 \times 10^{-12}$ M, about $1 \times 10^{-11}$ M to about $1 \times 10^{-13}$ M, about $1 \times 10^{-4}$ M to about $1 \times 10^{-5}$ M, about $1 \times 10^{-5}$ M to about $1 \times 10^{-6}$ M, about $1 \times 10^{-6}$ M to about $1 \times 10^{-7}$ M, about $1 \times 10^{-7}$ M to about $1 \times 10^{-8}$ M, about $1 \times 10^{-8}$ M to about $1 \times 10^{-9}$ M, about $1 \times 10^{-9}$ M to about $1 \times 10^{-10}$ M, about $1 \times 10^{-10}$ M to about $1 \times 10^{-11}$ M, about $1 \times 10^{-11}$ M to about $1 \times 10^{-12}$ M, or about $1 \times 10^{-12}$ M to about $1 \times 10^{-13}$ M (inclusive). Any of a variety of different methods known in the art can be used to determine the $K_D$ value of the binding of the first domain of the pair of affinity domains and the second domain of the pair of affinity domains (e.g., an electrophoretic mobility shift assay, a filter binding assay, surface plasmon resonance, and a biomolecular binding kinetics assay, etc.).

In some embodiments, a first chimeric polypeptide of a multi-chain chimeric polypeptide includes a first domain of a pair of affinity domains and a second chimeric polypeptide of the multi-chain chimeric polypeptide includes a second domain of a pair of affinity domains, wherein the first domain of the pair of affinity domains, the second domain of the pair of affinity domains, or both is about 10 to 100 amino acids in length. For example, a first domain of a pair of affinity domains, a second domain of a pair of affinity domains, or both can be about 10 to 100 amino acids in length, about 15 to 100 amino acids in length, about 20 to 100 amino acids in length, about 25 to 100 amino acids in length, about 30 to 100 amino acids in length, about 35 to 100 amino acids in length, about 40 to 100 amino acids in length, about 45 to 100 amino acids in length, about 50 to 100 amino acids in length, about 55 to 100 amino acids in length, about 60 to 100 amino acids in length, about 65 to 100 amino acids in length, about 70 to 100 amino acids in length, about 75 to 100 amino acids in length, about 80 to 100 amino acids in length, about 85 to 100 amino acids in length, about 90 to 100 amino acids in length, about 95 to 100 amino acids in length, about 10 to 95 amino acids in length, about 10 to 90 amino acids in length, about 10 to 85 amino acids in length, about 10 to 80 amino acids in length, about 10 to 75 amino acids in length, about 10 to 70 amino acids in length, about 10 to 65 amino acids in length, about 10 to 60 amino acids in length, about 10 to 55 amino acids in length, about 10 to 50 amino acids in length, about 10 to 45 amino acids in length, about 10 to 40 amino acids in length, about 10 to 35 amino acids in length, about 10 to 30 amino acids in length, about 10 to 25 amino acids in length, about 10 to 20 amino acids in length, about 10 to 15 amino acids in length, about 20 to 30 amino acids in length, about 30 to 40 amino acids in length, about 40 to 50 amino acids in length, about 50 to 60 amino acids in length, about 60 to 70 amino acids in length, about 70 to 80 amino acids in length, about 80 to 90 amino acids in length, about 90 to 100 amino acids in length, about 20 to 90 amino acids in length, about 30 to 80 amino acids in length, about 40 to 70 amino acids in length, about 50 to 60 amino acids in length, or any range in between. In some embodiments, a first domain of a pair of affinity domains, a second domain of a pair of affinity domains, or both is about 10, 15, 20, 25, 30, 35, 40, 45, 50, 55, 60, 65, 70, 75, 80, 85, 90, 95, or 100 amino acids in length.

In some embodiments, any of the first and/or second domains of a pair of affinity domains disclosed herein can include one or more additional amino acids (e.g., 1, 2, 3, 5, 6, 7, 8, 9, 10, or more amino acids) at its N-terminus and/or C-terminus, so long as the function of the first and/or second domains of a pair of affinity domains remains intact. For example, a sushi domain from an alpha chain of human IL-15 receptor (IL15Rα) can include one or more additional amino acids at the N-terminus and/or the C-terminus, while still retaining the ability to bind to a soluble IL-15. Additionally or alternatively, a soluble IL-15 can include one or more additional amino acids at the N-terminus and/or the C-terminus, while still retaining the ability to bind to a sushi domain from an alpha chain of human IL-15 receptor (IL15Rα).

A non-limiting example of a sushi domain from an alpha chain of IL-15 receptor alpha (IL15Rα) can include a sequence that is at least 70% identical, at least 75% identical, at least 80% identical, at least 85% identical, at least 90% identical, at least 95% identical, at least 99% identical, or 100% identical to (SEQ ID NO: 94)
ITCPPPMSVEHADIWVKSYSLYSRERYICNSGFKRKAGTSSLTECVLNK
ATNVAHWTTPSLKCIR.

In some embodiments, a sushi domain from an alpha chain of IL15Rα can be encoded by a nucleic acid including (SEQ ID NO: 95)
ATTACATGCCCCCCTCCCATGAGCGTGGAGCACGCCGACATCTGGGTGA

AGAGCTATAGCCTCTACAGCCGGGAGAGGTATATCTGTAACAGCGGCTT

CAAGAGGAAGGCCGGCACCAGCAGCCTCACCGAGTGCGTGCTGAATAAG

GCTACCAACGTGGCTCACTGGACAACACCCTCTTTAAAGTGCATCCGG.

In some embodiments, a soluble IL-15 can include a sequence that is at least 70% identical, at least 75% identical, at least 80% identical, at least 85% identical, at least 90% identical, at least 95% identical, at least 99% identical, or 100% identical to (SEQ ID NO: 96)
NWVNVISDLKKIEDLIQSMHIDATLYTESDVHPSCKVTAMKCFLLELQV

ISLESGDASIHDTVENLIILANNSLSSNGNVTESGCKECEELEEKNIKE

FLQSFVHIVQMFINTS.

In some embodiments, a soluble IL-15 can be encoded by a nucleic acid including the sequence of (SEQ ID NO: 97)
AACTGGGTGAACGTCATCAGCGATTTAAAGAAGATCGAAGATTTAATTC

AGTCCATGCATATCGACGCCACTTTATACACAGAATCCGACGTGCACCC

CTCTTGTAAGGTGACCGCCATGAAATGTTTTTTACTGGAGCTGCAAGTT

ATCTCTTTAGAGAGCGGAGACGCTAGCATCCACGACACCGTGGAGAATT

TAATCATTTTAGCCAATAACTCTTTATCCAGCAACGGCAACGTGACAGA

GTCCGGCTGCAAGGAGTGCGAAGAGCTGGAGGAGAAGAACATCAAGGAG

TTTCTGCAATCCTTTGTGCACATTGTCCAGATGTTCATCAATACCTCC.

Single Chain Chimeric Polypeptides

A single-chain chimeric polypeptide includes: a first target-binding domain (e.g., any of the target-binding domains described herein or known in the art), a soluble tissue factor domain (e.g., any of the exemplary soluble tissue factor domains described herein or known in the art), and a second target-binding domain (e.g., any of the target-binding domains described herein or known in the art).

In some embodiments of any of the single-chain chimeric polypeptides described herein, the first target-binding domain (e.g., any of the exemplary target-binding domains described herein or known in the art) and the soluble tissue factor domain (e.g., any of the exemplary soluble tissue factor domains described herein) directly abut each other. In some embodiments of any of the single-chain chimeric polypeptides described herein, the single-chain chimeric polypeptide further comprises a linker sequence (e.g., any of the exemplary linker sequences described herein or known in the art) between the first target-binding domain (e.g., any of the exemplary target-binding domains described herein or known in the art) and the soluble tissue factor domain (e.g., any of the exemplary soluble tissue factor domains described herein). In some embodiments of any of the single-chain chimeric polypeptides described herein, the soluble tissue factor domain (e.g., any of the exemplary soluble tissue factor domains described herein) and the second target-binding domain (e.g., any of the exemplary target-binding domains described herein or known in the art) directly abut each other. In some embodiments of any of the single-chain chimeric polypeptides described herein, the single-chain chimeric polypeptide further comprises a linker sequence (e.g., any of the exemplary linker sequences described herein or known in the art) between the soluble tissue factor domain (e.g., any of the exemplary soluble tissue factor domains described herein) and the second target-binding domain (e.g., any of the exemplary target-binding domains described herein or known in the art).

In some embodiments of any of the single-chain chimeric polypeptides described herein, the first target-binding domain (e.g., any of the exemplary target-binding domains described herein or known in the art) and the second target-binding domain (e.g., any of the exemplary target-binding domains described herein or known in the art) directly abut each other. In some embodiments of any of the single-chain chimeric polypeptides described herein, the single-chain chimeric polypeptide further comprises a linker sequence (e.g., any of the exemplary linker sequences described herein or known in the art) between the first target-binding domain (e.g., any of the exemplary target-binding domains described herein or known in the art) and the second target-binding domain (e.g., any of the exemplary target-binding domains described herein or known in the art). In some embodiments of any of the single-chain chimeric polypeptides described herein, the second target-binding domain (e.g., any of the exemplary target-binding domains described herein or known in the art) and the soluble tissue factor domain (e.g., any of the exemplary soluble tissue factor domains described herein) directly abut each other. In some embodiments of any of the single-chain chimeric polypeptides described herein, the single-chain chimeric polypeptide further comprises a linker sequence (e.g., any of the exemplary linker sequences described herein or known in the art) between the second target-binding domain (e.g., any of the exemplary target-binding domains described herein or known in the art) and the soluble tissue factor domain (e.g., any of the exemplary soluble tissue factor domains described herein or known in the art).

In some examples of any of the single-chain chimeric polypeptides described herein, the single-chain chimeric polypeptide can have a total length of about 50 amino acids to about 3000 amino acids, about 50 amino acids to about 2500 amino acids, about 50 amino acids to about 2000 amino acids, about 50 amino acids to about 1500 amino acids, about 50 amino acids to about 1000 amino acids, about 50 amino acids to about 950 amino acids, about 50 amino acids to about 900 amino acids, about 50 amino acids to about 850 amino acids, about 50 amino acids to about 800 amino acids, about 50 amino acids to about 750 amino acids, about 50 amino acids to about 700 amino acids, about 50 amino acids to about 650 amino acids, about 50 amino acids to about 600 amino acids, about 50 amino acids to about 550 amino acids, about 50 amino acids to about 500 amino acids, about 50 amino acids to about 480 amino acids, about 50 amino acids to about 460 amino acids, about 50 amino acids to about 440 amino acids, about 50 amino acids to about 420 amino acids, about 50 amino acids to about 400 amino acids, about 50 amino acids to about 380 amino acids, about 50 amino acids to about 360 amino acids, about 50 amino acids to about 340 amino acids, about 50 amino acids to about 320 amino acids, about 50 amino acids to about 300 amino acids, about 50 amino acids to about 280 amino acids, about 50 amino acids to about 260 amino acids, about 50 amino acids to about 240 amino acids, about 50 amino acids to about 220 amino acids, about 50 amino acids to about 200 amino acids, about 50 amino acids to about 150 amino acids, about 50 amino acids to about 100 amino acids, about 100 amino acids to about 3000 amino acids, about 100 amino acids to about 2500 amino acids, about 100 amino acids to about 2000 amino acids, about 100 amino acids to about 1500 amino acids, about 100 amino acids to about 1000 amino acids, about 100 amino acids to about 950 amino acids, about 100 amino acids to about 900 amino acids, about 100 amino acids to about 850 amino acids, about 100 amino acids to about 800 amino acids, about 100 amino acids to about 750 amino acids, about 100 amino acids to about 700 amino acids, about 100 amino acids to about 650 amino acids, about 100 amino acids to about 600 amino acids, about 100 amino acids to about 550 amino acids, about 100 amino acids to about 500 amino acids, about 100 amino acids to about 480 amino acids, about 100 amino acids to about 460 amino acids, about 100 amino acids to about 440 amino acids, about 100 amino acids to about 420 amino acids, about 100 amino acids to about 400 amino acids, about 100 amino acids to about 380 amino acids, about 100 amino acids to about 360 amino acids, about 100 amino acids to about 340 amino acids, about 100 amino acids to about 320 amino acids, about 100 amino acids to about 300 amino acids, about 100 amino acids to about 280 amino acids, about 100 amino acids to about 260 amino acids, about 100 amino acids to about 240 amino acids, about 100 amino acids to about 220 amino acids, about 100 amino acids to about 200 amino acids, about 150 amino acids, about 150 amino acids to about 3000 amino acids, about 150 amino acids to about 2500 amino acids, about 150 amino acids to about 2000 amino acids, about 150 amino acids to about 1500 amino acids, about 150 amino acids to about 1000 amino acids, about 150 amino acids to about 950 amino acids, about 150 amino acids to about 900 amino acids, about 150 amino acids to about 850 amino acids, about 150 amino acids to about 800 amino acids, about 150 amino acids to about 750 amino acids, about 150 amino acids to about 700 amino acids, about 150 amino acids to about 650 amino acids, about 150 amino acids to about 600 amino acids, about 150 amino acids to about 550 amino acids, about 150 amino acids to about 500 amino acids, about 150 amino acids to about 480 amino acids, about 150 amino acids to about 460 amino acids, about 150 amino acids to about 440 amino acids, about 150 amino acids to about 420 amino acids, about 150 amino acids to about 400 amino acids, about 150 amino acids to about 380 amino acids, about 150 amino acids to about 360 amino acids, about 150 amino acids to about 340 amino acids, about 150 amino acids to about 320 amino acids, about 150 amino acids to about 300 amino acids, about 150 amino acids to about 280 amino acids, about 150 amino acids to about 260 amino acids, about 150 amino acids to about 240 amino acids, about 150 amino acids to about 220 amino acids, about 150 amino acids to about 200 amino acids, about 200 amino acids to about 3000 amino acids, about 200 amino acids to about 2500 amino acids, about 200 amino acids to about 2000 amino acids, about 200 amino acids to about 1500 amino acids, about 200 amino acids to about 1000 amino acids, about 200 amino acids to about 950 amino acids, about 200 amino acids to about 900 amino acids, about 200 amino acids to about 850 amino acids, about 200 amino acids to about 800 amino acids, about 200 amino acids to about 750 amino acids, about 200 amino acids to about 700 amino acids, about 200 amino acids to about 650 amino acids, about 200 amino acids to about 600 amino acids, about 200 amino acids to about 550 amino acids, about 200 amino acids to about 500 amino acids, about 200 amino acids to about 480 amino acids, about 200 amino acids to about 460 amino acids, about 200 amino acids to about 440 amino acids, about 200 amino acids to about 420 amino acids, about 200 amino acids to about 400 amino acids, about 200 amino acids to about 380 amino acids, about 200 amino acids to about 360 amino acids, about 200 amino acids to about 340 amino acids, about 200 amino acids to about 320 amino acids, about 200 amino acids to about 300 amino acids, about 200 amino acids to about 280 amino acids, about 200 amino acids to about 260 amino acids, about 200 amino acids to about 240 amino acids, about 200 amino acids to about 220 amino acids, about 220 amino acids to about 3000 amino acids, about 220 amino acids to about 2500 amino acids, about 220 amino acids to about 2000 amino acids, about 220 amino acids to about 1500 amino acids, about 220 amino acids to about 1000 amino acids, about 220 amino acids to about 950 amino acids, about 220 amino acids to about 900 amino acids, about 220 amino acids to about 850 amino acids, about 220 amino acids to about 800 amino acids, about 220 amino acids to about 750 amino acids, about 220 amino acids to about 700 amino acids, about 220 amino acids to about 650 amino acids, about 220 amino acids to about 600 amino acids, about 220 amino acids to about 550 amino acids, about 220 amino acids to about 500 amino acids, about 220 amino acids to about 480 amino acids, about 220 amino acids to about 460 amino acids, about 220 amino acids to about 440 amino acids, about 220 amino acids to about 420 amino acids, about 220 amino acids to about 400 amino acids, about 220 amino acids to about 380 amino acids, about 220 amino acids to about 360 amino acids, about 220 amino acids to about 340 amino acids, about 220 amino acids to about 320 amino acids, about 220 amino acids to about 300 amino acids, about 220 amino acids to about 280 amino acids, about 220 amino acids to about 260 amino acids, about 220 amino acids to about 240 amino acids, about 240 amino acids to about 3000 amino acids, about 240 amino acids to about 2500 amino acids, about 240 amino acids to about 2000 amino acids, about 240 amino acids to about 1500 amino acids, about 240 amino acids to about 1000 amino acids, about 240 amino acids to about 950 amino acids, about 240 amino acids to about 900 amino acids, about 240 amino acids to about 850 amino acids, about 240 amino acids to about 800 amino acids, about 240 amino acids to about 750 amino acids, about 240 amino acids to about 700 amino acids, about 240 amino acids to about 650 amino acids, about 240 amino acids to about 600 amino acids, about 240 amino acids to about 550 amino acids, about 240 amino acids to about 500 amino acids, about 240 amino acids to about 480 amino acids, about 240 amino acids to about 460 amino acids, about 240 amino acids to about 440 amino acids, about 240 amino acids to about 420 amino acids, about 240 amino acids to about 400 amino acids, about 240 amino acids to about 380 amino acids, about 240 amino acids to about 360 amino acids, about 240 amino acids to about 340 amino acids, about 240 amino acids to about 320 amino acids, about 240 amino acids to about 300 amino acids, about 240 amino acids to about 280 amino acids, about 240 amino acids to about 260 amino acids, about 260 amino acids to about 3000 amino acids, about 260 amino acids to about 2500 amino acids, about 260 amino acids to about 2000 amino acids, about 260 amino acids to about 1500 amino acids, about 260 amino acids to about 1000 amino acids, about 260 amino acids to about 950 amino acids, about 260 amino acids to about 900 amino acids, about 260 amino acids to about 850 amino acids, about 260 amino acids to about 800 amino acids, about 260 amino acids to about 750 amino acids, about 260 amino acids to about 700 amino acids, about 260 amino acids to about 650 amino acids, about 260 amino acids to about 600 amino acids, about 260 amino acids to about 550 amino acids, about 260 amino acids to about 500 amino acids, about 260 amino acids to about 480 amino acids, about 260 amino acids to about 460 amino acids, about 260 amino acids to about 440 amino acids, about 260 amino acids to about 420 amino acids, about 260 amino acids to about 400 amino acids, about 260 amino acids to about 380 amino acids, about 260 amino acids to about 360 amino acids, about 260 amino acids to about 340 amino acids, about 260 amino acids to about 320 amino acids, about 260 amino acids to about 300 amino acids, about 260 amino acids to about 280 amino acids, about 280 amino acids to about 3000 amino acids, about 280 amino acids to about 2500 amino acids, about 280 amino acids to about 2000 amino acids, about 280 amino acids to about 1500 amino acids, about 280 amino acids to about 1000 amino acids, about 280 amino acids to about 950 amino acids, about 280 amino acids to about 900 amino acids, about 280 amino acids to about 850 amino acids, about 280 amino acids to about 800 amino acids, about 280 amino acids to about 750 amino acids, about 280 amino acids to about 700 amino acids, about 280 amino acids to about 650 amino acids, about 280 amino acids to about 600 amino acids, about 280 amino acids to about 550 amino acids, about 280 amino acids to about 500 amino acids, about 280 amino acids to about 480 amino acids, about 280 amino acids to about 460 amino acids, about 280 amino acids to about 440 amino acids, about 280 amino acids to about 420 amino acids, about 280 amino acids to about 400 amino acids, about 280 amino acids to about 380 amino acids, about 280 amino acids to about 360 amino acids, about 280 amino acids to about 340 amino acids, about 280 amino acids to about 320 amino acids, about 280 amino acids to about 300 amino acids, about 300 amino acids to about 3000 amino acids, about 300 amino acids to about 2500 amino acids, about 300 amino acids to about 2000 amino acids, about 300 amino acids to about 1500 amino acids, about 300 amino acids to about 1000 amino acids, about 300 amino acids to about 950 amino acids, about 300 amino acids to about 900 amino acids, about 300 amino acids to about 850 amino acids, about 300 amino acids to about 800 amino acids, about 300 amino acids to about 750 amino acids, about 300 amino acids to about 700 amino acids, about 300 amino acids to about 650 amino acids, about 300 amino acids to about 600 amino acids, about 300 amino acids to about 550 amino acids, about 300 amino acids to about 500 amino acids, about 300 amino acids to about 480 amino acids, about 300 amino acids to about 460 amino acids, about 300 amino acids to about 440 amino acids, about 300 amino acids to about 420 amino acids, about 300 amino acids to about 400 amino acids, about 300 amino acids to about 380 amino acids, about 300 amino acids to about 360 amino acids, about 300 amino acids to about 340 amino acids, about 320 amino acids to about 3000 amino acids, about 320 amino acids to about 2500 amino acids, about 320 amino acids to about 2000 amino acids, about 320 amino acids to about 1500 amino acids, about 320 amino acids to about 1000 amino acids, about 320 amino acids to about 950 amino acids, about 320 amino acids to about 900 amino acids, about 320 amino acids to about 850 amino acids, about 320 amino acids to about 800 amino acids, about 320 amino acids to about 750 amino acids, about 320 amino acids to about 700 amino acids, about 320 amino acids to about 650 amino acids, about 320 amino acids to about 600 amino acids, about 320 amino acids to about 550 amino acids, about 320 amino acids to about 500 amino acids, about 320 amino acids to about 480 amino acids, about 320 amino acids to about 460 amino acids, about 320 amino acids to about 440 amino acids, about 320 amino acids to about 420 amino acids, about 320 amino acids to about 400 amino acids, about 320 amino acids to about 380 amino acids, about 320 amino acids to about 360 amino acids, about 320 amino acids to about 340 amino acids, about 340 amino acids to about 3000 amino acids, about 340 amino acids to about 2500 amino acids, about 340 amino acids to about 2000 amino acids, about 340 amino acids to about 1500 amino acids, about 340 amino acids to about 1000 amino acids, about 340 amino acids to about 950 amino acids, about 340 amino acids to about 900 amino acids, about 340 amino acids to about 850 amino acids, about 340 amino acids to about 800 amino acids, about 340 amino acids to about 750 amino acids, about 340 amino acids to about 700 amino acids, about 340 amino acids to about 650 amino acids, about 340 amino acids to about 600 amino acids, about 340 amino acids to about 550 amino acids, about 340 amino acids to about 500 amino acids, about 340 amino acids to about 480 amino acids, about 340 amino acids to about 460 amino acids, about 340 amino acids to about 440 amino acids, about 340 amino acids to about 420 amino acids, about 340 amino acids to about 400 amino acids, about 340 amino acids to about 380 amino acids, about 340 amino acids to about 360 amino acids, about 360 amino acids to about 3000 amino acids, about 360 amino acids to about 2500 amino acids, about 360 amino acids to about 2000 amino acids, about 360 amino acids to about 1500 amino acids, about 360 amino acids to about 1000 amino acids, about 360 amino acids to about 950 amino acids, about 360 amino acids to about 900 amino acids to about 850 amino acids, about 360 amino acids to about 800 amino acids, about 360 amino acids to about 750 amino acids, about 360 amino acids to about 700 amino acids, about 360 amino acids to about 650 amino acids, about 360 amino acids to about 600 amino acids, about 360 amino acids to about 550 amino acids, about 360 amino acids to about 500 amino acids, about 360 amino acids to about 480 amino acids, about 360 amino acids to about 460 amino acids, about 360 amino acids to about 440 amino acids, about 360 amino acids to about 420 amino acids, about 360 amino acids to about 400 amino acids, about 360 amino acids to about 380 amino acids, about 380 amino acids to about 3000 amino acids, about 380 amino acids to about 2500 amino acids, about 380 amino acids to about 2000 amino acids, about 380 amino acids to about 1500 amino acids, about 380 amino acids to about 1000 amino acids, about 380 amino acids to about 950 amino acids, about 380 amino acids to about 900 amino acids, about 380 amino acids to about 850 amino acids, about 380 amino acids to about 800 amino acids, about 380 amino acids to about 750 amino acids, about 380 amino acids to about 700 amino acids, about 380 amino acids to about 650 amino acids, about 380 amino acids to about 600 amino acids, about 380 amino acids to about 550 amino acids, about 380 amino acids to about 500 amino acids, about 380 amino acids to about 480 amino acids, about 380 amino acids to about 460 amino acids, about 380 amino acids to about 440 amino acids, about 380 amino acids to about 420 amino acids, about 380 amino acids to about 400 amino acids, about 400 amino acids to about 3000 amino acids, about 400 amino acids to about 2500 amino acids, about 400 amino acids to about 2000 amino acids, about 400 amino acids to about 1500 amino acids, about 400 amino acids to about 1000 amino acids, about 400 amino acids to about 950 amino acids, about 400 amino acids to about 900 amino acids, about 400 amino acids to about 850 amino acids, about 400 amino acids to about 800 amino acids, about 400 amino acids to about 750 amino acids, about 400 amino acids to about 700 amino acids, about 400 amino acids to about 650 amino acids, about 400 amino acids to about 600 amino acids, about 400 amino acids to about 550 amino acids, about 400 amino acids to about 500 amino acids, about 400 amino acids to about 480 amino acids, about 400 amino acids to about 460 amino acids, about 400 amino acids to about 440 amino acids, about 400 amino acids to about 420 amino acids, about 420 amino acids to about 3000 amino acids, about 420 amino acids to about 2500 amino acids, about 420 amino acids to about 2000 amino acids, about 420 amino acids to about 1500 amino acids, about 420 amino acids to about 1000 amino acids, about 420 amino acids to about 950 amino acids, about 420 amino acids to about 900 amino acids, about 420 amino acids to about 850 amino acids, about 420 amino acids to about 800 amino acids, about 420 amino acids to about 750 amino acids, about 420 amino acids to about 700 amino acids, about 420 amino acids to about 650 amino acids, about 420 amino acids to about 600 amino acids, about 420 amino acids to about 550 amino acids, about 420 amino acids to about 500 amino acids, about 420 amino acids to about 480 amino acids, about 420 amino acids to about 460 amino acids, about 420 amino acids to about 440 amino acids, about 440 amino acids to about 3000 amino acids, about 440 amino acids to about 2500 amino acids, about 440 amino acids to about 2000 amino acids, about 440 amino acids to about 1500 amino acids, about 440 amino acids to about 1000 amino acids, about 440 amino acids to about 950 amino acids, about 440 amino acids to about 900 amino acids, about 440 amino acids to about 850 amino acids, about 440 amino acids to about 800 amino acids, about 440 amino acids to about 750 amino acids, about 440 amino acids to about 700 amino acids, about 440 amino acids to about 650 amino acids, about 440 amino acids to about 600 amino acids, about 440 amino acids to about 550 amino acids, about 440 amino acids to about 500 amino acids, about 440 amino acids to about 480 amino acids, about 440 amino acids to about 460 amino acids, about 460 amino acids to about 3000 amino acids, about 460 amino acids to about 2500 amino acids, about 460 amino acids to about 2000 amino acids, about 460 amino acids to about 1500 amino acids, about 460 amino acids to about 1000 amino acids, about 460 amino acids to about 950 amino acids, about 460 amino acids to about 900 amino acids, about 460 amino acids to about 850 amino acids, about 460 amino acids to about 800 amino acids, about 460 amino acids to about 750 amino acids, about 460 amino acids to about 700 amino acids, about 460 amino acids to about 650 amino acids, about 460 amino acids to about 600 amino acids, about 460 amino acids to about 550 amino acids, about 460 amino acids to about 500 amino acids, about 460 amino acids to about 480 amino acids, about 480 amino acids to about 3000 amino acids, about 480 amino acids to about 2500 amino acids, about 480 amino acids to about 2000 amino acids, about 480 amino acids to about 1500 amino acids, about 480 amino acids to about 1000 amino acids, about 480 amino acids to about 950 amino acids, about 480 amino acids to about 900 amino acids, about 480 amino acids to about 850 amino acids, about 480 amino acids to about 800 amino acids, about 480 amino acids to about 750 amino acids, about 480 amino acids to about 700 amino acids, about 480 amino acids to about 650 amino acids, about 480 amino acids to about 600 amino acids, about 480 amino acids to about 550 amino acids, about 480 amino acids to about 500 amino acids, about 500 amino acids to about 3000 amino acids, about 500 amino acids to about 2500 amino acids, about 500 amino acids to about 2000 amino acids, about 500 amino acids to about 1500 amino acids, about 500 amino acids to about 1000 amino acids, about 500 amino acids to about 950 amino acids, about 500 amino acids to about 900 amino acids, about 500 amino acids to about 850 amino acids, about 500 amino acids to about 800 amino acids, about 500 amino acids to about 750 amino acids, about 500 amino acids to about 700 amino acids, about 500 amino acids to about 650 amino acids, about 500 amino acids to about 600 amino acids, about 500 amino acids to about 550 amino acids, about 550 amino acids to about 3000 amino acids, about 550 amino acids to about 2500 amino acids, about 550 amino acids to about 2000 amino acids, about 550 amino acids to about 1500 amino acids, about 550 amino acids to about 1000 amino acids, about 550 amino acids to about 950 amino acids, about 550 amino acids to about 900 amino acids, about 550 amino acids to about 850 amino acids, about 550 amino acids to about 800 amino acids, about 550 amino acids to about 750 amino acids, about 550 amino acids to about 700 amino acids, about 550 amino acids to about 650 amino acids, about 550 amino acids to about 600 amino acids, about 600 amino acids to about 3000 amino acids, about 600 amino acids to about 2500 amino acids, about 600 amino acids to about 2000 amino acids, about 600 amino acids to about 1500 amino acids, about 600 amino acids to about 1000 amino acids, about 600 amino acids to about 950 amino acids, about 600 amino acids to about 900 amino acids, about 600 amino acids to about 850 amino acids, about 600 amino acids to about 800 amino acids, about 600 amino acids to about 750 amino acids, about 600 amino acids to about 700 amino acids, about 600 amino acids to about 650 amino acids, about 650 amino acids to about 3000 amino acids, about 650 amino acids to about 2500 amino acids, about 650 amino acids to about 2000 amino acids, about 650 amino acids to about 1500 amino acids, about 650 amino acids to about 1000 amino acids, about 650 amino acids to about 950 amino acids, about 650 amino acids to about 900 amino acids, about 650 amino acids to about 850 amino acids, about 650 amino acids to about 800 amino acids, about 650 amino acids to about 750 amino acids, about 650 amino acids to about 700 amino acids, about 700 amino acids to about 3000 amino acids, about 700 amino acids to about 2500 amino acids, about 700 amino acids to about 2000 amino acids, about 700 amino acids to about 1500 amino acids, about 700 amino acids to about 1000 amino acids, about 700 amino acids to about 950 amino acids, about 700 amino acids to about 900 amino acids, about 700 amino acids to about 850 amino acids, about 700 amino acids to about 800 amino acids, about 700 amino acids to about 750 amino acids, about 750 amino acids to about 3000 amino acids, about 750 amino acids to about 2500 amino acids, about 750 amino acids to about 2000 amino acids, about 750 amino acids to about 1500 amino acids, about 750 amino acids to about 1000 amino acids, about 750 amino acids to about 950 amino acids, about 750 amino acids to about 900 amino acids, about 750 amino acids to about 850 amino acids, about 750 amino acids to about 800 amino acids, about 800 amino acids to about 3000 amino acids, about 800 amino acids to about 2500 amino acids, about 800 amino acids to about 2000 amino acids, about 800 amino acids to about 1500 amino acids, about 800 amino acids to about 1000 amino acids, about 800 amino acids to about 950 amino acids, about 800 amino acids to about 900 amino acids, about 800 amino acids to about 850 amino acids, about 850 amino acids to about 3000 amino acids, about 850 amino acids to about 2500 amino acids, about 850 amino acids to about 2000 amino acids, about 850 amino acids to about 1500 amino acids, about 850 amino acids to about 1000 amino acids, about 850 amino acids to about 950 amino acids, about 850 amino acids to about 900 amino acids, about 900 amino acids to about 3000 amino acids, about 900 amino acids to about 2500 amino acids, about 900 amino acids to about 2000 amino acids, about 900 amino acids to about 1500 amino acids, about 900 amino acids to about 1000 amino acids, about 900 amino acids to about 950 amino acids, about 950 amino acids to about 3000 amino acids, about 950 amino acids to about 2500 amino acids, about 950 amino acids to about 2000 amino acids, about 950 amino acids to about 1500 amino acids, about 1000 amino acids to about 3000 amino acids, about 1000 amino acids to about 2500 amino acids, about 1000 amino acids to about 2000 amino acids, about 1000 amino acids to about 1500 amino acids, about 1500 amino acids to about 3000 amino acids, about 1500 amino acids to about 2500 amino acids, about 1500 amino acids to about 2000 amino acids, about 2000 amino acids to about 3000 amino acids, about 2000 amino acids to about 2500 amino acids, or about 2500 amino acids to about 3000 amino acids.

Exemplary IL-2 Receptor Activating Agents that are Single-Chain Chimeric Polypeptides In some embodiments, a single-chain chimeric polypeptide can be an IL-2 receptor activating agent. In such embodiments, one or both of the first target-binding domain and/or the second target-binding domain bind to a receptor for IL-2 (e.g., a human receptor for IL-2).

In some embodiments of any of the single-chain chimeric polypeptides that are an IL-2 receptor activating agent, the first target-binding domain and/or the second target-binding domain can be an agonistic antigen-binding domain that binds specifically to an IL-2 receptor (e.g., a human IL-2 receptor) (see, e.g., those described in Gaulton et al., *Clin. Immunol. Immunopathol.* 36(1): 18-29, 1985)).

In some embodiments of any of the single-chain chimeric polypeptides that are an IL-2 receptor activating agent, one or both of the first target-binding domain and the second target-binding domain can be a soluble interleukin 2 (IL-2) protein. An exemplary sequence of soluble IL-2 is provided below.

```
Human Soluble IL-2
                                    (SEQ ID NO: 1)
aptssstkkt qlqlehllld lqmilnginn yknpkltrml tfkfympkka telkhlqcle eelkpleevl nlaqsknfhl rprdlisnin vivlelkgse ttfmceyade tativeflnr witfcqsiis tlt
```

In some embodiments of these single-chain chimeric polypeptides, the first target-binding domain and the second target-binding domain is a soluble human IL-2 protein. A non-limiting example of an IL-2 protein that binds specifically to an IL-2 receptor can include a sequence that is at least 80% identical (e.g., at least 82% identical, at least 84% identical, at least 86% identical, at least 88% identical, at least 90% identical, at least 92% identical, at least 94% identical, at least 96% identical, at least 98% identical, at least 99% identical, or 100% identical) to SEQ ID NO: 1.

In some embodiments, a soluble human IL-2 protein can be encoded by a sequence that is at least 80% identical (e.g., at least 82% identical, at least 84% identical, at least 86% identical, at least 88% identical, at least 90% identical, at least 92% identical, at least 94% identical, at least 96% identical, at least 98% identical, at least 99% identical, or 100% identical) to:

```
                                   (SEQ ID NO: 31)
GCACCTACTTCAAGTTCTACAAAGAAAACACAGCTACAACTGGAGCATT

TACTGCTGGATTTACAGATGATTTTGAATGGAATTAATAATTACAAGAA

TCCCAAACTCACCAGGATGCTCACATTTAAGTTTTACATGCCCAAGAAG

GCCACAGAACTGAAACATCTTCAGTGTCTAGAAGAAGAACTCAAACCTC

TGGAGGAAGTGCTAAATTTAGCTCAAAGCAAAAACTTTCACTTAAGACC

CAGGGACTTAATCAGCAATATCAACGTAATAGTTCTGGAACTAAAGGGA

TCTGAAACAACATTCATGTGTGAATATGCTGATGAGACAGCAACCATTG

TAGAATTTCTGAACAGATGGATTACCTTTTGTCAAAGCATCATCTCAAC

ACTAACT.
```

In some embodiments, a soluble human IL-2 protein can be encoded by a sequence that is at least 80% identical (e.g., at least 82% identical, at least 84% identical, at least 86% identical, at least 88% identical, at least 90% identical, at least 92% identical, at least 94% identical, at least 96% identical, at least 98% identical, at least 99% identical, or 100% identical) to:

(SEQ ID NO: 32)
GCCCCCACCTCCTCCTCCACCAAGAAGACCCAGCTGCAGCTGGAGCATT

TACTGCTGGATTTACAGATGATTTTAAACGGCATCAACAACTACAAGAA

CCCCAAGCTGACTCGTATGCTGACCTTCAAGTTCTACATGCCCAAGAAG

GCCACCGAGCTGAAGCATTTACAGTGTTTAGAGGAGGAGCTGAAGCCCC

TCGAGGAGGTGCTGAATTTAGCCCAGTCCAAGAATTTCCATTTAAGGCC

CCGGGATTTAATCAGCAACATCAACGTGATCGTTTTAGAGCTGAAGGGC

TCCGAGACCACCTTCATGTGCGAGTACGCCGACGAGACCGCCACCATCG

TGGAGTTTTTAAATCGTTGGATCACCTTCTGCCAGTCCATCATCTCCAC

TTTAACC

In some embodiments, a single-chain chimeric polypeptide that is an IL-2 receptor activating agent can include a sequence that is at least 80% identical (e.g., at least 82% identical, at least 84% identical, at least 86% identical, at least 88% identical, at least 90% identical, at least 92% identical, at least 94% identical, at least 96% identical, at least 98% identical, at least 99% identical, or 100% identical) to:

(SEQ ID NO: 3)
APTSSSTKKTQLQLEHLLLDLQMILNGINNYKNPKLTRMLTFKFYMPKK

ATELKHLQCLEEELKPLEEVLNLAQSKNFHLRPRDLISNINVIVLELKG

SETTFMCEYADETATIVEFLNRWITFCQSIISTLTSGTTNTVAAYNLTW

KSTNFKTILEWEPKPVNQVYTVQISTKSGDWKSKCFYTTDTECDLTDEI
VKDVKQTYLARVFSYPAGNVESTGSAGEPLYENSPEFTPYLETNLGQPT
IQSFEQVGTKVNVTVEDERTLVRRNNTFLSLRDVFGKDLIYTLYYWKSS
SSGKKTAKTNTNEFLIDVDKGENYCFSVQAVIPSRTVNRKSTDSPVECM
GQEKGEFREAPTSSSTKKTQLQLEHLLLDLQMILNGINNYKNPKLTRML
TFKFYMPKKATELKHLQCLEEELKPLEEVLNLAQSKNFHLRPRDLISNI
NVIVLELKGSETTFMCEYADETATIVEFLNRWITFCQSIISTLT.

In some embodiments, a single-chain chimeric polypeptide that is an IL-2 receptor activating agent is encoded by a sequence that is at least 80% identical (e.g., at least 82% identical, at least 84% identical, at least 86% identical, at least 88% identical, at least 90% identical, at least 92% identical, at least 94% identical, at least 96% identical, at least 98% identical, at least 99% identical, or 100% identical) to:

(SEQ ID NO: 11)
GCCCCCACCTCCTCCTCCACCAAGAAGACCCAGCTGCAGCTGGAGCATT
TACTGCTGGATTTACAGATGATTTTAAACGGCATCAACAACTACAAGAA
CCCCAAGCTGACTCGTATGCTGACCTTCAAGTTCTACATGCCCAAGAAG
GCCACCGAGCTGAAGCATTTACAGTGTTTAGAGGAGGAGCTGAAGCCCC
TCGAGGAGGTGCTGAATTTAGCCCAGTCCAAGAATTTCCATTTAAGGCC
CCGGGATTTAATCAGCAACATCAACGTGATCGTTTTAGAGCTGAAGGGC
TCCGAGACCACCTTCATGTGCGAGTACGCCGACGAGACCGCCACCATCG
TGGAGTTTTTAAATCGTTGGATCACCTTCTGCCAGTCCATCATCTCCAC

-continued

TTTAACCAGCGGCACAACCAACACAGTCGCTGCCTATAACCTCACTTGG
AAGAGCACCAACTTCAAAACCATCCTCGAATGGGAACCCAAACCCGTTA
ACCAAGTTTACACCGTGCAGATCAGCACCAAGTCCGGCGACTGGAAGTC
CAAATGTTTCTATACCACCGACACCGAGTGCGATCTCACCGATGAGATC
GTGAAAGATGTGAAACAGACCTACCTCGCCCGGGTGTTTAGCTACCCCG
CCGGCAATGTGGAGAGCACTGGTTCCGCTGGCGAGCCTTTATACGAGAA
CAGCCCCGAATTTACCCCTTACCTCGAGACCAATTTAGGACAGCCCACC
ATCCAAAGCTTTGAGCAAGTTGGCACAAAGGTGAATGTGACAGTGGAGG
ACGAGCGGACTTTAGTGCGGCGGAACAACACCTTTCTCAGCCTCCGGGA
TGTGTTCGGCAAAGATTTAATCTACACACTGTATTACTGGAAGTCCTCT
TCCTCCGGCAAGAAGACAGCTAAAACCAACACAAACGAGTTTTTAATCG
ACGTGGATAAAGGCGAAAACTACTGTTTCAGCGTGCAAGCTGTGATCCC
CTCCCGGACCGTGAATAGGAAAAGCACCGATAGCCCCGTTGAGTGCATG
GGCCAAGAAAAGGGCGAGTTCCGGGAGGCACCTACTTCAAGTTCTACAA
AGAAAACACAGCTACAACTGGAGCATTTACTGCTGGATTTACAGATGAT
TTTGAATGGAATTAATAATTACAAGAATCCCAAACTCACCAGGATGCTC
ACATTTAAGTTTTACATGCCCAAGAAGGCCACAGAACTGAAACATCTTC
AGTGTCTAGAAGAAGAACTCAAACCTCTGGAGGAAGTGCTAAATTTAGC
TCAAAGCAAAAACTTTCACTTAAGACCCAGGGACTTAATCAGCAATATC
AACGTAATAGTTCTGGAACTAAAGGGATCTGAAACAACATTCATGTGTG
AATATGCTGATGAGACAGCAACCATTGTAGAATTTCTGAACAGATGGAT
TACCTTTTGTCAAAGCATCATCTCAACACTAACT.

In some embodiments, a single-chain chimeric polypeptide that is an IL-2 receptor activating agent can include a sequence that is at least 80% identical (e.g., at least 82% identical, at least 84% identical, at least 86% identical, at least 88% identical, at least 90% identical, at least 92% identical, at least 94% identical, at least 96% identical, at least 98% identical, at least 99% identical, or 100% identical) to:

(SEQ ID NO: 4)
MKWVTFISLLFLFSSAYSAPTSSSTKKTQLQLEHLLLDLQMILNGINNYK
NPKLTRMLTFKFYMPKKATELKHLQCLEEELKPLEEVLNLAQSKNFHLRP
RDLISNINVIVLELKGSETTFMCEYADETATIVEFLNRWITFCQSIISTL
TSGTTNTVAAYNLTWKSTNFKTILEWEPKPVNQVYTVQISTKSGDWKSKC
FYTTDTECDLTDEIVKDVKQTYLARVFSYPAGNVESTGSAGEPLYENSPE
FTPYLETNLGQPTIQSFEQVGTKVNVTVEDERTLVRRNNTFLSLRDVFGK
DLIYTLYYWKSSSSGKKTAKTNTNEFLIDVDKGENYCFSVQAVIPSRTVN
RKSTDSPVECMGQEKGEFREAPTSSSTKKTQLQLEHLLLDLQMILNGINN
YKNPKLTRMLTFKFYMPKKATELKHLQCLEEELKPLEEVLNLAQSKNFHL
RPRDLISNINVIVLELKGSETTFMCEYADETATIVEFLNRWITFCQSIIS
TLT.

In some embodiments, a single-chain chimeric polypeptide that is an IL-2 receptor activating agent is encoded by a sequence that is at least 80% identical (e.g., at least 82% identical, at least 84% identical, at least 86% identical, at least 88% identical, at least 90% identical, at least 92% identical, at least 94% identical, at least 96% identical, at least 98% identical, at least 99% identical, or 100% identical) to:

(SEQ ID NO: 12)
ATGAAGTGGGTGACCTTCATCAGCCTGCTGTTCCTGTTCTCCAGCGCCTA

CTCCGCCCCACCTCCTCCTCCACCAAGAAGACCCAGCTGCAGCTGGAGC

ATTTACTGCTGGATTTACAGATGATTTTAAACGGCATCAACAACTACAAG

AACCCCAAGCTGACTCGTATGCTGACCTTCAAGTTCTACATGCCCAAGAA

GGCCACCGAGCTGAAGCATTTACAGTGTTTAGAGGAGGAGCTGAAGCCCC

TCGAGGAGGTGCTGAATTTAGCCCAGTCCAAGAATTTCCATTTAAGGCCC

CGGGATTTAATCAGCAACATCAACGTGATCGTTTTAGAGCTGAAGGGCTC

CGAGACCACCTTCATGTGCGAGTACGCCGACGAGACCGCCACCATCGTGG

AGTTTTTAAATCGTTGGATCACCTTCTGCCAGTCCATCATCTCCACTTTA

ACCAGCGGCACAACCAACACAGTCGCTGCCTATAACCTCACTTGGAAGAG

CACCAACTTCAAAACCATCCTCGAATGGGAACCCAAACCCGTTAACCAAG

TTTACACCGTGCAGATCAGCACCAAGTCCGGCGACTGGAAGTCCAAATGT

TTCTATACCACCGACACCGAGTGCGATCTCACCGATGAGATCGTGAAAGA

TGTGAAACAGACCTACCTCGCCCGGGTGTTTAGCTACCCCGCCGGCAATG

TGGAGAGCACTGGTTCCGCTGGCGAGCCTTTATACGAGAACAGCCCCGAA

TTTACCCCTTACCTCGAGACCAATTTAGGACAGCCCACCATCCAAAGCTT

TGAGCAAGTTGGCACAAAGGTGAATGTGACAGTGGAGGACGAGCGGACTT

TAGTGCGGCGGAACAACACCTTTCTCAGCCTCCGGGATGTGTTCGGCAAA

GATTTAATCTACACACTGTATTACTGGAAGTCCTCTTCCTCCGGCAAGAA

GACAGCTAAAACCAACACAAACGAGTTTTTAATCGACGTGGATAAAGGCG

AAAACTACTGTTTCAGCGTGCAAGCTGTGATCCCCTCCCGGACCGTGAAT

AGGAAAAGCACCGATAGCCCCGTTGAGTGCATGGGCCAAGAAAAGGGCGA

GTTCCGGGAGGCACCTACTTCAAGTTCTACAAAGAAAACACAGCTACAAC

TGGAGCATTTACTGCTGGATTTACAGATGATTTTGAATGGAATTAATAAT

TACAAGAATCCCAAACTCACCAGGATGCTCACATTTAAGTTTTACATGCC

CAAGAAGGCCACAGAACTGAAACATCTTCAGTGTCTAGAAGAAGAACTCA

AACCTCTGGAGGAAGTGCTAAATTTAGCTCAAAGCAAAAACTTTCACTTA

AGACCCAGGGACTTAATCAGCAATATCAACGTAATAGTTCTGGAACTAAA

GGGATCTGAAACAACATTCATGTGTGAATATGCTGATGAGACAGCAACCA

TTGTAGAATTTCTGAACAGATGGATTACCTTTTGTCAAAGCATCATCTCA

ACACTAACT.

Exemplary CD3/CD38 Binding Agents that are Single-Chain Chimeric Polypeptides

In some embodiments where the single-chain chimeric polypeptide is an CD3/CD28 binding agent, the first target-binding domain binds specifically to CD3 (e.g., one or more of CD3δ (e.g., human CD3δ), CD3ε (e.g., human CD3ε), CD3γ (e.g., human CD3γ), and CD3ζ (e.g., human CD3ζ)) and the second target-binding domain binds specifically to CD28 (e.g., human CD28).

In some embodiments, the first target-binding domain that binds specifically to CD3 (e.g., one or more of CD3δ (e.g., human CD3δ), CD3ε (e.g., human CD3ε), CD3γ (e.g., human CD3γ), and CD3ζ (e.g., human CD3ζ)) is an antigen-binding domain (e.g., any of the exemplary antigen-binding domains described herein, e.g., an anti-CD3 scFv).

In some embodiments, the first target binding domain can be an anti-CD3 scFv. In some embodiments, the anti-CD3 scFv can include a heavy chain variable domain including a sequence that is at least 70% identical (e.g., at least 75% identical, at least 80% identical, at least 85% identical, at least 90% identical, at least 95% identical, at least 99% identical, or 100% identical) to:

(SEQ ID NO: 21)
QVQLQQSGAELARPGASVKMSCKASGYTFTRYTMHWVKQRPGQGLEWIGY

INPSRGYTNYNQKFKDKATLTTDKSSSTAYMQLSSLTSEDSAVYYCARYY

DDHYCLDYWGQGTTLTVSS and/or a light chain variable domain including a sequence that is at least 70% identical (e.g., at least 75% identical, at least 80% identical, at least 85% identical, at least 90% identical, at least 95% identical, at least 99% identical, or 100% identical) to:

(SEQ ID NO: 22)
QIVLTQSPAIMSASPGEKVTMTCSASSSVSYMNWYQQKSGTSPKRWIYDT

SKLASGVPAHFRGSGSGTSYSLTISGMEAEDAATYYCQQWSSNPFTFGSG

TKLEINR.

In some embodiments, a scFv (e.g., any of the scFvs described herein) can include a linker sequence (e.g., any of the exemplary linker sequences described herein or known in the art) between the heavy chain variable domain and the light chain variable domain.

In some embodiments, the anti-CD3 scFv can include a heavy chain variable domain encoded by a nucleic acid including a sequence that is at least 70% identical (e.g., at least 75% identical, at least 80% identical, at least 85% identical, at least 90% identical, at least 95% identical, at least 99% identical, or 100% identical) to:

(SEQ ID NO: 23)
CAAGTTCAGCTCCAGCAAAGCGGCGCCGAACTCGCTCGGCCCGGCGCTTC

CGTGAAGATGTCTTGTAAGGCCTCCGGCTATACCTTCACCCGGTACACAA

TGCACTGGGTCAAGCAACGGCCCGGTCAAGGTTTAGAGTGGATTGGCTAT

ATCAACCCCTCCCGGGGCTATACCAACTACAACCAGAAGTTCAAGGACAA

AGCCACCCTCACCACCGACAAGTCCAGCAGCACCGCTTACATGCAGCTGA

GCTCTTTAACATCCGAGGATTCCGCCGTGTACTACTGCGCTCGGTACTAC

GACGATCATTACTGCCTCGATTACTGGGGCCAAGGTACCACCTTAACAGT

CTCCTCC, and/or a light chain variable domain encoded by a nucleic acid including a sequence that is at least 70% identical (e.g., at least 75% identical, at least 80% identical, at least 85% identical, at least 90% identical, at least 95% identical, at least 99% identical, or 100% identical) to:

(SEQ ID NO: 24)
CAGATCGTGCTGACCCAGTCCCCCGCTATTATGAGCGCTAGCCCCGGTGA

AAAGGTGACTATGACATGCAGCGCCAGCTCTTCCGTGAGCTACATGAACT

GGTATCAGCAGAAGTCCGGCACCAGCCCTAAAAGGTGGATCTACGACACC

AGCAAGCTGGCCAGCGGCGTCCCCGCTCACTTTCGGGGCTCCGGCTCCGG

AACAAGCTACTCTCTGACCATCAGCGGCATGGAAGCCGAGGATGCCGCTA

CCTATTACTGTCAGCAGTGGAGCTCCAACCCCTTCACCTTTGGATCCGGC

ACCAAGCTCGAGATTAATCGT.

In some embodiments, an anti-CD3 scFv can include a sequence that is at least 70% identical (e.g., at least 75% identical, at least 80% identical, at least 85% identical, at least 90% identical, at least 95% identical, at least 99% identical, or 100% identical) to:

(SEQ ID NO: 5)
QIVLTQSPAIMSASPGEKVTMTCSASSSVSYMNWYQQKSGTSPKRWIYDT

SKLASGVPAHFRGSGSGTSYSLTISGMEAEDAATYYCQQWSSNPFTFGSG

TKLEINRGGGGSGGGGSGGGGSQVQLQQSGAELARPGASVKMSCKASGYT

FTRYTMHWVKQRPGQGLEWIGYINPSRGYTNYNQKFKDKATLTTDKSSST

AYMQLSSLTSEDSAVYYCARYYDDHYCLDYWGQGTTLTVSS.

In some embodiments, an anti-CD3 scFv can include the six CDRs present in SEQ ID NO: 5.

In some embodiments, an anti-CD3 scFv can include a sequence encoded by a nucleic acid sequence that is at least 70% identical (e.g., at least 75% identical, at least 80% identical, at least 85% identical, at least 90% identical, at least 95% identical, at least 99% identical, or 100% identical) to:

(SEQ ID NO: 25)
CAGATCGTGCTGACCCAGTCCCCCGCTATTATGAGCGCTAGCCCCGGTGA

AAAGGTGACTATGACATGCAGCGCCAGCTCTTCCGTGAGCTACATGAACT

GGTATCAGCAGAAGTCCGGCACCAGCCCTAAAAGGTGGATCTACGACACC

AGCAAGCTGGCCAGCGGCGTCCCCGCTCACTTTCGGGGCTCCGGCTCCGG

AACAAGCTACTCTCTGACCATCAGCGGCATGGAAGCCGAGGATGCCGCTA

CCTATTACTGTCAGCAGTGGAGCTCCAACCCCTTCACCTTTGGATCCGGC

ACCAAGCTCGAGATTAATCGTGGAGGCGGAGGTAGCGGAGGAGGCGGATC

CGGCGGTGGAGGTAGCCAAGTTCAGCTCCAGCAAAGCGGCGCCGAACTCG

CTCGGCCCGGCGCTTCCGTGAAGATGTCTTGTAAGGCCTCCGGCTATACC

TTCACCCGGTACACAATGCACTGGGTCAAGCAACGGCCCGGTCAAGGTTT

AGAGTGGATTGGCTATATCAACCCCTCCCGGGGCTATACCAACTACAACC

AGAAGTTCAAGGACAAAGCCACCCTCACCACCGACAAGTCCAGCAGCACC

GCTTACATGCAGCTGAGCTCTTTAACATCCGAGGATTCCGCCGTGTACTA

CTGCGCTCGGTACTACGACGATCATTACTGCCTCGATTACTGGGCCAAG

GTACCACCTTAACAGTCTCCTCC.

In some embodiments, the second target-binding domain that binds specifically to CD28 (e.g., human CD28) is an antigen-binding domain (e.g., any of the exemplary antigen-binding domains described herein, e.g., an anti-CD28 scFv).

In some embodiments, the anti-CD28 scFv can include a heavy chain variable domain including a sequence that is at least 70% identical (e.g., at least 75% identical, at least 80% identical, at least 85% identical, at least 90% identical, at least 95% identical, at least 99% identical, or 100% identical) to:

(SEQ ID NO: 26)
DIEMTQSPAIMSASLGERVTMTCTASSSVSSSYFHWYQQKPGSSPKLCIY

STSNLASGVPPRFSGSGSTSYSLTISSMEAEDAATYFCHQYHRSPTFGGG

TKLETKR and/or a light chain variable domain including a sequence that is at least 70% identical (e.g., at least 75% identical, at least 80% identical, at least 85% identical, at least 90% identical, at least 95% identical, at least 99% identical, or 100% identical) to:

(SEQ ID NO: 27)
VQLQQSGPELVKPGASVKMSCKASGYTFTSYVIQWVKQKPGQGLEWIGSI

NPYNDYTKYNEKFKGKATLTSDKSSITAYMEFSSLTSEDSALYYCARWGD

GNYWGRGTTLTVSS.

In some embodiments, the anti-CD28 scFv can include a heavy chain variable domain encoded by a nucleic acid including a sequence that is at least 70% identical (e.g., at least 75% identical, at least 80% identical, at least 85% identical, at least 90% identical, at least 95% identical, at least 99% identical, or 100% identical) to:

(SEQ ID NO: 28)
GACATCGAGATGACACAGTCCCCCGCTATCATGAGCGCCTCTTTAGGAGA

ACGTGTGACCATGACTTGTACAGCTTCCTCCAGCGTGAGCAGCTCCTATT

TCCACTGGTACCAGCAGAAACCCGGCTCCTCCCCTAAACTGTGTATCTAC

TCCACAAGCAATTTAGCTAGCGGCGTGCCTCCTCGTTTTAGCGGCTCCGG

CAGCACCTCTTACTCTTTAACCATTAGCTCTATGGAGGCCGAAGATGCCG

CCACATACTTTTGCCATCAGTACCACCGGTCCCCTACCTTTGGCGGAGGC

ACAAAGCTGGAGACCAAGCGG, and/or a light chain variable domain encoded by a nucleic acid including a sequence that is at least 70% identical (e.g., at least 75% identical, at least 80% identical, at least 85% identical, at least 90% identical, at least 95% identical, at least 99% identical, or 100% identical) to:

(SEQ ID NO: 29)
GTGCAGCTGCAGCAGTCCGGACCCGAACTGGTCAAGCCCGGTGCCTCCGT

GAAAATGTCTTGTAAGGCTTCTGGCTACACCTTTACCTCCTACGTCATCC

AATGGGTGAAGCAGAAGCCCGGTCAAGGTCTCGAGTGGATCGGCAGCATC

AATCCCTACAACGATTACACCAAGTATAACGAAAAGTTTAAGGGCAAGGC

CACTCTGACAAGCGACAAGAGCTCCATTACCGCCTACATGGAGTTTTCCT

CTTTAACTTCTGAGGACTCCGCTTTATACTATTGCGCTCGTTGGGGCGAT

GGCAATTATTGGGGCCGGGGAACTACTTTAACAGTGAGCTCC.

In some embodiments, an anti-CD28 scFv can include a sequence that is at least 70% identical (e.g., at least 75% identical, at least 80% identical, at least 85% identical, at least 90% identical, at least 95% identical, at least 99% identical, or 100% identical) to:

(SEQ ID NO: 6)
VQLQQSGPELVKPGASVKMSCKASGYTFTSYVIQWVKQKPGQGLEWIGSI

NPYNDYTKYNEFKGKATLTSDKSSITAYMEFSSLTSEDSALYYCARWGD

GNYWGRGTTLTVSSGGGGSGGGGSGGGGSDIEMTQSPAIMSASLGERVTM

TCTASSSVSSSYFHWYQQKPGSSPKLCIYSTSNLASGVPPRFSGSGSTSY

SLTISSMEAEDAATYFCHQYHRSPTFGGGTKLETKR.

In some embodiments, an anti-CD28 scFv can include the six CDRs present in SEQ ID NO: 6.

In some embodiments, an anti-CD28 scFv can include a sequence encoded by a nucleic acid sequence that is at least 70% identical (e.g., at least 75% identical, at least 80% identical, at least 85% identical, at least 90% identical, at least 95% identical, at least 99% identical, or 100% identical) to:

(SEQ ID NO: 30)
GTGCAGCTGCAGCAGTCCGGACCCGAACTGGTCAAGCCCGGTGCCTCCGT

GAAAATGTCTTGTAAGGCTTCTGGCTACACCTTTACCTCCTACGTCATCC

AATGGGTGAAGCAGAAGCCCGGTCAAGGTCTCGAGTGGATCGGCAGCATC

AATCCCTACAACGATTACACCAAGTATAACGAAAAGTTTAAGGGCAAGGC

CACTCTGACAAGCGACAAGAGCTCCATTACCGCCTACATGGAGTTTTCCT

CTTTAACTTCTGAGGACTCCGCTTTATACTATTGCGCTCGTTGGGGCGAT

GGCAATTATTGGGGCCGGGGAACTACTTTAACAGTGAGCTCCGGCGGCGG

CGGAAGCGGAGGTGGAGGATCTGGCGGTGGAGGCAGCGACATCGAGATGA

CACAGTCCCCCGCTATCATGAGCGCCTCTTTAGGAGAACGTGTGACCATG

ACTTGTACAGCTTCCTCCAGCGTGAGCAGCTCCTATTTCCACTGGTACCA

GCAGAAACCCGGCTCCTCCCCTAAACTGTGTATCTACTCCACAAGCAATT

TAGCTAGCGGCGTGCCTCCTCGTTTTAGCGGCTCCGGCAGCACCTCTTAC

TCTTTAACCATTAGCTCTATGGAGGCCGAAGATGCCGCCACATACTTTTG

CCATCAGTACCACCGGTCCCCTACCTTTGGCGGAGGCACAAAGCTGGAGA

CCAAGCGG.

In some embodiments, a single-chain chimeric polypeptide that is a CD3/CD28-binding agent can include a sequence that is at least 70% identical (e.g., at least 75% identical, at least 80% identical, at least 85% identical, at least 90% identical, at least 95% identical, at least 99% identical, or 100% identical) to:

(SEQ ID NO: 7)
QIVLTQSPAIMSASPGEKVTMTCSASSSVSYMNWYQQKSGTSPKRWIYDT

SKLASGVPAHFRGSGSGTSYSLTISGMEAEDAATYYCQQWSSNPFTFGSG

TKLEINRGGGGSGGGGSGGGGSQVQLQQSGAELARPGASVKMSCKASGYT

FTRYTMHWVKQRPGQGLEWIGYINPSRGYTNYNQKFKDKATLTTDKSSST

AYMQLSSLTSEDSAVYYCARYYDDHYCLDYWGQGTTLTVSSSGTTNTVAA

YNLTWKSTNFKTILEWEPKPVNQVYTVQISTKSGDWKSKCFYTTDTECDL

TDEIVKDVKQTYLARVFSYPAGNVESTGSAGEPLYENSPEFTPYLETNLG

QPTIQSFEQVGTKVNVTVEDERTLVRRNNTFLSLRDVFGKDLIYTLYYWK

SSSSGKKTAKTNTNEFLIDVDKGENYCFSVQAVIPSRTVNRKSTDSPVEC

MGQEKGEFREVQLQQSGPELVKPGASVKMSCKASGYTFTSYVIQWVKQKP

GQGLEWIGSINPYNDYTKYNEFKGKATLTSDKSSITAYMEFSSLTSEDS

ALYYCARWGDGNYWGRGTTLTVSSGGGGSGGGGSGGGGSDIEMTQSPAIM

SASLGERVTMTCTASSSVSSSYFHWYQQKPGSSPKLCIYSTSNLASGVPP

RFSGSGSTSYSLTISSMEAEDAATYFCHQYHRSPTFGGGTKLETKR.

In some embodiments, a single-chain chimeric polypeptide that is a CD3/CD28-binding agent is encoded by a nucleic acid that includes a sequence that is at least 70% identical (e.g., at least 75% identical, at least 80% identical, at least 85% identical, at least 90% identical, at least 95% identical, at least 99% identical, or 100% identical) to (SEQ ID NO: 9)
CAGATCGTGCTGACCCAAAGCCCCGCCATCATGAGCGCTAGCCCCGGTGA

GAAGGTGACCATGACATGCTCCGCTTCCAGCTCCGTGTCCTACATGAACT

GGTATCAGCAGAAAAGCGGAACCAGCCCCAAAAGGTGGATCTACGACACC

AGCAAGCTGGCCTCCGGAGTGCCCGCTCATTTCCGGGGCTCTGGATCCGG

CACCAGCTACTCTTTAACCATTTCCGGCATGGAAGCTGAAGACGCTGCCA

CCTACTATTGCCAGCAATGGAGCAGCAACCCCTTCACATTCGGATCTGGC

ACCAAGCTCGAAATCAATCGTGGAGGAGGTGGCAGCGGCGGCGGTGGATC

CGGCGGAGGAGGAAGCCAAGTTCAACTCCAGCAGAGCGGCGCTGAACTGG

CCCGGCCCGGCGCCTCCGTCAAGATGAGCTGCAAGGCTTCCGGCTATACA

TTTACTCGTTACACAATGCATTGGGTCAAGCAGAGGCCCGGTCAAGGTTT

AGAGTGGATCGGATATATCAACCCTTCCCGGGGCTACACCAACTATAACC

AAAAGTTCAAGGATAAAGCCACTTTAACCACTGACAAGAGCTCCTCCACC

GCCTACATGCAGCTGTCCTCTTTAACCAGCGAGGACTCCGCTGTTTACTA

CTGCGCTAGGTATTACGACGACCACTACTGTTTAGACTATTGGGACAAG

GTACCACTTTAACCGTCAGCAGCTCCGGCACCACCAATACCGTGGCCGCT

TATAACCTCACATGGAAGAGCACCAACTTCAAGACAATTCTGGAATGGGA

ACCCAAGCCCGTCAATCAAGTTTACACCGTGCAGATCTCCACCAAATCCG

GAGACTGGAAGAGCAAGTGCTTCTACACAACAGACACCGAGTGTGATTTA

ACCGACGAAATCGTCAAGGACGTCAAGCAAACCTATCTGGCTCGGGTCTT

TTCCTACCCCGCTGGCAATGTCGAGTCCACCGGCTCCGCTGGCGAGCCTC

TCTACGAGAATTCCCCCGAATTCACCCCTTATTTAGAGACCAATTTAGGC

CAGCCTACCATCCAGAGCTTCGAGCAAGTTGGCACCAAGGTGAACGTCAC

CGTCGAGGATGAAAGGACTTTAGTGCGGCGGAATAACACATTTTTATCCC

TCCGGGATGTGTTCGGCAAAGACCTCATCTACACACTGTACTATTGGAAG

TCCAGCTCCTCCGGCAAAAAGACCGCTAAGACCAACACCAACGAGTTTTT

-continued
```
AATTGACGTGGACAAAGGCGAGAACTACTGCTTCAGCGTGCAAGCCGTGA

TCCCTTCTCGTACCGTCAACCGGAAGAGCACAGATTCCCCCGTTGAGTGC

ATGGGCCAAGAAAAGGGCGAGTTCCGGGAGGTCCAGCTGCAGCAGAGCGG

ACCCGAACTCGTGAAACCCGGTGCTTCCGTGAAAATGTCTTGTAAGGCCA

GCGGATACACCTTCACCTCCTATGTGATCCAGTGGGTCAAACAGAAGCCC

GGACAAGGTCTCGAGTGGATCGGCAGCATCAACCCTTACAACGACTATAC

CAAATACAACGAGAAGTTTAAGGGAAAGGCTACTTTAACCTCCGACAAAA

GCTCCATCACAGCCTACATGGAGTTCAGCTCTTTAACATCCGAGGACAGC

GCTCTGTACTATTGCGCCCGGTGGGGCGACGGCAATTACTGGGGACGGGG

CACAACACTGACCGTGAGCAGCGGAGGCGGAGGCTCCGGCGGAGGCGGAT

CTGGCGGTGGCGGCTCCGACATCGAGATGACCCAGTCCCCCGCTATCATG

TCCGCCTCTTTAGGCGAGCGGGTCACAATGACTTGTACAGCCTCCTCCAG

CGTCTCCTCCTCCTACTTCCATTGGTACCAACAGAAACCCGGAAGCTCCC

CTAAACTGTGCATCTACAGCACCAGCAATCTCGCCAGCGGCGTGCCCCCT

AGGTTTTCCGGAAGCGGAAGCACCAGCTACTCTTTAACCATCTCCTCCAT

GGAGGCTGAGGATGCCGCCACCTACTTTTGTCACCAGTACCACCGGTCCC

CCACCTTCGGAGGCGGCACCAAACTGGAGACAAAGAGG.
```

In some embodiments, a single-chain chimeric polypeptide that is a CD3/CD28-binding agent can include a sequence that is at least 70% identical (e.g., at least 75% identical, at least 80% identical, at least 85% identical, at least 90% identical, at least 95% identical, at least 99% identical, or 100% identical) to:

```
                                       (SEQ ID NO: 8)
MKWVTFISLLFLFSSAYSQIVLTQSPAIMSASPGEKVTMTCSASSSVSYM

NWYQQKSGTSPKRWIYDTSKLASGVPAHFRGSGSGTSYSLTISGMEAEDA

ATYYCQQWSSNPFTFGSGTKLEINRGGGGSGGGGSGGGGSQVQLQQSGAE

LARPGASVKMSCKASGYTFTRYTMHWVKQRPGQGLEWIGYINPSRGYTNY

NQKFKDKATLTTDKSSSTAYMQLSSLTSEDSAVYYCARYYDDHYCLDYWG

QGTTLTVSSSGTTNTVAAYNLTWKSTNFKTILEWEPKPVNQVYTVQISTK

SGDWKSKCFYTTDTECDLTDEIVKDVKQTYLARVFSYPAGNVESTGSAGE

PLYENSPEFTPYLETNLGQPTIQSFEQVGTKVNVTVEDERTLVRRNNTFL

SLRDVFGKDLIYTLYYWKSSSSGKKTAKTNTNEFLIDVDKGENYCFSVQA

VIPSRTVNRKSTDSPVECMGQEKGEFREVQLQQSGPELVKPGASVKMSCK

ASGYTFTSYVIQWVKQKPGQGLEWIGSINPYNDYTKYNEKFKGKATLTSD

KSSITAYMEFSSLTSEDSALYYCARWGDGNYWGRGTTLTVSSGGGGSGGG

GSGGGGSDIEMTQSPAIMSASLGERVTMTCTASSSVSSSYFHWYQQKPGS

SPKLCIYSTSNLASGVPPRFSGSGSTSYSLTISSMEAEDAATYFCHQYHR

SPTFGGGTKLETKR.
```

In some embodiments, a single-chain chimeric polypeptide that is a CD3/CD28-binding agent is encoded by a nucleic acid that includes a sequence that is at least 70% identical (e.g., at least 75% identical, at least 80% identical, at least 85% identical, at least 90% identical, at least 95% identical, at least 99% identical, or 100% identical) to:

```
                                       (SEQ ID NO: 10)
ATGAAGTGGGTGACCTTCATCAGCTTATTATTTTTATTCAGCTCCGCCTA

TTCCCAGATCGTGCTGACCCAAAGCCCCGCCATCATGAGCGCTAGCCCCG

GTGAGAAGGTGACCATGACATGCTCCGCTTCCAGCTCCGTGTCCTACATG

AACTGGTATCAGCAGAAAAGCGGAACCAGCCCCAAAAGGTGGATCTACGA

CACCAGCAAGCTGGCCTCCGGAGTGCCCGCTCATTTCCGGGGCTCTGGAT

CCGGCACCAGCTACTCTTTAACCATTTCCGGCATGGAAGCTGAAGACGCT

GCCACCTACTATTGCCAGCAATGGAGCAGCAACCCCTTCACATTCGGATC

TGGCACCAAGCTCGAAATCAATCGTGGAGGAGGTGGCAGCGGCGGCGGTG

GATCCGGCGGAGGAGGAAGCCAAGTTCAACTCCAGCAGAGCGGCGCTGAA

CTGGCCCGGCCCGGCGCCTCCGTCAAGATGAGCTGCAAGGCTTCCGGCTA

TACATTTACTCGTTACACAATGCATTGGGTCAAGCAGAGGCCCGGTCAAG

GTTTAGAGTGGATCGGATATATCAACCCTTCCCGGGGCTACACCAACTAT

AACCAAAAGTTCAAGGATAAAGCCACTTTAACCACTGACAAGAGCTCCTC

CACCGCCTACATGCAGCTGTCCTCTTTAACCAGCGAGGACTCCGCTGTTT

ACTACTGCGCTAGGTATTACGACGACCACTACTGTTTAGACTATTGGGGA

CAAGGTACCACTTTAACCGTCAGCAGCTCCGGCACCACCAATACCGTGGC

CGCTTATAACCTCACATGGAAGAGCACCAACTTCAAGACAATTCTGGAAT

GGGAACCCAAGCCCGTCAATCAAGTTTACACCGTGCAGATCTCCACCAAA

TCCGGAGACTGGAAGAGCAAGTGCTTCTACACAACAGACACCGAGTGTGA

TTTAACCGACGAAATCGTCAAGGACGTCAAGCAAACCTATCTGGCTCGGG

TCTTTTCCTACCCCGCTGGCAATGTCGAGTCCACCGGCTCCGCTGGCGAG

CCTCTCTACGAGAATTCCCCCGAATTCACCCCTTATTTAGAGACCAATTT

AGGCCAGCCTACCATCCAGAGCTTCGAGCAAGTTGGCACCAAGGTGAACG

TCACCGTCGAGGATGAAAGGACTTTAGTGCGGCGGAATAACACATTTTTA

TCCCTCCGGGATGTGTTCGGCAAAGACCTCATCTACACACTGTACTATTG

GAAGTCCAGCTCCTCCGGCAAAAAGACCGCTAAGACCAACACCAACGAGT

TTTTAATTGACGTGGACAAAGGCGAGAACTACTGCTTCAGCGTGCAAGCC

GTGATCCCTTCTCGTACCGTCAACCGGAAGAGCACAGATTCCCCCGTTGA

GTGCATGGGCCAAGAAAAGGGCGAGTTCCGGGAGGTCCAGCTGCAGCAGA

GCGGACCCGAACTCGTGAAACCCGGTGCTTCCGTGAAAATGTCTTGTAAG

GCCAGCGGATACACCTTCACCTCCTATGTGATCCAGTGGGTCAAACAGAA

GCCCGGACAAGGTCTCGAGTGGATCGGCAGCATCAACCCTTACAACGACT

ATACCAAATACAACGAGAAGTTTAAGGGAAAGGCTACTTTAACCTCCGAC

AAAAGCTCCATCACAGCCTACATGGAGTTCAGCTCTTTAACATCCGAGGA

CAGCGCTCTGTACTATTGCGCCCGGTGGGGCGACGGCAATTACTGGGGAC

GGGGCACAACACTGACCGTGAGCAGCGGAGGCGGAGGCTCCGGCGGAGGC

GGATCTGGCGGTGGCGGCTCCGACATCGAGATGACCCAGTCCCCCGCTAT

CATGTCCGCCTCTTTAGGCGAGCGGGTCACAATGACTTGTACAGCCTCCT

CCAGCGTCTCCTCCTCCTACTTCCATTGGTACCAACAGAAACCCGGAAGC

TCCCCTAAACTGTGCATCTACAGCACCAGCAATCTCGCCAGCGGCGTGCC
```

```
                                -continued
CCCTAGGTTTTCCGGAAGCGGAAGCACCAGCTACTCTTTAACCATCTCCT

CCATGGAGGCTGAGGATGCCGCCACCTACTTTTGTCACCAGTACCACCGG

TCCCCCACCTTCGGAGGCGGCACCAAACTGGAGACAAAGAGG.
```

Additional Antigen-Binding Domains

Some embodiments of any of the single-chain chimeric polypeptides described herein can further include one or more (e.g., two, three, four, five, six, seven, eight, nine, or ten) additional target-binding domains (e.g., any of the exemplary target-binding domains described herein or known in the art) at its N- and/or C-terminus.

In some embodiments, the single-chain chimeric polypeptides can include one or more (e.g., two, three, four, five, six, seven, eight, nine, or ten) additional target-binding domains (e.g., any of the exemplary target-binding domains described herein or known in the art) at its N-terminus. In some embodiments, one of the one or more additional target-binding domains (e.g., any of the exemplary target-binding domains described herein or known in the art) at the N-terminus of the single-chain chimeric polypeptide can directly abut the first target-binding domain (e.g., any of the exemplary target-binding domains described herein or known in the art), the second target-binding domain (e.g., any of the exemplary target-binding domains described herein or known in the art), or the soluble tissue factor domain (e.g., any of the exemplary soluble tissue factor domains described herein). In some embodiments, the single-chain chimeric polypeptide further includes a linker sequence (e.g., any of the exemplary linker sequences described herein or known in the art) between one of the at least one additional target-binding domains (e.g., any of the exemplary target-binding domains described herein or known in the art) at the N-terminus of the single-chain chimeric polypeptide and the first target-binding domain (e.g., any of the exemplary target-binding domains described herein or known in the art), the second target-binding domain (e.g., any of the exemplary target-binding domains described herein or known in the art), or the soluble tissue factor domain (e.g., any of the exemplary soluble tissue factor domains described herein).

In some embodiments of any of the single-chain chimeric polypeptides described herein, the single-chain chimeric polypeptide includes one or more (e.g., two, three, four, five, six, seven, eight, nine, or ten) additional target-binding domains (e.g., any of the exemplary target-binding domains described herein or known in the art) at its C-terminus. In some embodiments, one of the one or more additional target-binding domains (e.g., any of the exemplary target-binding domains described herein or known in the art) at the C-terminus of the single-chain chimeric polypeptide directly abuts the first target-binding domain (e.g., any of the exemplary target-binding domains described herein or known in the art), the second target-binding domain (e.g., any of the exemplary target-binding domains described herein or known in the art), or the soluble tissue factor domain (e.g., any of the exemplary soluble tissue factor domains described herein or known in the art). In some embodiments, the single-chain chimeric polypeptide further comprises a linker sequence (e.g., any of the exemplary linker sequences described herein or known in the art) between one of the at least one additional target-binding domains (e.g., any of the exemplary target-binding domains described herein or known in the art) at the C-terminus of the single-chain chimeric polypeptide and the first target-binding domain (e.g., any of the exemplary target-binding domains described herein or known in the art), the second target-binding domain (e.g., any of the exemplary target-binding domains described herein or known in the art), or the soluble tissue factor domain (e.g., any of the exemplary soluble tissue factor domains described herein).

In some embodiments of any of the single-chain chimeric polypeptides described herein, the single-chain chimeric polypeptide comprises one or more (e.g., two, three, four, five, six, seven, eight, nine, or ten) additional target binding domains (e.g., any of the exemplary target-binding domains described herein or known in the art) at its N-terminus and its C-terminus. In some embodiments, one of the one or more additional antigen binding domains (e.g., any of the exemplary target-binding domains described herein or known in the art) at the N-terminus of the single-chain chimeric polypeptide directly abuts the first target-binding domain (e.g., any of the exemplary target-binding domains described herein or known in the art), the second target-binding domain (e.g., any of the exemplary target-binding domains described herein or known in the art), or the soluble tissue factor domain (e.g., any of the exemplary soluble tissue factor domains described herein). In some embodiments, the single-chain chimeric polypeptide further includes a linker sequence (e.g., any of the exemplary linker sequences described herein or known in the art) between one of the one or more additional antigen-binding domains (e.g., any of the exemplary target-binding domains described herein or known in the art) at the N-terminus and the first target-binding domain (e.g., any of the exemplary target-binding domains described herein or known in the art), the second target-binding domain (e.g., any of the exemplary target-binding domains described herein or known in the art), or the soluble tissue factor domain (e.g., any of the exemplary soluble tissue factor domains). In some embodiments, one of the one or more additional antigen binding domains (e.g., any of the exemplary target-binding domains described herein or known in the art) at the C-terminus directly abuts the first target-binding domain (e.g., any of the exemplary target-binding domains described herein or known in the art), the second target-binding domain (e.g., any of the exemplary target-binding domains described herein or known in the art), or the soluble tissue factor domain (e.g., any of the exemplary soluble tissue factor domains). In some embodiments, the single-chain chimeric polypeptide further includes a linker sequence (e.g., any of the exemplary linker sequences described herein or known in the art) between one of the one or more additional antigen-binding domains (e.g., any of the exemplary target-binding domains described herein or known in the art) at the C-terminus and the first target-binding domain (e.g., any of the exemplary target-binding domains described herein or known in the art), the second target-binding domain (e.g., any of the exemplary target-binding domains described herein or known in the art), or the soluble tissue factor domain (e.g., any of the exemplary soluble tissue factor domains described herein).

In some embodiments of any of the single-chain chimeric polypeptides described herein, two or more (e.g., three, four, five, six, seven, eight, nine, or ten) of the first target-binding domain (e.g., any of the exemplary target-binding domains described herein or known in the art), the second target-binding domain (e.g., any of the exemplary target-binding domains described herein or known in the art), and the one or more additional target-binding domains (e.g., any of the exemplary target-binding domains described herein or known in the art) bind specifically to the same antigen. In some embodiments, two or more (e.g., three, four, five, six, seven, eight, nine, or ten) of the first target-binding domain (e.g., any of the exemplary target-binding domains described herein or known in the art), the second target-binding domain (e.g., any of the exemplary target-binding domains described herein or known in the art), and the one or more additional target-binding domains (e.g., any of the exemplary target-binding domains described herein or known in the art) bind specifically to the same epitope. In some embodiments, two or more (e.g., three, four, five, six, seven, eight, nine, or ten) of the first target-binding domain (e.g., any of the exemplary target-binding domains described herein or known in the art), the second target-binding domain (e.g., any of the exemplary target-binding domains described herein or known in the art), and the one or more additional target-binding domains (e.g., any of the exemplary target-binding domains described herein or known in the art) include the same amino acid sequence.

In some embodiments of any of the single-chain chimeric polypeptides described herein, the first target-binding domain (e.g., any of the exemplary target-binding domains described herein or known in the art), the second target-binding domain (e.g., any of the exemplary target-binding domains described herein or known in the art), and the one or more (e.g., two, three, four, five, six, seven, eight, nine, or ten) additional target-binding domains (e.g., any of the exemplary target-binding domains described herein or known in the art) each bind specifically to the same antigen. In some embodiments, the first target-binding domain (e.g., any of the exemplary target-binding domains described herein or known in the art), the second target-binding domain (e.g., any of the exemplary target-binding domains described herein or known in the art), and the one or more (e.g., two, three, four, five, six, seven, eight, nine, or ten) additional target-binding domains (e.g., any of the exemplary target-binding domains described herein or known in the art) each bind specifically to the same epitope. In some embodiments, the first target-binding domain, the second target-binding domain, and the one or more (e.g., two, three, four, five, six, seven, eight, nine, or ten) additional target-binding domains each comprise the same amino acid sequence.

In some embodiments of any of the single-chain chimeric polypeptides described herein, the first target-binding domain (e.g., any of the exemplary target-binding domains described herein or known in the art), the second target-binding domain (e.g., any of the exemplary target-binding domains described herein or known in the art), and the one or more (e.g., two, three, four, five, six, seven, eight, nine, or ten) additional target-binding domains (e.g., any of the exemplary target-binding domains described herein or known in the art) bind specifically to different antigens.

In some embodiments of any of the single-chain chimeric polypeptides, one or more of the first target-binding domain, the second target-binding domain, and the one or more target-binding domains is an antigen-binding domain (e.g., any of the exemplary antigen-binding domains described herein or known in the art). In some embodiments of any of the single-chain chimeric polypeptides described herein, the first target-binding domain, the second target-binding domain, and the one or more additional target-binding domains are each an antigen-binding domain (e.g., any of the exemplary antigen-binding domains described herein or known in the art). In some embodiments, the antigen-binding domain can include a scFv or a single domain antibody.

In some embodiments of any of the single-chain chimeric polypeptides described herein, one or more (e.g., two, three, four, five, six, seven, eight, nine, or ten) of the first target-binding domain (e.g., any of the exemplary target-binding domains described herein or known in the art), the second target-binding domain (e.g., any of the exemplary target-binding domains described herein or known in the art), and the one or more additional target-binding domains (e.g., any of the exemplary target-binding domains described herein or known in the art) bind specifically to CD28, CD3, or a receptor for IL-2.

In some embodiments of any of the single-chain chimeric polypeptides described herein, one or more of the first target-binding domain (e.g., any of the exemplary target-binding domains described herein or known in the art), the second target-binding domain (e.g., any of the exemplary target-binding domains described herein or known in the art), and the one or more additional target-binding domains (e.g., any of the exemplary target-binding domains described herein or known in the art) is a soluble IL-2.

In some embodiments of any of the multi-chain chimeric polypeptides, the first chimeric polypeptide further includes one or more (e.g., two, three, four, five, six, seven, eight, nine, or ten) additional target-binding domain(s) (e.g., any of the exemplary target-binding domains described herein or known in the art), where at least one of the one or more additional antigen-binding domain(s) is positioned between the soluble tissue factor domain (e.g., any of the exemplary soluble tissue factor domains described herein or known in the art) and the first domain of the pair of affinity domains (e.g., any of the exemplary first domains of any of the exemplary pairs of affinity domains described herein). In some embodiments, the first chimeric polypeptide can further include a linker sequence (e.g., any of the exemplary linker sequences described herein or known in the art) between the soluble tissue factor domain (e.g., any of the exemplary soluble tissue factor domains described herein) and the at least one of the one or more additional target-binding domain(s) (e.g., any of the exemplary target-binding domains described herein or known in the art), and/or a linker sequence (e.g., any of the exemplary linker sequences described herein or known in the art) between the at least one of the one or more additional target-binding domain(s) (e.g., any of the exemplary target-binding domains described herein or known in the art) and the first domain of the pair of affinity domains (e.g., any of the exemplary first domains described herein of any of the exemplary pairs of affinity domains described herein).

In some embodiments of any of the multi-chain chimeric polypeptides described herein, the first chimeric polypeptide further includes one or more (e.g., two, three, four, five, six, seven, eight, nine, or ten) additional target-binding domains at the N-terminal and/or C-terminal end of the first chimeric polypeptide. In some embodiments, at least one of the one or more additional target-binding domains (e.g., any of the exemplary target-binding domains described herein or known in the art) directly abuts the first domain of the pair of affinity domains (e.g., any of the exemplary first domains described herein of any of the exemplary pairs of affinity domains described herein) in the first chimeric polypeptide. In some embodiments, the first chimeric polypeptide further includes a linker sequence (e.g., any of the exemplary linker sequences described herein or known in the art) between the at least one of the one or more additional target-binding domains (e.g., any of the exemplary target-binding domains described herein or known in the art) and the first domain of the pair of affinity domains (e.g., any of the exemplary first domains described herein of any of the exemplary pairs of affinity domains described herein). In some embodiments, the at least one of the one or more additional target-binding domains (e.g., any of the exemplary target-binding domains described herein or known in the art) directly abuts the first target-binding domain (e.g., any of the exemplary target-binding domains described herein or known in the art) in the first chimeric polypeptide. In some embodiments, the first chimeric polypeptide further comprises a linker sequence (e.g., any of the exemplary linker sequences described herein or known in the art) between the at least one of the one or more additional target-binding domains (e.g., any of the exemplary target-binding domains described herein or known in the art) and the first target-binding domain (e.g., any of the exemplary target-binding domains described herein or known in the art).

In some embodiments of any of the multi-chain chimeric polypeptides described herein, at least one of the one or more additional target-binding domains (e.g., any of the exemplary target-binding domains described herein or known in the art) is disposed at the N- and/or C-terminus of the first chimeric polypeptide, and at least one of the one or more additional target-binding domains (e.g., any of the exemplary target-binding domains described herein or known in the art) is positioned between the soluble tissue factor domain (e.g., any of the exemplary soluble tissue factor domains described herein or known in the art) and the first domain of the pair of affinity domains (e.g., any of the exemplary first domains of any of the exemplary pairs of affinity domains described herein) in the first chimeric polypeptide. In some embodiments, the at least one additional target-binding domain (e.g., any of the exemplary target-binding domains described herein or known in the art) of the one or more additional target-binding domains disposed at the N-terminus directly abuts the first target-binding domain (e.g., any of the exemplary target-binding domains described herein or known in the art) or the first domain of the pair of affinity domains (e.g., any of the exemplary first domains described herein of any of the exemplary pairs of affinity domains described herein) in the first chimeric polypeptide. In some embodiments, the first chimeric polypeptide further comprises a linker sequence (e.g., any of the linker sequences described herein or known in the art) disposed between the at least one additional target-binding domain (e.g., any of the exemplary target-binding domains described herein or known in the art) and the first target-binding domain (e.g., any of the exemplary target-binding domains described herein or known in the art) or the first domain of the pair of affinity domains (e.g., any of the exemplary first domains described herein of any of the exemplary pairs of affinity domains described herein) in the first chimeric polypeptide. In some embodiments, the at least one additional target-binding domain (e.g., any of the exemplary target-binding domains described herein or known in the art) of the one or more additional target-binding domains disposed at the C-terminus directly abuts the first target-binding domain (e.g., any of the exemplary target-binding domains described herein or known in the art) or the first domain of the pair of affinity domains (e.g., any of the exemplary first domains of any of the exemplary pairs of affinity domains described herein) in the first chimeric polypeptide. In some embodiments, the first chimeric polypeptide further includes a linker sequence (e.g., any of the exemplary linker sequences described herein or known in the art) disposed between the at least one additional target-binding domain (e.g., any of the exemplary target-binding domains described herein or known in the art) and the first target-binding domain (e.g., any of the exemplary target-binding domains described herein or known in the art) or the first domain of the pair of affinity domains (e.g., any of the exemplary first domains described herein of any of the exemplary pairs of affinity domains described herein) in the first chimeric polypeptide. In some embodiments, the at least one of the one or more additional target-binding domains (e.g., any of the exemplary target-binding domains described herein or known in the art) positioned between the soluble tissue factor domain (e.g., any of the exemplary soluble tissue factor domains described herein) and the first domain of the pair of affinity domains (e.g., any of the first domains described herein or any of the exemplary pairs of affinity domains described herein), directly abuts the soluble tissue factor domain and/or the first domain of the pair of affinity domains. In some embodiments, the first chimeric polypeptide further comprises a linker sequence (e.g., any of the exemplary linker sequences described herein or known in the art) disposed (i) between the soluble tissue factor domain (e.g., any of the exemplary soluble tissue factor domains described herein) and the at least one of the one or more additional target-binding domains (e.g., any of the exemplary target-binding domains described herein or known in the art) positioned between the soluble tissue factor domain (e.g., any of the exemplary soluble tissue factor domains described herein) and the first domain of the pair of affinity domains (e.g., any of the exemplary first domains of any of the exemplary pairs of affinity domains described herein), and/or (ii) between the first domain of the pair of affinity domains and the at least one of the one or more additional target-binding domains positioned between the soluble tissue factor domain and the first domain of the pair of affinity domains.

In some embodiments of any of the multi-chain chimeric polypeptides described herein, the second chimeric polypeptide further includes one or more (e.g., two, three, four, five, six, seven, eight, nine, or ten) additional target-binding domains (e.g., any of the exemplary target-binding domains described herein or known in the art) at the N-terminal end and/or the C-terminal end of the second chimeric polypeptide. In some embodiments, at least one of the one or more additional target-binding domains (e.g., any of the exemplary target-binding domains described herein or known in the art) directly abuts the second domain of the pair of affinity domains (e.g., any of the exemplary second domains of any of the exemplary pairs of affinity domains described herein) in the second chimeric polypeptide. In some embodiments, the second chimeric polypeptide further includes a linker sequence (e.g., any of the exemplary linker sequences described herein or known in the art) between at least one of the one or more additional target-binding domains (e.g., any of the exemplary target-binding domains described herein or known in the art) and the second domain of the pair of affinity domains (e.g., any of the second domains described herein of any of the exemplary pairs of affinity domains described herein) in the second chimeric polypeptide. In some embodiments, at least one of the one or more additional target-binding domains (e.g., any of the exemplary target-binding domains described herein or known in the art) directly abuts the second target-binding domain (e.g., any of the target-binding domains described herein or known in the art) in the second chimeric polypeptide. In some embodiments, the second chimeric polypeptide further includes a linker sequence (e.g., any of the exemplary linker sequences described herein or known in the art) between at least one of the one or more additional target-binding domains (e.g., any of the exemplary target binding domains described herein or known in the art) and the second target-binding domain (e.g., any of the exemplary target binding domains described herein or known in the art) in the second chimeric polypeptide.

In some embodiments of any of the multi-chain chimeric polypeptides described herein, two or more (e.g., three or more, four or more, five or more, six or more, seven or more, eight or more, nine or more, or ten or more) of the first target-binding domain, the second target-binding domain, and the one or more additional target-binding domains bind specifically to the same antigen. In some embodiments, two or more (e.g., three or more, four or more, five or more, six or more, seven or more, eight or more, nine or more, or ten or more) of the first target-binding domain, the second target-binding domain, and the one or more additional target-binding domains bind specifically to the same epitope. In some embodiments, two or more (e.g., three or more, four or more, five or more, six or more, seven or more, eight or more, nine or more, or ten or more) of the first target-binding domain, the second target-binding domain, and the one or more additional target-binding domains include the same amino acid sequence. In some embodiments, the first target-binding domain, the second target-binding domain, and the one or more additional target-binding domains each bind specifically to the same antigen. In some embodiments, the first target-binding domain, the second target-binding domain, and the one or more additional target-binding domains each bind specifically to the same epitope. In some embodiments, the first target-binding domain, the second target-binding domain, and the one or more additional target-binding domains each include the same amino acid sequence.

In some embodiments of any of the multi-chain chimeric polypeptides described herein, the first target-binding domain, the second target-binding domain, and the one or more additional target-binding domains bind specifically to different antigens. In some embodiments of any of the multi-chain chimeric polypeptides described herein, one or more (e.g., two or more, three or more, four or more, five or more, six or more, seven or more, eight or more, nine or more, or ten or more) of the first target-binding domain, the second target-binding domain, and the one or more additional target-binding domains is an antigen-binding domain. In some embodiments, the first target-binding domain, the second target-binding domain, and the one or more additional target-binding domains are each an antigen-binding domain (e.g., a scFv or a single-domain antibody).

Signal Sequence

In some embodiments, a single-chain chimeric polypeptide, a first chimeric polypeptide, or a second chimeric polypeptide described herein can further include a signal sequence at its N-terminal end. As will be understood by those of ordinary skill in the art, a signal sequence is an amino acid sequence that is present at the N-terminus of a number of endogenously produced proteins that directs the protein to the secretory pathway (e.g., the protein is directed to reside in certain intracellular organelles, to reside in the cell membrane, or to be secreted from the cell). Signal sequences are heterogeneous and differ greatly in their primary amino acid sequences. However, signal sequences are typically 16 to 30 amino acids in length and include a hydrophilic, usually positively charged N-terminal region, a central hydrophobic domain, and a C-terminal region that contains the cleavage site for signal peptidase.

In some embodiments, a single-chain chimeric polypeptide, a first chimeric polypeptide, or a second chimeric polypeptide can include a signal sequence having an amino acid sequence MKWVTFISLLFLFSSAYS (SEQ ID NO: 33). In some embodiments, a single-chain chimeric polypeptide, a first chimeric polypeptide, or a second chimeric polypeptide can include a signal sequence encoded by the nucleic acid sequence:

```
                                      (SEQ ID NO: 34)
ATGAAATGGGTGACCTTTATTTCTTTACTGTTCCTCTTTAGCAGCGCCTA

CTCC, (SEQ ID NO: 35)
ATGAAGTGGGTCACATTTATCTCTTTACTGTTCCTCTTCTCCAGCGCCTA

CAGC, (SEQ ID NO: 36)
ATGAAATGGGTGACCTTTATTTCTTTACTGTTCCTCTTTAGCAGCGCCTA

CTCC,
or (SEQ ID NO: 101)
ATGAAATGGGTCACCTTCATCTCTTTACTGTTTTATTTAGCAGCGCCTA

CAGC.
```

In some embodiments, a single-chain chimeric polypeptide, a first chimeric polypeptide, or a second chimeric polypeptide can include a signal sequence having an amino acid sequence MKCLLYLAFLFLGVNC (SEQ ID NO: 37). In some embodiments, a single-chain chimeric polypeptide, a first chimeric polypeptide, or a second chimeric polypeptide can include a signal sequence having an amino acid sequence: MGQIVTMFEALPHIIDEVINIVIIV-LIIITSIKAVYNFATCGILALVSFLFLAGRSCG (SEQ ID NO: 38). In some embodiments, a single-chain chimeric polypeptide, a first chimeric polypeptide, or a second chimeric polypeptide can include a signal sequence having an amino acid sequence:

```
                                      (SEQ ID NO: 39)
MPNHQSGSPTGSSDLLLSGKKQRPHLALRRKRRREMRKINRKVRRMNLAP

IKEKTAWQHLQALISEAEEVLKTSQTPQNSLTLFLALLSVLGPPVTG.
```

In some embodiments, a single-chain chimeric polypeptide, a first chimeric polypeptide, or a second chimeric polypeptide can include a signal sequence having an amino acid sequence MDSKGSSQKGSRLLLLL-VVSNLLLCQGVVS (SEQ ID NO: 40). Those of ordinary skill in the art will be aware of other appropriate signal sequences for use in a single-chain chimeric polypeptide.

In some embodiments, a single-chain chimeric polypeptide, a first chimeric polypeptide, or a second chimeric polypeptide can include a signal sequence that is about 10 to 100 amino acids in length. For example, a signal sequence can be about 10 to 100 amino acids in length, about 15 to 100 amino acids in length, about 20 to 100 amino acids in length, about 25 to 100 amino acids in length, about 30 to 100 amino acids in length, about 35 to 100 amino acids in length, about 40 to 100 amino acids in length, about 45 to 100 amino acids in length, about 50 to 100 amino acids in length, about 55 to 100 amino acids in length, about 60 to 100 amino acids in length, about 65 to 100 amino acids in length, about 70 to 100 amino acids in length, about 75 to 100 amino acids in length, about 80 to 100 amino acids in length, about 85 to 100 amino acids in length, about 90 to 100 amino acids in length, about 95 to 100 amino acids in length, about 10 to 95 amino acids in length, about 10 to 90 amino acids in length, about 10 to 85 amino acids in length, about 10 to 80 amino acids in length, about 10 to 75 amino acids in length, about 10 to 70 amino acids in length, about 10 to 65 amino acids in length, about 10 to 60 amino acids in length, about 10 to 55 amino acids in length, about 10 to 50 amino acids in length, about 10 to 45 amino acids in length, about 10 to 40 amino acids in length, about 10 to 35 amino acids in length, about 10 to 30 amino acids in length, about 10 to 25 amino acids in length, about 10 to 20 amino acids in length, about 10 to 15 amino acids in length, about 20 to 30 amino acids in length, about 30 to 40 amino acids in length, about 40 to 50 amino acids in length, about 50 to 60 amino acids in length, about 60 to 70 amino acids in length, about 70 to 80 amino acids in length, about 80 to 90 amino acids in length, about 90 to 100 amino acids in length, about 20 to 90 amino acids in length, about 30 to 80 amino acids in length, about 40 to 70 amino acids in length, about 50 to 60 amino acids in length, or any range in between. In some embodiments, a signal sequence is about 10, 15, 20, 25, 30, 35, 40, 45, 50, 55, 60, 65, 70, 75, 80, 85, 90, 95, or 100 amino acids in length.

In some embodiments, any of the signal sequences disclosed herein can include one or more additional amino acids (e.g., 1, 2, 3, 5, 6, 7, 8, 9, 10, or more amino acids) at its N-terminus and/or C-terminus, so long as the function of the signal sequence remains intact. For example, a signal sequence having the amino acid sequence MKWVTFISLL-FLFSSAYS (SEQ ID NO: 33) can include one or more additional amino acids at the N-terminus or C-terminus, while still retaining the ability to direct the single-chain chimeric polypeptide, the first chimeric polypeptide, or the second chimeric polypeptide to the secretory pathway.

In some embodiments, a single-chain chimeric polypeptide, a first chimeric polypeptide, or a second chimeric polypeptide can include a signal sequence that directs the single-chain chimeric polypeptide, the first chimeric polypeptide, or the second chimeric polypeptide into the extracellular space. Such embodiments are useful in producing single-chain chimeric polypeptides, first chimeric polypeptides, and second chimeric polypeptides that are relatively easy to be isolated and/or purified.

Peptide Tags

In some embodiments, a single-chain chimeric polypeptide, a first chimeric polypeptide, or a second chimeric polypeptide can include a peptide tag (e.g., at the N-terminal end or the C-terminal end of the single-chain chimeric polypeptide, the first chimeric polypeptide, or the second chimeric polypeptide). In some embodiments, a single-chain chimeric polypeptide, a first chimeric polypeptide, or a second chimeric polypeptide includes two or more peptide tags.

Exemplary peptide tags that can be included in a single-chain chimeric polypeptide, a first chimeric polypeptide, or a second chimeric polypeptide include, without limitation: AviTag (GLNDIFEAQKIEWHE; SEQ ID NO: 41), a calmodulin-tag (KRRWKKNFIAVSAANRFKKISSSGAL; SEQ ID NO: 42), a polyglutamate tag (EEEEEE; SEQ ID NO: 43), an E-tag (GAPVPYPDPLEPR; SEQ ID NO: 44), a FLAG-tag (DYKDDDDK; SEQ ID NO: 45), an HA-tag, a peptide from hemagglutinin (YPYDVPDYA; SEQ ID NO: 46), a his-tag (HHHHH (SEQ ID NO: 47); HHHHHH (SEQ ID NO: 48); HHHHHHH (SEQ ID NO: 49); HHHHHHHH (SEQ ID NO: 50); HHHHHHHHH (SEQ ID NO: 51); or HHHHHHHHHH (SEQ ID NO: 52)), a myc-tag (EQKLISEEDL; SEQ ID NO: 53), NE-tag (TKENPRSNQEESYDDNES; SEQ ID NO: 54), S-tag, (KETAAAKFERQHMDS; SEQ ID NO: 55), SBP-tag (MDEKTTGWRGGHVVEGLAGELEQLRAR-LEHHPQGQREP; SEQ ID NO: 56), Softag 1 (SLAELLNAGLGGS; SEQ ID NO: 57), Softag 3 (TQDPSRVG; SEQ ID NO: 58), Spot-tag (PDRVRAVSHWSS; SEQ ID NO: 59), Strep-tag (WSHPQFEK; SEQ ID NO: 60), TC tag (CCPGCC; SEQ ID NO: 61), Ty tag (EVHTNQDPLD; SEQ ID NO: 62), V5 tag (GKPIPNPLLGLDST; SEQ ID NO: 63), VSV-tag (YTDIEMNRLGK; SEQ ID NO: 64), and Xpress tag (DLYDDDDK; SEQ ID NO: 65). In some embodiments, tissue factor protein is a peptide tag.

Peptide tags that can be included in a single-chain chimeric polypeptide, a first chimeric polypeptide, or a second chimeric polypeptide can be used in any of a variety of applications related to the single-chain chimeric polypeptide, the first chimeric polypeptide, or the second chimeric polypeptide. For example, a peptide tag can be used in the purification of a single-chain chimeric polypeptide, a first chimeric polypeptide, or a second chimeric polypeptide. As one non-limiting example, a single-chain chimeric polypeptide, a first chimeric polypeptide, or a second chimeric polypeptide can include a myc tag; and can be purified using an antibody that recognizes the myc tag(s). One non-limiting example of an antibody that recognizes a myc tag is 9E10, available from the non-commercial Developmental Studies Hybridoma Bank. As another non-limiting example, a single-chain chimeric polypeptide, a first chimeric polypeptide, or a second chimeric polypeptide can include a histidine tag, and can be purified using a nickel or cobalt chelate. Those of ordinary skill in the art will be aware of other suitable tags and agent that bind those tags for use in purifying a single-chain chimeric polypeptide, a first chimeric polypeptide, or a second chimeric polypeptide. In some embodiments, a peptide tag is removed from the single-chain chimeric polypeptide, the first chimeric polypeptide, or the second chimeric polypeptide after purification. In some embodiments, a peptide tag is not removed from the single-chain chimeric polypeptide, the first chimeric polypeptide, or the second chimeric polypeptide after purification.

Peptide tags that can be included in a single-chain chimeric polypeptide, a first chimeric polypeptide, or a second chimeric polypeptide can be used, for example, in immunoprecipitation of the single-chain chimeric polypeptide, the first chimeric polypeptide, or the second chimeric polypeptide, imaging of the single-chain chimeric polypeptide, the first chimeric polypeptide, or the second chimeric polypeptide (e.g., via Western blotting, ELISA, flow cytometry, and/or immunocytochemistry), and/or solubilization of the single-chain chimeric polypeptide, the first chimeric polypeptide, or the second chimeric polypeptide.

In some embodiments, a single-chain chimeric polypeptide, a first chimeric polypeptide, or a second chimeric polypeptide can include a peptide tag that is about 10 to 100 amino acids in length. For example, a peptide tag can be about 10 to 100 amino acids in length, about 15 to 100 amino acids in length, about 20 to 100 amino acids in length, about 25 to 100 amino acids in length, about 30 to 100 amino acids in length, about 35 to 100 amino acids in length, about 40 to 100 amino acids in length, about 45 to 100 amino acids in length, about 50 to 100 amino acids in length, about 55 to 100 amino acids in length, about 60 to 100 amino acids in length, about 65 to 100 amino acids in length, about 70 to 100 amino acids in length, about 75 to 100 amino acids in length, about 80 to 100 amino acids in length, about 85 to 100 amino acids in length, about 90 to 100 amino acids in length, about 95 to 100 amino acids in length, about 10 to 95 amino acids in length, about 10 to 90 amino acids in length, about 10 to 85 amino acids in length, about 10 to 80 amino acids in length, about 10 to 75 amino acids in length, about 10 to 70 amino acids in length, about 10 to 65 amino acids in length, about 10 to 60 amino acids in length, about 10 to 55 amino acids in length, about 10 to 50 amino acids in length, about 10 to 45 amino acids in length, about 10 to 40 amino acids in length, about 10 to 35 amino acids in length, about 10 to 30 amino acids in length, about 10 to 25 amino acids in length, about 10 to 20 amino acids in length, about 10 to 15 amino acids in length, about 20 to 30 amino acids in length, about 30 to 40 amino acids in length, about 40 to 50 amino acids in length, about 50 to 60 amino acids in length, about 60 to 70 amino acids in length, about 70 to 80 amino acids in length, about 80 to 90 amino acids in length, about 90 to 100 amino acids in length, about 20 to 90 amino acids in length, about 30 to 80 amino acids in length, about 40 to 70 amino acids in length, about 50 to 60 amino acids in length, or any range in between. In some embodiments, a peptide tag is about 10, 15, 20, 25, 30, 35, 40, 45, 50, 55, 60, 65, 70, 75, 80, 85, 90, 95, or 100 amino acids in length.

Peptide tags included in a single-chain chimeric polypeptide, a first chimeric polypeptide, or a second chimeric polypeptide can be of any suitable length. For example, peptide tags can be 5, 6, 7, 8, 9, 10, 11, 12, 13, 14, 15, 16, 17, 18, 19, 20, or more amino acids in length. In embodiments in which a single-chain chimeric polypeptide, a first chimeric polypeptide, or a second chimeric polypeptide includes two or more peptide tags, the two or more peptide tags can be of the same or different lengths. In some embodiments, any of the peptide tags disclosed herein may include one or more additional amino acids (e.g., 1, 2, 3, 5, 6, 7, 8, 9, 10, or more amino acids) at the N-terminus and/or C-terminus, so long as the function of the peptide tag remains intact. For example, a myc tag having the amino acid sequence EQKLISEEDL (SEQ ID NO: 53) can include one or more additional amino acids (e.g., at the N-terminus and/or the C-terminus of the peptide tag), while still retaining the ability to be bound by an antibody (e.g., 9E10).

CD3/CD28-Binding Agents

Provided herein are methods that include the use of one or more CD3/CD28-binding agent(s). A CD3/CD28-binding agent can be, for example, a single-chain chimeric polypeptide, a multi-chain chimeric polypeptide, a bi-specific antibody, or an anti-CD3/anti-CD28 bead.

Single-Chain Chimeric Polypeptides

Non-limiting examples of CD3/CD28-binding agents are single-chain chimeric polypeptides that include a first target-binding domain, a soluble tissue factor domain, and a second target-binding domain, where: the first target-binding domain of the single-chain chimeric polypeptide binds to CD3 and the second target-binding domain of the single-chain chimeric polypeptide binds to CD28. Non-limiting examples of single-chain chimeric polypeptides that are CD3/CD28-binding agents are described herein.

Multi-Chain Chimeric Polypeptides

Non-limiting examples of CD3/CD28-binding agents are multi-chain chimeric polypeptides that include a first chimeric polypeptide including (i) a first target-binding domain; (ii) a soluble tissue factor domain; and (iii) a first domain of a pair of affinity domains; and a second chimeric polypeptide comprising: (i) a second domain of a pair of affinity domains; and (ii) a second target-binding domain, wherein: the first chimeric polypeptide and the second chimeric polypeptide associate through the binding of the first domain and the second domain of the pair of affinity domains; and wherein the first target-binding domain binds to CD3 and the second target-binding domain binds to CD28, or the first target-binding domain binds to CD28 and the second target-binding domain to CD3.

In some embodiments, the liquid culture medium further includes an IgG1 antibody construct that comprises at least one antigen-binding domain that binds specifically to the soluble tissue factor domain of the multi-chain chimeric polypeptide. In some embodiments, the IgG1 antibody construct comprises a heavy chain variable domain comprising CDRs of SEQ ID NOs: 66, 67 or 74, and 68, and a light chain variable domain comprising CDRs of SEQ ID NOs: 69, 70, and 71. In some embodiments, the heavy chain variable domain comprises a sequence that is at least 90% identical to SEQ ID NO: 72, and the light chain variable domain comprises a sequence that is at least 90% identical to SEQ ID NO: 73. In some embodiments, the heavy chain variable domain comprises SEQ ID NO: 72, and the light chain variable domain comprises SEQ ID NO: 73.

In some embodiments, the first target-binding domain of the first chimeric polypeptide and the soluble tissue factor domain directly abut each other. In some embodiments, the first chimeric polypeptide further comprises a linker sequence between the first target-binding domain and the soluble tissue factor domain. In some embodiments, the soluble tissue factor domain and the second target-binding domain of the second chimeric polypeptide directly abut each other. In some embodiments, the second chimeric polypeptide further comprises a linker sequence between the soluble tissue factor domain and the second target-binding domain.

In some embodiments, the CD3 is human CD3. In some embodiments, the first target-binding domain of the first chimeric polypeptide comprises a sequence that is at least 80%, at least 85%, at least 90%, at least 95%, at least 99%, or 100% identical to SEQ ID NO: 5.

In some embodiments, the soluble tissue factor domain of the first chimeric polypeptide is a soluble human tissue factor domain. In some embodiments, the soluble human tissue factor domain of the first chimeric polypeptide comprises a sequence that is at least 80%, at least 85%, at least 90%, at least 95%, at least 99%, or 100% identical to SEQ ID NO: 2. In some embodiments, the soluble tissue factor domain of the first chimeric polypeptide comprises or consists of a sequence from a wildtype soluble human tissue factor.

In some embodiments, the soluble tissue factor domain of the first chimeric polypeptide does not include any of: a lysine at an amino acid position that corresponds to amino acid position 20 of mature wildtype human tissue factor protein; an isoleucine at an amino acid position that corresponds to amino acid position 22 of mature wildtype human tissue factor protein; a tryptophan at an amino acid position that corresponds to amino acid position 45 of mature wildtype human tissue factor protein; an aspartic acid at an amino acid position that corresponds to amino acid position 58 of mature wildtype human tissue factor protein; a tyrosine at an amino acid position that corresponds to amino acid position 94 of mature wildtype human tissue factor protein; an arginine at an amino acid position that corresponds to amino acid position 135 of mature wildtype human tissue factor protein; and a phenylalanine at an amino acid position that corresponds to amino acid position 140 of mature wildtype human tissue factor protein.

In some embodiments, the soluble tissue factor domain of the first chimeric polypeptide includes one or more of: a lysine at an amino acid position that corresponds to amino acid position 20 of mature wildtype human tissue factor protein; an isoleucine at an amino acid position that corresponds to amino acid position 22 of mature wildtype human tissue factor protein; a tryptophan at an amino acid position that corresponds to amino acid position 45 of mature wildtype human tissue factor protein; an aspartic acid at an amino acid position that corresponds to amino acid position 58 of mature wildtype human tissue factor protein; a tyrosine at an amino acid position that corresponds to amino acid position 94 of mature wildtype human tissue factor protein; an arginine at an amino acid position that corresponds to amino acid position 135 of mature wildtype human tissue factor protein; and a phenylalanine at an amino acid position that corresponds to amino acid position 140 of mature wildtype human tissue factor protein.

In some embodiments, the soluble tissue factor domain of the first chimeric polypeptide does not initiate blood coagulation. In some embodiments, the first chimeric polypeptide comprises a sequence that is at least 80%, at least 85%, at least 90%, at least 95%, at least 99%, or 100% identical to SEQ ID NO: 102. In some embodiments, the first chimeric polypeptide comprises a sequence that is at least 80%, least 85%, at least 90%, at least 95%, at least 99%, or 100% identical to SEQ ID NO: 104.

In some embodiments, the CD28 is human CD28. In some embodiments, the second target-binding domain of the second chimeric polypeptide comprises a sequence that is at least 80%, at least 85%, at least 90%, at least 95%, at least 99%, or 100% identical to SEQ ID NO: 6. In some embodiments, the second chimeric polypeptide comprises a sequence that is at least 80%, at least 85%, at least 90%, at least 95%, at least 99%, or 100% identical to SEQ ID NO: 106. In some embodiments, the second chimeric polypeptide comprises a sequence that is at least 80%, at least 85%, at least 90%, at least 95%, at least 99%, or 100% identical to SEQ ID NO: 108. In some embodiments, the multi-chain chimeric polypeptide does not initiate blood coagulation.

In some embodiments, the liquid culture medium comprises about 10 nM to about 1000 nM (or any of the subranges of this range described herein) of the multi-chain chimeric polypeptide. In some embodiments, the liquid culture medium comprises about 50 nM to about 300 nM (or any of the subranges of this range described herein) of the multi-chain chimeric polypeptide.

```
Exemplary Mature First Chimeric Polypeptide
                                               (SEQ ID NO: 102)
QIVLTQSPAIMSASPGEKVTMTCSASSSVSYMNWYQQKSGTSPKRWIYDTSKLA

SGVPAHFRGSGSGTSYSLTISGMEAEDAATYYCQQWSSNPFTFGSGTKLEINRGG

GGSGGGGSGGGGSQVQLQQSGAELARPGASVKMSCKASGYTFTRYTMHWVKQ

RPGQGLEWIGYINPSRGYTNYNQKFKDKATLTTDKSSSTAYMQLSSLTSEDSAV

YYCARYYDDHYCLDYWGQGTTLTVSSSGTTNTVAAYNLTWKSTNFKTILEWEP

KPVNQVYTVQISTKSGDWKSKCFYTTDTECDLTDEIVKDVKQTYLARVFSYPAG

NVESTGSAGEPLYENSPEFTPYLETNLGQPTIQSFEQVGTKVNVTVEDERTLVRR

NNTFLSLRDVFGKDLIYTLYYWKSSSSGKKTAKTNTNEFLIDVDKGENYCFSVQ

AVIPSRTVNRKSTDSPVECMGQEKGEFRENWVNVISNLKKIEDLIQSMHIDATLY

TESDVHPSCKVTAMKCFLLELQVISLESGDASIHDTVENLIILANNSLSSNGNVTE

SGCKECEELEEKNIKEFLQSFVHIVQMFINTS

Exemplary DNA Encoding Mature First Chimeric Polypeptide
                                               (SEQ ID NO: 103)
CAGATCGTGCTGACCCAAAGCCCCGCCATCATGAGCGCTAGCCCCGGTGAGA

AGGTGACCATGACATGCTCCGCTTCCAGCTCCGTGTCCTACATGAACTGGTAT

CAGCAGAAAAGCGGAACCAGCCCCAAAAGGTGGATCTACGACACCAGCAAG

CTGGCCTCCGGAGTGCCCGCTCATTTCCGGGGCTCTGGATCCGGCACCAGCTA

CTCTTTAACCATTTCCGGCATGGAAGCTGAAGACGCTGCCACCTACTATTGCC

AGCAATGGAGCAGCAACCCCTTCACATTCGGATCTGGCACCAAGCTCGAAAT

CAATCGTGGAGGAGGTGGCAGCGGCGGCGGTGGATCCGGCGGAGGAGGAAG

CCAAGTTCAACTCCAGCAGAGCGGCGCTGAACTGGCCCGGCCCGGCGCCTCC

GTCAAGATGAGCTGCAAGGCTTCCGGCTATACATTTACTCGTTACACAATGCA

TTGGGTCAAGCAGAGGCCCGGTCAAGGTTTAGAGTGGATCGGATATATCAAC

CCTTCCCGGGGCTACACCAACTATAACCAAAAGTTCAAGGATAAAGCCACTT

TAACCACTGACAAGAGCTCCTCCACCGCCTACATGCAGCTGTCCTCTTTAACC

AGCGAGGACTCCGCTGTTTACTACTGCGCTAGGTATTACGACGACCACTACTG

TTTAGACTATTGGGGACAAGGTACCACTTTAACCGTCAGCAGCTCCGGCACC
```

-continued

ACCAATACCGTGGCCGCTTATAACCTCACATGGAAGAGCACCAACTTCAAGA

CAATTCTGGAATGGGAACCCAAGCCCGTCAATCAAGTTTACACCGTGCAGAT

CTCCACCAAATCCGGAGACTGGAAGAGCAAGTGCTTCTACACAACAGACACC

GAGTGTGATTTAACCGACGAAATCGTCAAGGACGTCAAGCAAACCTATCTGG

CTCGGGTCTTTTCCTACCCCGCTGGCAATGTCGAGTCCACCGGCTCCGCTGGC

GAGCCTCTCTACGAGAATTCCCCCGAATTCACCCCTTATTTAGAGACCAATTT

AGGCCAGCCTACCATCCAGAGCTTCGAGCAAGTTGGCACCAAGGTGAACGTC

ACCGTCGAGGATGAAAGGACTTTAGTGCGGCGGAATAACACATTTTTATCCC

TCCGGGATGTGTTCGGCAAAGACCTCATCTACACACTGTACTATTGGAAGTCC

AGCTCCTCCGGCAAAAAGACCGCTAAGACCAACACCAACGAGTTTTTAATTG

ACGTGGACAAAGGCGAGAACTACTGCTTCAGCGTGCAAGCCGTGATCCCTTC

TCGTACCGTCAACCGGAAGAGCACAGATTCCCCCGTTGAGTGCATGGGCCAA

GAAAAGGGCGAGTTCCGGGAGAACTGGGTGAACGTCATCAGCAATTTAAAG

AAGATCGAAGATTTAATTCAGTCCATGCATATCGACGCCACTTTATACACAG

AATCCGACGTGCACCCCTCTTGTAAGGTGACCGCCATGAAATGTTTTTTACTG

GAGCTGCAAGTTATCTCTTTAGAGAGCGGAGACGCTAGCATCCACGACACCG

TGGAGAATTTAATCATTTTAGCCAATAACTCTTTATCCAGCAACGGCAACGTG

ACAGAGTCCGGCTGCAAGGAGTGCGAAGAGCTGGAGGAGAAGAACATCAAG

GAGTTTCTGCAATCCTTTGTGCACATTGTCCAGATGTTCATCAATACCTCC

Exemplary Precursor First Chimeric Polypeptide
(SEQ ID NO: 104)
MKWVTFISLLFLFSSAYSQIVLTQSPAIMSASPGEKVTMTCSASSSVSYMNWYQQ

KSGTSPKRWIYDTSKLASGVPAHFRGSGSGTSYSLTISGMEAEDAATYYCQQWS

SNPFTFGSGTKLEINRGGGGSGGGGSGGGGSQVQLQQSGAELARPGASVKMSCK

ASGYTFTRYTMHWVKQRPGQGLEWIGYINPSRGYTNYNQKFKDKATLTTDKSS

STAYMQLSSLTSEDSAVYYCARYYDDHYCLDYWGQGTTLTVSSSGTTNTVAAY

NLTWKSTNFKTILEWEPKPVNQVYTVQISTKSGDWKSKCFYTTDTECDLTDEIVK

DVKQTYLARVFSYPAGNVESTGSAGEPLYENSPEFTPYLETNLGQPTIQSFEQVG

TKVNVTVEDERTLVRRNNTFLSLRDVFGKDLIYTLYYWKSSSSGKKTAKTNTNE

FLIDVDKGENYCFSVQAVIPSRTVNRKSTDSPVECMGQEKGEFRENWVNVISNL

KKIEDLIQSMHIDATLYTESDVHPSCKVTAMKCFLLELQVISLESGDASIHDTVEN

LIILANNSLSSNGNVTESGCKECEELEEKNIKEFLQSFVHIVQMFINTS

Exemplary DNA Encoding Precursor First Chimeric Polypeptide
(SEQ ID NO: 105)
ATGAAGTGGGTGACCTTCATCAGCTTATTATTTTTATTCAGCTCCGCCTATTCC

CAGATCGTGCTGACCCAAAGCCCCGCCATCATGAGCGCTAGCCCCGGTGAGA

AGGTGACCATGACATGCTCCGCTTCCAGCTCCGTGTCCTACATGAACTGGTAT

CAGCAGAAAAGCGGAACCAGCCCCAAAAGGTGGATCTACGACACCAGCAAG

CTGGCCTCCGGAGTGCCCGCTCATTTCCGGGGCTCTGGATCCGGCACCAGCTA

CTCTTTAACCATTTCCGGCATGGAAGCTGAAGACGCTGCCACCTACTATTGCC

AGCAATGGAGCAGCAACCCCTTCACATTCGGATCTGGCACCAAGCTCGAAAT

CAATCGTGGAGGAGGTGGCAGCGGCGGCGGTGGATCCGGCGGAGGAGGAAG

CCAAGTTCAACTCCAGCAGAGCGGCGCTGAACTGGCCCGGCCCGGCGCCTCC

-continued

```
GTCAAGATGAGCTGCAAGGCTTCCGGCTATACATTTACTCGTTACACAATGCA

TTGGGTCAAGCAGAGGCCCGGTCAAGGTTTAGAGTGGATCGGATATATCAAC

CCTTCCCGGGGCTACACCAACTATAACCAAAAGTTCAAGGATAAAGCCACTT

TAACCACTGACAAGAGCTCCTCCACCGCCTACATGCAGCTGTCCTCTTTAACC

AGCGAGGACTCCGCTGTTTACTACTGCGCTAGGTATTACGACGACCACTACTG

TTTAGACTATTGGGGACAAGGTACCACTTTAACCGTCAGCAGCTCCGGCACC

ACCAATACCGTGGCCGCTTATAACCTCACATGGAAGAGCACCAACTTCAAGA

CAATTCTGGAATGGGAACCCAAGCCCGTCAATCAAGTTTACACCGTGCAGAT

CTCCACCAAATCCGGAGACTGGAAGAGCAAGTGCTTCTACACAACAGACACC

GAGTGTGATTTAACCGACGAAATCGTCAAGGACGTCAAGCAAACCTATCTGG

CTCGGGTCTTTTCCTACCCCGCTGGCAATGTCGAGTCCACCGGCTCCGCTGGC

GAGCCTCTCTACGAGAATTCCCCCGAATTCACCCCTTATTTAGAGACCAATTT

AGGCCAGCCTACCATCCAGAGCTTCGAGCAAGTTGGCACCAAGGTGAACGTC

ACCGTCGAGGATGAAAGGACTTTAGTGCGGCGGAATAACACATTTTTATCCC

TCCGGGATGTGTTCGGCAAAGACCTCATCTACACACTGTACTATTGGAAGTCC

AGCTCCTCCGGCAAAAAGACCGCTAAGACCAACACCAACGAGTTTTTAATTG

ACGTGGACAAAGGCGAGAACTACTGCTTCAGCGTGCAAGCCGTGATCCCTTC

TCGTACCGTCAACCGGAAGAGCACAGATTCCCCCGTTGAGTGCATGGGCCAA

GAAAAGGGCGAGTTCCGGGAGAACTGGGTGAACGTCATCAGCAATTTAAAG

AAGATCGAAGATTTAATTCAGTCCATGCATATCGACGCCACTTTATACACAG

AATCCGACGTGCACCCCTCTTGTAAGGTGACCGCCATGAAATGTTTTTTACTG

GAGCTGCAAGTTATCTCTTTAGAGAGCGGAGACGCTAGCATCCACGACACCG

TGGAGAATTTAATCATTTTAGCCAATAACTCTTTATCCAGCAACGGCAACGTG

ACAGAGTCCGGCTGCAAGGAGTGCGAAGAGCTGGAGGAGAAGAACATCAAG

GAGTTTCTGCAATCCTTTGTGCACATTGTCCAGATGTTCATCAATACCTCC
```

Exemplary Mature Second Chimeric Polypeptide
(SEQ ID NO: 106)

```
VQLQQSGPELVKPGASVKMSCKASGYTFTSYVIQWVKQPGQGLEWIGSINPYN

DYTKYNEKFKGKATLTSDKSSITAYMEFSSLTSEDSALYYCARWGDGNYWGRG

TTLTVSSGGGGSGGGGSGGGGSDIEMTQSPAIMSASLGERVTMTCTASSSVSSSY

FHWYQQKPGSSPKLCIYSTSNLASGVPPRFSGSGSTSYSLTISSMEAEDAATYFCH

QYHRSPTFGGGTKLETKRITCPPPMSVEHADIWVKSYSLYSRERYICNSGFKRKA

GTSSLTECVLNKATNVAHWTTPSLKCIR
```

Exemplary DNA Encoding Mature Second Chimeric Polypeptide
(SEQ ID NO: 107)

```
GTGCAGCTGCAGCAGTCCGGACCCGAACTGGTCAAGCCCGGTGCCTCCGTGA

AAATGTCTTGTAAGGCTTCTGGCTACACCTTTACCTCCTACGTCATCCAATGG

GTGAAGCAGAAGCCCGGTCAAGGTCTCGAGTGGATCGGCAGCATCAATCCCT

ACAACGATTACACCAAGTATAACGAAAAGTTTAAGGGCAAGGCCACTCTGAC

AAGCGACAAGAGCTCCATTACCGCCTACATGGAGTTTTCCTCTTTAACTTCTG

AGGACTCCGCTTTATACTATTGCGCTCGTTGGGGCGATGGCAATTATTGGGGC

CGGGGAACTACTTTAACAGTGAGCTCCGGCGGCGGCGGAAGCGGAGGTGGA
```

-continued

```
GGATCTGGCGGTGGAGGCAGCGACATCGAGATGACACAGTCCCCCGCTATCA

TGAGCGCCTCTTTAGGAGAACGTGTGACCATGACTTGTACAGCTTCCTCCAGC

GTGAGCAGCTCCTATTTCCACTGGTACCAGCAGAAACCCGGCTCCTCCCCTAA

ACTGTGTATCTACTCCACAAGCAATTTAGCTAGCGGCGTGCCTCCTCGTTTTA

GCGGCTCCGGCAGCACCTCTTACTCTTTAACCATTAGCTCTATGGAGGCCGAA

GATGCCGCCACATACTTTTGCCATCAGTACCACCGGTCCCCTACCTTTGGCGG

AGGCACAAAGCTGGAGACCAAGCGGATTACATGCCCCCCTCCCATGAGCGTG

GAGCACGCCGACATCTGGGTGAAGAGCTATAGCCTCTACAGCCGGGAGAGGT

ATATCTGTAACAGCGGCTTCAAGAGGAAGGCCGGCACCAGCAGCCTCACCGA

GTGCGTGCTGAATAAGGCTACCAACGTGGCTCACTGGACAACACCCTCTTTA

AAGTGCATCCGG

Exemplary Precursor Second Chimeric Polypeptide
                                         (SEQ ID NO: 108)
MKWVTFISLLFLFSSAYSVQLQQSGPELVKPGASVKMSCKASGYTFTSYVIQWV

KQKPGQGLEWIGSINPYNDYTKYNEKFKGKATLTSDKSSITAYMEFSSLTSEDSA

LYYCARWGDGNYWGRGTTLTVSSGGGGSGGGGSGGGGSDIEMTQSPAIMSASL

GERVTMTCTASSSVSSSYFHWYQQKPGSSPKLCIYSTSNLASGVPPRFSGSGSTSY

SLTISSMEAEDAATYFCHQYHRSPTFGGGTKLETKRITCPPPMSVEHADIWVKSY

SLYSRERYICNSGFKRKAGTSSLTECVLNKATNVAHWTTPSLKCIR

Exemplary DNA Encoding Precursor Second Chimeric Polypeptide
                                         (SEQ ID NO: 109)
ATGAAATGGGTCACCTTCATCTCTTTACTGTTTTTATTTAGCAGCGCCTACAG

CGTGCAGCTGCAGCAGTCCGGACCCGAACTGGTCAAGCCCGGTGCCTCCGTG

AAAATGTCTTGTAAGGCTTCTGGCTACACCTTTACCTCCTACGTCATCCAATG

GGTGAAGCAGAAGCCCGGTCAAGGTCTCGAGTGGATCGGCAGCATCAATCCC

TACAACGATTACACCAAGTATAACGAAAAGTTTAAGGGCAAGGCCACTCTGA

CAAGCGACAAGAGCTCCATTACCGCCTACATGGAGTTTTCCTCTTTAACTTCT

GAGGACTCCGCTTTATACTATTGCGCTCGTTGGGGCGATGGCAATTATTGGGG

CCGGGGAACTACTTTAACAGTGAGCTCCGGCGGCGGCGGAAGCGGAGGTGG

AGGATCTGGCGGTGGAGGCAGCGACATCGAGATGACACAGTCCCCCGCTATC

ATGAGCGCCTCTTTAGGAGAACGTGTGACCATGACTTGTACAGCTTCCTCCAG

CGTGAGCAGCTCCTATTTCCACTGGTACCAGCAGAAACCCGGCTCCTCCCCTA

AACTGTGTATCTACTCCACAAGCAATTTAGCTAGCGGCGTGCCTCCTCGTTTT

AGCGGCTCCGGCAGCACCTCTTACTCTTTAACCATTAGCTCTATGGAGGCCGA

AGATGCCGCCACATACTTTTGCCATCAGTACCACCGGTCCCCTACCTTTGGCG

GAGGCACAAAGCTGGAGACCAAGCGGATTACATGCCCCCCTCCCATGAGCGT

GGAGCACGCCGACATCTGGGTGAAGAGCTATAGCCTCTACAGCCGGGAGAG

GTATATCTGTAACAGCGGCTTCAAGAGGAAGGCCGGCACCAGCAGCCTCACC

GAGTGCGTGCTGAATAAGGCTACCAACGTGGCTCACTGGACAACACCCTCTT

TAAAGTGCATCCGG
```

Anti-CD3/anti-CD28 Beads

In some embodiments, a CD3/CD28-binding agent can be an anti-CD3/anti-CD28 bead. An anti-CD3/anti-CD28 bead can include an anti-CD3 antibody or an antigen-binding fragment thereof and an anti-CD28 antibody or an antigen-binding fragment thereof, both of which are covalently or non-covalently linked to the beads. In some embodiments, the anti-CD3 antibody or antigen-binding fragment thereof is an anti-CD3 scFv (e.g., an of the exemplary anti-CD3 scFvs described herein). In some embodiments, the anti-CD28 antibody or antigen-binding fragment thereof is an anti-CD28 scFv (e.g., any anti-CD28 scFvs described herein). The beads can be any suitable spherical polymer particles known in the art. An average diameter of the beads can be about 0.5 to about 20 micrometers (e.g., about 0.5 to about 10, about 0.8 to about 8, or about 1 to about 5 micrometers). In some embodiments, the beads can include one or more paramagnetic material, such as but not limited to dynabeads. Non-limiting examples of anti-CD3/anti-CD28 beads include anti-CD3/anti-CD28 dynabeads, such as those developed by ThermoFisher Scientific, Gibco, and Invitrogen. Additional commercial sources of anti-CD3/anti-CD28 beads are known in the art.

IL-2 Receptor-Activating Agents

Provided herein are methods that include the use of one or more IL-2 receptor-activating agent(s). Non-limiting examples of the IL-2 receptor-activating agents include single-chain chimeric polypeptides, multi-chain chimeric polypeptides, soluble IL-2 (e.g., recombinant human IL-2), and an agonistic antibody that binds specifically to an IL-2 receptor (e.g., a human IL-2 receptor).

Single-Chain Chimeric Polypeptides

In some embodiments, the IL-2 receptor-activating agents are single-chain chimeric polypeptides that include a first target-binding domain, a soluble tissue factor domain, and a second target-binding domain, wherein the first target-binding domain and the second target-binding domain bind to a receptor for IL-2. Non-limiting examples of single-chain chimeric polypeptides that are IL-2 receptor activating agents are described herein.

Soluble IL-2

In some examples, an IL-2 receptor-activating agent can be a soluble IL-2 (e.g., any of the soluble IL-2 proteins described herein). In some embodiments, a soluble IL-2 protein can include a sequence that is at least 80% identical, at least 82% identical, at least 84% identical, at least 86% identical, at least 88% identical, at least 90% identical, at least 92% identical, at least 94% identical, at least 96% identical, at least 98% identical, at least 99% identical, or 100% identical to SEQ ID NO: 1.

Agonistic Antibodies

In some examples, an IL-2 receptor activating agent can be an agonistic antibody that binds specifically to an IL-2 receptor (e.g., a human IL-2 receptor) (see, e.g., those described in Gaulton et al., *Clinical Immunology and Immunopathology* 36(1): 18-29, 1985), or an antigen-binding fragment thereof.

IgG1 Antibody Constructs

An IgG1 antibody construct can be an IgG1 antibody (e.g., a monoclonal or a polyclonal IgG1 antibody that binds specifically to a soluble tissue factor domain, e.g., any of the soluble tissue factor domains described herein). In some embodiments, an IgG1 antibody construct can be an antibody or an antibody fragment that includes an IgG1 Fc region (e.g., a human IgG1 Fc region). As is known in the art, the IgG1 Fc region binds to CD16a (FcRgammaIII) (e.g., human CD16a) and induces its intracellular signaling. In some embodiments, an IgG1 antibody construct can be a single-chain or a multi-chain polypeptide that includes an Fc region that is capable of binding specifically to CD16a (FcRgammaIII) (e.g., human CD16a) and is capable of inducing its intracellular signaling in a natural killer cell (e.g., a human natural killer cell), and specifically binds to the soluble tissue factor domain. In some embodiments, an IgG1 antibody construct can be a single chain or a multi-chain polypeptide that includes an Fc region that includes a sequence that is at least 80% identical (e.g., at least 82% identical, at least 84% identical, at least 86% identical, at least 88% identical, at least 90% identical, at least 92% identical, at least 94% identical, at least 96% identical, at least 98% identical, or at least 99% identical) to a wildtype IgG1 Fc domain (e.g., a wildtype human IgG1 Fc domain, e.g., SEQ ID NO: 98) and is capable of binding specifically to CD16a (FcRgammaIII) (e.g., human CD16a), and is capable of inducing its intracellular signaling in a natural killer cell (e.g., a human natural killer cell), and specifically binds to the soluble tissue factor domain. In some embodiments, the IgG1 antibody construct binds specifically to a soluble tissue factor domain (e.g., any of the soluble tissue factor domains described herein) and includes a non-human Fc region (e.g., a Fc region from a non-human antibody) that has been altered (e.g., by substituting 1, 2, 3, 4, 5, 6, 7, 8, 9, 10, 11, 12, 13, 14, 15, 16, 17, 18, 19, or 20 amino acids in the wildtype non-human Fc region) such that the non-human Fc region is capable of binding to human CD16a (human FcRgammaIII) and inducing its intracellular signaling in a natural killer cell (e.g., a human natural killer cell).

```
Wildtype Human IgG1 Fc Region
                                        (SEQ ID NO: 98)
PCPAPELLGGPSVFLFPPKPKDTLMISRTPEVTCVVVDVSHEDPEVKENW

YVDGVEVHNAKTKPREEQYNSTYRVVSVLIVLHQDWINGKEYKCKVSNKA

LPAPIEKTISKAKGQPREPQVYTLPPSRDELTKNQVSITCLVKGFYPSDI

AVEWESNGQPENNYKTTPPVLDSDGSFFLYSKLTVDKSRWQQGNVFSCSV

MHEALHNHYTQKSLSLSPGK
```

In some examples, the IgG1 antibody construct is a humanized or fully human anti-tissue factor antibody (see, e.g., the anti-tissue factor antibodies described in U.S. Pat. Nos. 7,968,094 and 8,007,795).

In some embodiments, the IgG1 antibody construct can include a heavy chain variable domain that includes the following set of CDR sequences: a CDR1 including DYNVY (SEQ ID NO: 66); a CDR2 including YIDPYN-GITIYDQNFKG (SEQ ID NO: 67); and a CDR3 including DVTTALDF (SEQ ID NO: 68).

In some embodiments, the IgG1 antibody construct can include a heavy chain variable domain that includes the following set of CDR sequences: a CDR1 including DYNVY (SEQ ID NO: 66); a CDR2 including YIDPYN-GITIYDQNLKG (SEQ ID NO: 74); and a CDR3 including DVTTALDF (SEQ ID NO: 68).

```
Exemplary heavy chain variable domain
                                        (SEQ ID NO: 72)
QIQLVQSGGEVKKPGASVRVSCKASGYSFTDYNVYWVRQSPGKGLEWIGY

IDPYNGITIYDQNFKGKATLTVDKSTSTAYMELSSLRSEDTAVYFCARDV

TTALDFWGQGTTVTVSS
```

In some embodiments, the IgG1 antibody construct can include a heavy chain variable domain that includes a sequence that is at least 70% identical (e.g., at least 72%, at least 74%, at least 75%, at least 76%, at least 78%, at least 80%, at least 82%, at least 84%, at least 85%, at least 86%, at least 88%, at least 90%, at least 92%, at least 94%, at least 95%, at least 96%, at least 97%, at least 98%, at least 99%, or 100% identical) to SEQ ID NO: 72.

In some embodiments, the IgG1 antibody construct can include a light chain variable domain that includes the following set of CDR sequences: a CDR1 including LASQTIDTWLA (SEQ ID NO: 69); a CDR2 including AATNLAD (SEQ ID NO: 70); and a CDR3 including QQVYSSPFT (SEQ ID NO: 71).

```
Exemplary light chain variable domain
                                         (SEQ ID NO: 73)
DIQMTQSPASLSASVGDRVTITCLASQTIDTWLAWYLQKPGKSPQLLIYA

ATNLADGVPSRFSGSGSGTDFSFTISSLQPEDFATYYCQQVYSSPFTFGQ

GTKLEIK
```

In some embodiments, the IgG1 antibody construct can include a light chain variable domain that includes a sequence that is at least 70% identical (e.g., at least 72%, at least 74%, at least 75%, at least 76%, at least 78%, at least 80%, at least 82%, at least 84%, at least 85%, at least 86%, at least 88%, at least 90%, at least 92%, at least 94%, at least 95%, at least 96%, at least 97%, at least 98%, at least 99%, or 100% identical) to SEQ ID NO: 73.

Non-limiting examples of the IgG1 antibody construct can include: a heavy chain variable domain including a sequence that is at least 70% identical (e.g., at least 72%, at least 74%, at least 75%, at least 76%, at least 78%, at least 80%, at least 82%, at least 84%, at least 85%, at least 86%, at least 88%, at least 90%, at least 92%, at least 94%, at least 95%, at least 96%, at least 97%, at least 98%, at least 99%, or 100% identical) to SEQ ID NO: 72, and a light chain variable domain including a sequence that is at least 70% identical (e.g., at least 72%, at least 74%, at least 75%, at least 76%, at least 78%, at least 80%, at least 82%, at least 84%, at least 85%, at least 86%, at least 88%, at least 90%, at least 92%, at least 94%, at least 95%, at least 96%, at least 97%, at least 98%, at least 99%, or 100% identical) to SEQ ID NO: 73.

mTOR Inhibitors

Non-limiting examples of mTOR inhibitors include rapamycin (also called sirolimus), Zortress (also called everolimus and RAD001), Torisel (also called temsirolimus and CCI-779), Afinitor (everolimus), dactolisib (also called NVP-BEZ235), GSK2126458, XL765, AZD8055, INK128 (also called MLN0128), OSI027, and RapaLinks.

Exemplary Methods of Stimulating or Increasing Proliferation of a $T_{reg}$ Cell Provided herein are methods of stimulating or increasing the proliferation of a $T_{reg}$ cell that include culturing a $T_{reg}$ cell in a liquid culture medium over a period of time, where at the beginning of the period of time, the liquid culture medium includes: a CD3/CD28-binding agent (e.g., any of the exemplary CD3/CD28-binding agents described herein); and a single-chain chimeric polypeptide including a first target-binding domain, a soluble tissue factor domain, and a second target-binding domain, where the first target-binding domain and the second target-binding domain bind to a receptor for IL-2. In some examples, the liquid culture medium further includes an IgG1 antibody construct that includes at least one antigen-binding domain that binds specifically to the soluble tissue factor domain of the single-chain chimeric polypeptide (e.g., any of the exemplary IgG1 antibody constructs described herein). In some examples, the single-chain chimeric polypeptide includes a sequence that is at least 80% identical (e.g., at least 82% identical, at least 84% identical, at least 86% identical, at least 88% identical, at least 90% identical, at least 92% identical, at least 94% identical, at least 96% identical, at least 98% identical, at least 99% identical, or 100% identical) to SEQ ID NO: 3. In some examples, the single-chain chimeric polypeptide includes a sequence that is at least 80% identical (e.g., at least 82% identical, at least 84% identical, at least 86% identical, at least 88% identical, at least 90% identical, at least 92% identical, at least 94% identical, at least 96% identical, at least 98% identical, at least 99% identical, or 100% identical) to SEQ ID NO: 4.

In some embodiments, the liquid culture medium includes about 10 nM to about 500 nM (e.g., about 10 nM to about 450 nM, about 10 nM to about 400 nM, about 10 nM to about 350 nM, about 10 nM to about 300 nM, about 10 nM to about 250 nM, about 10 nM to about 200 nM, about 10 nM to about 150 nM, about 10 nM to about 100 nM, about 10 nM to about 50 nM, about 50 nM to about 500 nM, about 50 nM to about 450 nM, about 50 nM to about 400 nM, about 50 nM to about 350 nM, about 50 nM to about 300 nM, about 50 nM to about 250 nM, about 50 nM to about 200 nM, about 50 nM to about 150 nM, about 50 nM to about 100 nM, about 100 nM to about 500 nM, about 100 nM to about 450 nM, about 100 nM to about 400 nM, about 100 nM to about 350 nM, about 100 nM to about 300 nM, about 100 nM to about 250 nM, about 100 nM to about 200 nM, about 100 nM to about 150 nM, about 150 nM to about 500 nM, about 150 nM to about 450 nM, about 150 nM to about 400 nM, about 150 nM to about 350 nM, about 150 nM to about 300 nM, about 150 nM to about 250 nM, about 150 nM to about 200 nM, about 200 nM to about 500 nM, about 200 nM to about 450 nM, about 200 nM to about 400 nM, about 200 nM to about 350 nM, about 200 nM to about 300 nM, about 200 nM to about 250 nM, about 250 nM to about 500 nM, about 250 nM to about 450 nM, about 250 nM to about 400 nM, about 250 nM to about 350 nM, about 250 nM to about 300 nM, about 300 nM to about 500 nM, about 300 nM to about 450 nM, about 300 nM to about 400 nM, about 300 nM to about 350 nM, about 350 nM to about 500 nM, about 350 nM to about 450 nM, about 350 nM to about 400 nM, about 400 nM to about 500 nM, about 400 nM to about 450 nM, or about 450 nM to about 500 nM), of the single-chain chimeric polypeptide.

In some embodiments, the CD3/CD28-binding agent is an anti-CD3/anti-CD28 bead (e.g., any of the exemplary anti-CD3/anti-CD28 beads described herein or known in the art). In some embodiments the liquid culture medium includes the anti-CD3/anti-CD28 bead at a ratio of about 1:1 to about 6:1 beads/cell (e.g., about 1:1 to about 5:1, about 1:1 to about 4:1, about 1:1 to about 3:1, about 1:1 to about 2:1, about 2:1 to about 6:1, about 2:1 to about 5:1, about 2:1 to about 4:1, about 2:1 to about 3:1, about 3:1 to about 6:1, about 3:1 to about 5:1, about 3:1 to about 4:1, about 4:1 to about 6:1, about 4:1 to about 5:1, about 5:1 to about 6:1 beads/cell).

In some embodiments, the CD3/CD28-binding agent is an additional single-chain chimeric polypeptide including a first antigen-binding domain, a soluble tissue factor domain, and a second target-binding domain, where the first target-binding domain of the additional single-chain chimeric polypeptide specifically binds to CD3 and the second target-binding domain of the additional single-chain chimeric polypeptide specifically binds to CD28. In some embodiments, the liquid culture medium further includes an IgG1 antibody construct (e.g., any of the exemplary IgG1 antibody constructs described herein) that includes at least one antigen-binding domain that binds specifically to the soluble tissue factor domain of the additional single-chain chimeric polypeptide.

In some embodiments, the additional single-chain chimeric polypeptide comprises a sequence that is at least 80% identical (e.g., at least 82% identical, at least 84% identical, at least 86% identical, at least 88% identical, at least 90% identical, at least 92% identical, at least 94% identical, at least 96% identical, at least 98% identical, at least 99% identical, or 100% identical) to SEQ ID NO: 7. In some embodiments, the additional single-chain chimeric polypeptide comprises a sequence that is at least 80% identical (e.g., at least 82% identical, at least 84% identical, at least 86% identical, at least 88% identical, at least 90% identical, at least 92% identical, at least 94% identical, at least 96% identical, at least 98% identical, at least 99% identical, or 100% identical) to SEQ ID NO: 8. In some embodiments, the liquid culture medium includes about 10 nM to about 1000 nM (e.g., about 10 nM to about 950 nM, about 10 nM to about 900 nM, about 10 nM to about 850 nM, about 10 nM to about 800 nM, about 10 nM to about 750 nM, about 10 nM to about 700 nM, about 10 nM to about 650 nM, about 10 nM to about 600 nM, about 10 nM to about 550 nM, about 10 nM to about 500 nM, about 10 nM to about 450 nM, about 10 nM to about 400 nM, about 10 nM to about 350 nM, about 10 nM to about 300 nM, about 10 nM to about 250 nM, about 10 nM to about 200 nM, about 10 nM to about 150 nM, about 10 nM to about 100 nM, about 10 nM to about 50 nM, about 25 nM to about 1000 nM, about 25 nM to about 950 nM, about 25 nM to about 900 nM, about 25 nM to about 850 nM, about 25 nM to about 800 nM, about 25 nM to about 750 nM, about 25 nM to about 700 nM, about 25 nM to about 650 nM, about 25 nM to about 600 nM, about 25 nM to about 550 nM, about 25 nM to about 500 nM, about 25 nM to about 450 nM, about 25 nM to about 400 nM, about 25 nM to about 350 nM, about 25 nM to about 300 nM, about 25 nM to about 250 nM, about 25 nM to about 200 nM, about 25 nM to about 150 nM, about 25 nM to about 100 nM, about 25 nM to about 50 nM, about 50 nM to about 1000 nM, about 50 nM to about 950 nM, about 50 nM to about 900 nM, about 50 nM to about 850 nM, about 50 nM to about 800 nM, about 50 nM to about 750 nM, about 50 nM to about 700 nM, about 50 nM to about 650 nM, about 50 nM to about 600 nM, about 50 nM to about 550 nM, about 50 nM to about 500 nM, about 50 nM to about 450 nM, about 50 nM to about 400 nM, about 50 nM to about 350 nM, about 50 nM to about 300 nM, about 50 nM to about 250 nM, about 50 nM to about 200 nM, about 50 nM to about 150 nM, about 50 nM to about 100 nM, about 100 nM to about 1000 nM, about 100 nM to about 950 nM, about 100 nM to about 900 nM, about 100 nM to about 850 nM, about 100 nM to about 800 nM, about 100 nM to about 750 nM, about 100 nM to about 700 nM, about 100 nM to about 650 nM, about 100 nM to about 600 nM, about 100 nM to about 550 nM, about 100 nM to about 500 nM, about 100 nM to about 450 nM, about 100 nM to about 400 nM, about 100 nM to about 350 nM, about 100 nM to about 300 nM, about 100 nM to about 250 nM, about 100 nM to about 200 nM, about 100 nM to about 150 nM, about 150 nM to about 1000 nM, about 150 nM to about 950 nM, about 150 nM to about 900 nM, about 150 nM to about 850 nM, about 150 nM to about 800 nM, about 150 nM to about 750 nM, about 150 nM to about 700 nM, about 150 nM to about 650 nM, about 150 nM to about 600 nM, about 150 nM to about 550 nM, about 150 nM to about 500 nM, about 150 nM to about 450 nM, about 150 nM to about 400 nM, about 150 nM to about 350 nM, about 150 nM to about 300 nM, about 150 nM to about 250 nM, about 150 nM to about 200 nM, about 200 nM to about 1000 nM, about 200 nM to about 950 nM, about 200 nM to about 900 nM, about 200 nM to about 850 nM, about 200 nM to about 800 nM, about 200 nM to about 750 nM, about 200 nM to about 700 nM, about 200 nM to about 650 nM, about 200 nM to about 600 nM, about 200 nM to about 550 nM, about 200 nM to about 500 nM, about 200 nM to about 450 nM, about 200 nM to about 400 nM, about 200 nM to about 350 nM, about 200 nM to about 300 nM, about 200 nM to about 250 nM, about 250 nM to about 1000 nM, about 250 nM to about 950 nM, about 250 nM to about 900 nM, about 250 nM to about 850 nM, about 250 nM to about 800 nM, about 250 nM to about 750 nM, about 250 nM to about 700 nM, about 250 nM to about 650 nM, about 250 nM to about 600 nM, about 250 nM to about 550 nM, about 250 nM to about 500 nM, about 250 nM to about 450 nM, about 250 nM to about 400 nM, about 250 nM to about 350 nM, about 250 nM to about 300 nM, about 300 nM to about 1000 nM, about 300 nM to about 950 nM, about 300 nM to about 900 nM, about 300 nM to about 850 nM, about 300 nM to about 800 nM, about 300 nM to about 750 nM, about 300 nM to about 700 nM, about 300 nM to about 650 nM, about 300 nM to about 600 nM, about 300 nM to about 550 nM, about 300 nM to about 500 nM, about 300 nM to about 450 nM, about 300 nM to about 400 nM, about 300 nM to about 350 nM, about 350 nM to about 1000 nM, about 350 nM to about 950 nM, about 350 nM to about 900 nM, about 350 nM to about 850 nM, about 350 nM to about 800 nM, about 350 nM to about 750 nM, about 350 nM to about 700 nM, about 350 nM to about 650 nM, about 350 nM to about 600 nM, about 350 nM to about 550 nM, about 350 nM to about 500 nM, about 350 nM to about 450 nM, about 350 nM to about 400 nM, about 400 nM to about 1000 nM, about 400 nM to about 950 nM, about 400 nM to about 900 nM, about 400 nM to about 850 nM, about 400 nM to about 800 nM, about 400 nM to about 750 nM, about 400 nM to about 700 nM, about 400 nM to about 650 nM, about 400 nM to about 600 nM, about 400 nM to about 550 nM, about 400 nM to about 500 nM, about 400 nM to about 450 nM, about 450 nM to about 1000 nM, about 450 nM to about 950 nM, about 450 nM to about 900 nM, about 450 nM to about 850 nM, about 450 nM to about 800 nM, about 450 nM to about 750 nM, about 450 nM to about 700 nM, about 450 nM to about 650 nM, about 450 nM to about 600 nM, about 450 nM to about 550 nM, about 450 nM to about 500 nM, about 500 nM to about 1000 nM, about 500 nM to about 950 nM, about 500 nM to about 900 nM, about 500 nM to about 850 nM, about 500 nM to about 800 nM, about 500 nM to about 750 nM, about 500 nM to about 700 nM, about 500 nM to about 650 nM, about 500 nM to about 600 nM, about 500 nM to about 550 nM, about 550 nM to about 1000 nM, about 550 nM to about 950 nM, about 550 nM to about 900 nM, about 550 nM to about 850 nM, about 550 nM to about 800 nM, about 550 nM to about 750 nM, about 550 nM to about 700 nM, about 550 nM to about 650 nM, about 550 nM to about 600 nM, about 600 nM to about 1000 nM, about 600 nM to about 950 nM, about 600 nM to about 900 nM, about 600 nM to about 850 nM, about 600 nM to about 800 nM, about 600 nM to about 750 nM, about 600 nM to about 700 nM, about 600 nM to about 650 nM, about 650 nM to about 1000 nM, about 650 nM to about 950 nM, about 650 nM to about 900 nM, about 650 nM to about 850 nM, about 650 nM to about 800 nM, about 650 nM to about 750 nM, about 650 nM to about 700 nM, about 700 nM to about 1000 nM, about 700 nM to about 950 nM, about 700 nM to about 900 nM, about 700 nM to about 850 nM, about 700 nM to about 800 nM, about 700 nM to about 750 nM, about 750 nM to about 1000 nM, about 750 nM to about 950 nM, about 750 nM to about 900 nM, about 750 nM to about 850 nM, about 750 nM to about 800 nM, about 800 nM to about 1000 nM, about 800 nM to about 950 nM, about 800 nM to about 900 nM, about 800 nM to about 850 nM, about 850 nM to about 1000 nM, about 850 nM to about 950 nM, about 850 nM to about 900 nM, about 900 nM to about 1000 nM, about 900 nM to about 950 nM, or about 950 nM to about 1000 nM) of the additional single-chain chimeric polypeptide.

In some embodiments, the CD3/CD28-binding agent is multi-chain chimeric polypeptide that includes a first chimeric polypeptide including (i) a first target-binding domain; (ii) a soluble tissue factor domain; and (iii) a first domain of a pair of affinity domains; and a second chimeric polypeptide comprising: (i) a second domain of a pair of affinity domains; and (ii) a second target-binding domain, wherein: the first chimeric polypeptide and the second chimeric polypeptide associate through the binding of the first domain and the second domain of the pair of affinity domains; and wherein the first target-binding domain binds to CD3 and the second target-binding domain binds to CD28, or the first target-binding domain binds to CD28 and the second target-binding domain to CD3. In some embodiments, the liquid culture medium further includes an IgG1 antibody construct (e.g., any of the exemplary IgG1 antibody constructs described herein) that includes at least one antigen-binding domain that binds specifically to the soluble tissue factor domain of the multi-chain chimeric polypeptide.

In some embodiments, the first chimeric polypeptide comprises a sequence that is at least 80% identical (e.g., at least 82% identical, at least 84% identical, at least 86% identical, at least 88% identical, at least 90% identical, at least 92% identical, at least 94% identical, at least 96% identical, at least 98% identical, at least 99% identical, or 100% identical) to SEQ ID NO: 102. In some embodiments, the first chimeric polypeptide comprises a sequence that is at least 80% identical (e.g., at least 82% identical, at least 84% identical, at least 86% identical, at least 88% identical, at least 90% identical, at least 92% identical, at least 94% identical, at least 96% identical, at least 98% identical, at least 99% identical, or 100% identical) to SEQ ID NO: 104. In some embodiments, the second chimeric polypeptide comprises a sequence that is at least 80% identical (e.g., at least 82% identical, at least 84% identical, at least 86% identical, at least 88% identical, at least 90% identical, at least 92% identical, at least 94% identical, at least 96% identical, at least 98% identical, at least 99% identical, or 100% identical) to SEQ ID NO: 106. In some embodiments, the second chimeric polypeptide comprises a sequence that is at least 80% identical (e.g., at least 82% identical, at least 84% identical, at least 86% identical, at least 88% identical, at least 90% identical, at least 92% identical, at least 94% identical, at least 96% identical, at least 98% identical, at least 99% identical, or 100% identical) to SEQ ID NO: 108. In some embodiments, the liquid culture medium includes about 10 nM to about 1000 nM (e.g., or any of the subranges of this range described herein) of the multi-chain chimeric polypeptide. In some embodiments, the liquid culture medium further comprises an mTOR inhibitor (e.g., any of the mTOR inhibitors described herein, e.g., rapamycin). In some embodiments, the liquid culture medium includes about 10 nM to about 500 nM (e.g., or any of the subranges of this range described herein) of the mTOR inhibitor. In some embodiments, the liquid culture medium does not include an mTOR inhibitor.

Some embodiments further include periodically adding to the liquid culture medium, after each 36 hours to about 60 hours (e.g., about 36 to about 56 hours, about 36 to about 52 hours, about 36 to about 48 hours, about 36 to about 44 hours, about 36 to about 40 hours, about 40 to about 60 hours, about 40 to about 56 hours, about 40 to about 52 hours, about 40 to about 48 hours, about 40 to about 44 hours, about 44 to about 60 hours, about 44 to about 56 hours, about 44 to about 52 hours, about 44 to about 48 hours, about 48 to about 60 hours, about 48 to about 56 hours, about 48 to about 52 hours, about 52 to about 60 hours, about 52 to about 56 hours, or about 56 to about 60 hours) after the start of the period of time, the single-chain chimeric polypeptide (e.g., any of the single-chain chimeric polypeptides described herein). In some embodiments, the periodic addition of the single-chain chimeric polypeptide is performed to result in a concentration of about 10 nM to about 500 nM (e.g., or any of the subranges of this range described herein) of the single-chain chimeric polypeptide in the liquid culture medium.

Some embodiments further include periodically adding to the liquid culture medium, after each about 4 days to about 10 days (e.g., after each about 4 days to about 9 days, after each about 4 days to about 8 days, after each about 4 days to about 7 days, after each about 4 days to about 6 days, after each about 4 days to about 5 days, after each about 5 days to about 10 days, after each about 5 days to about 9 days, after each about 5 days to about 8 days, after each about 5 days to about 7 days, after each about 5 days to about 6 days, after each about 6 days to about 10 days, after each about 6 days to about 9 days, after each about 6 days to about 8 days, after each about 6 days to about 7 days, after each about 7 days to about 10 days, after each about 7 days to about 9 days, after each about 7 days to about 8 days, after each about 8 days to about 10 days, after each about 8 days to about 9 days, or after each about 9 days to about 10 days) after the start of the period of time, the CD3/CD28-binding agent.

In some embodiments of any of the methods of stimulating or increasing the proliferation of a $T_{reg}$ cell described herein, the liquid culture medium can further include an mTOR inhibitor (e.g., any of the mTOR inhibitors described herein). In some embodiments, the liquid culture medium includes about 10 nM to about 500 nM (e.g., or any of the subranges of this range described herein) of the mTOR inhibitor (e.g., any of the mTOR inhibitors described herein).

In some examples of these methods, the liquid culture medium is a serum-free liquid culture medium. In some embodiments of any of the methods described herein, the liquid culture medium is a chemically-defined liquid culture medium.

In some embodiments, the period of time is about 7 days to about 56 days (e.g., about 7 days to about 56 days, about 7 days to about 54 days, about 7 days to about 46 days, about 7 days to about 38 days, about 7 days to about 32 days, about 7 days to about 28 days, about 7 days to about 25 days, about 7 days to about 23 days, about 7 days to about 21 days, about 7 days to about 19 days, about 7 days to about 17 days, about 7 days to about 15 days, about 7 days to about 13 days, about 7 days to about 11 days, about 7 days to about 9 days, about 9 days to about 56 days, about 9 days to about 54 days, about 9 days to about 46 days, about 9 days to about 38 days, about 9 days to about 32 days, about 9 days to about 28 days, about 9 days to about 25 days, about 9 days to about 23 days, about 9 days to about 21 days, about 9 days to about 19 days, about 9 days to about 17 days, about 9 days to about 15 days, about 9 days to about 13 days, about 9 days to about 11 days, about 11 days to about 56 days, about 11 days to about 54 days, about 11 days to about 46 days, about 11 days to about 38 days, about 11 days to about 32 days, about 11 days to about 28 days, about 11 days to about 25 days, about 11 days to about 23 days, about 11 days to about 21 days, about 11 days to about 19 days, about 11 days to about 17 days, about 11 days to about 15 days, about 11 days to about 13 days, about 13 days to about 56 days, about 13 days to about 54 days, about 13 days to about 46 days, about 13 days to about 38 days, about 13 days to about 32 days, about 13 days to about 28 days, about 13 days to about 25 days, about 13 days to about 23 days, about 13 days to about 21 days, about 13 days to about 19 days, about 13 days to about 17 days, about 13 days to about 15 days, about 15 days to about 56 days, about 15 days to about 54 days, about 15 days to about 46 days, about 15 days to about 38 days, about 15 days to about 32 days, about 15 days to about 28 days, about 15 days to about 25 days, about 15 days to about 23 days, about 15 days to about 21 days, about 15 days to about 19 days, about 15 days to about 17 days, about 17 days to about 56 days, about 17 days to about 54 days, about 17 days to about 46 days, about 17 days to about 38 days, about 17 days to about 32 days, about 17 days to about 28 days, about 17 days to about 25 days, about 17 days to about 23 days, about 17 days to about 21 days, about 17 days to about 19 days, about 19 days to about 56 days, about 19 days to about 54 days, about 19 days to about 46 days, about 19 days to about 38 days, about 19 days to about 32 days, about 19 days to about 28 days, about 19 days to about 25 days, about 19 days to about 23 days, about 19 days to about 21 days, about 21 days to about 56 days, about 21 days to about 54 days, about 21 days to about 46 days, about 21 days to about 38 days, about 21 days to about 32 days, about 21 days to about 28 days, about 21 days to about 25 days, about 21 days to about 23 days, about 23 days to about 56 days, about 23 days to about 54 days, about 23 days to about 46 days, about 23 days to about 38 days, about 23 days to about 32 days, about 23 days to about 28 days, about 23 days to about 25 days, about 25 days to about 56 days, about 25 days to about 54 days, about 25 days to about 46 days, about 25 days to about 38 days, about 25 days to about 32 days, about 25 days to about 28 days, about 28 days to about 56 days, about 28 days to about 54 days, about 28 days to about 50 days, about 28 days to about 46 days, about 28 days to about 38 days, about 28 days to about 32 days, about 32 days to about 56 days, about 32 days to about 54 days, about 32 days to about 46 days, about 32 days to about 38 days, about 38 days to about 56 days, about 38 days to about 54 days, about 38 days to about 46 days, about 46 days to about 56 days, about 46 days to about 54 days, about 54 days to about 56 days).

Some embodiments further include, before the culturing step, a step of isolating the $T_{reg}$ cell from a sample obtained from a subject (e.g., using any of the methods of isolating described herein).

Exemplary Methods of Stimulating or Increasing Proliferation of a $T_{reg}$ Cell Also provided are methods of stimulating or increasing the proliferation of a $T_{reg}$ cell that include: culturing a $T_{reg}$ cell in a liquid culture medium over a period of time, where at the beginning of the period of time, the liquid culture medium includes: an IL-2 receptor-activating agent (e.g., any of the IL-2 receptor activating agents described herein); and a single-chain chimeric polypeptide comprising a first target-binding domain, a soluble tissue factor domain, and a second target-binding domain, where: the first target-binding domain of the single-chain chimeric polypeptide binds to CD3 and the second target-binding domain of the single-chain chimeric polypeptide binds to CD28. In some examples, the liquid culture medium further includes an IgG1 antibody construct that comprises at least one antigen-binding domain that binds specifically to the soluble tissue factor domain of the single-chain chimeric polypeptide (e.g., any of the exemplary IgG1 antibody constructs described herein).

In some embodiments, the single-chain chimeric polypeptide includes a sequence that is at least 80% identical (e.g., at least 82% identical, at least 84% identical, at least 86% identical, at least 88% identical, at least 90% identical, at least 92% identical, at least 94% identical, at least 96% identical, at least 98% identical, at least 99% identical, or 100% identical) to SEQ ID NO: 7. In some embodiments, the single-chain chimeric polypeptide includes a sequence that is at least 80% identical (e.g., at least 82% identical, at least 84% identical, at least 86% identical, at least 88% identical, at least 90% identical, at least 92% identical, at least 94% identical, at least 96% identical, at least 98% identical, at least 99% identical, or 100% identical) to SEQ ID NO: 8.

In some embodiments, the liquid culture medium includes about 10 nM to about 1000 nM (e.g., or any of the subranges of this range described herein) of the single-chain chimeric polypeptide (e.g., any of the single-chain chimeric polypeptides described herein)

In some embodiments, the IL-2 receptor-activating agent is a soluble IL-2. In some embodiments, the human soluble IL-2 includes a sequence that is at least 80% identical (e.g., at least 82% identical, at least 84% identical, at least 86% identical, at least 88% identical, at least 90% identical, at least 92% identical, at least 94% identical, at least 96% identical, at least 98% identical, at least 99% identical, or 100% identical) to SEQ ID NO: 1. In some embodiments, the liquid culture medium includes about 100 IU/mL to about 800 IU/mL (e.g., about 100 IU/mL to about 800 IU/mL, about 100 IU/mL to about 700 IU/mL, about 100 IU/mL to about 600 IU/mL, about 100 IU/mL to about 500 IU/mL, about 100 IU/mL to about 400 IU/mL, about 100 IU/mL to about 300 IU/mL, about 100 IU/mL to about 200 IU/mL, about 200 IU/mL to about 800 IU/mL, about 200 IU/mL to about 700 IU/mL, about 200 IU/mL to about 600 IU/mL, about 200 IU/mL to about 500 IU/mL, about 200 IU/mL to about 400 IU/mL, about 200 IU/mL to about 300 IU/mL, about 300 IU/mL to about 800 IU/mL, about 300 IU/mL to about 700 IU/mL, about 300 IU/mL to about 600 IU/mL, about 300 IU/mL to about 500 IU/mL, about 300 IU/mL to about 400 IU/mL, about 400 IU/mL to about 800 IU/mL, about 400 IU/mL to about 700 IU/mL, about 400 IU/mL to about 600 IU/mL, about 400 IU/mL to about 500 IU/mL, about 500 IU/mL to about 800 IU/mL, about 500 IU/mL to about 700 IU/mL, about 500 IU/mL to about 600 IU/mL, about 600 IU/mL to about 800 IU/mL, about 600 IU/mL to about 700 IU/mL, or about 700 IU/mL to about 800 IU/mL) of the human soluble IL-2.

In some embodiments, the liquid culture medium further includes an mTOR inhibitor (e.g., any of the exemplary mTOR inhibitors described herein, e.g., rapamycin). In some embodiments, the liquid culture medium includes about 10 nM to about 500 nM (e.g., or any of the subranges of this range described herein) of the mTOR inhibitor.

Some embodiments of these methods further include periodically adding to the liquid culture medium, after each 36 hours to about 60 hours (e.g., about 36 to about 56 hours, about 36 to about 52 hours, about 36 to about 48 hours, about 36 to about 44 hours, about 36 to about 40 hours, about 40 to about 60 hours, about 40 to about 56 hours, about 40 to about 52 hours, about 40 to about 48 hours, about 40 to about 44 hours, about 44 to about 60 hours, about 44 to about 56 hours, about 44 to about 52 hours, about 44 to about 48 hours, about 48 to about 60 hours, about 48 to about 56 hours, about 48 to about 52 hours, about 52 to about 60 hours, about 52 to about 56 hours, or about 56 to about 60 hours) after the start of the period of time, the IL-2 receptor-activating agent (e.g., any of the IL-2 receptor-activating agents described herein). In some embodiments, the periodic addition of the IL-2 receptor activating agent is performed to result in a concentration of about 10 nM to about 1000 nM (e.g., or any of the subranges of this range described herein) of the IL-2 receptor-activating agent in the liquid culture medium.

Some embodiments of these methods further include periodically adding to the liquid culture medium, after each about 4 days to about 10 days (e.g., after each about 4 days to about 9 days, after each about 4 days to about 8 days, after each about 4 days to about 7 days, after each about 4 days to about 6 days, after each about 4 days to about 5 days, after each about 5 days to about 10 days, after each about 5 days to about 9 days, after each about 5 days to about 8 days, after each about 5 days to about 7 days, after each about 5 days to about 6 days, after each about 6 days to about 10 days, after each about 6 days to about 9 days, after each about 6 days to about 8 days, after each about 6 days to about 7 days, after each about 7 days to about 10 days, after each about 7 days to about 9 days, after each about 7 days to about 8 days, after each about 8 days to about 10 days, after each about 8 days to about 9 days, or after each about 9 days to about 10 days) after the start of the period of time, the single-chain chimeric polypeptide (e.g., any of the exemplary single-chain chimeric polypeptides described herein).

In some embodiments of any of these methods, the period of time is about 7 to about 56 days (e.g., or any of the subranges of this range described herein).

Some embodiments further include, before the culturing step, a step of isolating the $T_{reg}$ cell from a sample obtained from a subject (e.g., using any of the methods of isolating described herein).

Exemplary Methods of Stimulating or Increasing Proliferation of a $T_{reg}$ Cell Also provided are methods of stimulating or increasing the proliferation of a $T_{reg}$ cell that include: culturing a $T_{reg}$ cell in a liquid culture medium over a period of time, where at the beginning of the period of time, the liquid culture medium includes: a CD3/CD28-binding agent (e.g., any of the CD3/CD28-binding agents described herein); and a multi-chain chimeric polypeptide that includes: (a) a first chimeric polypeptide including: (i) a first target-binding domain; (ii) a soluble tissue factor domain; and (iii) a first domain of a pair of affinity domains; and (b) a second chimeric polypeptide including: (i) a second domain of a pair of affinity domains; and (ii) a second target-binding domain, where the first chimeric polypeptide and the second chimeric polypeptide associate through the binding of the first domain and the second domain of the pair of affinity domains (e.g., any of the multi-chain chimeric polypeptides described herein). In some embodiments, the liquid culture medium further includes an IgG1 antibody construct that comprises at least one antigen-binding domain that binds specifically to the soluble tissue factor domain of the multi-chain chimeric polypeptide (e.g., any of the IgG1 antibody constructs described herein).

In some embodiments, the CD3/CD28-binding agent is an anti-CD3/anti-CD28 bead (e.g., any of the anti-CD3/anti-CD28 beads described herein). In some embodiments of any of the methods described herein, the liquid culture medium includes the anti-CD3/anti-CD28 bead at a ratio of about 1:1 to about 6:1 beads/cell (e.g., about 1:1 to about 5:1, about 1:1 to about 4:1, about 1:1 to about 3:1, about 1:1 to about 2:1, about 2:1 to about 6:1, about 2:1 to about 5:1, about 2:1 to about 4:1, about 2:1 to about 3:1, about 3:1 to about 6:1, about 3:1 to about 5:1, about 3:1 to about 4:1, about 4:1 to about 6:1, about 4:1 to about 5:1, about 5:1 to about 6:1 beads/cell).

In some embodiments, the CD3/CD28-binding agent is an single-chain chimeric polypeptide including a first target-binding domain, a soluble tissue factor domain, and a second target-binding domain, where: the first target-binding domain of the single-chain chimeric polypeptide binds to CD3 and the second target-binding domain of the single-chain chimeric polypeptide binds to CD28 (e.g., any of the exemplary single-chain chimeric polypeptides described herein). In some embodiments, the single-chain chimeric polypeptide includes a sequence that is at least 80% identical (e.g., at least 82% identical, at least 84% identical, at least 86% identical, at least 88% identical, at least 90% identical, at least 92% identical, at least 94% identical, at least 96% identical, at least 98% identical, at least 99% identical, or 100% identical) to SEQ ID NO: 7. In some embodiments, the single-chain chimeric polypeptide includes a sequence that is at least 80% identical (e.g., at least 82% identical, at least 84% identical, at least 86% identical, at least 88% identical, at least 90% identical, at least 92% identical, at least 94% identical, at least 96% identical, at least 98% identical, at least 99% identical, or 100% identical) to SEQ ID NO: 8. In some embodiments, the liquid culture medium includes about 10 nM to about 1000 nM (e.g., or any of the subranges of this range described herein) of the single-chain chimeric polypeptide.

In some embodiments, the CD3/CD28-binding agent is multi-chain chimeric polypeptide that includes a first chimeric polypeptide including (i) a first target-binding domain; (ii) a soluble tissue factor domain; and (iii) a first domain of a pair of affinity domains; and a second chimeric polypeptide comprising: (i) a second domain of a pair of affinity domains; and (ii) a second target-binding domain, wherein: the first chimeric polypeptide and the second chimeric polypeptide associate through the binding of the first domain and the second domain of the pair of affinity domains; and wherein the first target-binding domain binds to CD3 and the second target-binding domain binds to CD28, or the first target-binding domain binds to CD28 and the second target-binding domain to CD3. In some embodiments, the liquid culture medium further includes an IgG1 antibody construct (e.g., any of the exemplary IgG1 antibody constructs described herein) that includes at least one antigen-binding domain that binds specifically to the soluble tissue factor domain of the multi-chain chimeric polypeptide.

In some embodiments, the first chimeric polypeptide comprises a sequence that is at least 80% identical (e.g., at least 82% identical, at least 84% identical, at least 86% identical, at least 88% identical, at least 90% identical, at least 92% identical, at least 94% identical, at least 96% identical, at least 98% identical, at least 99% identical, or 100% identical) to SEQ ID NO: 102. In some embodiments, the first chimeric polypeptide comprises a sequence that is at least 80% identical (e.g., at least 82% identical, at least 84% identical, at least 86% identical, at least 88% identical, at least 90% identical, at least 92% identical, at least 94% identical, at least 96% identical, at least 98% identical, at least 99% identical, or 100% identical) to SEQ ID NO: 104. In some embodiments, the second chimeric polypeptide comprises a sequence that is at least 80% identical (e.g., at least 82% identical, at least 84% identical, at least 86% identical, at least 88% identical, at least 90% identical, at least 92% identical, at least 94% identical, at least 96% identical, at least 98% identical, at least 99% identical, or 100% identical) to SEQ ID NO: 106. In some embodiments, the second chimeric polypeptide comprises a sequence that is at least 80% identical (e.g., at least 82% identical, at least 84% identical, at least 86% identical, at least 88% identical, at least 90% identical, at least 92% identical, at least 94% identical, at least 96% identical, at least 98% identical, at least 99% identical, or 100% identical) to SEQ ID NO: 108. In some embodiments, the liquid culture medium includes about 10 nM to about 1000 nM (e.g., or any of the subranges of this range described herein) of the multi-chain chimeric polypeptide.

In some embodiments, the liquid culture medium further includes an mTOR inhibitor (e.g., any of the mTOR inhibitors described herein, e.g., rapamycin). In some embodiments, the liquid culture medium includes about 10 nM to about 500 nM of the mTOR inhibitor (e.g., or any of the subranges of this range described herein). In some embodiments, the liquid culture medium does not include an mTOR inhibitor.

Some embodiments of these methods further include periodically adding to the liquid culture medium, after each 36 hours to about 60 hours (e.g., about 36 to about 56 hours, about 36 to about 52 hours, about 36 to about 48 hours, about 36 to about 44 hours, about 36 to about 40 hours, about 40 to about 60 hours, about 40 to about 56 hours, about 40 to about 52 hours, about 40 to about 48 hours, about 40 to about 44 hours, about 44 to about 60 hours, about 44 to about 56 hours, about 44 to about 52 hours, about 44 to about 48 hours, about 48 to about 60 hours, about 48 to about 56 hours, about 48 to about 52 hours, about 52 to about 60 hours, about 52 to about 56 hours, or about 56 to about 60 hours) after the start of the period of time, the multi-chain chimeric polypeptide (e.g., any of the multi-chain chimeric polypeptides described herein). In some embodiments, the periodic addition of the multi-chain chimeric polypeptide is performed to result in a concentration of about 10 nM to about 500 nM (e.g., or any of the subranges of this range described herein) of the multi-chain chimeric polypeptide in the liquid culture medium.

Some embodiments of these methods further include periodically adding to the liquid culture medium, after each about 4 days to about 10 days (e.g., after each about 4 days to about 9 days, after each about 4 days to about 8 days, after each about 4 days to about 7 days, after each about 4 days to about 6 days, after each about 4 days to about 5 days, after each about 5 days to about 10 days, after each about 5 days to about 9 days, after each about 5 days to about 8 days, after each about 5 days to about 7 days, after each about 5 days to about 6 days, after each about 6 days to about 10 days, after each about 6 days to about 9 days, after each about 6 days to about 8 days, after each about 6 days to about 7 days, after each about 7 days to about 10 days, after each about 7 days to about 9 days, after each about 7 days to about 8 days, after each about 8 days to about 10 days, after each about 8 days to about 9 days, or after each about 9 days to about 10 days) after the start of the period of time, the CD3/CD28-binding agent (e.g., any of the exemplary CD3/CD28-binding agents described herein).

In some embodiments of any of these methods, the period of time is about 7 to about 56 days (e.g., or any of the subranges of this range described herein).

Some embodiments further include, before the culturing step, a step of isolating the Treg cell from a sample obtained from a subject (e.g., using any of the methods of isolating described herein).

Methods of Isolating $T_{reg}$ Cells from a Sample

Any of the methods of stimulating or increasing the proliferation of a $T_{reg}$ cell as described herein can further include, before the culturing step, a step of isolating the $T_{reg}$ cell from a sample obtained from a subject.

The sample can be a blood sample (e.g., a peripheral blood sample or a cord blood sample), lymphoid tissue, or a thymus sample (e.g., pediatric thymus sample). Some embodiments of any of the methods described herein further include obtaining a sample from the subject.

Methods of isolating $T_{reg}$ cells from samples obtained from a subject are well known in the art. For example, magnetic-activated cell sorting (MACS) and/or fluorescence-activated cell sorting (FACS) can be used to isolate $T_{reg}$ cells based on marker expression. Non-limiting examples of FACS instruments include FACSAria (Becton Dickinson), FX500 fluidics cell sorter (Sony), and MACSQuant Tyto cell sorter (Miltenyi Biotec). Exemplary cell surface proteins for isolating $T_{reg}$ cells from samples include CD4, CD25, and CD127. An intracellular marker for $T_{reg}$ cells is Foxp3. For example, expression levels of CD4 and CD25 can be used to isolate $T_{reg}$ cells from a sample (e.g., a cord blood sample). Expression levels of CD127 can be used as an additional marker for isolating $T_{reg}$ cells from a sample (e.g., a peripheral blood sample). In some instances, isolating $T_{reg}$ cells from samples include sorting for $T_{reg}$ cells that are $CD4^+CD25^+Foxp3^+$ and/or are $CD4^+CD25^+CD127^{dim}$. Kits for isolating $T_{reg}$ cells include $CD4^+CD25^+CD127^{dim}$ regulatory T cell isolation kit II reagent (Miltenyi Biotec). Additional kits for isolating a $T_{reg}$ cell are commercially available from StemCell Technologies (EasySep™ Human $CD4^+CD127^{low}$, $CD25^+$ Regulatory T cell Isolation Kit), Miltenyi Biotec (Human $CD4^+CD25^+$ Regulatory T Cell Isolation Kit), and R&D Systems (MagCellect Human $CD4^+CD25^+$ Regulatory T Cell Isolation Kit).

Also provided herein are methods of isolating a Treg cell from a sample obtained from a subject that include separating the Treg cell from the sample based on its expression of CD39, thereby isolating the Treg cell. Some embodiments of these methods include mixing the sample with an antibody or ligand capable of binding CD39 under conditions that allow binding of the antibody or ligand to Treg cells expressing CD39; and separating the Treg cell bound to the antibody or ligand from other components in the sample, thereby isolating the Treg cell. In some embodiments of these methods, the antibody is a mouse, a humanized, or a human antibody or antigen-binding fragment thereof; and/or the antibody or the ligand is labeled with at least one of biotin, avidin, streptavidin, or a fluorochrome, or is bound to a particle, bead, resin, or solid support. In some embodiments of these methods, the separating comprises the use of flow cytometry, fluorescence-activated cell sorting (FACS), centrifugation, or column, plate, particle, or bead-based methods. Some embodiments of these methods further include: mixing the sample with a biotinylated antibody or ligand capable of binding CD39 under conditions that allow binding of the antibody or the ligand to the Treg cell; capturing the Treg cell bound to the biotinylated antibody or the ligand using streptavidin-coated magnetic particles; separating the magnetic particle-bound Treg cell using a magnet; washing the magnet particle-bound Treg cell to remove other components in the sample; and releasing the magnetic particle-bound Treg cell from the magnet into a solution, thereby isolating the Treg cell.

In some examples, the Treg cell is an autologous Treg cell, a haploidentical Treg cell, or an allogeneic Treg cell isolated from a sample comprising fresh or frozen peripheral blood, umbilical cord blood, peripheral blood mononuclear cells, lymphocytes, CD4+ T cells or Treg cells. In some examples, the Treg cell is a CD4+CD25+Foxp3+ cell. In some examples, the Treg cell is a CD4+CD25+CD127$^{dim}$ cell. In some examples, the Treg cells comprises a chimeric antigen receptor. In some examples, the Treg cells are immunosuppressive in vitro and in vivo.

Also provided herein are populations of isolated Treg cells generated and/or isolated using any of the methods described here. In some examples, the isolated population of Treg cells are greater than 70% (e.g., greater than 75%, greater than 80%, greater than 80%, greater than 85%, greater than 90%, greater than 95%, or greater than 99% CD39+ cells). In some examples, the isolated Treg cell or populations of isolated Treg cells provided herein are further expanded in vitro. Also provided are methods of expanding any of the populations of isolated Treg cells described herein that include culturing the population of isolated Treg cells under conditions that allow for proliferation of the isolated Treg cells.

Also provided herein are compositions comprising any of the populations of isolated Treg cells described herein and a pharmaceutically acceptable carrier. Also provided herein are methods of treating a subject in need thereof that include administering to the subject a therapeutically effective amount of any of the compositions described herein. In some examples, the subject has been identified or diagnosed as having an aging-related disease or an inflammatory disease. In some examples, the aging-related disease is selected from the group of: Alzheimer's disease, aneurysm, cystic fibrosis, fibrosis in pancreatitis, glaucoma, hypertension, idiopathic pulmonary fibrosis, inflammatory bowel disease, intervertebral disc degeneration, macular degeneration, osteoarthritis, type 2 diabetes mellitus, adipose atrophy, lipodystrophy, atherosclerosis, cataracts, COPD, idiopathic pulmonary fibrosis, kidney transplant failure, liver fibrosis, loss of bone mass, myocardial infarction, sarcopenia, wound healing, alopecia, cardiomyocyte hypertrophy, osteoarthritis, Parkinson's disease, age-associated loss of lung tissue elasticity, macular degeneration, cachexia, glomerulosclerosis, liver cirrhosis, NAFLD, osteoporosis, amyotrophic lateral sclerosis, Huntington's disease, spinocerebellar ataxia, multiple sclerosis, neurodegeneration, stroke, dementia, vascular disease, infection susceptibility, chronic inflammation, and renal dysfunction. In some examples, the inflammatory disease is selected from the group of: rheumatoid arthritis, inflammatory bowel disease, lupus erythematosus, lupus nephritis, diabetic nephropathy, CNS injury, Alzheimer's disease, Parkinson's disease, amyotrophic lateral sclerosis, Crohn's disease, multiple sclerosis, Guillain-Barre syndrome, psoriasis, Grave's disease, ulcerative colitis, nonalcoholic steatohepatitis, and mood disorders.

$T_{reg}$ Cells

In some embodiments of any of the methods, compositions, and kits described herein, the $T_{reg}$ cell can be an autologous $T_{reg}$ cell, a haploidentical $T_{reg}$ cell, or an allogeneic $T_{reg}$ cell isolated from peripheral blood or umbilical cord blood. In some embodiments of any of the methods, compositions, and kits described herein, the $T_{reg}$ cell can be a CD4+CD25+Foxp3+ cell. In some embodiments of any of the methods, compositions, and kits described herein, the $T_{reg}$ cell can be a CD4+CD25+CD127$^{dim}$ cell.

In some embodiments of any of the methods, compositions, and kits described herein, the $T_{reg}$ cell can include a chimeric antigen receptor or a recombinant T-cell receptor. In some examples, the $T_{reg}$ cell has previously been genetically-modified to express a chimeric antigen receptor or a recombinant T-cell receptor. In some examples, the $T_{reg}$ cell has previously been genetically-modified to express a recombinant T-cell receptor recognizing a peptide of interest in the target tissue or a co-stimulatory molecule (e.g., ICOS).

Some embodiments of these methods can further include, after the culturing step, introducing into the $T_{reg}$ cell a nucleic acid encoding a chimeric antigen-receptor or a recombinant T-cell receptor. Some embodiments of these methods can further include, after the culturing step, introducing into the $T_{reg}$ cell a nucleic acid encoding a co-stimulatory molecule (e.g., ICOS).

Some embodiments of these methods can further include, before the culturing step, introducing into the $T_{reg}$ cell a nucleic acid encoding a chimeric antigen-receptor or a recombinant T-cell receptor. Some embodiments of these methods can further include, before the culturing step, introducing into the $T_{reg}$ cell a nucleic acid encoding a co-stimulatory molecule (e.g., ICOS).

Detection of the proliferation of a $T_{reg}$ cell can be performed using methods known in the art, e.g., cytometry (e.g., fluorescence-assisted flow cytometry), microscopy, and immunofluorescence microscopy. For example, proliferation of $T_{reg}$ cells can be determined by staining with dyes (e.g., trypan blue) and counting the number of viable cells. In some examples, proliferation and/or activation of $T_{reg}$ cells can be determined by detecting the levels of surface markers on the $T_{reg}$ cells such as but not limited to: Helios, CTLA-4, CD39, CD62L, CD25, CD103, CD69, PD1 and CD49b. The detection of these surface markers can be performed using FACS. Activation of $T_{reg}$ cells can also be determined by detecting the levels of glucose metabolism in the $T_{reg}$ cells. In some examples, glucose metabolism can be determined by measuring the extracellular acidification rate (ECAR), which involves the stages of non-glycolytic acidification (without drugs), glycolysis (addition of glucose), glycolytic capacity (addition of oligomycin), and glycolytic reserve (addition of 2-deoxyglucose). An extracellular flux analyzer (Agilent) can be used for measuring ECAR.

In some examples, the proliferation and/or activation of $T_{reg}$ cells can be determined by detecting an increase in the level of IL-10 secretion. For example, the methods provided herein can result in an increase of about 1% to about 800% (e.g., about 1% to about 750%, about 1% to about 700%, about 1% to about 650%, about 1% to about 600%, about 1% to about 550%, about 1% to about 500%, about 1% to about 450%, about 1% to about 400%, about 1% to about 350%, about 1% to about 300%, about 1% to about 280%, about 1% to about 260%, about 1% to about 240%, about 1% to about 220%, about 1% to about 200%, about 1% to about 180%, about 1% to about 160%, about 1% to about 140%, about 1% to about 120%, about 1% to about 100%, about 1% to about 90%, about 1% to about 80%, about 1% to about 70%, about 1% to about 60%, about 1% to about 50%, about 1% to about 45%, about 1% to about 40%, about 1% to about 35%, about 1% to about 30%, about 1% to about 25%, about 1% to about 20%, about 1% to about 15%, about 1% to about 10%, about 1% to about 5%, about 5% to about 800%, about 5% to about 750%, about 5% to about 700%, about 5% to about 650%, about 5% to about 600%, about 5% to about 550%, about 5% to about 500%, about 5% to about 450%, about 5% to about 400%, about 5% to about 350%, about 5% to about 300%, about 5% to about 280%, about 5% to about 260%, about 5% to about 240%, about 5% to about 220%, about 5% to about 200%, about 5% to about 180%, about 5% to about 160%, about 5% to about 140%, about 5% to about 120%, about 5% to about 100%, about 5% to about 90%, about 5% to about 80%, about 5% to about 70%, about 5% to about 60%, about 5% to about 50%, about 5% to about 45%, about 5% to about 40%, about 5% to about 35%, about 5% to about 30%, about 5% to about 25%, about 5% to about 20%, about 5% to about 15%, about 5% to about 10%, about 10% to about 800%, about 10% to about 750%, about 10% to about 700%, about 10% to about 650%, about 10% to about 600%, about 10% to about 550%, about 10% to about 500%, about 10% to about 450%, about 10% to about 400%, about 10% to about 350%, about 10% to about 300%, about 10% to about 280%, about 10% to about 260%, about 10% to about 240%, about 10% to about 220%, about 10% to about 200%, about 10% to about 180%, about 10% to about 160%, about 10% to about 140%, about 10% to about 120%, about 10% to about 100%, about 10% to about 90%, about 10% to about 80%, about 10% to about 70%, about 10% to about 60%, about 10% to about 50%, about 10% to about 45%, about 10% to about 40%, about 10% to about 35%, about 10% to about 30%, about 10% to about 25%, about 10% to about 20%, about 10% to about 15%, about 15% to about 800%, about 15% to about 750%, about 15% to about 700%, about 15% to about 650%, about 15% to about 600%, about 15% to about 550%, about 15% to about 500%, about 15% to about 450%, about 15% to about 400%, about 15% to about 350%, about 15% to about 300%, about 15% to about 280%, about 15% to about 260%, about 15% to about 240%, about 15% to about 220%, about 15% to about 200%, about 15% to about 180%, about 15% to about 160%, about 15% to about 140%, about 15% to about 120%, about 15% to about 100%, about 15% to about 90%, about 15% to about 80%, about 15% to about 70%, about 15% to about 60%, about 15% to about 50%, about 15% to about 45%, about 15% to about 40%, about 15% to about 35%, about 15% to about 30%, about 15% to about 25%, about 15% to about 20%, about 20% to about 800%, about 20% to about 750%, about 20% to about 700%, about 20% to about 650%, about 20% to about 600%, about 20% to about 550%, about 20% to about 500%, about 20% to about 450%, about 20% to about 400%, about 20% to about 350%, about 20% to about 300%, about 20% to about 280%, about 20% to about 260%, about 20% to about 240%, about 20% to about 220%, about 20% to about 200%, about 20% to about 180%, about 20% to about 160%, about 20% to about 140%, about 20% to about 120%, about 20% to about 100%, about 20% to about 90%, about 20% to about 80%, about 20% to about 70%, about 20% to about 60%, about 20% to about 50%, about 20% to about 45%, about 20% to about 40%, about 20% to about 35%, about 20% to about 30%, about 20% to about 25%, about 25% to about 800%, about 25% to about 750%, about 25% to about 700%, about 25% to about 650%, about 25% to about 600%, about 25% to about 550%, about 25% to about 500%, about 25% to about 450%, about 25% to about 400%, about 25% to about 350%, about 25% to about 300%, about 25% to about 280%, about 25% to about 260%, about 25% to about 240%, about 25% to about 220%, about 25% to about 200%, about 25% to about 180%, about 25% to about 160%, about 25% to about 140%, about 25% to about 120%, about 25% to about 100%, about 25% to about 90%, about 25% to about 80%, about 25% to about 70%, about 25% to about 60%, about 25% to about 50%, about 25% to about 45%, about 25% to about 40%, about 25% to about 35%, about 35% to about 800%, about 35% to about 750%, about 35% to about 700%, about 35% to about 650%, about 35% to about 600%, about 35% to about 550%, about 35% to about 500%, about 35% to about 450%, about 35% to about 400%, about 35% to about 350%, about 35% to about 300%, about 35% to about 280%, about 35% to about 260%, about 35% to about 240%, about 35% to about 220%, about 35% to about 200%, about 35% to about 180%, about 35% to about 160%, about 35% to about 140%, about 35% to about 120%, about 35% to about 100%, about 35% to about 90%, about 35% to about 80%, about 35% to about 70%, about 35% to about 60%, about 35% to about 50%, about 35% to about 45%, about 35% to about 40%, about 40% to about 800%, about 40% to about 750%, about 40% to about 700%, about 40% to about 650%, about 40% to about 600%, about 40% to about 550%, about 40% to about 500%, about 40% to about 450%, about 40% to about 400%, about 40% to about 350%, about 40% to about 300%, about 40% to about 280%, about 40% to about 260%, about 40% to about 240%, about 40% to about 220%, about 40% to about 200%, about 40% to about 180%, about 40% to about 160%, about 40% to about 140%, about 40% to about 120%, about 40% to about 100%, about 40% to about 90%, about 40% to about 80%, about 40% to about 70%, about 40% to about 60%, about 40% to about 50%, about 40% to about 45%, about 45% to about 800%, about 45% to about 750%, about 45% to about 700%, about 45% to about 650%, about 45% to about 600%, about 45% to about 550%, about 45% to about 500%, about 45% to about 450%, about 45% to about 400%, about 45% to about 350%, about 45% to about 300%, about 45% to about 280%, about 45% to about 260%, about 45% to about 240%, about 45% to about 220%, about 45% to about 200%, about 45% to about 180%, about 45% to about 160%, about 45% to about 140%, about 45% to about 120%, about 45% to about 100%, about 45% to about 90%, about 45% to about 80%, about 45% to about 70%, about 45% to about 60%, about 45% to about 50%, about 50% to about 800%, about 50% to about 750%, about 50% to about 700%, about 50% to about 650%, about 50% to about 600%, about 50% to about 550%, about 50% to about 500%, about 50% to about 450%, about 50% to about 400%, about 50% to about 350%, about 50% to about 300%, about 50% to about 280%, about 50% to about 260%, about 50% to about 240%, about 50% to about 220%, about 50% to about 200%, about 50% to about 180%, about 50% to about 160%, about 50% to about 140%, about 50% to about 120%, about 50% to about 100%, about 50% to about 90%, about 50% to about 80%, about 50% to about 70%, about 50% to about 60%, about 60% to about 800%, about 60% to about 750%, about 60% to about 700%, about 60% to about 650%, about 60% to about 600%, about 60% to about 550%, about 60% to about 500%, about 60% to about 450%, about 60% to about 400%, about 60% to about 350%, about 60% to about 300%, about 60% to about 280%, about 60% to about 260%, about 60% to about 240%, about 60% to about 220%, about 60% to about 200%, about 60% to about 180%, about 60% to about 160%, about 60% to about 140%, about 60% to about 120%, about 60% to about 100%, about 60% to about 90%, about 60% to about 80%, about 60% to about 70%, about 70% to about 800%, about 70% to about 750%, about 70% to about 700%, about 70% to about 650%, about 70% to about 600%, about 70% to about 550%, about 70% to about 500%, about 70% to about 450%, about 70% to about 400%, about 70% to about 350%, about 70% to about 300%, about 70% to about 280%, about 70% to about 260%, about 70% to about 240%, about 70% to about 220%, about 70% to about 200%, about 70% to about 180%, about 70% to about 160%, about 70% to about 140%, about 70% to about 120%, about 70% to about 100%, about 70% to about 90%, about 70% to about 80%, about 80% to about 800%, about 80% to about 750%, about 80% to about 700%, about 80% to about 650%, about 80% to about 600%, about 80% to about 550%, about 80% to about 500%, about 80% to about 450%, about 80% to about 400%, about 80% to about 350%, about 80% to about 300%, about 80% to about 280%, about 80% to about 260%, about 80% to about 240%, about 80% to about 220%, about 80% to about 200%, about 80% to about 180%, about 80% to about 160%, about 80% to about 140%, about 80% to about 120%, about 80% to about 100%, about 80% to about 90%, about 90% to about 800%, about 90% to about 750%, about 90% to about 700%, about 90% to about 650%, about 90% to about 600%, about 90% to about 550%, about 90% to about 500%, about 90% to about 450%, about 90% to about 400%, about 90% to about 350%, about 90% to about 300%, about 90% to about 280%, about 90% to about 260%, about 90% to about 240%, about 90% to about 220%, about 90% to about 200%, about 90% to about 180%, about 90% to about 160%, about 90% to about 140%, about 90% to about 120%, about 90% to about 100%, about 100% to about 800%, about 100% to about 750%, about 100% to about 700%, about 100% to about 650%, about 100% to about 600%, about 100% to about 550%, about 100% to about 500%, about 100% to about 450%, about 100% to about 400%, about 100% to about 350%, about 100% to about 300%, about 100% to about 280%, about 100% to about 260%, about 100% to about 240%, about 100% to about 220%, about 100% to about 200%, about 100% to about 180%, about 100% to about 160%, about 100% to about 140%, about 100% to about 120%, about 120% to about 800%, about 120% to about 750%, about 120% to about 700%, about 120% to about 650%, about 120% to about 600%, about 120% to about 550%, about 120% to about 500%, about 120% to about 450%, about 120% to about 400%, about 120% to about 350%, about 120% to about 300%, about 120% to about 280%, about 120% to about 260%, about 120% to about 240%, about 120% to about 220%, about 120% to about 200%, about 120% to about 180%, about 120% to about 160%, about 120% to about 140%, about 140% to about 800%, about 140% to about 750%, about 140% to about 700%, about 140% to about 650%, about 140% to about 600%, about 140% to about 550%, about 140% to about 500%, about 140% to about 450%, about 140% to about 400%, about 140% to about 350%, about 140% to about 300%, about 140% to about 280%, about 140% to about 260%, about 140% to about 240%, about 140% to about 220%, about 140% to about 200%, about 140% to about 180%, about 140% to about 160%, about 160% to about 800%, about 160% to about 750%, about 160% to about 700%, about 160% to about 650%, about 160% to about 600%, about 160% to about 550%, about 160% to about 500%, about 160% to about 450%, about 160% to about 400%, about 160% to about 350%, about 160% to about 300%, about 160% to about 280%, about 160% to about 260%, about 160% to about 240%, about 160% to about 220%, about 160% to about 200%, about 160% to about 180%, about 180% to about 800%, about 180% to about 750%, about 180% to about 700%, about 180% to about 650%, about 180% to about 600%, about 180% to about 550%, about 180% to about 500%, about 180% to about 450%, about 180% to about 400%, about 180% to about 350%, about 180% to about 300%, about 180% to about 280%, about 180% to about 260%, about 180% to about 240%, about 180% to about 220%, about 180% to about 200%, about 200% to about 800%, about 200% to about 750%, about 200% to about 700%, about 200% to about 650%, about 200% to about 600%, about 200% to about 550%, about 200% to about 500%, about 200% to about 450%, about 200% to about 400%, about 200% to about 350%, about 200% to about 300%, about 200% to about 280%, about 200% to about 260%, about 200% to about 240%, about 200% to about 220%, about 220% to about 800%, about 220% to about 750%, about 220% to about 700%, about 220% to about 650%, about 220% to about 600%, about 220% to about 550%, about 220% to about 500%, about 220% to about 450%, about 220% to about 400%, about 220% to about 350%, about 220% to about 300%, about 220% to about 280%, about 220% to about 260%, about 220% to about 240%, about 240% to about 800%, about 240% to about 750%, about 240% to about 700%, about 240% to about 650%, about 240% to about 600%, about 240% to about 550%, about 240% to about 500%, about 240% to about 450%, about 240% to about 400%, about 240% to about 350%, about 240% to about 300%, about 240% to about 280%, about 240% to about 260%, about 260% to about 800%, about 260% to about 750%, about 260% to about 700%, about 260% to about 650%, about 260% to about 600%, about 260% to about 550%, about 260% to about 500%, about 260% to about 450%, about 260% to about 400%, about 260% to about 350%, about 260% to about 300%, about 260% to about 280%, about 280% to about 800%, about 280% to about 750%, about 280% to about 700%, about 280% to about 650%, about 280% to about 600%, about 280% to about 550%, about 280% to about 500%, about 280% to about 450%, about 280% to about 400%, about 280% to about 350%, about 280% to about 300%, about 300% to about 800%, about 300% to about 750%, about 300% to about 700%, about 300% to about 650%, about 300% to about 600%, about 300% to about 550%, about 300% to about 500%, about 300% to about 450%, about 300% to about 400%, about 300% to about 350%, about 350% to about 800%, about 350% to about 750%, about 350% to about 700%, about 350% to about 650%, about 350% to about 600%, about 350% to about 550%, about 350% to about 500%, about 350% to about 450%, about 350% to about 400%, about 400% to about 800%, about 400% to about 750%, about 400% to about 700%, about 400% to about 650%, about 400% to about 600%, about 400% to about 550%, about 400% to about 500%, about 400% to about 450%, about 450% to about 800%, about 450% to about 750%, about 450% to about 700%, about 450% to about 650%, about 450% to about 600%, about 450% to about 550%, about 450% to about 500%, about 500% to about 800%, about 500% to about 750%, about 500% to about 700%, about 500% to about 650%, about 500% to about 600%, about 500% to about 550%, about 550% to about 800%, about 550% to about 750%, about 550% to about 700%, about 550% to about 650%, about 550% to about 600%, about 600% to about 800%, about 600% to about 750%, about 600% to about 700%, about 600% to about 650%, about 650% to about 800%, about 650% to about 750%, about 650% to about 700%, about 700% to about 800%, about 700% to about 750%, or about 750% to about 800%) in the level of secreted IL-10 by the $T_{reg}$ cells (e.g., at the end of the period of time as compared to the start of the period of time).

The methods provided herein can result in an increase (e.g., about 1% to about 800% increase, or any of the subranges of this range described herein) in the concentration or number of the $T_{reg}$ cells (e.g., at the end of the period of time as compared to the start of the period of time).

In some embodiments, the methods provided herein can result in an increase in the concentration or number of $T_{reg}$ cells (e.g., about a 0.1-fold increase to about a 100-fold increase, about a 0.1-fold increase to about a 90-fold increase, about a 0.1-fold increase to about a 80-fold increase, about a 0.1-fold increase to about a 70-fold increase, about a 0.1-fold increase to about a 60-fold increase, about a 0.1-fold increase to about a 50-fold increase, about a 0.1-fold increase to about a 45-fold increase, about a 0.1-fold increase to about a 40-fold increase, about a 0.1-fold increase to about a 35-fold increase, about a 0.1-fold increase to about a 30-fold increase, about a 0.1-fold increase to about a 25-fold increase, about a 0.1-fold increase to about a 20-fold increase, about a 0.1-fold increase to about a 15-fold increase, about a 0.1-fold increase to about a 10-fold increase, about a 0.1-fold increase to about a 8-fold increase, about a 0.1-fold increase to about a 6-fold increase, about a 0.1-fold increase to about a 4-fold increase, about a 0.1-fold increase to about a 2-fold increase, about a 0.1-fold increase to about a 1.5-fold increase, about a 0.1-fold increase to about a 1-fold increase, about a 0.1-fold increase to about a 0.5-fold increase, about a 0.5-fold increase to about a 100-fold increase, about a 0.5-fold increase to about a 90-fold increase, about a 0.5-fold increase to about a 80-fold increase, about a 0.5-fold increase to about a 70-fold increase, about a 0.5-fold increase to about a 60-fold increase, about a 0.5-fold increase to about a 50-fold increase, about a 0.5-fold increase to about a 45-fold increase, about a 0.5-fold increase to about a 40-fold increase, about a 0.5-fold increase to about a 35-fold increase, about a 0.5-fold increase to about a 30-fold increase, about a 0.5-fold increase to about a 25-fold increase, about a 0.5-fold increase to about a 20-fold increase, about a 0.5-fold increase to about a 15-fold increase, about a 0.5-fold increase to about a 10-fold increase, about a 0.5-fold increase to about a 8-fold increase, about a 0.5-fold increase to about a 6-fold increase, about a 0.5-fold increase to about a 4-fold increase, about a 0.5-fold increase to about a 2-fold increase, about a 0.5-fold increase to about a 1.5-fold increase, about a 0.5-fold increase to about a 1-fold increase, about a 1-fold increase to about a 100-fold increase, about a 1-fold increase to about a 90-fold increase, about a 1-fold increase to about a 80-fold increase, about a 1-fold increase to about a 70-fold increase, about a 1-fold increase to about a 60-fold increase, about a 1-fold increase to about a 50-fold increase, about a 1-fold increase to about a 45-fold increase, about a 1-fold increase to about a 40-fold increase, about a 1-fold increase to about a 35-fold increase, about a 1-fold increase to about a 30-fold increase, about a 1-fold increase to about a 25-fold increase, about a 1-fold increase to about a 20-fold increase, about a 1-fold increase to about a 15-fold increase, about a 1-fold increase to about a 10-fold increase, about a 1-fold increase to about a 8-fold increase, about a 1-fold increase to about a 6-fold increase, about a 1-fold increase to about a 4-fold increase, about a 1-fold increase to about a 2-fold increase, about a 1-fold increase to about a 1.5-fold increase, about a 1.5-fold increase to about a 100-fold increase, about a 1.5-fold increase to about a 90-fold increase, about a 1.5-fold increase to about a 80-fold increase, about a 1.5-fold increase to about a 70-fold increase, about a 1.5-fold increase to about a 60-fold increase, about a 1.5-fold increase to about a 50-fold increase, about a 1.5-fold increase to about a 45-fold increase, about a 1.5-fold increase to about a 40-fold increase, about a 1.5-fold increase to about a 35-fold increase, about a 1.5-fold increase to about a 30-fold increase, about a 1.5-fold increase to about a 25-fold increase, about a 1.5-fold increase to about a 20-fold increase, about a 1.5-fold increase to about a 15-fold increase, about a 1.5-fold increase to about a 10-fold increase, about a 1.5-fold increase to about a 8-fold increase, about a 1.5-fold increase to about a 6-fold increase, about a 1.5-fold increase to about a 4-fold increase, about a 1.5-fold increase to about a 2-fold increase, about a 2-fold increase to about a 100-fold increase, about a 2-fold increase to about a 90-fold increase, about a 2-fold increase to about a 80-fold increase, about a 2-fold increase to about a 70-fold increase, about a 2-fold increase to about a 60-fold increase, about a 2-fold increase to about a 50-fold increase, about a 2-fold increase to about a 45-fold increase, about a 2-fold increase to about a 40-fold increase, about a 2-fold increase to about a 35-fold increase, about a 2-fold increase to about a 30-fold increase, about a 2-fold increase to about a 25-fold increase, about a 2-fold increase to about a 20-fold increase, about a 2-fold increase to about a 15-fold increase, about a 2-fold increase to about a 10-fold increase, about a 2-fold increase to about a 8-fold increase, about a 2-fold increase to about a 6-fold increase, about a 2-fold increase to about a 4-fold increase, about a 4-fold increase to about a 100-fold increase, about a 4-fold increase to about a 90-fold increase, about a 4-fold increase to about a 80-fold increase, about a 4-fold increase to about a 70-fold increase, about a 4-fold increase to about a 60-fold increase, about a 4-fold increase to about a 50-fold increase, about a 4-fold increase to about a 45-fold increase, about a 4-fold increase to about a 40-fold increase, about a 4-fold increase to about a 35-fold increase, about a 4-fold increase to about a 30-fold increase, about a 4-fold increase to about a 25-fold increase, about a 4-fold increase to about a 20-fold increase, about a 4-fold increase to about a 15-fold increase, about a 4-fold increase to about a 10-fold increase, about a 4-fold increase to about a 8-fold increase, about a 4-fold increase to about a 6-fold increase, about a 6-fold increase to about a 100-fold increase, about a 6-fold increase to about a 90-fold increase, about a 6-fold increase to about a 80-fold increase, about a 6-fold increase to about a 70-fold increase, about a 6-fold increase to about a 60-fold increase, about a 6-fold increase to about a 50-fold increase, about a 6-fold increase to about a 45-fold increase, about a 6-fold increase to about a 40-fold increase, about a 6-fold increase to about a 35-fold increase, about a 6-fold increase to about a 30-fold increase, about a 6-fold increase to about a 25-fold increase, about a 6-fold increase to about a 20-fold increase, about a 6-fold increase to about a 15-fold increase, about a 6-fold increase to about a 10-fold increase, about a 6-fold increase to about a 8-fold increase, about a 8-fold increase to about a 100-fold increase, about a 8-fold increase to about a 90-fold increase, about a 8-fold increase to about a 80-fold increase, about a 8-fold increase to about a 70-fold increase, about a 8-fold increase to about a 60-fold increase, about a 8-fold increase to about a 50-fold increase, about a 8-fold increase to about a 45-fold increase, about a 8-fold increase to about a 40-fold increase, about a 8-fold increase to about a 35-fold increase, about a 8-fold increase to about a 30-fold increase, about a 8-fold increase to about a 25-fold increase, about a 8-fold increase to about a 20-fold increase, about a 8-fold increase to about a 15-fold increase, about a 8-fold increase to about a 10-fold increase, about a 10-fold increase to about a 100-fold increase, about a 10-fold increase to about a 90-fold increase, about a 10-fold increase to about a 80-fold increase, about a 10-fold increase to about a 70-fold increase, about a 10-fold increase to about a 60-fold increase, about a 10-fold increase to about a 50-fold increase, about a 10-fold increase to about a 45-fold increase, about a 10-fold increase to about a 40-fold increase, about a 10-fold increase to about a 35-fold increase, about a 10-fold increase to about a 30-fold increase, about a 10-fold increase to about a 25-fold increase, about a 10-fold increase to about a 20-fold increase, about a 10-fold increase to about a 15-fold increase, about a 15-fold increase to about a 100-fold increase, about a 15-fold increase to about a 90-fold increase, about a 15-fold increase to about a 80-fold increase, about a 15-fold increase to about a 70-fold increase, about a 15-fold increase to about a 60-fold increase, about a 15-fold increase to about a 50-fold increase, about a 15-fold increase to about a 45-fold increase, about a 15-fold increase to about a 40-fold increase, about a 15-fold increase to about a 35-fold increase, about a 15-fold increase to about a 30-fold increase, about a 15-fold increase to about a 25-fold increase, about a 15-fold increase to about a 20-fold increase, about a 20-fold increase to about a 100-fold increase, about a 20-fold increase to about a 90-fold increase, about a 20-fold increase to about a 80-fold increase, about a 20-fold increase to about a 70-fold increase, about a 20-fold increase to about a 60-fold increase, about a 20-fold increase to about a 50-fold increase, about a 20-fold increase to about a 45-fold increase, about a 20-fold increase to about a 40-fold increase, about a 20-fold increase to about a 35-fold increase, about a 20-fold increase to about a 30-fold increase, about a 20-fold increase to about a 25-fold increase, about a 25-fold increase to about a 100-fold increase, about a 25-fold increase to about a 90-fold increase, about a 25-fold increase to about a 80-fold increase, about a 25-fold increase to about a 70-fold increase, about a 25-fold increase to about a 60-fold increase, about a 25-fold increase to about a 50-fold increase, about a 25-fold increase to about a 45-fold increase, about a 25-fold increase to about a 40-fold increase, about a 25-fold increase to about a 35-fold increase, about a 25-fold increase to about a 30-fold increase, about a 30-fold increase to about a 100-fold increase, about a 30-fold increase to about a 90-fold increase, about a 30-fold increase to about a 80-fold increase, about a 30-fold increase to about a 70-fold increase, about a 30-fold increase to about a 60-fold increase, about a 30-fold increase to about a 50-fold increase, about a 30-fold increase to about a 45-fold increase, about a 30-fold increase to about a 40-fold increase, about a 30-fold increase to about a 35-fold increase, about a 35-fold increase to about a 100-fold increase, about a 35-fold increase to about a 90-fold increase, about a 35-fold increase to about a 80-fold increase, about a 35-fold increase to about a 70-fold increase, about a 35-fold increase to about a 60-fold increase, about a 35-fold increase to about a 50-fold increase, about a 35-fold increase to about a 45-fold increase, about a 35-fold increase to about a 40-fold increase, about a 40-fold increase to about a 100-fold increase, about a 40-fold increase to about a 90-fold increase, about a 40-fold increase to about a 80-fold increase, about a 40-fold increase to about a 70-fold increase, about a 40-fold increase to about a 60-fold increase, about a 40-fold increase to about a 50-fold increase, about a 40-fold increase to about a 45-fold increase, about a 45-fold increase to about a 100-fold increase, about a 45-fold increase to about a 90-fold increase, about a 45-fold increase to about a 80-fold increase, about a 45-fold increase to about a 70-fold increase, about a 45-fold increase to about a 60-fold increase, about a 45-fold increase to about a 50-fold increase, about a 50-fold increase to about a 100-fold increase, about a 50-fold increase to about a 90-fold increase, about a 50-fold increase to about a 80-fold increase, about a 50-fold increase to about a 70-fold increase, about a 50-fold increase to about a 60-fold increase, about a 60-fold increase to about a 100-fold increase, about a 60-fold increase to about a 90-fold increase, about a 60-fold increase to about a 80-fold increase, about a 60-fold increase to about a 70-fold increase, about a 70-fold increase to about a 100-fold increase, about a 70-fold increase to about a 90-fold increase, about a 70-fold increase to about a 80-fold increase, about a 80-fold increase to about a 100-fold increase, about a 80-fold increase to about a 90-fold increase, or about a 90-fold increase to about a 100-fold increase) (e.g., at the end of the period of time as compared to the start of the period of time).

Compositions and Kits

Also provided herein populations of $T_{reg}$ cells produced using any of the methods described herein. Also provided herein are compositions (e.g., pharmaceutical compositions) that include a $T_{reg}$ cell produced using any of the methods described herein or a population of $T_{reg}$ cells produced using any of the methods described herein. In some embodiments, the pharmaceutical compositions can include a pharmaceutically acceptable carrier (e.g., phosphate buffered saline). The compositions can be used to treat a subject in need thereof (e.g., any of the exemplary subjects described herein).

Single or multiple administrations of pharmaceutical compositions can be given to a subject in need thereof depending on for example: the dosage and frequency as required and tolerated by the subject. The formulation should provide a sufficient quantity of $T_{reg}$ cells to effectively treat, prevent, or ameliorate conditions, diseases, or symptoms in the subject.

Also provided herein are kits that include (i) a CD3/CD28-binding agent (e.g., any of the CD3/CD28-binding agents described herein); (ii) a single-chain chimeric polypeptide comprising a first target-binding domain, a soluble tissue factor domain, and a second target-binding domain, wherein the first target-binding domain and the second target-binding domain bind to a receptor for IL-2 (e.g., any of such single-chain chimeric polypeptides described herein); and (iii) an mTOR inhibitor (e.g., any mTOR inhibitors described herein). Some embodiments of these kits can further include an IgG1 antibody construct that includes at least one antigen-binding domain that binds specifically to the soluble tissue factor domain of the single-chain chimeric polypeptide (e.g., any of the exemplary IgG1 antibody constructs described herein). In some embodiments of these kits, the CD3/CD28-binding agent is an anti-CD3/anti-CD28 bead (e.g., any of the exemplary anti-CD3/anti-CD28 beads described herein). In some embodiments, the CD3/CD28-binding agent is an additional single-chain chimeric polypeptide comprising a first target-binding domain, a soluble tissue factor domain, and a second target-binding domain, where: the first target-binding domain of the additional single-chain chimeric polypeptide binds to CD3 and the second target-binding domain of the additional single-chain chimeric polypeptide binds to CD28 (e.g., any of the examples of such single-chain chimeric polypeptides described herein). In some embodiments, the kit can further include an IgG1 antibody construct that includes at least one antigen-binding domain that binds specifically to the soluble tissue factor domain of the additional single-chain chimeric polypeptide (e.g., any of the exemplary IgG1 antibody constructs described herein).

Also provided herein are kits that include (i) an interleukin-2 receptor-activating agent (e.g., any of the interleukin-2 receptor-activating agents described herein); (ii) a single-chain chimeric polypeptide including a first target-binding domain, a soluble tissue factor domain, and a second target-binding domain, where: the first target-binding domain binds to CD3 and the second target-binding domain binds to CD28; or the first target-binding domain binds to CD28 and the second target-binding domain binds to CD3 (e.g., any of such single-chain chimeric polypeptides described herein); and (iii) an mTOR inhibitor (e.g., any mTOR inhibitors described herein). In some embodiments, the kits can further include an IgG1 antibody construct that includes at least one antigen-binding domain that binds specifically to the soluble tissue factor domain of the single-chain chimeric polypeptide (e.g., any of the exemplary IgG1 antibody constructs described herein).

Also provided herein are kits that include: a CD3/CD28-binding agent (e.g., any of the CD3/CD28-binding agents described herein); a multi-chain chimeric polypeptide comprising: (a) a first chimeric polypeptide comprising: (i) a first target-binding domain; (ii) a soluble tissue factor domain; and (iii) a first domain of a pair of affinity domains; and (b) a second chimeric polypeptide comprising: (i) a second domain of a pair of affinity domains; and (ii) a second target-binding domain, where the first chimeric polypeptide and the second chimeric polypeptide associate through the binding of the first domain and the second domain of the pair of affinity domains (e.g., any of the exemplary multi-chain chimeric polypeptides described herein); and an mTOR inhibitor (e.g., any of the exemplary mTOR inhibitors described herein). Some embodiments of these kits further include an IgG1 antibody construct that comprises at least one antigen-binding domain that binds specifically to the soluble tissue factor domain of the multi-chain chimeric polypeptide (e.g., any of the exemplary IgG1 antibody constructs described herein). In some embodiments, the CD3/CD28-binding agent is an anti-CD3/anti-CD28 bead (e.g., any of the anti-CD3/anti-CD28 beads described herein). In some embodiments, the CD3/CD28-binding agent is an single-chain chimeric polypeptide including a first target-binding domain, a soluble tissue factor domain, and a second target-binding domain, where the first target-binding domain of the additional single-chain chimeric polypeptide binds to CD3 and the second target-binding domain of the additional single-chain chimeric polypeptide binds to CD28 (e.g., any of the examples of such single-chain chimeric polypeptides described herein). In some embodiments, the kit further includes an IgG1 antibody construct that comprises at least one antigen-binding domain that binds specifically to the soluble tissue factor domain of the single-chain chimeric polypeptide (e.g., any of the exemplary IgG1 antibody constructs described herein).

Nucleic Acids/Vectors

Also provided herein are nucleic acids that encode any of the single-chain chimeric polypeptides or multi-chain chimeric polypeptides described herein. Also provided herein are vectors that include any of the nucleic acids encoding any of the single-chain chimeric polypeptides or multi-chain chimeric polypeptides described herein.

Any of the vectors described herein can be an expression vector. For example, an expression vector can include a promoter sequence operably linked to the sequence encoding the single-chain chimeric polypeptide.

Non-limiting examples of vectors include plasmids, transposons, cosmids, and viral vectors (e.g., any adenoviral vectors (e.g., pSV or pCMV vectors), adeno-associated virus (AAV) vectors, lentivirus vectors, and retroviral vectors), and any Gateway® vectors. A vector can, e.g., include sufficient cis-acting elements for expression; other elements for expression can be supplied by the host mammalian cell or in an in vitro expression system. Skilled practitioners will be capable of selecting suitable vectors and mammalian cells for making any of the single-chain chimeric polypeptides or multi-chain chimeric polypeptides described herein.

Cells

Also provided herein are cells (e.g., any of the exemplary cells described herein or known in the art) comprising any of the nucleic acids described herein that encode any of the single-chain chimeric polypeptides or any of the multi-chain chimeric polypeptides described herein.

Also provided herein are cells (e.g., any of the exemplary cells described herein or known in the art) that include any of the vectors described herein that encode any of the single-chain chimeric polypeptides or any of the multi-chain chimeric polypeptides described herein.

In some embodiments of any of the methods described herein, the cell can be a eukaryotic cell. As used herein, the term "eukaryotic cell" refers to a cell having a distinct, membrane-bound nucleus. Such cells may include, for example, mammalian (e.g., rodent, non-human primate, or human), insect, fungal, or plant cells. In some embodiments, the eukaryotic cell is a yeast cell, such as *Saccharomyces cerevisiae*. In some embodiments, the eukaryotic cell is a higher eukaryote, such as mammalian, avian, plant, or insect cells. Non-limiting examples of mammalian cells include Chinese hamster ovary cells and human embryonic kidney cells (e.g., HEK293 cells).

Methods of introducing nucleic acids and expression vectors into a cell (e.g., an eukaryotic cell) are known in the art. Non-limiting examples of methods that can be used to introduce a nucleic acid into a cell include lipofection, transfection, electroporation, microinjection, calcium phosphate transfection, dendrimer-based transfection, cationic polymer transfection, cell squeezing, sonoporation, optical transfection, impalefection, hydrodynamic delivery, magnetofection, viral transduction (e.g., adenoviral and lentiviral transduction), and nanoparticle transfection.

Methods of Producing Single-Chain or Multi-Chain Chimeric Polypeptides

Also provided herein are methods of producing any of the single-chain chimeric polypeptides or multi-chain chimeric polypeptides described herein that include culturing any of the cells described herein in a culture medium under conditions sufficient to result in the production of the single-chain chimeric polypeptide or a multi-chain chimeric polypeptide; and recovering the single-chain chimeric polypeptide or the multi-chain chimeric polypeptide from the cell and/or the culture medium.

The recovery of the single-chain chimeric polypeptide or the multi-chain chimeric polypeptide from a culture medium or a cell (e.g., a eukaryotic cell) can be performed using techniques well-known in the art (e.g., ammonium sulfate precipitation, polyethylene glycol precipitation, ion-exchange chromatography (anion or cation), chromatography based on hydrophobic interaction, metal-affinity chromatography, ligand-affinity chromatography, and size exclusion chromatography).

Methods of culturing cells are well known in the art. Cells can be maintained in vitro under conditions that favor proliferation, differentiation and growth. Briefly, cells can be cultured by contacting a cell (e.g., any cell) with a cell culture medium that includes the necessary growth factors and supplements to support cell viability and growth.

Also provided herein are single-chain chimeric polypeptides (e.g., any of the single-chain chimeric polypeptides described herein) or multi-chain chimeric polypeptides (e.g., any of the multi-chain chimeric polypeptides) produced by any of the methods described herein.

Methods of Treatment

Also provided herein are methods of treating a subject in need thereof (e.g., any of the exemplary subjects described herein) that include administering to the subject a therapeutically effective amount of a population of $T_{reg}$ cells generated using any of the methods described herein or any of the compositions (e.g., pharmaceutical compositions) comprising a $T_{reg}$ cell or a population of $T_{reg}$ cells generated using any of the methods described herein.

In some embodiments of these methods, the subject has been identified or diagnosed as having an aging-related disease or an inflammatory disease. In some embodiments, the aging-related disease is selected from the group of: Alzheimer's disease, aneurysm, cystic fibrosis, fibrosis in pancreatitis, glaucoma, hypertension, idiopathic pulmonary fibrosis, inflammatory bowel disease, intervertebral disc degeneration, macular degeneration, osteoarthritis, type 2 diabetes mellitus, adipose atrophy, lipodystrophy, atherosclerosis, cataracts, COPD, idiopathic pulmonary fibrosis, kidney transplant failure, liver fibrosis, loss of bone mass, myocardial infarction, sarcopenia, wound healing, alopecia, cardiomyocyte hypertrophy, osteoarthritis, Parkinson's disease, age-associated loss of lung tissue elasticity, macular degeneration, cachexia, glomerulosclerosis, liver cirrhosis, NAFLD, osteoporosis, amyotrophic lateral sclerosis, Huntington's disease, spinocerebellar ataxia, multiple sclerosis, neurodegeneration, stroke, dementia, vascular disease, infection susceptibility, chronic inflammation, and renal dysfunction.

In some embodiments, the inflammatory disease is selected from the group of: rheumatoid arthritis, inflammatory bowel disease, lupus erythematosus, lupus nephritis, diabetic nephropathy, CNS injury, Alzheimer's disease, Parkinson's disease, amyotrophic lateral sclerosis, Crohn's disease, multiple sclerosis, Guillain-Barre syndrome, psoriasis, Grave's disease, ulcerative colitis, nonalcoholic steatohepatitis, and mood disorders.

In some embodiments, these methods can result in a reduction in the number, severity, or frequency of one or more symptoms of the cancer in the subject (e.g., as compared to the number, severity, or frequency of the one or more symptoms of the aging-related disease or the inflammatory disease in the subject prior to treatment). In some examples, the methods can result in a decrease (e.g., about 1% decrease to about 99% decrease, an about 1% decrease to about 95% decrease, about 1% decrease to about 90% decrease, about 1% decrease to about 85% decrease, about 1% decrease to about 80% decrease, about 1% decrease to about 75% decrease, about 1% to about 70% decrease, about 1% decrease to about 65% decrease, about 1% decrease to about 60% decrease, about 1% decrease to about 55% decrease, about 1% decrease to about 50% decrease, about 1% decrease to about 45% decrease, about 1% decrease to about 40% decrease, about 1% decrease to about 35% decrease, about 1% decrease to about 30% decrease, about 1% decrease to about 25% decrease, about 1% decrease to about 20% decrease, about 1% decrease to about 15% decrease, about 1% decrease to about 10% decrease, about 1% decrease to about 5% decrease, about 5% decrease to about 99% decrease, an about 5% decrease to about 95% decrease, about 5% decrease to about 90% decrease, about 5% decrease to about 85% decrease, about 5% decrease to about 80% decrease, about 5% decrease to about 75% decrease, about 5% to about 70% decrease, about 5% decrease to about 65% decrease, about 5% decrease to about 60% decrease, about 5% decrease to about 55% decrease, about 5% decrease to about 50% decrease, about 5% decrease to about 45% decrease, about 5% decrease to about 40% decrease, about 5% decrease to about 35% decrease, about 5% decrease to about 30% decrease, about 5% decrease to about 25% decrease, about 5% decrease to about 20% decrease, about 5% decrease to about 15% decrease, about 5% decrease to about 10% decrease, about 10% decrease to about 99% decrease, an about 10% decrease to about 95% decrease, about 10% decrease to about 90% decrease, about 10% decrease to about 85% decrease, about 10% decrease to about 80% decrease, about 10% decrease to about 75% decrease, about 10% to about 70% decrease, about 10% decrease to about 65% decrease, about 10% decrease to about 60% decrease, about 10% decrease to about 55% decrease, about 10% decrease to about 50% decrease, about 10% decrease to about 45% decrease, about 10% decrease to about 40% decrease, about 10% decrease to about 35% decrease, about 10% decrease to about 30% decrease, about 10% decrease to about 25% decrease, about 10% decrease to about 20% decrease, about 10% decrease to about 15% decrease, about 15% decrease to about 99% decrease, an about 15% decrease to about 95% decrease, about 15% decrease to about 90% decrease, about 15% decrease to about 85% decrease, about 15% decrease to about 80% decrease, about 15% decrease to about 75% decrease, about 15% to about 70% decrease, about 15% decrease to about 65% decrease, about 15% decrease to about 60% decrease, about 15% decrease to about 55% decrease, about 15% decrease to about 50% decrease, about 15% decrease to about 45% decrease, about 15% decrease to about 40% decrease, about 15% decrease to about 35% decrease, about 15% decrease to about 30% decrease, about 15% decrease to about 25% decrease, about 15% decrease to about 20% decrease, about 20% decrease to about 99% decrease, an about 20% decrease to about 95% decrease, about 20% decrease to about 90% decrease, about 20% decrease to about 85% decrease, about 20% decrease to about 80% decrease, about 20% decrease to about 75% decrease, about 20% to about 70% decrease, about 20% decrease to about 65% decrease, about 20% decrease to about 60% decrease, about 20% decrease to about 55% decrease, about 20% decrease to about 50% decrease, about 20% decrease to about 45% decrease, about 20% decrease to about 40% decrease, about 20% decrease to about 35% decrease, about 20% decrease to about 30% decrease, about 20% decrease to about 25% decrease, about 25% decrease to about 99% decrease, an about 25% decrease to about 95% decrease, about 25% decrease to about 90% decrease, about 25% decrease to about 85% decrease, about 25% decrease to about 80% decrease, about 25% decrease to about 75% decrease, about 25% to about 70% decrease, about 25% decrease to about 65% decrease, about 25% decrease to about 60% decrease, about 25% decrease to about 55% decrease, about 25% decrease to about 50% decrease, about 25% decrease to about 45% decrease, about 25% decrease to about 40% decrease, about 25% decrease to about 35% decrease, about 25% decrease to about 30% decrease, about 30% decrease to about 99% decrease, an about 30% decrease to about 95% decrease, about 30% decrease to about 90% decrease, about 30% decrease to about 85% decrease, about 30% decrease to about 80% decrease, about 30% decrease to about 75% decrease, about 30% to about 70% decrease, about 30% decrease to about 65% decrease, about 30% decrease to about 60% decrease, about 30% decrease to about 55% decrease, about 30% decrease to about 50% decrease, about 30% decrease to about 45% decrease, about 30% decrease to about 40% decrease, about 30% decrease to about 35% decrease, about 35% decrease to about 99% decrease, an about 35% decrease to about 95% decrease, about 35% decrease to about 90% decrease, about 35% decrease to about 85% decrease, about 35% decrease to about 80% decrease, about 35% decrease to about 75% decrease, about 35% to about 70% decrease, about 35% decrease to about 65% decrease, about 35% decrease to about 60% decrease, about 35% decrease to about 55% decrease, about 35% decrease to about 50% decrease, about 35% decrease to about 45% decrease, about 35% decrease to about 40% decrease, about 40% decrease to about 99% decrease, an about 40% decrease to about 95% decrease, about 40% decrease to about 90% decrease, about 40% decrease to about 85% decrease, about 40% decrease to about 80% decrease, about 40% decrease to about 75% decrease, about 40% to about 70% decrease, about 40% decrease to about 65% decrease, about 40% decrease to about 60% decrease, about 40% decrease to about 55% decrease, about 40% decrease to about 50% decrease, about 40% decrease to about 45% decrease, about 45% decrease to about 99% decrease, an about 45% decrease to about 95% decrease, about 45% decrease to about 90% decrease, about 45% decrease to about 85% decrease, about 45% decrease to about 80% decrease, about 45% decrease to about 75% decrease, about 45% to about 70% decrease, about 45% decrease to about 65% decrease, about 45% decrease to about 60% decrease, about 45% decrease to about 55% decrease, about 45% decrease to about 50% decrease, about 50% decrease to about 99% decrease, an about 50% decrease to about 95% decrease, about 50% decrease to about 90% decrease, about 50% decrease to about 85% decrease, about 50% decrease to about 80% decrease, about 50% decrease to about 75% decrease, about 50% to about 70% decrease, about 50% decrease to about 65% decrease, about 50% decrease to about 60% decrease, about 50% decrease to about 55% decrease, about 55% decrease to about 99% decrease, an about 55% decrease to about 95% decrease, about 55% decrease to about 90% decrease, about 55% decrease to about 85% decrease, about 55% decrease to about 80% decrease, about 55% decrease to about 75% decrease, about 55% to about 70% decrease, about 55% decrease to about 65% decrease, about 55% decrease to about 60% decrease, about 60% decrease to about 99% decrease, an about 60% decrease to about 95% decrease, about 60% decrease to about 90% decrease, about 60% decrease to about 85% decrease, about 60% decrease to about 80% decrease, about 60% decrease to about 75% decrease, about 60% to about 70% decrease, about 60% decrease to about 65% decrease, about 65% decrease to about 99% decrease, an about 65% decrease to about 95% decrease, about 65% decrease to about 90% decrease, about 65% decrease to about 85% decrease, about 65% decrease to about 80% decrease, about 65% decrease to about 75% decrease, about 65% to about 70% decrease, about 70% decrease to about 99% decrease, an about 70% decrease to about 95% decrease, about 70% decrease to about 90% decrease, about 70% decrease to about 85% decrease, about 70% decrease to about 80% decrease, about 70% decrease to about 75% decrease, about 75% decrease to about 99% decrease, an about 75% decrease to about 95% decrease, about 75% decrease to about 90% decrease, about 75% decrease to about 85% decrease, about 75% decrease to about 80% decrease, about 80% decrease to about 99% decrease, an about 80% decrease to about 95% decrease, about 80% decrease to about 90% decrease, about 80% decrease to about 85% decrease, about 85% decrease to about 99% decrease, an about 85% decrease to about 95% decrease, about 85% decrease to about 90% decrease, about 90% decrease to about 99% decrease, an about 90% decrease to about 95% decrease, or about 95% decrease to about 99% decrease) in the number of senescent cells in the subject (e.g., a decrease in the number of senescent cells in one or more specific tissues involved and/or implicated in the aging-related disease or the inflammatory disease in the subject), e.g., as compared to the number of senescent cells in the subject prior to treatment.

The term "subject" refers to any mammal. In some embodiments, the subject or "subject in need of treatment" may be a canine (e.g., a dog), feline (e.g., a cat), equine (e.g., a horse), ovine, bovine, porcine, caprine, primate, e.g., a simian (e.g., a monkey (e.g., marmoset, baboon), or an ape (e.g., a gorilla, chimpanzee, orangutan, or gibbon) or a human; or rodent (e.g., a mouse, a guinea pig, a hamster, or a rat). In some embodiments, the subject or "subject in need of treatment" may be a non-human mammal, especially mammals that are conventionally used as models for demonstrating therapeutic efficacy in humans (e.g., murine, lapine, porcine, canine or primate animals) may be employed.

Senescent Cells

Senescence is a form of irreversible growth arrest accompanied by phenotypic changes, resistance to apoptosis and activation of damage-sensing signaling pathways. Cellular senescence was first described in cultured human fibroblast cells that lost their ability to proliferate, reaching permanent arrest after about 50 population doublings (referred to as the Hayflick limit). Senescence is considered a stress response that can be induced by a wide range of intrinsic and extrinsic insults, including oxidative and genotoxic stress, DNA damage, telomere attrition, oncogenic activation, mitochondrial dysfunction, or chemotherapeutic agents.

Senescent cells remain metabolically active and can influence the tissue hemostasis, disease and aging through their secretory phenotype. Senescence is considered as a physiologic process and is important in promoting wound healing, tissue homeostasis, regeneration, and fibrosis regulation. For instance, transient induction of senescent cells is observed during would healing and contributes to wound resolution. Perhaps one of the most important roles of senescence is its role in tumor suppression. However, the accumulation of senescent cells also drives aging- and aging-related diseases and conditions. The senescent phenotype also can trigger chronic inflammatory responses and consequently augment chronic inflammatory conditions to promote tumor growth. The connection between senescence and aging was initially based on observations that senescent cells accumulate in aged tissue. The use of transgenic models has enabled the detection of senescent cells systematically in many age-related pathologies. Strategies to selectively eliminate senescent cells has demonstrated that senescent cells can indeed play a causal role in aging and related pathologies.

Senescent cells display important and unique properties which include changes in morphology, chromatin organization, gene expression, and metabolism. There are several biochemical and functional properties associated with cellular senescence, such as (i) increased expression of p16 and p21, inhibitors of cyclin-dependent kinases, (ii) presence of senescence-associated β-galactosidase, a marker of lysosomal activity, (iii) appearance of senescence-associated heterochromatin foci and downregulation of lamin B1 levels, (iv) resistance to apoptosis caused by an increased expression of anti-apoptotic BCL-family protein, and (v) upregulation of CD26 (DPP4), CD36 (Scavenger receptor), forkhead box 4 (FOXO4), and secretory carrier membrane protein 4 (SCAMP4). Senescent cells also express an inflammatory signature, the so-called senescence-associated secretory phenotype (SASP). Through SASP, the senescent cells produce a wide range of inflammatory cytokines (IL-6, IL-8), growth factors (TGF-β), chemokines (CCL-2), and matrix metalloproteinases (MMP-3, MMP-9) that operate in a cell-autonomous manner to reinforce senescence (autocrine effects) and communicate with and modify the microenvironment (paracrine effects). SASP factors can contribute to tumor suppression by triggering senescence surveillance, an immune-mediated clearance of senescent cells. However, chronic inflammation is also a known driver of tumorigenesis, and accumulating evidence indicates that chronic SASP can also boost cancer and aging-related diseases.

The secretion profile of senescent cells is context dependent. For instance, the mitochondrial dysfunction-associated senescence (MiDAS), induced by different mitochondrial dysfunction in human fibroblasts, led to the appearance of a SASP that was deficient in IL-1-dependent inflammatory factors. A decrease in the NAD+/NADH ratio activated AMPK signaling which induced MiDAS through the activation of p53. As a result, p53 inhibited NF-κB signaling which is a crucial inducer of pro-inflammatory SASP. In contrast, the cellular senescence caused by persistent DNA damage in human cells induced an inflammatory SASP, which was dependent on the activation of ataxia-telangiectasia mutated (ATM) kinase but not on that of p53. In particular, the expression and secretion levels of IL-6 and IL-8 were increased. It was also demonstrated that cellular senescence caused by the ectopic expression p16INK4a and p21CIP1 induced the senescent phenotype in human fibroblasts without an inflammatory SASP indicating that the growth arrest itself did not stimulate SASP.

One of the most defining characteristics of senescence is stable growth arrest. This is achieved by two important pathways, the p16/Rb and the p53/p21, both of which are central in tumor suppression. DNA damage results in: (1) high deposition of γH2Ax (histone coding gene) and 53BP1 (involved in DNA damage response) in chromatin: this leads to activation of a kinase cascade eventually resulting in p53 activation, and (2) activation of p16INK4a and ARF (both encoded by CDKN2A) and P15INK4b (encoded by CDKN2B): p53 induces transcription of cyclin-dependent kinase inhibitor (p21) and along with both p16INK4a and p15INK4b block genes for cell cycle progression (CDK4 and CDK6). This eventually leads to hypophosphorylation of Retinoblastoma protein (Rb) and cell cycle arrest at the G1 phase.

Selectively killing senescent cells has been shown to significantly improve the health span of mice in the context of normal aging and ameliorates the consequences of age-related disease or cancer therapy (Ovadya, *J Clin Invest.* 128(4): 1247-1254, 2018). In nature, the senescent cells are normally removed by the innate immune cells. Induction of senescence not only prevents the potential proliferation and transformation of damaged/altered cells, but also favors tissue repair through the production of SASP factors that function as chemoattractants mainly for Natural Killer (NK) cells (such as IL-15 and CCL2) and macrophages (such as CFS-1 and CCL2). These innate immune cells mediate the immunosurveillance mechanism for eliminating stressed cells. Senescent cells usually up-regulate the NK-cell activating receptor NKG2D and DNAM1 ligands, which belong to a family of stress-inducible ligands: an important component of the frontline immune defense against infectious diseases and malignancies. Upon receptor activation, NK cells can then specifically induce the death of senescent cells through their cytolytic machinery. A role for NK cells in the immune surveillance of senescent cells has been pointed out in liver fibrosis (Sagiv, Oncogene 32(15): 1971-1977, 2013), hepatocellular carcinoma (Iannello, *J Exp Med* 210(10): 2057-2069, 2013), multiple myeloma (Soriani, *Blood* 113 (15): 3503-3511, 2009), and glioma cells stressed by dysfunction of the mevalonate pathway (Ciaglia, *Int J Cancer* 142(1): 176-190, 2018). Endometrial cells undergo acute cellular senescence and do not differentiate into decidual cells. The differentiated decidual cells secrete IL-15 and thereby recruit uterine NK cells to target and eliminate the undifferentiated senescent cells thus helping to re-model and rejuvenate the endometrium (Brighton, *Elife* 6: e31274, 2017). With a similar mechanism, during liver fibrosis, p53-expressing senescent liver satellite cells skewed the polarization of resident Kupfer macrophages and freshly infiltrated macrophages toward the pro-inflammatory M1 phenotype, which display senolytic activity. F4/80+ macrophages have been shown to play a key role in the clearance of mouse uterine senescent cells to maintain postpartum uterine function.

Senescent cells recruit NK cells by mainly upregulating ligands to NKG2D (expressed on NK cells), chemokines, and other SASP factors. In vivo models of liver fibrosis have shown effective clearance of senescent cells by activated NK cells (Krizhanovsky, *Cell* 134(4): 657-667, 2008). Studies have described various models to study senescence including liver fibrosis (Krizhanovsky, *Cell* 134(4): 657-667, 2008), osteoarthritis (Xu, *J Gerontol A Biol Sci Med Sci* 72(6): 780-785, 2017), and Parkinson's disease (Chinta, *Cell Rep* 22(4): 930-940, 2018). Animal models for studying senescent cells are described in: Krizhanovsky, *Cell* 134(4): 657-667, 2008; Baker, *Nature* 479(7372): 232-236, 2011; Farr, *Nat Med* 23(9): 1072-1079, 2017; Bourgeois, *FEBS Lett* 592(12): 2083-2097, 2018; Xu, *Nat Med* 24(8): 1246-1256, 2018).

Additional Therapeutic Agents

Some embodiments of any of the methods described herein can further include administering to a subject (e.g., any of the subjects described herein) a therapeutically effective amount of one or more additional therapeutic agents. The one or more additional therapeutic agents can be administered to the subject at substantially the same time as a $T_{reg}$ cell generated by any of the methods described herein or any of the compositions (e.g., pharmaceutical compositions) comprising a population of $T_{reg}$ cells produced using any of the methods described herein. In some embodiments, one or more additional therapeutic agents can be administered to the subject prior to administration of a $T_{reg}$ cell or a composition (e.g., a pharmaceutical composition) comprising a population of $T_{reg}$ cells produced using any of the methods described herein. In some embodiments, one or more additional therapeutic agents can be administered to the subject after administration of a $T_{reg}$ cell or a composition (e.g., a pharmaceutical composition) comprising a population of $T_{reg}$ cells produced using any of the methods described herein to the subject.

Non-limiting examples of additional therapeutic agents include: anti-cancer drugs, activating receptor agonists, immune checkpoint inhibitors, agents for blocking HLA-specific inhibitory receptors, Glucogen Synthase Kinase (GSK) 3 inhibitors, and antibodies.

Non-limiting examples of anticancer drugs include anti-metabolic drugs (e.g., 5-fluorouracil (5-FU), 6-mercaptopurine (6-MP), capecitabine, cytarabine, floxuridine, fludarabine, gemcitabine, hydroxycarbamide, methotrexate, 6-thioguanine, cladribine, nelarabine, pentostatin, or pemetrexed), plant alkaloids (e.g., vinblastine, vincristine, vindesine, camptothecin, 9-methoxycamptothecin, coronaridine, taxol, naucleaorals, diprenylated indole alkaloid, montamine, schischkiniin, protoberberine, berberine, sanguinarine, chelerythrine, chelidonine, liriodenine, clivorine, β-carboline, antofine, tylophorine, cryptolepine, neocryptolepine, corynoline, sampangine, carbazole, crinamine, montanine, ellipticine, paclitaxel, docetaxel, etoposide, tenisopide, irinotecan, topotecan, or acridone alkaloids), proteasome inhibitors (e.g., lactacystin, disulfiram, epigallocatechin-3-gallate, marizomib (salinosporamide A), oprozomib (ONX-0912), delanzomib (CEP-18770), epoxomicin, MG132, beta-hydroxy beta-methylbutyrate, bortezomib, carfilzomib, or ixazomib), antitumor antibiotics (e.g., doxorubicin, daunorubicin, epirubicin, mitoxantrone, idarubicin, actinomycin, plicamycin, mitomycin, or bleomycin), histone deacetylase inhibitors (e.g., vorinostat, panobinostat, belinostat, givinostat, abexinostat, depsipeptide, entinostat, phenyl butyrate, valproic acid, trichostatin A, dacinostat, mocetinostat, pracinostat, nicotinamide, cambinol, tenovin 1, tenovin 6, sirtinol, ricolinostat, tefinostat, kevetrin, quisinostat, resminostat, tacedinaline, chidamide, or selisistat), tyrosine kinase inhibitors (e.g., axitinib, dasatinib, encorafinib, erlotinib, imatinib, nilotinib, pazopanib, and sunitinib), and chemotherapeutic agents (e.g., all-trans retinoic acid, azacitidine, azathioprine, doxifluridine, epothilone, hydroxyurea, imatinib, teniposide, tioguanine, valrubicin, vemurafenib, and lenalidomide). Additional examples of chemotherapeutic agents include alkylating agents, e.g., mechlorethamine, cyclophosphamide, chlorambucil, melphalan, ifosfamide, thiotepa, hexamethylmelamine, busulfan, altretamine, procarbazine, dacarbazine, temozolomide, carmustine, lumustine, streptozocin, carboplatin, cisplatin, and oxaliplatin.

EXAMPLES

The invention is further described in the following examples, which do not limit the scope of the invention described in the claims.

Example 1. Production of αCD3scFv/TF/αCD28scFv

The nucleic acid and amino acid sequences of αCD3scFv/TF/αCD28scFv are shown below.

Nucleic Acid Encoding αCD3scFv/TF/αCD28scFv
(SEQ ID NO: 10)
(Signal peptide)
ATGAAGTGGGTGACCTTCATCAGCTTATTATTTTTATTCAGCTCCGCCT

ATTCC (αCD3 light chain variable region)
CAGATCGTGCTGACCCAAAGCCCCGCCATCATGAGCGCTAGCCCCGGTGA

GAAGGTGACCATGACATGCTCCGCTTCCAGCTCCGTGTCCTACATGAACT

GGTATCAGCAGAAAAGCGGAACCAGCCCCAAAAGGTGGATCTACGACACC

AGCAAGCTGGCCTCCGGAGTGCCCGCTCATTTCCGGGGCTCTGGATCCGG

CACCAGCTACTCTTTAACCATTTCCGGCATGGAAGCTGAAGACGCTGCCA

CCTACTATTGCCAGCAATGGAGCAGCAACCCCTTCACATTCGGATCTGGC

ACCAAGCTCGAAATCAATCGT (Linker)
GGAGGAGGTGGCAGCGGCGGCGGTGGATCCGGCGGAGGAGGAAGC (αCD3 heavy chain variable region)
CAAGTTCAACTCCAGCAGAGCGGCGCTGAACTGGCCCGGCCCGGCGCCTC

CGTCAAGATGAGCTGCAAGGCTTCCGGCTATACATTTACTCGTTACACAA

TGCATTGGGTCAAGCAGAGGCCCGGTCAAGGTTTAGAGTGGATCGGATAT

ATCAACCCTTCCCGGGGCTACACCAACTATAACCAAAAGTTCAAGGATAA

AGCCACTTTAACCACTGACAAGAGCTCCTCCACCGCCTACATGCAGCTGT

CCTCTTTAACCAGCGAGGACTCCGCTGTTTACTACTGCGCTAGGTATTAC

GACGACCACTACTGTTTAGACTATTGGGGACAAGGTACCACTTTAACCGT

CAGCAGC (Human tissue factor 219 form)
TCCGGCACCACCAATACCGTGGCCGCTTATAACCTCACATGGAAGAGCAC

CAACTTCAAGACAATTCTGGAATGGGAACCCAAGCCCGTCAATCAAGTTT

ACACCGTGCAGATCTCCACCAAATCCGGAGACTGGAAGAGCAAGTGCTTC

TACACAACAGACACCGAGTGTGATTTAACCGACGAAATCGTCAAGGACGT

CAAGCAAACCTATCTGGCTCGGGTCTTTTCCTACCCCGCTGGCAATGTCG

AGTCCACCGGCTCCGCTGGCGAGCCTCTCTACGAGAATTCCCCCGAATTC

ACCCCTTATTTAGAGACCAATTTAGGCCAGCCTACCATCCAGAGCTTCGA

GCAAGTTGGCACCAAGGTGAACGTCACCGTCGAGGATGAAAGGACTTTAG

TGCGGCGGAATAACACATTTTTATCCCTCCGGGATGTGTTCGGCAAAGAC

CTCATCTACACACTGTACTATTGGAAGTCCAGCTCCTCCGGCAAAAAGAC

CGCTAAGACCAACACCAACGAGTTTTTAATTGACGTGGACAAAGGCGAGA

ACTACTGCTTCAGCGTGCAAGCCGTGATCCCTTCTCGTACCGTCAACCGG

AAGAGCACAGATTCCCCCGTTGAGTGCATGGGCCAAGAAAAGGGCGAGTT

CCGGGAG (αCD28 light chain variable region)
GTCCAGCTGCAGCAGAGCGGACCCGAACTCGTGAAACCCGGTGCTTCCGT

GAAAATGTCTTGTAAGGCCAGCGGATACACCTTCACCTCCTATGTGATCC

AGTGGGTCAAACAGAAGCCCGGACAAGGTCTCGAGTGGATCGGCAGCATC

AACCCTTACAACGACTATACCAAATACAACGAGAAGTTTAAGGGAAAGGC

TACTTTAACCTCCGACAAAAGCTCCATCACAGCCTACATGGAGTTCAGCT

CTTTAACATCCGAGGACAGCGCTCTGTACTATTGCGCCCGGTGGGGCGAC

GGCAATTACTGGGGACGGGGCACAACACTGACCGTGAGCAGC

-continued (Linker)
GGAGGCGGAGGCTCCGGCGGAGGCGGATCTGGCGGTGGCGGCTCC (αCD28 light chain variable region)
GACATCGAGATGACCCAGTCCCCCGCTATCATGTCCGCCTCTTTAGGCGA

GCGGGTCACAATGACTTGTACAGCCTCCTCCAGCGTCTCCTCCTCCTACT

TCCATTGGTACCAACAGAAACCCGGAAGCTCCCCTAAACTGTGCATCTAC

AGCACCAGCAATCTCGCCAGCGGCGTGCCCCCTAGGTTTTCCGGAAGCGG

AAGCACCAGCTACTCTTTAACCATCTCCTCCATGGAGGCTGAGGATGCCG

CCACCTACTTTTGTCACCAGTACCACCGGTCCCCCACCTTCGGAGGCGGC

ACCAAACTGGAGACAAAGAGG

αCD3scFv/TF/αCD28scFv
(SEQ ID NO: 8)
(Signal peptide)
MKWVTFISLLFLFSSAYS (αCD3 light chain variable region)
QIVLTQSPAIMSASPGEKVTMTCSASSSVSYMNWYQQKSGTSPKRWIYDT

SKLASGVPAHFRGSGSGTSYSLTISGMEAEDAATYYCQQWSSNPFTFGSG

TKLEINR (Linker)
GGGGSGGGGSGGGGS (αCD3 heavy chain variable region)
QVQLQQSGAELARPGASVKMSCKASGYTFTRYTMHWVKQRPGQGLEWIGY

INPSRGYTNYNQKFKDKATLTTDKSSSTAYMQLSSLTSEDSAVYYCARYY

DDHYCLDYWGQGTTLTVSS (Human tissue factor 219)
SGTTNTVAAYNLTWKSTNFKTILEWEPKPVNQVYTVQISTKSGDWKSKCF

YTTDTECDLTDEIVKDVKQTYLARVFSYPAGNVESTGSAGEPLYENSPEF

TPYLETNLGQPTIQSFEQVGTKVNVTVEDERTLVRRNNTFLSLRDVFGKD

LIYTLYYWKSSSSGKKTAKTNTNEFLIDVDKGENYCFSVQAVIPSRTVNR

KSTDSPVECMGQEKGEFRE (αCD28 light chain variable region)
VQLQQSGPELVKPGASVKMSCKASGYTFTSYVIQWVKQKPGQGLEWIGSI

NPYNDYTKYNEKFKGKATLTSDKSSITAYMEFSSLTSEDSALYYCARWGD

GNYWGRGTTLTVSS (Linker)
GGGGSGGGGSGGGGS (αCD28 heavy chain variable region)
DIEMTQSPAIMSASLGERVTMTCTASSSVSSSYFHWYQQKPGSSPKLCIY

STSNLASGVPPRFSGSGSTSYSLTISSMEAEDAATYFCHQYHRSPTFGGG

TKLETKR

The nucleic acid encoding αCD3scFv/TF/αCD28scFv was cloned into a modified retrovirus expression vectors as described previously (Hughes et al., *Hum Gene Ther* 16:457-72, 2005). The expression vector encoding αCD3scFv/TF/αCD28scFv was transfected into CHO-K1 cells. Expression of the expression vector in CHO-K1 cells allowed for secretion of the soluble αCD3scFv/TF/αCD28scFv single-chain chimeric polypeptide (referred to as 3t28), which can be purified by anti-TF antibody affinity and other chromatography methods.

An anti-tissue factor antibody affinity column was used to purify the αCD3scFv/TF/αCD28scFv single-chain chimeric polypeptide. The anti-tissue factor antibody affinity column was connected to a GE Healthcare AKTA Avant system. A flow rate of 4 mL/min was used for all steps except the elution step, which was 2 mL/min.

Cell culture harvest including αCD3scFv/TF/αCD28scFv single-chain chimeric polypeptide was adjusted to pH 7.4 with 1M Tris base and loaded onto the anti-TF antibody affinity column (described above) which was equilibrated with 5 column volumes of PBS. After sample loading, the column was washed with 5 column volumes PBS, followed by elution with 6 column volumes 0.1 M acetic acid, pH 2.9. An A280 elution peak was collected and then neutralized to pH 7.5-8.0 by adding 1 M Tris base. The neutralized sample was then buffer exchanged into PBS using Amicon centrifugal filters with a 30 kDa molecular weight cutoff.

After each elution, the anti-tissue factor antibody affinity column was stripped using 6 column volumes of 0.1 M glycine, pH 2.5. The column was then neutralized using 10 column volumes of PBS, 0.05% NaN$_3$, and stored at 2-8° C.

Example 2. Production of IL-2/TF/IL-2

The nucleic acid and amino acid sequences of IL-2/TF/IL-2 are shown below.

Nucleic Acid Encoding IL-2/TF/IL-2
(SEQ ID NO: 12)
(Signal peptide)
ATGAAGTGGGTGACCTTCATCAGCCTGCTGTTCCTGTTCTCCAGCGCCT

ACTCC (First IL-2 fragment)
GCCCCCACCTCCTCCTCCACCAAGAAGACCCAGCTGCAGCTGGAGCATTT

ACTGCTGGATTTACAGATGATTTTAAACGGCATCAACAACTACAAGAACC

CCAAGCTGACTCGTATGCTGACCTTCAAGTTCTACATGCCCAAGAAGGCC

ACCGAGCTGAAGCATTTACAGTGTTTAGAGGAGGAGCTGAAGCCCCTCGA

GGAGGTGCTGAATTTAGCCCAGTCCAAGAATTTCCATTTAAGGCCCCGGG

ATTTAATCAGCAACATCAACGTGATCGTTTTAGAGCTGAAGGGCTCCGAG

ACCACCTTCATGTGCGAGTACGCCGACGAGACCGCCACCATCGTGGAGTT

TTTAAATCGTTGGATCACCTTCTGCCAGTCCATCATCTCCACTTTAACC (Human tissue factor 219 form)
AGCGGCACAACCAACACAGTCGCTGCCTATAACCTCACTTGGAAGAGCAC

CAACTTCAAAACCATCCTCGAATGGGAACCCAAACCCGTTAACCAAGTTT

ACACCGTGCAGATCAGCACCAAGTCCGGCGACTGGAAGTCCAAATGTTTC

TATACCACCGACACCGAGTGCGATCTCACCGATGAGATCGTGAAAGATGT

GAAACAGACCTACCTCGCCCGGGTGTTTAGCTACCCCGCCGGCAATGTGG

AGAGCACTGGTTCCGCTGGCGAGCCTTTATACGAGAACAGCCCCGAATTT

ACCCCTTACCTCGAGACCAATTTAGGACAGCCCACCATCCAAAGCTTTGA

GCAAGTTGGCACAAAGGTGAATGTGACAGTGGAGGACGAGCGGACTTTAG

TGCGGCGGAACAACACCTTTCTCAGCCTCCGGGATGTGTTCGGCAAAGAT

TTAATCTACACACTGTATTACTGGAAGTCCTCTTCCTCCGGCAAGAAGAC

AGCTAAAACCAACACAAACGAGTTTTTAATCGACGTGGATAAAGGCGAAA

```
-continued
ACTACTGTTTCAGCGTGCAAGCTGTGATCCCCTCCCGGACCGTGAATAGG

AAAAGCACCGATAGCCCCGTTGAGTGCATGGGCCAAGAAAAGGGCGAGTT

CCGGGAG (Second IL-2 fragment)
GCACCTACTTCAAGTTCTACAAAGAAAACACAGCTACAACTGGAGCATTT

ACTGCTGGATTTACAGATGATTTTGAATGGAATTAATAATTACAAGAATC

CCAAACTCACCAGGATGCTCACATTTAAGTTTTACATGCCCAAGAAGGCC

ACAGAACTGAAACATCTTCAGTGTCTAGAAGAAGAACTCAAACCTCTGGA

GGAAGTGCTAAATTTAGCTCAAAGCAAAAACTTTCACTTAAGACCCAGGG

ACTTAATCAGCAATATCAACGTAATAGTTCTGGAACTAAAGGGATCTGAA

ACAACATTCATGTGTGAATATGCTGATGAGACAGCAACCATTGTAGAATT

TCTGAACAGATGGATTACCTTTTGTCAAAGCATCATCTCAACACTAACT

IL-2/TF/IL-2
                                                    (SEQ ID NO: 4)
(Signal peptide)
MKWVTFISLLFLFSSAYS (Human IL-2)
APTSSSTKKTQLQLEHLLLDLQMILNGINNYKNPKLTRMLTFKFYMPKKA

TELKHLQCLEEELKPLEEVLNLAQSKNFHLRPRDLISNINVIVLELKGSE

TTFMCEYADETATIVEFLNRWITFCQSIISTLT (Human Tissue Factor 219)
SGTTNTVAAYNLTWKSTNFKTILEWEPKPVNQVYTVQISTKSGDWKSKCF

YTTDTECDLTDEIVKDVKQTYLARVFSYPAGNVESTGSAGEPLYENSPEF

TPYLETNLGQPTIQSFEQVGTKVNVTVEDERTLVRRNNTFLSLRDVFGKD

LIYTLYYWKSSSSGKKTAKTNTNEFLIDVDKGENYCFSVQAVIPSRTVNR

KSTDSPVECMGQEKGEFRE (Human IL-2)
APTSSSTKKTQLQLEHLLLDLQMILNGINNYKNPKLTRMLTFKFYMPKKA

TELKHLQCLEEELKPLEEVLNLAQSKNFHLRPRDLISNINVIVLELKGSE

TTFMCEYADETATIVEFLNRWITFCQSIISTLT
```

The nucleic acid encoding IL-2/TF/IL-2 was cloned into a modified retrovirus expression vector as described previously (Hughes et al., Hum Gene Ther 16:457-72, 2005). The expression vector encoding IL-2/TF/IL-2 was transfected into CHO-K1 cells. Expression of the expression vector in CHO-K1 cells allowed for secretion of the soluble IL-2/TF/IL-2 single-chain chimeric polypeptide (referred to as 2t2), which can be purified by anti-TF antibody affinity and other chromatography methods.

Example 3: Stimulation of Foxp3+ $T_{reg}$ Cells by 2t2 with Anti-CD3/Anti-CD28 Beads and Rapamycin Compared with Commercial Recombinant Human IL-2

Fresh human leukocytes (3 donors) were obtained from the blood bank and CD4+CD25+CD127$^{dim}$ $T_{reg}$ cells were isolated with the CD4+CD25+CD127$^{dim}$ regulatory T cell isolation kit II reagent (Miltenyi Biotec). The purity of Foxp3+ $T_{reg}$ cells was >35% and confirmed by staining with CD4-Alexa Fluro 488, CD25-APC, CD3 APC-Cy7, Foxp3-PE (Intracellular staining, Invitrogen), and CD127-Alex Fluro 700 (BioLegend). The cells were counted and resuspended in 1×10$^6$/mL in a 48-well flat-bottom plate in complete media (RPMI 1640 (Gibco) supplemented with 2 mM L-glutamine (Thermo Life Technologies), penicillin (Thermo Life Technologies), streptomycin (Thermo Life Technologies), and 10% FBS (Hyclone)). The cells were stimulated with either (1) hIL-2 cytokine (500 IU/mL) (Proleukin), anti-CD3/anti-CD28 beads (4:1,Beads: Cells) (Dynabeads, Life Technologies), and rapamycin (100 nM) (Sigma) or (2) 100 nM of 2t2, anti-CD3/anti-CD28 beads (4:1 Beads: Cells) (Dynabeads, Life Technologies), and rapamycin (100 nM) (Sigma) and incubated for 21 days at 37° C., 5% $CO_2$. During the expansion period, the cells were re-stimulated with either (1) hIL-2 cytokine (500 IU/mL) (Proleukin) and rapamycin (100 nM) (Sigma) or (2) 100 nM of 2t2 and rapamycin (100 nM) (Sigma) every alternate day. Every 7 days, the cells were re-stimulated with anti-CD3/anti-CD28 beads (1:1 Beads: Cells) (Dynabeads, Life Technologies). The cells were maintained for 21 days at 1×10$^6$/mL concentration with fresh complete media containing either (1) hIL-2 cytokine (500 IU/mL) (Proleukin) and rapamycin (100 nM) (Sigma) or (2) 100 nM of 2t2 and rapamycin (100 nM) (Sigma) every alternate day. At Days 7, 14, and 21, the cells were stained with CD4-Alexa Fluro 488, CD25-PE, CD3 APC-Cy7, Foxp3-PE (intracellular staining using Foxp3 staining kit, Invitrogen), and CD127-Alex Fluro 700 (BioLegend) to assess the expansion of Foxp3+ $T_{reg}$ cells by flow cytometry. Fold-expansion of Foxp3+ $T_{reg}$ cells was measured by counting in a trypan blue (0.4%, Invitrogen) viability assay. FIG. 1 shows a 145-fold increase in Foxp3+ $T_{reg}$ cells which were stimulated with 100 nM of 2t2, anti-CD3/anti-CD28 beads (4:1 Beads: Cells) (Dynabeads, Life Technologies), and rapamycin (100 nM) (Sigma) compared to a 100-fold increase with hIL-2 (500 IU/mL) (Proleukin), anti-CD3/anti-CD28 beads (4:1 Beads: Cells) (Dynabeads, Life Technologies), and rapamycin (100 nM) (Sigma).

Example 4: Detection of Helios, CTLA-4, CD39, CD62L, CD25, CD103, CD69, PD1 and CD49b Markers Fresh human leukocytes (3 donors) were obtained from the blood bank and CD4+CD25+CD127$^{dim}$ $T_{reg}$ cells were isolated with the CD4+CD25+CD127$^{dim}$ regulatory T cell isolation kit II reagent (Miltenyi Biotec). The purity of Foxp3+ $T_{reg}$ cells was >35% and confirmed by staining with CD4-Alexa Fluro 488, CD25-APC, CD3 APC-Cy7, Foxp3-PE (Intracellular staining, Invitrogen), and CD127-Alex Fluro 700 (BioLegend). The cells were counted and resuspended in 1×10$^6$/mL in a 48-well flat-bottom plate in complete media (RPMI 1640 (Gibco) supplemented with 2 mM L-glutamine (Thermo Life Technologies), penicillin (Thermo Life Technologies), streptomycin (Thermo Life Technologies), and 10% FBS (Hyclone)). The cells were stimulated with either (1) hIL-2 cytokine (500 IU/mL) (Proleukin), anti-CD3/anti-CD28 beads (4:1 Beads: Cells) (Dynabeads, Life Technologies), and rapamycin (100 nM) (Sigma) or (2) 100 nM of 2t2, anti-CD3/anti-CD28 beads (4:1 Beads: Cells) (Dynabeads, Life Technologies), and rapamycin (100 nM) (Sigma), then incubated for 21 days at 37° C., 5% $CO_2$. During the expansion period, the cells were re-stimulated with either (1) hIL-2 (500 IU/mL) (Proleukin) and rapamycin (100 nM) (Sigma) or (2) 100 nM of 2t2 and rapamycin (100 nM) (Sigma) every alternate day. Every 7 days, the cells were re-stimulated with anti-CD3/anti-CD28 beads (1:1,Beads: Cells) (Dynabeads, Life Technologies). The cells were maintained for 21 days at 1×10$^6$/mL concentration with fresh complete media containing either (1) hIL-2 (500 IU/mL) (Proleukin) and rapamycin (100 nM) (Sigma) or (2) 100 nM of 2t2 and rapamycin (100 nM) (Sigma), every alternate day. The cells were stained with CD4-Alexa Fluro 488, CD25-PE, CD3 APC-Cy7, Foxp3-PE (Intracellular staining using Foxp3 staining kit, Invitrogen), and CD127-Alex Fluro 700 (BioLegend) to assess the expansion of Foxp3$^+$ T$_{reg}$ cells by flow cytometry. Fold-expansion of Foxp3$^+$ T$_{reg}$ cells was measured by counting in a trypan blue (0.4%, Invitrogen) viability assay. On day 21, the cells were harvested, and surface stained for CD4-Alexa Fluro 488, CD25-PE, CD3 APC-Cy7, Foxp3-PE (Intracellular staining using Foxp3 staining kit, Invitrogen), CD127-Alex Fluro 700, Helios PE-Cy7, CTLA-4 Brilliant Violet 605, CD39 APC, CD62L PECy7, CD25 PE, CD103 Per-CP.Cy5.5, CD69 APC Fire 750, PD1 Alexa Fluro 750, and CD49b APC, and intracellularly stained using Foxp3-Pacific Blue (BioLegend) (Intracellular staining kit, Invitrogen). For surface staining, the cells were washed (1500 RPM for 5 minutes at room temperature) in FACS buffer (1×PBS (Hyclone) with 0.5% BSA (EMD Millipore) and 0.001% sodium azide (Sigma). After two washes, the cells were analyzed by Flow Cytometry (Celesta-BD Bioscience). For intracellularly cell staining, the cells were fixed in fixative buffer (Invitrogen) for 20 minutes at room temperature. After fixation steps, the cells were washed (1500 RPM for 5 minutes in room temperature) in 1× Permeabilized Buffer (eBioscience) and stained using Foxp3-Pacific Blue (Biolegend) for 30 minutes at room temperature. The cells were washed once again with 1× Permeabilized Buffer and then washed with FACS buffer. The cell pellets were resuspended in 300 µL of FACS Buffer for analysis by Flow Cytometry (Celesta-BD Bioscience). (The cells were gated on CD4$^+$CD25$^+$Foxp3$^+$ cells and plotted Data-%$^+$ of surface markers, 3 healthy donors). FIGS. 2A-2I show comparable surface markers on Foxp3$^+$ T$_{reg}$ cells which were stimulated with either (1) 100 nM of 2t2, anti-CD3/anti-CD28 beads (4:1 Beads: Cells) (Dynabeads, Life Technologies) and rapamycin (100 nM) (Sigma) or (2) hIL-2 (500 IU/mL) (Proleukin), anti-CD3/anti-CD28 beads (4:1 Beads: Cells) (Dynabeads, Life Technologies), and rapamycin (100 nM) (Sigma) for 21 days.

Example 5: Activation of Human Regulatory T Cells Displays a High Level of Glucose Metabolism Fresh human leukocytes (3 donors) were obtained from the blood bank and CD4$^+$CD25$^+$CD127$^{dim}$ T$_{reg}$ cells were isolated using CD4$^+$CD25$^+$CD127$^{dim}$ T$_{reg}$ cell isolation kit II (Miltenyi Biotec). The purity of Foxp3$^+$ T$_{reg}$ cells was >35% and confirmed by staining with CD4-Alexa Fluro 488, CD25-APC, CD3 APC-Cy7, Foxp3-PE (Intracellular staining, Invitrogen), and CD127-Alex Fluro 700 (BioLegend). The cells were counted and resuspended in 1×10$^6$/mL in a 24-well flat-bottom plate in complete media (RPMI 1640 (Gibco) supplemented with 2 mM L-glutamine (Thermo Life Technologies), penicillin (Thermo Life Technologies), streptomycin (Thermo Life Technologies), and 10% FBS (Hyclone)). The cells were stimulated with either (1) hIL-2 (500 IU/mL) (Proleukin), anti-CD3/anti-CD28 beads (4:1 Beads: Cells) (Dynabeads, Life Technologies), and rapamycin (100 nM) (Sigma) or (2) 100 nM of 2t2, anti-CD3/anti-CD28 beads (4:1 Beads: Cells) (Dynabeads, Life Technologies), and rapamycin (100 nM) (Sigma), then incubated overnight at 37° C. at 5% CO$_2$. The next day, the cells were harvested, counted, and resuspended in 4×10$^6$/mL in a 96-well plate and 50 µL/well were seeded in Cell-Tak-coated Seahorse Bioanalyzer XFe96 culture plates in Seahorse XF RPMI medium, pH 7.4 supplemented with 2 mM L-glutamine. The cells were allowed to attach to the plate for 30 mins at 37° C. Additional 130 µL of assay medium was added to each well of the plate (also the background wells). The plate was incubated in 37° C., non-CO$_2$ incubator for 1 hr. For the calibration plate: the 10× solution of glucose/oligomycin/2-deoxyglucose were prepared in Seahorse assay media. 20 µL volume of glucose/oligomycin/2-deoxyglucose were added to ports A, B, and C of the extracellular flux plate that was calibrated overnight. Extracellular acidification rate (ECAR) was measured using an XFe96 Extracellular Flux Analyzer. Complete ECAR analysis consisted of four stages: non-glycolytic acidifications (without drugs), glycolysis (10 mM glucose), glycolytic capacity (2 µM oligomycin), and glycolytic reserve (100 mM 2-deoxyglucose) which was calculated by using Seahorse Xfe96 software, wave. The results (FIGS. 3A-3D) showed that the activated human T$_{reg}$ cells displayed a high level of glucose metabolism.

Figure 4:
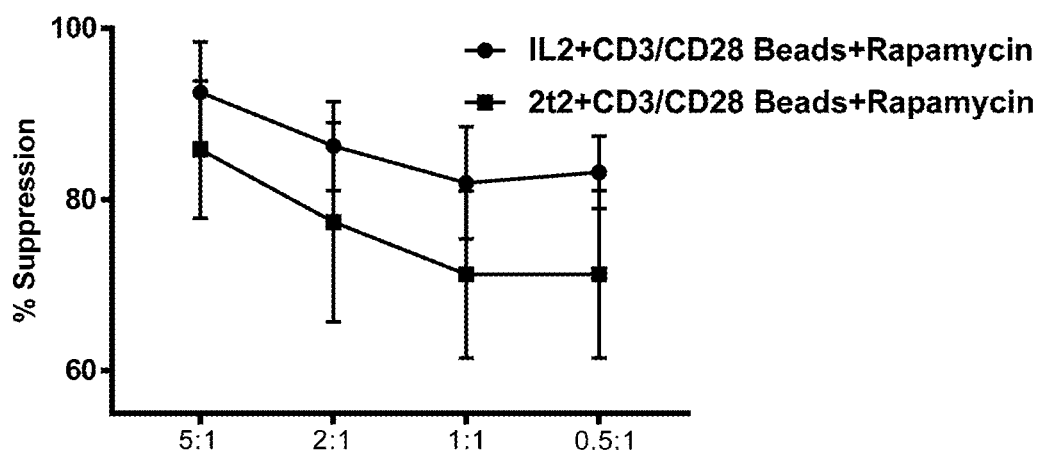
FIG. 4 is a diagram showing the suppression of autologous T responder cells by $T_{reg}$ cells previously stimulated with (1) 2t2, CD3/CD28 beads, and rapamycin, or (2) recombinant human IL-2, CD3/CD28 beads, and rapamycin.

Example 6: Measurement of Suppression of Autologous T Responder Cells by Expanded Regulatory T Cell Fresh human leukocytes (3 donors) were obtained from the blood bank and CD4$^+$CD25$^+$CD127$^{dim-}$ T$_{reg}$ cells were isolated with the CD4$^+$CD25$^+$CD127$^{dim-}$ regulatory T cell isolation kit II reagent (Miltenyi Biotec). The purity of Foxp3$^+$ T$_{reg}$ cells was >35% and confirmed by staining with CD4-Alexa Fluro 488, CD25-APC, CD3 APC-Cy7, Foxp3-PE (Intracellular staining, Invitrogen), and CD127-Alex Fluro 700 (BioLegend). The cells were counted and resuspended in 1×10$^6$/mL in a 24-well flat-bottom plate in complete media (RPMI 1640 (Gibco) supplemented with 2 mM L-glutamine (Thermo Life Technologies), penicillin (Thermo Life Technologies), streptomycin (Thermo Life Technologies), and 10% FBS (Hyclone)). The cells were stimulated with either (1) hIL-2 (500 IU/mL) (Proleukin), anti-CD3/anti-CD28 beads (4:1 Beads: Cells) (Dynabeads, Life Technologies), and rapamycin (100 nM) (Sigma) or (2) 100 nM of 2t2, anti-CD3/anti-CD28 beads (4:1 Beads: Cells) (Dynabeads, Life Technologies), and rapamycin (100 nM) (Sigma), and then incubated for 21 days at 37° C., 5% CO$_2$. During the expansion period, the cells were re-stimulated with either (1) hIL-2 cytokine (500 IU/mL) (Proleukin) and rapamycin (100 nM) (Sigma) or (2) 100 nM of 2t2 and rapamycin (100 nM) (Sigma), every alternate day. Every 7 days, the cells were re-stimulated with anti-CD3/anti-CD28 beads (1:1 Beads: Cells) (Dynabeads, Life Technologies). The cells were maintained for 21 days at 1×10$^6$/mL concentration with fresh complete media containing either (1) hIL-2 (500 IU/mL) (Proleukin) and rapamycin (100 nM) (Sigma) or (2) 100 nM of 2t2 and rapamycin (100 nM) (Sigma), every alternate day. Fold-expansion of Foxp3$^+$ T$_{reg}$ cells was measured by counting in trypan blue (0.4%, Invitrogen) viability assay. On day 21, frozen autologous T responder (Tresp) cells were thawed and labelled with Cell Trace Violet (Invitrogen). Expanded T$_{reg}$ cells were harvested and counted. T$_{reg}$ cells were cultured with T responder cells at various ratios (5:1, 2:1, 1:1, 0.5:1, T$_{reg}$ cells: T responder cells). The cells were re-stimulated with either (1) anti-CD3/anti-CD28 beads (Beads:Cell 1:70) and 2t2 (25 nM) or (2) anti-CD3/anti-CD28 beads (Beads:Cell 1:70) and IL2 (50 IU/mL), and cultured for 5 days. The cells were harvested and washed (1500 RPM for 5 minutes at room temperature) in FACS buffer (1×PBS (Hyclone) with 0.5% BSA (EMD Millipore) and 0.001% Sodium Azide (Sigma)). After two washes, the cells were analyzed by flow cytometry (Celesta-BD Bioscience). (Plotted %+ of CFSE+ proliferating cells). FIG. 4 shows suppression capacity of Foxp3+ $T_{reg}$ cells which were stimulated with 100 nM of 2t2, anti-CD3/anti-CD28 beads (4:1 Beads: Cells) (Dynabeads, Life Technologies), and rapamycin (100 nM) compared to cells stimulated with hIL-2 (500 IU/mL) (Proleukin), anti-CD3/anti-CD28 beads (4:1 Beads: Cells) (Dynabeads, Life Technologies), and rapamycin (100 nM) (Sigma).

Example 7: Measurement of IL-10 from Suppression Assay

Figure 5:
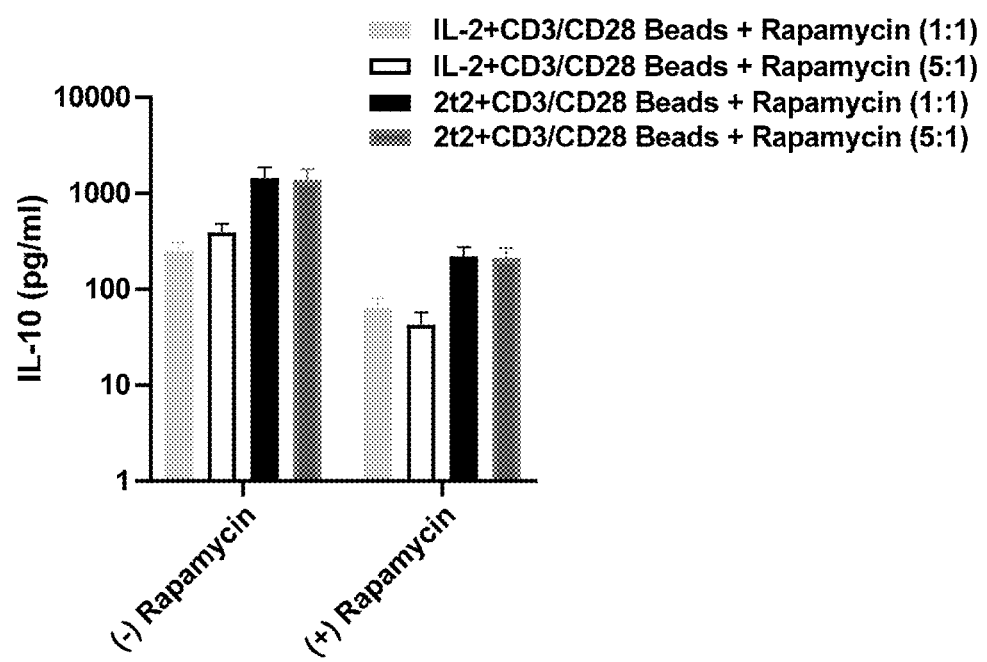
FIG. 5 is a diagram showing the levels of IL-10 secretion by $T_{reg}$ cells in a T responder cell suppression assay, where the $T_{reg}$ cells were previously stimulated with either (1) 2t2 and CD3/CD28 beads in the presence or absence of rapamycin, or (2) recombinant human IL-2 and CD3/CD28 beads in the presence or absence of rapamycin.

Fresh human leukocytes (3 donors) were obtained from the blood bank and CD4+CD25+CD127$^{dim}$ $T_{reg}$ cells were isolated with the CD4+CD25+CD127$^{dim}$ regulatory T cell isolation kit II reagent (Miltenyi Biotec). The purity of Foxp3+ $T_{reg}$ cells was >35% and confirmed by staining with CD4-Alexa Fluro 488, CD25-APC, CD3 APC-Cy7, Foxp3-PE (Intracellular staining, Invitrogen), and CD127-Alex Fluro 700 (BioLegend). The cells were counted and resuspended in 1×10$^6$/mL in a 24-well flat-bottom plate in complete media (RPMI 1640 (Gibco) supplemented with 2 mM L-glutamine (Thermo Life Technologies), penicillin (Thermo Life Technologies), streptomycin (Thermo Life Technologies), and 10% FBS (Hyclone)). The cells were stimulated with either (1) hIL-2 (500 IU/mL) (Proleukin), anti-CD3/anti-CD28 beads (4:1 Beads: Cells) (Dynabeads, Life Technologies), and rapamycin (100 nM) (Sigma) or (2) 100 nM of 2t2, anti-CD3/anti-CD28 beads (4:1 Beads: Cells) (Dynabeads, Life Technologies), and rapamycin (100 nM) (Sigma), and then incubated for 21 days at 37° C. and 5% CO$_2$. During the expansion period, the cells were re-stimulated with either (1) hIL-2 cytokine (500 IU/mL) (Proleukin) and rapamycin (100 nM) (Sigma) or (2) 100 nM of 2t2 and rapamycin (100 nM) (Sigma), every alternate day. Every 7 days, the cells were re-stimulated with anti-CD3/anti-CD28 beads (1:1 Beads:Cells) (Dynabeads, Life Technologies). The cells were maintained for 21 days at 1×10$^6$/mL concentration with fresh complete media containing either (1) hIL-2 (500 IU/mL) (Proleukin) and rapamycin (100 nM) (Sigma) or (2) 100 nM of 2t2 and rapamycin (100 nM) (Sigma), every alternate day. Fold-expansion of Foxp3+ $T_{reg}$ cells was measured by counting in a trypan blue (0.4%, Invitrogen) viability assay. On day 21, frozen autologous T responder (Tresp) cells were thawed and labelled with Cell Trace Violet (Invitrogen). The expanded $T_{reg}$ cells were harvested and counted. The $T_{reg}$ cells were cultured with T responder cells at various ratios (5:1, 1:1, $T_{reg}$ cells: T responder cells). The cells were re-stimulated with (1) anti-CD3/anti-CD28 beads (Beads:Cell 1:70) and 2t2 (25 nM) or (2) anti-CD3/anti-CD28 beads (Beads:Cell 1:70) and IL2 (50 IU/mL), and cultured for 5 days. The cell-free liquid culture medium was collected and analyzed by LEGEND-plex multi-analyte flow assay kit (Biolegend) according to the manufacturer's instructions. FIG. 5 shows IL-10 in the cell-free liquid culture medium from a suppression assay where IL-10 secretion was significantly higher in 2t2-expanded $T_{reg}$ cells compared to IL-2 expanded $T_{reg}$ cells, both in the presences or absence of rapamycin.

Example 8. Generation and Characterization of 3t15*-28s Fusion Protein Complex

Construction and production of 3115*-28s

Figure 6A:
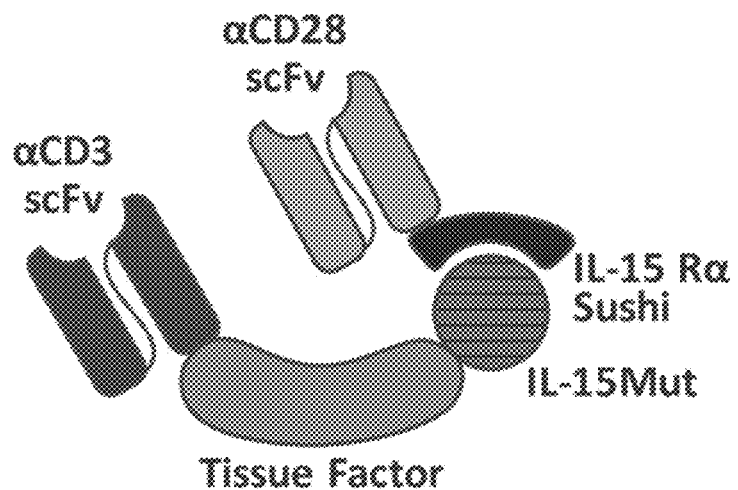
FIGS. 6A-6B show exemplary diagrams for a fusion protein generated including anti-CD3scFv/TF/IL15D8N mutant (3t15*) and anti-CD28scFv/IL15RαSu (28s) fusion proteins.
Figure 6B:
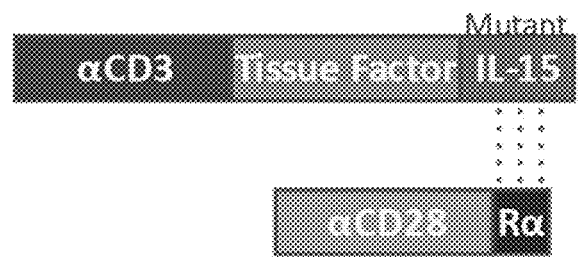

A fusion protein was generated comprising anti-CD3scFv/TF/IL15D8N mutant and anti-CD28scFv/IL15RαSu fusion proteins. The anti-CD3 antibody (αCD3) variable regions, human tissue factor, IL15D8N mutant, anti-CD28 antibody (αCD28) variable regions, and IL15RαSu sequences were obtained from the UniProt website and DNA for these sequences was synthesized by Genewiz. Specifically, the construct was made linking αCD3 light chain variable region sequence by a (G4S) 3 linker to αCD3 heavy chain variable region sequence to form an αCD3scFv. The αCD3scFv was linked to the N-terminus coding region of tissue factor 219 followed by a linkage to the N-terminus coding region of IL15D8N mutant (FIGS. 6A-6B). The nucleic acid and protein sequences of a construct are shown below.

The nucleic acid sequence of the αCD3scFv/TF/IL15D8N construct (including signal peptide sequence) is as follows (SEQ ID NO: 105):

(Signal peptide)
ATGAAGTGGGTGACCTTCATCAGCTTATTATTTTTATTCAGCTCCGCCT

ATTCC (αCD3 light chain variable region)
CAGATCGTGCTGACCCAAAGCCCCGCCATCATGAGCGCTAGCCCCGGTGA

GAAGGTGACCATGACATGCTCCGCTTCCAGCTCCGTGTCCTACATGAACT

GGTATCAGCAGAAAAGCGGAACCAGCCCCAAAAGGTGGATCTACGACACC

AGCAAGCTGGCCTCCGGAGTGCCCGCTCATTTCCGGGGCTCTGGATCCGG

CACCGCTACTCTTTAACCATTTCCGGCATGGAAGCTGAAGACGCTGCCA

CCTACTATTGCCAGCAATGGAGCAGCAACCCCTTCACATTCGGATCTGGC

ACCAAGCTCGAAATCAATCGT (Linker)
GGAGGAGGTGGCAGCGGCGGCGGTGGATCCGGCGGAGGAGGAAGC (αCD3 heavy chain variable region)
CAAGTTCAACTCCAGCAGAGCGGCGCTGAACTGGCCCGGCCCGGCGCCTC

CGTCAAGATGAGCTGCAAGGCTTCCGGCTATACATTTACTCGTTACACAA

TGCATTGGGTCAAGCAGAGGCCCGGTCAAGGTTTAGAGTGGATCGGATAT

ATCAACCCTTCCCGGGGCTACACCAACTATAACCAAAAGTTCAAGGATAA

AGCCACTTTAACCACTGACAAGAGCTCCTCCACCGCCTACATGCAGCTGT

CCTCTTTAACCAGCGAGGACTCCGCTGTTTACTACTGCGCTAGGTATTAC

GACGACCACTACTGTTTAGACTATTGGGACAAGGTACCACTTTAACCGT

CAGCAGC (Human tissue factor 219 form)
TCCGGCACCACCAATACCGTGGCCGCTTATAACCTCACATGGAAGAGCAC

CAACTTCAAGACAATTCTGGAATGGGAACCCAAGCCCGTCAATCAAGTTT

ACACCGTGCAGATCTCCACCAAATCCGGAGACTGGAAGAGCAAGTGCTTC

TACACAACAGACACCGAGTGTGATTTAACCGACGAAATCGTCAAGGACGT

CAAGCAAACCTATCTGGCTCGGGTCTTTTCCTACCCCGCTGGCAATGTCG

AGTCCACCGGCTCCGCTGGCGAGCCTCTCTACGAGAATTCCCCCCGAATTC

-continued

```
ACCCCTTATTTAGAGACCAATTTAGGCCAGCCTACCATCCAGAGCTTCGA

GCAAGTTGGCACCAAGGTGAACGTCACCGTCGAGGATGAAAGGACTTTAG

TGCGGCGGAATAACACATTTTTATCCCTCCGGGATGTGTTCGGCAAAGAC

CTCATCTACACACTGTACTATTGGAAGTCCAGCTCCTCCGGCAAAAAGAC

CGCTAAGACCAACACCAACGAGTTTTTAATTGACGTGGACAAAGGCGAGA

ACTACTGCTTCAGCGTGCAAGCCGTGATCCCTTCTCGTACCGTCAACCGG

AAGAGCACAGATTCCCCCGTTGAGTGCATGGGCCAAGAAAAGGGCGAGTT

CCGGGAG (Human IL15D8N mutant)
AACTGGGTGAACGTCATCAGCAATTTAAAGAAGATCGAAGATTTAATTCA

GTCCATGCATATCGACGCCACTTTATACACAGAATCCGACGTGCACCCCT

CTTGTAAGGTGACCGCCATGAAATGTTTTTTACTGGAGCTGCAAGTTATC

TCTTTAGAGAGCGGAGACGCTAGCATCCACGACACCGTGGAGAATTTAAT

CATTTTAGCCAATAACTCTTTATCCAGCAACGGCAACGTGACAGAGTCCG

GCTGCAAGGAGTGCGAAGAGCTGGAGGAGAAGAACATCAAGGAGTTTCTG

CAATCCTTTGTGCACATTGTCCAGATGTTCATCAATACCTCC
```

The amino acid sequence of the αCD3scFv/TF/IL15D8N construct (including signal peptide sequence) is as follows (SEQ ID NO: 104):

```
(Signal peptide)
MKWVTFISLLFLFSSAYS (αCD3 light chain variable region)
QIVLTQSPAIMSASPGEKVTMTCSASSSVSYMNWYQQKSGTSPKRWIYDT

SKLASGVPAHFRGSGSGTSYSLTISGMEAEDAATYYCQQWSSNPFTFGSG

TKLEINR (Linker)
GGGGSGGGGSGGGGS (αCD3 heavy chain variable region)
QVQLQQSGAELARPGASVKMSCKASGYTFTRYTMHWVKQRPGQGLEWIGY

INPSRGYTNYNQKFKDKATLTTDKSSSTAYMQLSSLTSEDSAVYYCARYY

DDHYCLDYWGQGTTLTVSS (Human tissue factor 219)
SGTTNTVAAYNLTWKSTNFKTILEWEPKPVNQVYTVQISTKSGDWKSKCF

YTTDTECDLTDEIVKDVKQTYLARVFSYPAGNVESTGSAGEPLYENSPEF

TPYLETNLGQPTIQSFEQVGTKVNVTVEDERTLVRRNNTFLSLRDVFGKD

LIYTLYYWKSSSSGKKTAKTNTNEFLIDVDKGENYCFSVQAVIPSRTVNR

KSTDSPVECMGQEKGEFRE (Human IL15D8N mutant)
NWVNVISNLKKIEDLIQSMHIDATLYTESDVHPSCKVTAMKCFLLELQVI

SLESGDASIHDTVENLIILANNSLSSNGNVTESGCKECEELEEKNIKEFL

QSFVHIVQMFINTS
```

Another construct was made by linking αCD28scFv which was constructed by linking αCD28 light chain variable region sequence by a (G4S) 3 linker to αCD28 heavy chain variable region sequence, to the N-terminus coding region of IL15RαSu. The final construct αCD28scFv/ IL15RαSu fusion protein sequence was synthesized by Genewiz. The nucleic acid and protein sequences of a construct are shown below.

The nucleic acid sequence of the αCD28scFv/IL15RαSu construct (including signal peptide sequence) is as follows (SEQ ID NO: 109):

```
(Signal peptide)
ATGAAATGGGTCACCTTCATCTCTTTACTGTTTTTATTTAGCAGCGCCT

ACAGC (αCD28 light chain variable region)
GTGCAGCTGCAGCAGTCCGGACCCGAACTGGTCAAGCCCGGTGCCTCCGT

GAAAATGTCTTGTAAGGCTTCTGGCTACACCTTTACCTCCTACGTCATCC

AATGGGTGAAGCAGAAGCCCGGTCAAGGTCTCGAGTGGATCGGCAGCATC

AATCCCTACAACGATTACACCAAGTATAACGAAAAGTTTAAGGGCAAGGC

CACTCTGACAAGCGACAAGAGCTCCATTACCGCCTACATGGAGTTTTCCT

CTTTAACTTCTGAGGACTCCGCTTTATACTATTGCGCTCGTTGGGGCGAT

GGCAATTATTGGGGCCGGGGAACTACTTTAACAGTGAGCTCC (Linker)
GGCGGCGGCGGAAGCGGAGGTGGAGGATCTGGCGGTGGAGGCAGC (αCD28 heavy chain variable region)
GACATCGAGATGACACAGTCCCCCGCTATCATGAGCGCCTCTTTAGGAGA

ACGTGTGACCATGACTTGTACAGCTTCCTCCAGCGTGAGCAGCTCCTATT

TCCACTGGTACCAGCAGAAACCCGGCTCCTCCCCTAAACTGTGTATCTAC

TCCACAAGCAATTTAGCTAGCGGCGTGCCTCCTCGTTTTAGCGGCTCCGG

CAGCACCTCTTACTCTTTAACCATTAGCTCTATGGAGGCCGAAGATGCCG

CCACATACTTTTGCCATCAGTACCACCGGTCCCCTACCTTTGGCGGAGGC

ACAAAGCTGGAGACCAAGCGG (Human IL15RαSu)
ATTACATGCCCCCCTCCCATGAGCGTGGAGCACGCCGACATCTGGGTGAA

GAGCTATAGCCTCTACAGCCGGGAGAGGTATATCTGTAACAGCGGCTTCA

AGAGGAAGGCCGGCACCAGCAGCCTCACCGAGTGCGTGCTGAATAAGGCT

ACCAACGTGGCTCACTGGACAACACCCTCTTTAAAGTGCATCCGG
```

The amino acid sequence of the αCD28scFv/IL15RαSu construct (including signal peptide sequence) is as follows (SEQ ID NO: 108):

```
(Signal peptide)
MKWVTFISLLFLFSSAYS (αCD28 light chain variable region)
VQLQQSGPELVKPGASVKMSCKASGYTFTSYVIQWVKQKPGQGLEWIGS

INPYNDYTKYNEKFKGKATLTSDKSSITAYMEFSSLTSEDSALYYCARWG

DGNYWGRGTTLTVSS (Linker)
GGGGSGGGGSGGGGS (αCD28 heavy chain variable region)
DIEMTQSPAIMSASLGERVTMTCTASSSVSSSYFHWYQQKPGSSPKLCIY

STSNLASGVPPRFSGSGSTSYSLTISSMEAEDAATYFCHQYHRSPTFGGG

TKLETKR
```

-continued (Human IL-15R α sushi domain)
ITCPPPMSVEHADIWVKSYSLYSRERYICNSGFKRKAGTSSLTECVLNKA

TNVAHWTTPSLKCIR

In some cases, the leader peptide is cleaved from the intact polypeptide to generate the mature form that may be soluble or secreted.

The αCD3scFv/TF/IL15D8N and αCD28scFv/IL15RαSu constructs were cloned into a modified retrovirus expression vectors with different antibiotics selection markers as described previously (Hughes et al., *Hum Gene Ther* 16:457-72, 2005), and the expression vectors were co-transfected into CHO-K1 cells. Expression of the construct in CHO-K1 cells allowed for secretion of the soluble αCD3scFv/TF/IL15D8N:αCD28scFv/IL15RαSu fusion protein (referred to as 3t15*-28s), which can be purified by anti-TF antibody affinity chromatography and other chromatographic methods.

Purification of 3115*-28s by immunoaffinity chromatography

The anti-TF antibody affinity column was connected to a GE Healthcare AKTA Avant system. The flow rate was 4 mL/min for all steps except the elution step, which was 2 mL/min.

Figure 7:
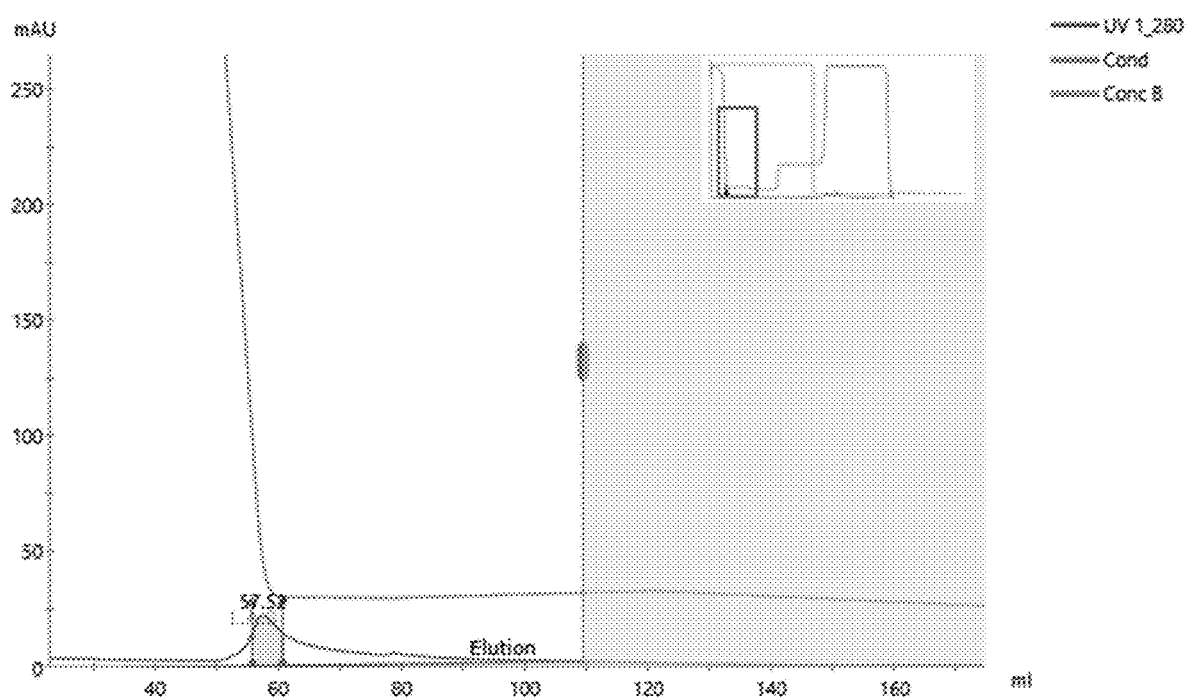
FIG. 7 is a graph showing 3t15*-28s purification elution by immunoaffinity chromatography from an anti-TF antibody affinity column.

Cell culture harvest of 3t15*-28s was adjusted to pH 7.4 with 1M Tris base and loaded onto the anti-TF antibody affinity column (described above) which was equilibrated with 5 column volumes of PBS. After sample loading, the column was washed with washed with 5 column volumes PBS, followed by elution with 6 column volumes 0.1M Acetic Acid, pH 2.9. A280 elution peak was collected and then neutralized to pH 7.5-8.0 by adding 1M Tris base. The neutralized sample was then buffer exchanged into PBS using Amicon centrifugal filters with a 30 KDa molecular weight cutoff. As shown in FIG. 7, it is clear that the anti-TF antibody affinity column can bind 3t15*-28s which contains TF as a fusion partner of 3t15*-28s. The buffer-exchanged protein sample is stored at 2-8° C. for further biochemical analysis and biological activity test.

After each elution, the anti-TF antibody affinity column was then stripped using 6 column volumes 0.1M Glycine, pH 2.5. The column was then neutralized using 10 column volumes PBS, 0.05% NaN₃ and stored at 2-8° C.

Analytical Size Exclusion Chromatography (SEC) Analysis of 3t15*-28s

Figure 8:
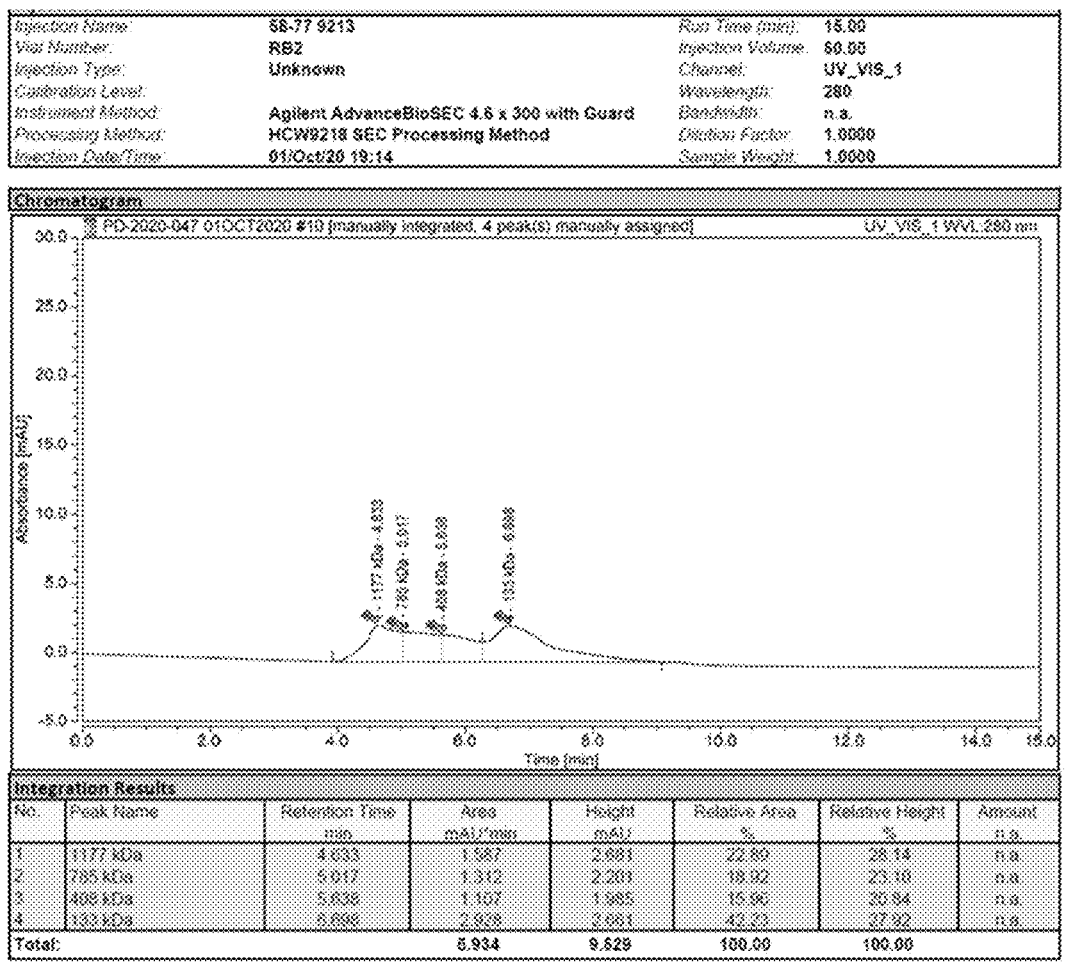
FIG. 8 shows size exclusion chromatography analysis of 3t15*-28s.

A Superdex 200 Increase 10/300 GL gel filtration column (from GE Healthcare) was connected to an AKTA Avant system (from GE Healthcare). The column was equilibrated with 2 column volumes of PBS. The flow rate was 0.8 mL/min. A 200 μL sample of 3t15*-28s (1 mg/mL) was injected onto the column using a capillary loop. The injection was then chased with 1.25 column volumes of PBS. The SEC chromatograph was shown in FIG. 8. The result indicated that there are 4 protein peaks, likely representing a monomer and dimer or other different forms of 3t15*-28s.

SDS PAGE Analysis of 3t15*-28s

Figure 9:
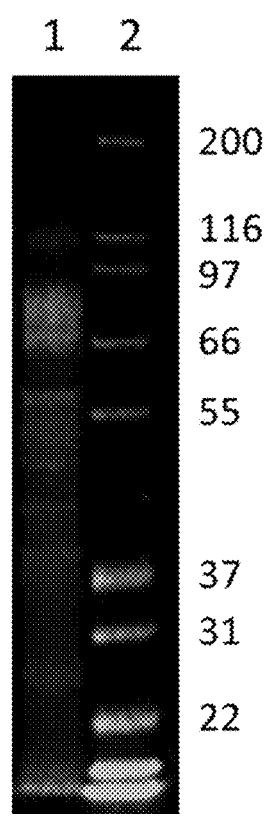
FIG. 9 shows an SDS gel of 3t15*-28s purified from anti-TF antibody affinity chromatography. Lane 1: 3t15*-28s; Lane 2: SeeBlue Plus 2 prestained standards (numbers on the left side indicate molecular weights in kilodaltons).
Figure 10A:
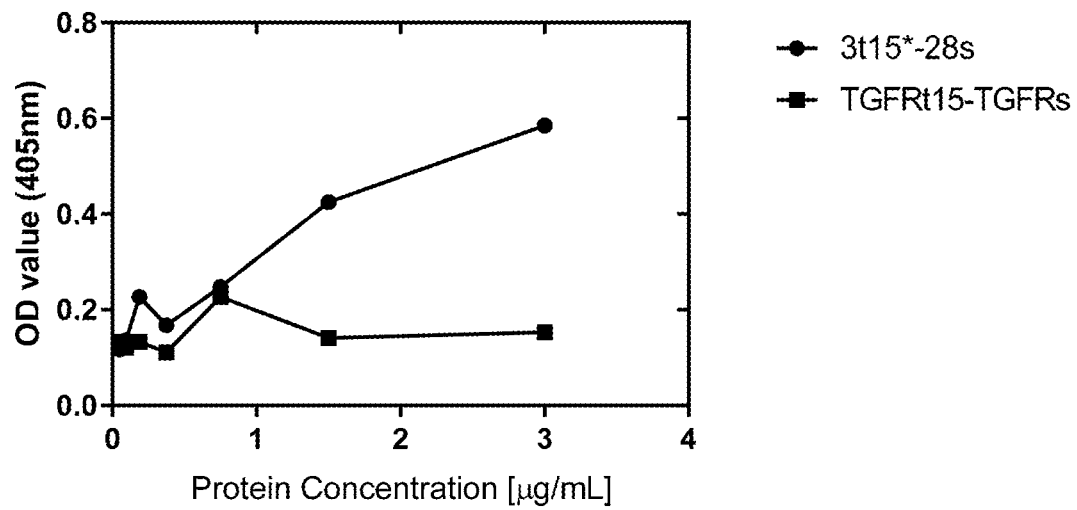
FIG. 10A is a graph showing interaction between 3t15*-28s and CD28.
Figure 10B:
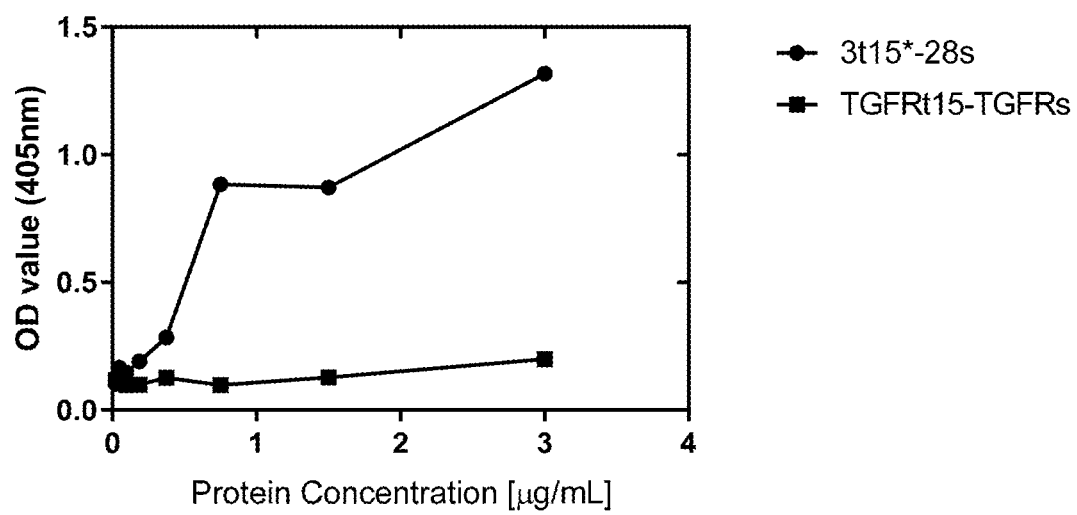
FIG. 10B is a graph showing interaction between 3t15*-28s and CD3.

To determine the purity and protein molecular weight, the purified 3t15*-28s protein sample from anti-TF antibody affinity chromatography was analyzed by standard sodium dodecyl sulfate polyacrylamide gel (4-12% NuPage Bis-Tris gel) electrophoresis (SDS-PAGE) method under reduced conditions. The gel was stained with InstantBlue for about 30 min, followed by destaining overnight with purified water. FIG. 9 shows the SDS gel of 3t15*-28s purified from anti-TF antibody affinity chromatography. The results indicated that purified 3t15*-28s contains protein bands with expected molecular weight (72 kDa) in reduced SDS PAGE.

In Vitro Characterization of the Activities of 3115*-28s Fusion Protein Complex

ELISA-based methods confirmed the formation of the 3t15*-28s fusion protein complex. To assess whether 3t15*-28s interacts with CD28 and CD3 (FIGS. 10A-10B), 10 μg/mL of human CD28-Fc (Cat #CD8-H525a, Acro Biosystems) or 10 μg/mL of human CD3E/CD3D heterodimer-Llama Fc/Llama Fc (Cat #CDD-H5258, Acro Biosystems) in 50 mM carbonate buffer pH 9.4 (100 μl/well) was applied to an ELISA plate (Cat #80040LE 0910, ThermoFisher) and incubated overnight at 4° C. Next day, the plate was washed 3 times with ELISA washing buffer (phosphate-buffered saline with 0.05% Tween 20) and blocked with the blocking buffer (1% BSA-PBS) for 1 hour. Descending concentrations (3 to 0.00243 μg/mL in blocking buffer) of 3t15*-28s or a negative control fusion protein (HCW9218 which contains the same TF domain) were added to the plate and the plate was incubated for 1 hour at 25° C. The plate was washed for 3 times with ELISA washing buffer. A detection antibody, biotinylated anti-TF antibody (Cat #BAF2339, R&D Systems) at 0.1 μg/mL was added to the plate and incubated at 25° C. for 1 hour. The plate was washed and Horseradish peroxidase-streptavidin (code #016-030-084, Jackson ImmunoResearch) at 0.25 μg/mL was added to the plate and incubated at 25° C. for 30 minutes. The plate was washed and a substrate of HRP, ABTS (Cat #ABTS-1000-01, Surmodics) was added to the plate and incubated for 20 minutes at 25° C. The plate was read with a microplate reader (Multiscan Sky, Thermo Scientific) at OD405 nm. As shown in FIGS. 10A-10B, 3t15*-28s interacted with CD28 and CD3 while the control fusion protein HCW9218 did not. The αCD3scFv and αCD28scFv domains of 3t15*-28s fusion protein complex were capable of binding CD3 and CD28. Binding of the αCD28scFv and TF domains to CD28 and anti-TF antibody, respectively (FIG. 10A), confirmed the purified protein was comprised of the 3t15*-28s heterodimeric complex.

Example 9. Expansion of Foxp3⁺ Regulatory T Cells Using 2t2 and 3t15*-28s

Figure 11:
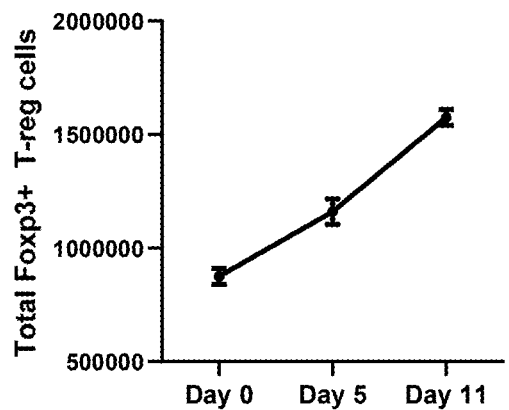
FIG. 11 is a graph showing the expansion of Foxp3$^+$ regulatory T cells in media containing 2t2 and 3t15*-28s.

Fresh human leukocytes (3 donors) were obtained from the blood bank and CD4⁺CD25⁺CD127$^{low}$ T regulatory cells were isolated with the EasySep Human CD4⁺CD25⁺CD127$^{low}$ regulatory T cells isolation kit (StemCell Technology). The purity of Foxp3+ regulatory T cells was >35% and confirmed by staining with CD4-Alexa Fluro 488, CD25-PE, CD3 APC-Cy7 and Foxp3-PacBlue antibodies (Abs) (BioLegend). Cells were counted and resuspended in 1×10⁶/mL in 24 well flat bottom plates in complete media (RPMI 1640 (Gibco) supplemented with 2 mM L-glutamine (Thermo Life Technologies), penicillin (Thermo Life Technologies), streptomycin (Thermo Life Technologies), and 10% FBS (Hyclone). Cells were stimulated with 2t2 (100 nM) and 3t15*-28s (200 nM) and incubated for 11 days at 37° C., 5% CO₂. During the expansion period, cells were maintained for 11 days at 1×10⁶/mL concentration with fresh complete media containing 2t2 (100 nM) and 3t28 (200 nM) every alternate day. Cells were then stained with CD4-Alexa Fluro 488, CD25-PE, CD3 APC-Cy7 and Foxp3-PacBlue Abs (BioLegend) to assess the expansion of Foxp3⁺ regulatory T cells by flow cytometry. Fold expansion of Foxp3⁺ regulatory T cells was measured by counting using trypan blue (0.4%, Invitrogen) exclusion. FIG. 11 shows 2.5-fold increase in Foxp3+ regulatory T cells at 11 days.

Example 10. Expansion of Human Immune Cells Using 2t2 and 3t15*-28s Plus Anti-Tissue Factor Antibody Fresh human leukocytes (2 donors) were obtained from the blood bank and PBMC (peripheral blood mononuclear cells) were isolated with Ficoll separation. Cells were counted and resuspended at a density of $1 \times 10^7$ cells/mL in PBS. 2 μM of final concentration of Cell-Trace Violet Dye (Life Technologies) was added in the cells and incubated for 20 minutes in 37° C. under an atmosphere of 5% $CO_2$. Cells were resuspended at 10 times volume in fresh pre-warmed RPMI 1640 medium (Gibco) supplemented with 2 mM L-glutamine (Thermo Life Technologies), antibiotics (penicillin, 10,000 units/mL; streptomycin, 10,000 μg/mL; Thermo Life Technologies), and 10% FBS (Hyclone) for 5 minutes at room temperature. Cells were washed 2 times at 1200 rpm for 10 minutes at counted and resuspended at a density of $2 \times 10^6$ cells/mL in RPMI 1640 medium (Gibco) supplemented with 2 mM L-glutamine (Thermo Life Technologies), antibiotics (penicillin, 10,000 units/mL; streptomycin, 10,000 μg/mL; Thermo Life Technologies), and 10% FBS (Hyclone). Cells (0.1 mL) were transferred in a 96 well flat bottom plate and incubated with 2t2 (100 nM) and 3t15*-28s (0.01-1000 nM) with or without the anti-tissue factor antibody (αTF Ab, 0.01-100 nM). Complex of 3t15*-28s and anti-tissue factor antibody was made in 2:1 ratio, 15 minutes prior to stimulation. Half of the media was removed and replaced with fresh 2t2 (100 nM) and 3t15*-28s with or without anti-tissue factor antibody every 48 to 72 hrs. Cells were stained with CD4-Alexa Fluro 488, CD3-PE, CD8-PerCP Cy5.5 Abs (BioLegend) to assess dilution of Cell Trace Violet by flow cytometry.

Figure 12:
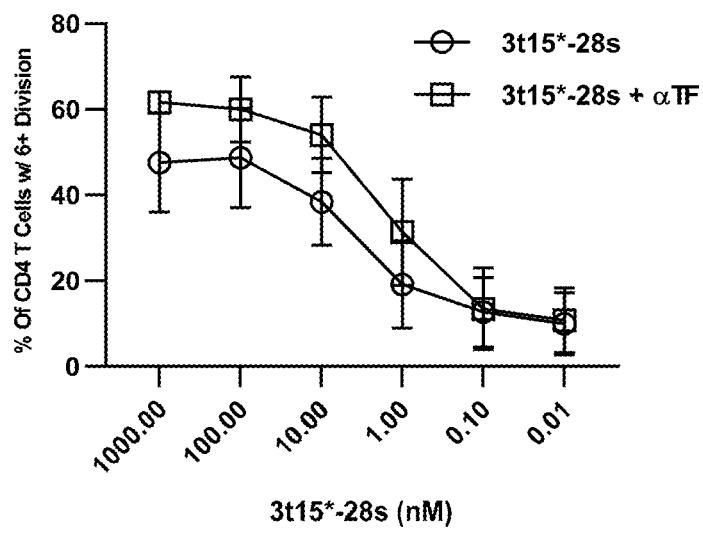
FIG. 12 is a graph showing the level of proliferating human immune cells following incubation in media containing 2t2 and 3t15*-28s with or without anti-TF antibody.

FIG. 12 shows the percent of CD4+ T cells undergoing six or more cell division under different culture conditions. Incubation with 3t15*-28s:αTF Ab complex plus 2t2 was capable of supporting cell proliferation at a lower 3t15*-28s concentration than was observed with 3t15*-28s plus 2t2 (without αTF Ab). This result suggests that immune cells derived from PBMC could be optimally stimulated to proliferate using a complex of anti-tissue factor antibody and 3t28.

Figure 13A:
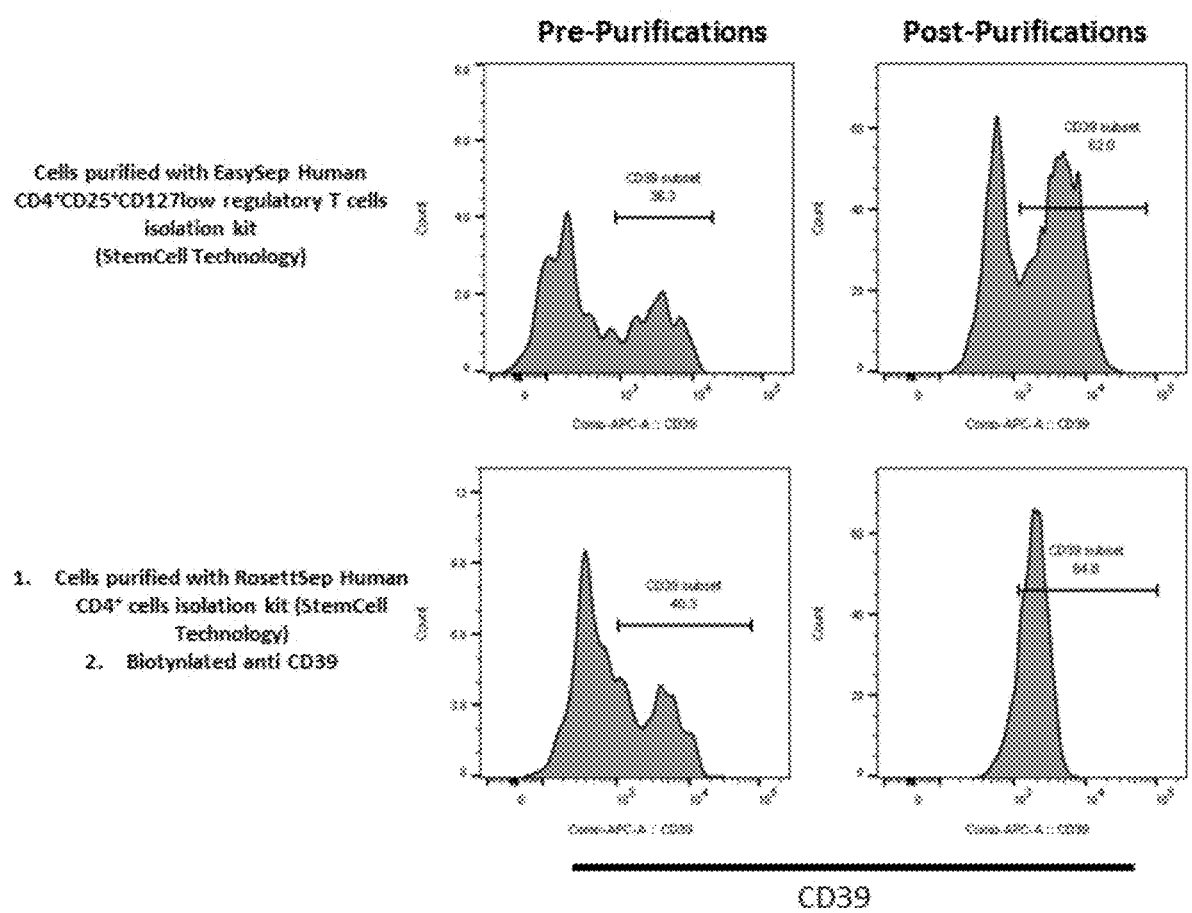
FIG. 13A shows flow cytometry histograms indicating the purity of CD39$^+$ regulatory T cells isolated with different purification schemes.

Example 11. Purification of CD39+Foxp3+ Regulatory T Cells Using an Anti-CD39 IgG1$_k$ Reagent Fresh human leukocytes were obtained from the blood bank. Half of the leukocytes were used to purify CD4+ CD25+CD127$^{low}$ T regulatory cells with the EasySep Human CD4+CD25+CD127$^{low}$ regulatory T cells isolation kit (StemCell Technology). The purity of Foxp3+ regulatory T cells was >60% and confirmed by staining with CD4-Alexa Fluro 488, CD39-APC, CD3 PE, Foxp3-PacBlue (BioLegend). The other half of the leukocytes were used to purify CD39+ Foxp3+ regulatory T cells by two step process. First CD4+ T cells were isolated with the RosetteSep Human CD4+ cells isolation kit (StemCell Technology). After enriching CD4+ T cells, CD39+CD4+ cells were isolated using a novel biotinylated anti CD39 antibody reagent (HCW Biologic) and magnetic particles per manufacturer's instructions (EasySep Human Biotin Positive Selection Kit, StemCell Technology). Cells were stained with CD4-Alexa Fluro 488, CD39-APC, CD3 PE, Foxp3-PacBlue Abs (BioLegend) to assess the purity of CD39+ Foxp3+ regulatory T cells by flow cytometry (Cells were gated on CD3+CD4+ Foxp3+). Post-purification purity analysis by flow cytometer showed that cell purified using biotinylated anti CD39 Ab were 84.8% CD39+ compared to 62% for cells isolated with the EasySep Human CD4+CD25+CD127$^{low}$ regulatory T cells isolation kit (StemCell Technology). This data demonstrates a novel strategy to isolated highly pure and phenotypical active regulatory T cells (FIG. 13A). These cells can be expanded in media containing hIL-2, anti-CD3/anti-CD28 beads, rapamycin, 2t2, 3t15*, and or 3t15*-28s: αTF Ab complex by the methods described above.

Figure 13B:
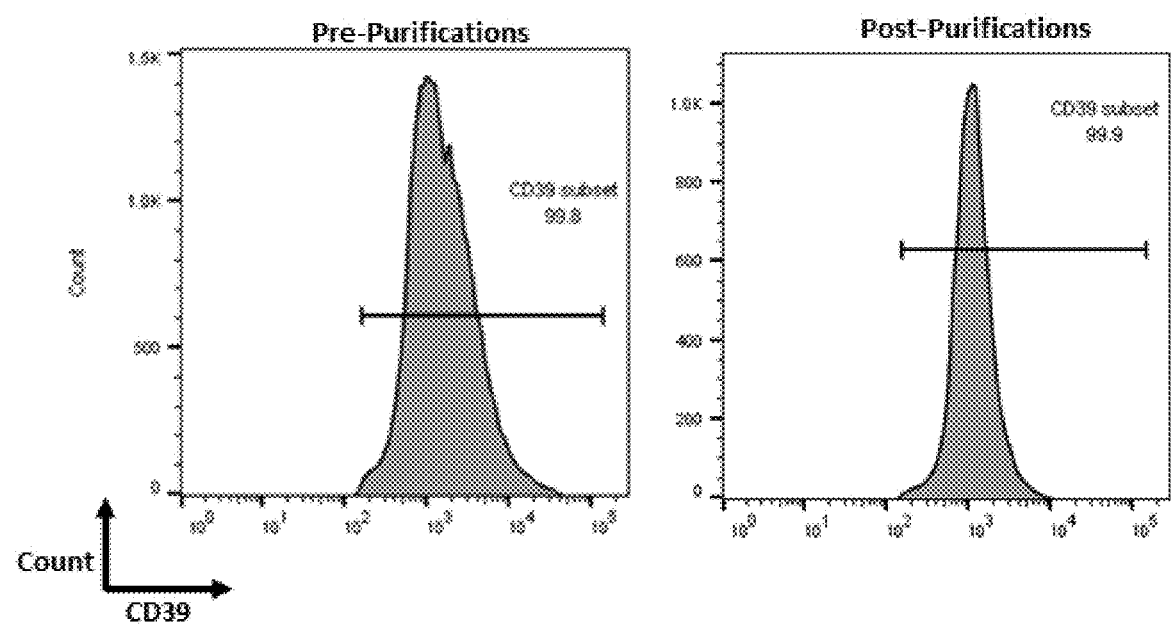
FIG. 13B shows a flow cytometry histogram indicating the purity of CD39$^+$ regulatory T cells isolated using an anti-CD39 Ab reagent.

In a second study, Foxp3+ regulatory T cells were first expanded with 2t2 from purified CD4+CD25+CD127$^{low}$ T regulatory cells, and then frozen. The cells were thawed and maintained at $2 \times 10^6$/mL in T25 flask with 2t2 (100 nM) in complete media (RPMI 1640 (Gibco) supplemented with 2 mM L-glutamine (Thermo Life Technologies), penicillin (Thermo Life Technologies), streptomycin (Thermo Life Technologies), and 10% FBS (Hyclone). CD39+CD4+ cells were isolated using a novel biotinylated anti CD39 Ab reagent (HCW Biologic) and magnetic particles per manufacturer's instructions (EasySep Human Biotin Positive Selection Kit, StemCell Technology). Cells were stained with CD4-Alexa Fluro 488, CD39-APC, CD3 PE, Foxp3-PacBlue Abs (BioLegend) to assess the purity of CD39+ Foxp3+ regulatory T cells by flow cytometry (Cells were gated on CD3+CD4+Foxp3+). Post-purification purity analysis by flow cytometer shows that cell purified using biotinylated anti CD39 antibody yielded a Foxp3+ regulatory T cells that are 99.9% enriched for the highly suppressive CD39+ subset (FIG. 13B). These cells can be expanded in media containing hIL-2, anti-CD3/anti-CD28 beads, rapamycin, 2t2, 3t15*, and or 3t15*-28s:αTF Ab complex by the methods described above.

Figure 14:
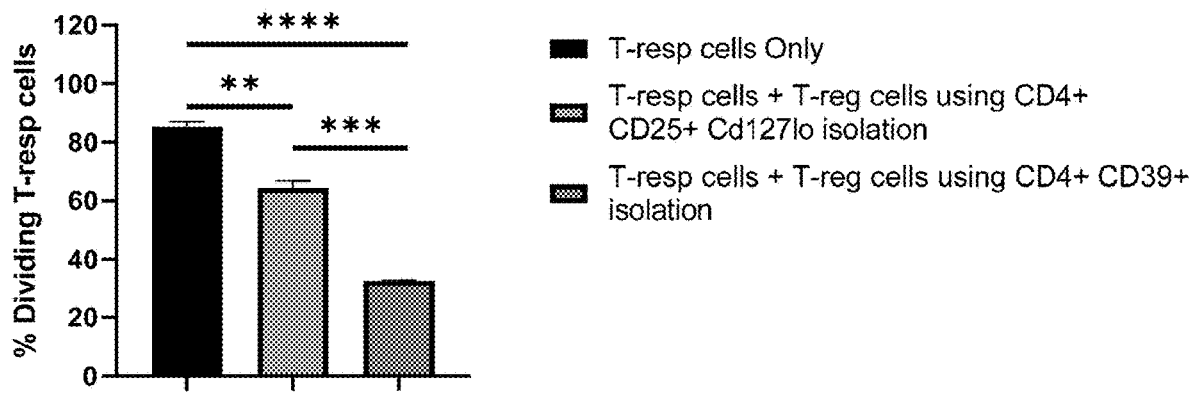
FIG. 14 shows a bar graph depicting the level of T responder cell proliferation following incubation with regulatory T cells isolated with different methods.

Example 12. Suppression of Autologous T Responder Cells by Purified CD39+ Regulatory T Cells Fresh human leukocytes were obtained from the blood bank. Half of the leukocytes were used to purify CD4+ CD25+CD127$^{low}$ T regulatory cells with the Easy Sep Human CD4+CD25+CD127$^{low}$ regulatory T cells isolation kit (StemCell Technology). The purity of Foxp3+ regulatory T cells was >60% and confirmed by staining with CD4-Alexa Fluro 488, CD39-APC, CD3 PE, Foxp3-PacBlue (BioLegend). The other half of the leukocytes were used to purify CD39+ Foxp3+ regulatory T cells by two step process. First CD4+ T cells were isolated with the RosetteSep Human CD4+ cells isolation kit (StemCell Technology). After enriching CD4+ T cells, CD39+ CD4+ cells were isolated using a novel biotinylated anti CD39 antibody reagent (HCW Biologics) and magnetic particles per manufacturer's instructions (EasySep Human Biotin Positive Selection Kit, StemCell Technology). Cells were stained with CD4-Alexa Fluro 488, CD39-APC, CD3 PE, Foxp3-PacBlue Abs (BioLegend) to assess the purity of CD39+ Foxp3+ regulatory T cells by flow cytometry (Cells gated on CD3+CD4+ Foxp3+). Autologous T responder (Tresp) cells were labelled with Cell Trace Violet (Invitrogen). The purified Foxp3+ T cells were cultured with T responder cells (1:1 regulatory T cells: T responder cells). Cells were re-stimulated with 2t2 (10 nM) and cultured for 5 days. Cells were harvested, washed (1500 RPM for 5 minutes at room temperature) in FACS buffer (1×PBS (Hyclone) with 0.5% BSA (EMD Millipore) and 0.001% Sodium Azide (Sigma)). After two washes, cells were analyzed by flow cytometry (Celesta-BD Bioscience) and % of dividing Tresp cells were determined based on Cell Trace Violet dilution. FIG. 14 shows that purified CD39$^+$Foxp3$^+$ regulatory T cells were more effective at suppressing T responder cell proliferation when compared to cells isolated based on CD4$^+$CD25$^+$CD127$^{low}$ T regulatory cells.

Example 13. Suppression of THP-1 Monocyte Cells by Expanded and CD39$^+$-Purified T Regulatory Cells Fresh human leukocytes were obtained from the blood bank. CD4$^+$CD25$^+$CD127$^{low}$ T regulatory cells with the EasySep Human CD4+CD25+CD127low regulatory T cells isolation kit (StemCell Technology). The purity of Foxp3$^+$ regulatory T cells was >60% and confirmed by staining with CD4-Alexa Fluro 488, CD39-APC, CD3 PE, Foxp3-PacBlue (BioLegend). Cells were counted and resuspended in 1×10$^6$/mL in 24 wells flat bottom plate in complete media (RPMI 1640 (Gibco) supplemented with 2 mM L-glutamine (Thermo Life Technologies), penicillin (Thermo Life Technologies), streptomycin (Thermo Life Technologies), and 10% FBS (Hyclone). Cells were stimulated with 100 nM of 2t2 with CD3/CD28 beads (4:1,Beads: Cells) (Dynabeads, Life Technologies) and incubated for 21 days at 37°, 5% CO$_2$. During the expansion period, cells were re-stimulated with 100 nM of 2t2 with every alternate day and every 7 days cells were re-stimulated with CD3/CD28 beads (1:1, Beads: Cells) (Dynabeads, Life Technologies). Cells were maintained up to 21 days at 1×10$^6$/mL concentration with fresh complete media containing 100 nM of 2t2 every alternate day.

On day 21 cells were stained with CD4-Alexa Fluro 488, CD25-PE, CD3 APC-Cy7, Foxp3-PE (Intracellular staining using Foxp3 staining kit, Invitrogen), CD127-Alex Fluro 700 (BioLegend) to assess the expansion of Foxp3$^+$ regulatory T cells by flow cytometry and frozen at 20 ×10$^6$/mL. Previously expanded cells were thawed and maintained at 2×10$^6$/mL in T25 flask in complete media (RPMI 1640 (Gibco) supplemented with 2 mM L-glutamine (Thermo Life Technologies), penicillin (Thermo Life Technologies), streptomycin (Thermo Life Technologies), and 10% FBS (Hyclone) for an hour and washed before isolating CD39$^+$ CD4$^+$T reg cells. CD39 CD4+ cells were isolated using a novel biotinylated anti-CD39 Ab reagent (HCW Biologics; EasySep Human Biotin Positive Selection Kit, StemCell Technology). Cells were stained with CD4-Alexa Fluro 488, CD39-APC, CD3 PE, Foxp3-PacBlue Abs (BioLegend) to assess the purity of CD39$^+$ Foxp3$^+$ regulatory T cells by flow cytometry (cells were gated on CD3$^+$CD4$^+$Foxp3$^+$). Post-purification purity analysis by flow cytometer shows that cell purified using biotinylated anti CD39 antibody yielded a Foxp3$^+$ regulatory T cells that are 99.9% enriched for the highly suppressive CD39$^+$ subset. Suppression assay was setup with THP-1 (Human Monocyte Cells) and purified CD39$^+$ Foxp3$^+$ T Reg cells or CD39– Foxp3$^+$ T Reg cells or Total CD4$^+$ T Reg cells (1:1 ratio). Cells were cultured for 3 days in (RPMI 1640 (Gibco) supplemented with 2 mM L-glutamine (Thermo Life Technologies), penicillin (Thermo Life Technologies), streptomycin (Thermo Life Technologies), and 10% FBS (Hyclone) supplemented with 50 ng/mL LPS. Cells supernatant was collected on day 3 to analyze IL-10 by ELISA (R&D System).

Figure 15:
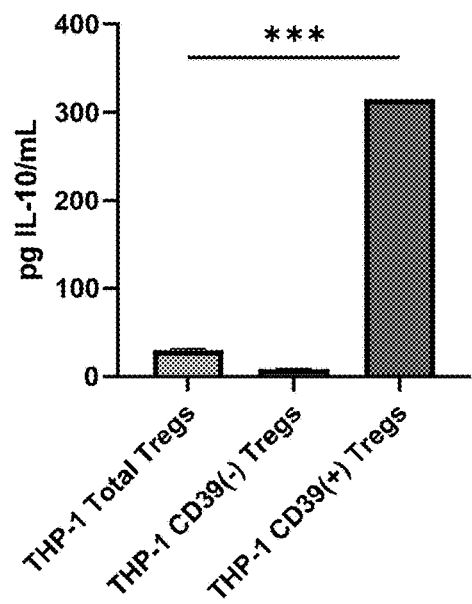
FIG. 15 shows a graph showing T responder cell proliferation (as assessed by levels of IL-10) following incubation with T regulatory cells isolated using different methods.

FIG. 15 shows that purified CD39$^+$Foxp3$^+$ regulatory T cells secret significantly more IL-10 compare to CD39– Foxp3$^+$ T Reg cells or Total CD4+ T Reg cells. This data shows that CD39$^+$ Foxp3$^+$ T Reg has more suppressive capacity compare to CD39– Foxp3$^+$ T Reg cells or Total CD4$^+$ T Reg cells.

OTHER EMBODIMENTS

It is to be understood that while the invention has been described in conjunction with the detailed description thereof, the foregoing description is intended to illustrate and not limit the scope of the invention, which is defined by the scope of the appended claims. Other aspects, advantages, and modifications are within the scope of the following claims.

---

What is claimed is:

1. A method of stimulating or increasing the proliferation of a $T_{reg}$ cell, wherein the method comprises:
 culturing a $T_{reg}$ cell in a liquid culture medium over a period of time, wherein the period of time is 7 days to 56 days and at the beginning of the period of time, the liquid culture medium comprises:
 a CD3/CD28-binding agent; and
 a single-chain chimeric polypeptide comprising a first target-binding domain, a soluble tissue factor domain, and a second target-binding domain, wherein:
  the first target-binding domain comprises a sequence that is at least 90% identical to SEQ ID NO: 1;
  the soluble tissue factor domain comprises a sequence that is at least 90% identical to SEQ ID NO: 2;
  the second target-binding domain comprises a sequence that is at least 90% identical to SEQ ID NO: 1; and
  the single-chain chimeric polypeptide does not stimulate blood coagulation in a mammal; and
 wherein the CD3/CD28-binding agent is:
 (1) an additional single-chain chimeric polypeptide comprising a sequence that is at least 90% identical to SEQ ID NO: 7; or
 (2) a multi-chain chimeric polypeptide comprising:
 (a) a first chimeric polypeptide comprising:
  (i) a first target-binding domain;
  (ii) a soluble tissue factor domain comprising a sequence that is at least 90% identical to SEQ ID NO: 2; and
  (iii) a first domain of a pair of affinity domains comprising a sequence that is at least 90% identical to SEQ ID NO: 96; and
 (b) a second chimeric polypeptide comprising:
  (i) a second domain of a pair of affinity domains comprising a sequence that is at least 90% identical to SEQ ID NO: 94; and
  (ii) a second target-binding domain,
 wherein:
 the first chimeric polypeptide and the second chimeric polypeptide associate through the binding of the first domain and the second domain of the pair of affinity domains;
 the first target-binding domain of the first chimeric polypeptide comprises a sequence that is at least 90% identical to SEQ ID NO: 5 and the second target-binding domain of the second chimeric polypeptide comprises a sequence that is at least 90% identical to SEQ ID NO: 6, or the first target-binding domain of the first chimeric polypeptide comprises a sequence that is at least 90% identical to SEQ ID NO: 6 and the second target-binding domain of the second chimeric polypeptide comprises a sequence that is at least 90% identical to SEQ ID NO: 5; and the multi-chain chimeric polypeptide would not stimulate blood coagulation if administered to a mammal.

2. The method of claim 1, wherein the liquid culture medium further includes an IgG1 antibody construct that comprises at least one antigen-binding domain that binds specifically to the soluble tissue factor domain of the single-chain chimeric polypeptide.

3. The method of claim 1, wherein the CD3/CD28 binding agent is the multi-chain chimeric polypeptide.

4. The method of claim 1, wherein the method further comprises, before the culturing step, a step of isolating the $T_{reg}$ cell from a sample obtained from a subject.

5. The method of claim 1, wherein the method further comprises, after the culturing step, a step of isolating the $T_{reg}$ cell from the liquid culture medium.

6. The method of claim 1, wherein the $T_{reg}$ cells comprises a chimeric antigen receptor.

7. The method of claim 1, wherein:
the first target-binding domain of the single-chain chimeric polypeptide comprises SEQ ID NO: 1;
the soluble tissue factor domain of the single-chain chimeric polypeptide comprises SEQ ID NO: 2; and
the second target-binding domain of the single-chain chimeric polypeptide comprises SEQ ID NO: 1.

8. The method of claim 1, wherein the single-chain chimeric polypeptide comprises a sequence at least 90% identical to SEQ ID NO: 3.

9. The method of claim 1, wherein the single-chain chimeric polypeptide comprises SEQ ID NO: 3.

10. The method of claim 1, wherein the CD3/CD28-binding agent is the additional single-chain chimeric polypeptide.

11. The method of claim 3, wherein:
the first target-binding domain of the first chimeric polypeptide comprises SEQ ID NO: 5;
the soluble tissue factor domain of the first chimeric polypeptide comprises SEQ ID NO: 2;
the first domain of the pair of affinity domains comprises SEQ ID NO: 96;
the second domain of the pair of affinity domains comprises SEQ ID NO: 94; and
the second target-binding domain of the second chimeric polypeptide comprises SEQ ID NO: 6.

12. The method of claim 3, wherein:
the first chimeric polypeptide comprises a sequence at least 90% identical to SEQ ID NO: 102; and
the second chimeric polypeptide comprises a sequence at least 90% identical to SEQ ID NO: 106.

13. The method of claim 10, wherein the additional single-chain chimeric polypeptide comprises SEQ ID NO: 7.

14. The method of claim 12, wherein:
the first chimeric polypeptide comprises SEQ ID NO: 102; and
the second chimeric polypeptide comprises SEQ ID NO: 106.

* * * * *

SEQUENCE LISTING

```
<160> NUMBER OF SEQ ID NOS: 112

<210> SEQ ID NO 1
<211> LENGTH: 133
<212> TYPE: PRT
<213> ORGANISM: Homo sapiens

<400> SEQUENCE: 1

Ala Pro Thr Ser Ser Thr Lys Lys Thr Gln Leu Gln Leu Glu His
1               5                   10                  15

Leu Leu Leu Asp Leu Gln Met Ile Leu Asn Gly Ile Asn Asn Tyr Lys
                20                  25                  30

Asn Pro Lys Leu Thr Arg Met Leu Thr Phe Lys Phe Tyr Met Pro Lys
                35                  40                  45

Lys Ala Thr Glu Leu Lys His Leu Gln Cys Leu Glu Glu Glu Leu Lys
    50                  55                  60

Pro Leu Glu Glu Val Leu Asn Leu Ala Gln Ser Lys Asn Phe His Leu
65                  70                  75                  80

Arg Pro Arg Asp Leu Ile Ser Asn Ile Asn Val Ile Val Leu Glu Leu
                85                  90                  95
```

-continued

```
Lys Gly Ser Glu Thr Thr Phe Met Cys Glu Tyr Ala Asp Glu Thr Ala
            100                 105                 110

Thr Ile Val Glu Phe Leu Asn Arg Trp Ile Thr Phe Cys Gln Ser Ile
        115                 120                 125

Ile Ser Thr Leu Thr
    130

<210> SEQ ID NO 2
<211> LENGTH: 219
<212> TYPE: PRT
<213> ORGANISM: Homo sapiens

<400> SEQUENCE: 2

Ser Gly Thr Thr Asn Thr Val Ala Ala Tyr Asn Leu Thr Trp Lys Ser
1               5                   10                  15

Thr Asn Phe Lys Thr Ile Leu Glu Trp Glu Pro Lys Pro Val Asn Gln
            20                  25                  30

Val Tyr Thr Val Gln Ile Ser Thr Lys Ser Gly Asp Trp Lys Ser Lys
        35                  40                  45

Cys Phe Tyr Thr Thr Asp Thr Glu Cys Asp Leu Thr Asp Glu Ile Val
    50                  55                  60

Lys Asp Val Lys Gln Thr Tyr Leu Ala Arg Val Phe Ser Tyr Pro Ala
65                  70                  75                  80

Gly Asn Val Glu Ser Thr Gly Ser Ala Gly Glu Pro Leu Tyr Glu Asn
                85                  90                  95

Ser Pro Glu Phe Thr Pro Tyr Leu Glu Thr Asn Leu Gly Gln Pro Thr
            100                 105                 110

Ile Gln Ser Phe Glu Gln Val Gly Thr Lys Val Asn Val Thr Val Glu
        115                 120                 125

Asp Glu Arg Thr Leu Val Arg Arg Asn Asn Thr Phe Leu Ser Leu Arg
    130                 135                 140

Asp Val Phe Gly Lys Asp Leu Ile Tyr Thr Leu Tyr Tyr Trp Lys Ser
145                 150                 155                 160

Ser Ser Ser Gly Lys Lys Thr Ala Lys Thr Asn Thr Asn Glu Phe Leu
                165                 170                 175

Ile Asp Val Asp Lys Gly Glu Asn Tyr Cys Phe Ser Val Gln Ala Val
            180                 185                 190

Ile Pro Ser Arg Thr Val Asn Arg Lys Ser Thr Asp Ser Pro Val Glu
        195                 200                 205

Cys Met Gly Gln Glu Lys Gly Glu Phe Arg Glu
    210                 215

<210> SEQ ID NO 3
<211> LENGTH: 485
<212> TYPE: PRT
<213> ORGANISM: Artificial Sequence
<220> FEATURE:
<223> OTHER INFORMATION: Description of Artificial Sequence: Synthetic
      polypeptide

<400> SEQUENCE: 3

Ala Pro Thr Ser Ser Ser Thr Lys Lys Thr Gln Leu Gln Leu Glu His
1               5                   10                  15

Leu Leu Leu Asp Leu Gln Met Ile Leu Asn Gly Ile Asn Asn Tyr Lys
            20                  25                  30

Asn Pro Lys Leu Thr Arg Met Leu Thr Phe Lys Phe Tyr Met Pro Lys
        35                  40                  45
```

```
Lys Ala Thr Glu Leu Lys His Leu Gln Cys Leu Glu Glu Leu Lys
    50                  55                  60

Pro Leu Glu Glu Val Leu Asn Leu Ala Gln Ser Lys Asn Phe His Leu
65                  70                  75                  80

Arg Pro Arg Asp Leu Ile Ser Asn Ile Asn Val Ile Val Leu Glu Leu
                85                  90                  95

Lys Gly Ser Glu Thr Thr Phe Met Cys Glu Tyr Ala Asp Glu Thr Ala
            100                 105                 110

Thr Ile Val Glu Phe Leu Asn Arg Trp Ile Thr Phe Cys Gln Ser Ile
            115                 120                 125

Ile Ser Thr Leu Thr Ser Gly Thr Thr Asn Thr Val Ala Ala Tyr Asn
    130                 135                 140

Leu Thr Trp Lys Ser Thr Asn Phe Lys Thr Ile Leu Glu Trp Glu Pro
145                 150                 155                 160

Lys Pro Val Asn Gln Val Tyr Thr Val Gln Ile Ser Thr Lys Ser Gly
                165                 170                 175

Asp Trp Lys Ser Lys Cys Phe Tyr Thr Thr Asp Thr Glu Cys Asp Leu
            180                 185                 190

Thr Asp Glu Ile Val Lys Asp Val Lys Gln Thr Tyr Leu Ala Arg Val
    195                 200                 205

Phe Ser Tyr Pro Ala Gly Asn Val Glu Ser Thr Gly Ser Ala Gly Glu
210                 215                 220

Pro Leu Tyr Glu Asn Ser Pro Glu Phe Thr Pro Tyr Leu Glu Thr Asn
225                 230                 235                 240

Leu Gly Gln Pro Thr Ile Gln Ser Phe Glu Gln Val Gly Thr Lys Val
                245                 250                 255

Asn Val Thr Val Glu Asp Glu Arg Thr Leu Val Arg Arg Asn Asn Thr
            260                 265                 270

Phe Leu Ser Leu Arg Asp Val Phe Gly Lys Asp Leu Ile Tyr Thr Leu
    275                 280                 285

Tyr Tyr Trp Lys Ser Ser Ser Gly Lys Lys Thr Ala Lys Thr Asn
    290                 295                 300

Thr Asn Glu Phe Leu Ile Asp Val Asp Lys Gly Glu Asn Tyr Cys Phe
305                 310                 315                 320

Ser Val Gln Ala Val Ile Pro Ser Arg Thr Val Asn Arg Lys Ser Thr
                325                 330                 335

Asp Ser Pro Val Glu Cys Met Gly Gln Glu Lys Gly Glu Phe Arg Glu
            340                 345                 350

Ala Pro Thr Ser Ser Ser Thr Lys Lys Thr Gln Leu Gln Leu Glu His
    355                 360                 365

Leu Leu Leu Asp Leu Gln Met Ile Leu Asn Gly Ile Asn Asn Tyr Lys
370                 375                 380

Asn Pro Lys Leu Thr Arg Met Leu Thr Phe Lys Phe Tyr Met Pro Lys
385                 390                 395                 400

Lys Ala Thr Glu Leu Lys His Leu Gln Cys Leu Glu Glu Glu Leu Lys
                405                 410                 415

Pro Leu Glu Glu Val Leu Asn Leu Ala Gln Ser Lys Asn Phe His Leu
            420                 425                 430

Arg Pro Arg Asp Leu Ile Ser Asn Ile Asn Val Ile Val Leu Glu Leu
    435                 440                 445

Lys Gly Ser Glu Thr Thr Phe Met Cys Glu Tyr Ala Asp Glu Thr Ala
450                 455                 460

Thr Ile Val Glu Phe Leu Asn Arg Trp Ile Thr Phe Cys Gln Ser Ile
```

```
                     465                 470                 475                 480
Ile Ser Thr Leu Thr
                485

<210> SEQ ID NO 4
<211> LENGTH: 503
<212> TYPE: PRT
<213> ORGANISM: Artificial Sequence
<220> FEATURE:
<223> OTHER INFORMATION: Description of Artificial Sequence: Synthetic
      polypeptide

<400> SEQUENCE: 4

Met Lys Trp Val Thr Phe Ile Ser Leu Leu Phe Leu Phe Ser Ser Ala
1               5                   10                  15

Tyr Ser Ala Pro Thr Ser Ser Ser Thr Lys Lys Thr Gln Leu Gln Leu
            20                  25                  30

Glu His Leu Leu Leu Asp Leu Gln Met Ile Leu Asn Gly Ile Asn Asn
        35                  40                  45

Tyr Lys Asn Pro Lys Leu Thr Arg Met Leu Thr Phe Lys Phe Tyr Met
50                  55                  60

Pro Lys Lys Ala Thr Glu Leu Lys His Leu Gln Cys Leu Glu Glu Glu
65                  70                  75                  80

Leu Lys Pro Leu Glu Glu Val Leu Asn Leu Ala Gln Ser Lys Asn Phe
                85                  90                  95

His Leu Arg Pro Arg Asp Leu Ile Ser Asn Ile Asn Val Ile Val Leu
            100                 105                 110

Glu Leu Lys Gly Ser Glu Thr Thr Phe Met Cys Glu Tyr Ala Asp Glu
        115                 120                 125

Thr Ala Thr Ile Val Glu Phe Leu Asn Arg Trp Ile Thr Phe Cys Gln
130                 135                 140

Ser Ile Ile Ser Thr Leu Thr Ser Gly Thr Thr Asn Thr Val Ala Ala
145                 150                 155                 160

Tyr Asn Leu Thr Trp Lys Ser Thr Asn Phe Lys Thr Ile Leu Glu Trp
                165                 170                 175

Glu Pro Lys Pro Val Asn Gln Val Tyr Thr Val Gln Ile Ser Thr Lys
            180                 185                 190

Ser Gly Asp Trp Lys Ser Lys Cys Phe Tyr Thr Thr Asp Thr Glu Cys
        195                 200                 205

Asp Leu Thr Asp Glu Ile Val Lys Asp Val Lys Gln Thr Tyr Leu Ala
210                 215                 220

Arg Val Phe Ser Tyr Pro Ala Gly Asn Val Glu Ser Thr Gly Ser Ala
225                 230                 235                 240

Gly Glu Pro Leu Tyr Glu Asn Ser Pro Glu Phe Thr Pro Tyr Leu Glu
                245                 250                 255

Thr Asn Leu Gly Gln Pro Thr Ile Gln Ser Phe Glu Gln Val Gly Thr
            260                 265                 270

Lys Val Asn Val Thr Val Glu Asp Glu Arg Thr Leu Val Arg Arg Asn
        275                 280                 285

Asn Thr Phe Leu Ser Leu Arg Asp Val Phe Gly Lys Asp Leu Ile Tyr
290                 295                 300

Thr Leu Tyr Tyr Trp Lys Ser Ser Ser Gly Lys Lys Thr Ala Lys
305                 310                 315                 320

Thr Asn Thr Asn Glu Phe Leu Ile Asp Val Asp Lys Gly Glu Asn Tyr
                325                 330                 335
```

```
Cys Phe Ser Val Gln Ala Val Ile Pro Ser Arg Thr Val Asn Arg Lys
            340                 345                 350

Ser Thr Asp Ser Pro Val Glu Cys Met Gly Gln Glu Lys Gly Glu Phe
            355                 360                 365

Arg Glu Ala Pro Thr Ser Ser Ser Thr Lys Lys Thr Gln Leu Gln Leu
        370                 375                 380

Glu His Leu Leu Leu Asp Leu Gln Met Ile Leu Asn Gly Ile Asn Asn
385                 390                 395                 400

Tyr Lys Asn Pro Lys Leu Thr Arg Met Leu Thr Phe Lys Phe Tyr Met
                405                 410                 415

Pro Lys Lys Ala Thr Glu Leu Lys His Leu Gln Cys Leu Glu Glu Glu
            420                 425                 430

Leu Lys Pro Leu Glu Glu Val Leu Asn Leu Ala Gln Ser Lys Asn Phe
        435                 440                 445

His Leu Arg Pro Arg Asp Leu Ile Ser Asn Ile Asn Val Ile Val Leu
    450                 455                 460

Glu Leu Lys Gly Ser Glu Thr Thr Phe Met Cys Glu Tyr Ala Asp Glu
465                 470                 475                 480

Thr Ala Thr Ile Val Glu Phe Leu Asn Arg Trp Ile Thr Phe Cys Gln
                485                 490                 495

Ser Ile Ile Ser Thr Leu Thr
            500

<210> SEQ ID NO 5
<211> LENGTH: 241
<212> TYPE: PRT
<213> ORGANISM: Artificial Sequence
<220> FEATURE:
<223> OTHER INFORMATION: Description of Artificial Sequence: Synthetic
      polypeptide

<400> SEQUENCE: 5

Gln Ile Val Leu Thr Gln Ser Pro Ala Ile Met Ser Ala Ser Pro Gly
1               5                   10                  15

Glu Lys Val Thr Met Thr Cys Ser Ala Ser Ser Ser Val Ser Tyr Met
            20                  25                  30

Asn Trp Tyr Gln Gln Lys Ser Gly Thr Ser Pro Lys Arg Trp Ile Tyr
        35                  40                  45

Asp Thr Ser Lys Leu Ala Ser Gly Val Pro Ala His Phe Arg Gly Ser
    50                  55                  60

Gly Ser Gly Thr Ser Tyr Ser Leu Thr Ile Ser Gly Met Glu Ala Glu
65                  70                  75                  80

Asp Ala Ala Thr Tyr Tyr Cys Gln Gln Trp Ser Ser Asn Pro Phe Thr
                85                  90                  95

Phe Gly Ser Gly Thr Lys Leu Glu Ile Asn Arg Gly Gly Gly Gly Ser
            100                 105                 110

Gly Gly Gly Gly Ser Gly Gly Gly Ser Gln Val Gln Leu Gln Gln
        115                 120                 125

Ser Gly Ala Glu Leu Ala Arg Pro Gly Ala Ser Val Lys Met Ser Cys
    130                 135                 140

Lys Ala Ser Gly Tyr Thr Phe Thr Arg Tyr Thr Met His Trp Val Lys
145                 150                 155                 160

Gln Arg Pro Gly Gln Gly Leu Glu Trp Ile Gly Tyr Ile Asn Pro Ser
                165                 170                 175

Arg Gly Tyr Thr Asn Tyr Asn Gln Lys Phe Lys Asp Lys Ala Thr Leu
            180                 185                 190
```

```
Thr Thr Asp Lys Ser Ser Thr Ala Tyr Met Gln Leu Ser Ser Leu
        195                 200                 205

Thr Ser Glu Asp Ser Ala Val Tyr Tyr Cys Ala Arg Tyr Tyr Asp Asp
210                 215                 220

His Tyr Cys Leu Asp Tyr Trp Gly Gln Gly Thr Thr Leu Thr Val Ser
225                 230                 235                 240

Ser

<210> SEQ ID NO 6
<211> LENGTH: 236
<212> TYPE: PRT
<213> ORGANISM: Artificial Sequence
<220> FEATURE:
<223> OTHER INFORMATION: Description of Artificial Sequence: Synthetic
      polypeptide

<400> SEQUENCE: 6

Val Gln Leu Gln Gln Ser Gly Pro Glu Leu Val Lys Pro Gly Ala Ser
1               5                   10                  15

Val Lys Met Ser Cys Lys Ala Ser Gly Tyr Thr Phe Thr Ser Tyr Val
            20                  25                  30

Ile Gln Trp Val Lys Gln Lys Pro Gly Gln Gly Leu Glu Trp Ile Gly
        35                  40                  45

Ser Ile Asn Pro Tyr Asn Asp Tyr Thr Lys Tyr Asn Glu Lys Phe Lys
    50                  55                  60

Gly Lys Ala Thr Leu Thr Ser Asp Lys Ser Ser Ile Thr Ala Tyr Met
65                  70                  75                  80

Glu Phe Ser Ser Leu Thr Ser Glu Asp Ser Ala Leu Tyr Tyr Cys Ala
                85                  90                  95

Arg Trp Gly Asp Gly Asn Tyr Trp Gly Arg Gly Thr Thr Leu Thr Val
            100                 105                 110

Ser Ser Gly Gly Gly Gly Ser Gly Gly Gly Ser Gly Gly Gly Gly
        115                 120                 125

Ser Asp Ile Glu Met Thr Gln Ser Pro Ala Ile Met Ser Ala Ser Leu
    130                 135                 140

Gly Glu Arg Val Thr Met Thr Cys Thr Ala Ser Ser Ser Val Ser Ser
145                 150                 155                 160

Ser Tyr Phe His Trp Tyr Gln Gln Lys Pro Gly Ser Ser Pro Lys Leu
                165                 170                 175

Cys Ile Tyr Ser Thr Ser Asn Leu Ala Ser Gly Val Pro Pro Arg Phe
            180                 185                 190

Ser Gly Ser Gly Ser Thr Ser Tyr Ser Leu Thr Ile Ser Ser Met Glu
        195                 200                 205

Ala Glu Asp Ala Ala Thr Tyr Phe Cys His Gln Tyr His Arg Ser Pro
    210                 215                 220

Thr Phe Gly Gly Gly Thr Lys Leu Glu Thr Lys Arg
225                 230                 235

<210> SEQ ID NO 7
<211> LENGTH: 696
<212> TYPE: PRT
<213> ORGANISM: Artificial Sequence
<220> FEATURE:
<223> OTHER INFORMATION: Description of Artificial Sequence: Synthetic
      polypeptide

<400> SEQUENCE: 7
```

```
Gln Ile Val Leu Thr Gln Ser Pro Ala Ile Met Ser Ala Ser Pro Gly
1               5                   10                  15

Glu Lys Val Thr Met Thr Cys Ser Ala Ser Ser Val Ser Tyr Met
            20                  25                  30

Asn Trp Tyr Gln Gln Lys Ser Gly Thr Ser Pro Lys Arg Trp Ile Tyr
        35                  40                  45

Asp Thr Ser Lys Leu Ala Ser Gly Val Pro Ala His Phe Arg Gly Ser
    50                  55                  60

Gly Ser Gly Thr Ser Tyr Ser Leu Thr Ile Ser Gly Met Glu Ala Glu
65                  70                  75                  80

Asp Ala Ala Thr Tyr Tyr Cys Gln Gln Trp Ser Ser Asn Pro Phe Thr
                85                  90                  95

Phe Gly Ser Gly Thr Lys Leu Glu Ile Asn Arg Gly Gly Gly Gly Ser
            100                 105                 110

Gly Gly Gly Gly Ser Gly Gly Gly Ser Gln Val Gln Leu Gln Gln
        115                 120                 125

Ser Gly Ala Glu Leu Ala Arg Pro Gly Ala Ser Val Lys Met Ser Cys
    130                 135                 140

Lys Ala Ser Gly Tyr Thr Phe Thr Arg Tyr Thr Met His Trp Val Lys
145                 150                 155                 160

Gln Arg Pro Gly Gln Gly Leu Glu Trp Ile Gly Tyr Ile Asn Pro Ser
                165                 170                 175

Arg Gly Tyr Thr Asn Tyr Asn Gln Lys Phe Lys Asp Lys Ala Thr Leu
            180                 185                 190

Thr Thr Asp Lys Ser Ser Ser Thr Ala Tyr Met Gln Leu Ser Ser Leu
        195                 200                 205

Thr Ser Glu Asp Ser Ala Val Tyr Tyr Cys Ala Arg Tyr Tyr Asp Asp
    210                 215                 220

His Tyr Cys Leu Asp Tyr Trp Gly Gln Gly Thr Thr Leu Thr Val Ser
225                 230                 235                 240

Ser Ser Gly Thr Thr Asn Thr Val Ala Ala Tyr Asn Leu Thr Trp Lys
                245                 250                 255

Ser Thr Asn Phe Lys Thr Ile Leu Glu Trp Glu Pro Lys Pro Val Asn
            260                 265                 270

Gln Val Tyr Thr Val Gln Ile Ser Thr Lys Ser Gly Asp Trp Lys Ser
        275                 280                 285

Lys Cys Phe Tyr Thr Thr Asp Thr Glu Cys Asp Leu Thr Asp Glu Ile
    290                 295                 300

Val Lys Asp Val Lys Gln Thr Tyr Leu Ala Arg Val Phe Ser Tyr Pro
305                 310                 315                 320

Ala Gly Asn Val Glu Ser Thr Gly Ser Ala Gly Glu Pro Leu Tyr Glu
                325                 330                 335

Asn Ser Pro Glu Phe Thr Pro Tyr Leu Glu Thr Asn Leu Gly Gln Pro
            340                 345                 350

Thr Ile Gln Ser Phe Glu Gln Val Gly Thr Lys Val Asn Val Thr Val
        355                 360                 365

Glu Asp Glu Arg Thr Leu Val Arg Arg Asn Asn Thr Phe Leu Ser Leu
    370                 375                 380

Arg Asp Val Phe Gly Lys Asp Leu Ile Tyr Thr Leu Tyr Tyr Trp Lys
385                 390                 395                 400

Ser Ser Ser Ser Gly Lys Lys Thr Ala Lys Thr Asn Thr Asn Glu Phe
                405                 410                 415

Leu Ile Asp Val Asp Lys Gly Glu Asn Tyr Cys Phe Ser Val Gln Ala
```

```
                    420              425              430
Val Ile Pro Ser Arg Thr Val Asn Arg Lys Ser Thr Asp Ser Pro Val
            435              440              445

Glu Cys Met Gly Gln Glu Lys Gly Glu Phe Arg Glu Val Gln Leu Gln
        450              455              460

Gln Ser Gly Pro Glu Leu Val Lys Pro Gly Ala Ser Val Lys Met Ser
465              470              475              480

Cys Lys Ala Ser Gly Tyr Thr Phe Thr Ser Tyr Val Ile Gln Trp Val
            485              490              495

Lys Gln Lys Pro Gly Gln Gly Leu Glu Trp Ile Gly Ser Ile Asn Pro
        500              505              510

Tyr Asn Asp Tyr Thr Lys Tyr Asn Glu Lys Phe Lys Gly Lys Ala Thr
            515              520              525

Leu Thr Ser Asp Lys Ser Ile Thr Ala Tyr Met Glu Phe Ser Ser
        530              535              540

Leu Thr Ser Glu Asp Ser Ala Leu Tyr Tyr Cys Ala Arg Trp Gly Asp
545              550              555              560

Gly Asn Tyr Trp Gly Arg Gly Thr Thr Leu Thr Val Ser Ser Gly Gly
            565              570              575

Gly Gly Ser Gly Gly Gly Ser Gly Gly Gly Ser Asp Ile Glu
        580              585              590

Met Thr Gln Ser Pro Ala Ile Met Ser Ala Ser Leu Gly Glu Arg Val
        595              600              605

Thr Met Thr Cys Thr Ala Ser Ser Ser Val Ser Ser Tyr Phe His
        610              615              620

Trp Tyr Gln Gln Lys Pro Gly Ser Ser Pro Lys Leu Cys Ile Tyr Ser
625              630              635              640

Thr Ser Asn Leu Ala Ser Gly Val Pro Pro Arg Phe Ser Gly Ser Gly
            645              650              655

Ser Thr Ser Tyr Ser Leu Thr Ile Ser Ser Met Glu Ala Glu Asp Ala
            660              665              670

Ala Thr Tyr Phe Cys His Gln Tyr His Arg Ser Pro Thr Phe Gly Gly
            675              680              685

Gly Thr Lys Leu Glu Thr Lys Arg
        690              695

<210> SEQ ID NO 8
<211> LENGTH: 714
<212> TYPE: PRT
<213> ORGANISM: Artificial Sequence
<220> FEATURE:
<223> OTHER INFORMATION: Description of Artificial Sequence: Synthetic
      polypeptide

<400> SEQUENCE: 8

Met Lys Trp Val Thr Phe Ile Ser Leu Leu Phe Leu Phe Ser Ser Ala
1               5                   10                  15

Tyr Ser Gln Ile Val Leu Thr Gln Ser Pro Ala Ile Met Ser Ala Ser
            20                  25                  30

Pro Gly Glu Lys Val Thr Met Thr Cys Ser Ala Ser Ser Ser Val Ser
        35                  40                  45

Tyr Met Asn Trp Tyr Gln Gln Lys Ser Gly Thr Ser Pro Lys Arg Trp
    50                  55                  60

Ile Tyr Asp Thr Ser Lys Leu Ala Ser Gly Val Pro Ala His Phe Arg
65                  70                  75                  80
```

```
Gly Ser Gly Ser Gly Thr Ser Tyr Ser Leu Thr Ile Ser Gly Met Glu
                85                  90                  95
Ala Glu Asp Ala Ala Thr Tyr Tyr Cys Gln Gln Trp Ser Ser Asn Pro
            100                 105                 110
Phe Thr Phe Gly Ser Gly Thr Lys Leu Glu Ile Asn Arg Gly Gly Gly
            115                 120                 125
Gly Ser Gly Gly Gly Gly Ser Gly Gly Gly Gly Ser Gln Val Gln Leu
            130                 135                 140
Gln Gln Ser Gly Ala Glu Leu Ala Arg Pro Gly Ala Ser Val Lys Met
145                 150                 155                 160
Ser Cys Lys Ala Ser Gly Tyr Thr Phe Thr Arg Tyr Thr Met His Trp
                165                 170                 175
Val Lys Gln Arg Pro Gly Gln Gly Leu Glu Trp Ile Gly Tyr Ile Asn
            180                 185                 190
Pro Ser Arg Gly Tyr Thr Asn Tyr Asn Gln Lys Phe Lys Asp Lys Ala
            195                 200                 205
Thr Leu Thr Thr Asp Lys Ser Ser Thr Ala Tyr Met Gln Leu Ser
    210                 215                 220
Ser Leu Thr Ser Glu Asp Ser Ala Val Tyr Tyr Cys Ala Arg Tyr Tyr
225                 230                 235                 240
Asp Asp His Tyr Cys Leu Asp Tyr Trp Gly Gln Gly Thr Thr Leu Thr
                245                 250                 255
Val Ser Ser Gly Thr Thr Asn Thr Val Ala Ala Tyr Asn Leu Thr
                260                 265                 270
Trp Lys Ser Thr Asn Phe Lys Thr Ile Leu Glu Trp Glu Pro Lys Pro
            275                 280                 285
Val Asn Gln Val Tyr Thr Val Gln Ile Ser Thr Lys Ser Gly Asp Trp
            290                 295                 300
Lys Ser Lys Cys Phe Tyr Thr Thr Asp Thr Glu Cys Asp Leu Thr Asp
305                 310                 315                 320
Glu Ile Val Lys Asp Val Lys Gln Thr Tyr Leu Ala Arg Val Phe Ser
                325                 330                 335
Tyr Pro Ala Gly Asn Val Glu Ser Thr Gly Ser Ala Gly Glu Pro Leu
            340                 345                 350
Tyr Glu Asn Ser Pro Glu Phe Thr Pro Tyr Leu Glu Thr Asn Leu Gly
            355                 360                 365
Gln Pro Thr Ile Gln Ser Phe Glu Gln Val Gly Thr Lys Val Asn Val
            370                 375                 380
Thr Val Glu Asp Glu Arg Thr Leu Val Arg Arg Asn Asn Thr Phe Leu
385                 390                 395                 400
Ser Leu Arg Asp Val Phe Gly Lys Asp Leu Ile Tyr Thr Leu Tyr Tyr
                405                 410                 415
Trp Lys Ser Ser Ser Gly Lys Lys Thr Ala Lys Thr Asn Thr Asn
            420                 425                 430
Glu Phe Leu Ile Asp Val Asp Lys Gly Glu Asn Tyr Cys Phe Ser Val
            435                 440                 445
Gln Ala Val Ile Pro Ser Arg Thr Val Asn Arg Lys Ser Thr Asp Ser
    450                 455                 460
Pro Val Glu Cys Met Gly Gln Glu Lys Gly Glu Phe Arg Glu Val Gln
465                 470                 475                 480
Leu Gln Gln Ser Gly Pro Glu Leu Val Lys Pro Gly Ala Ser Val Lys
                485                 490                 495
Met Ser Cys Lys Ala Ser Gly Tyr Thr Phe Thr Ser Tyr Val Ile Gln
```

```
                500               505                510
Trp Val Lys Gln Lys Pro Gly Gln Gly Leu Glu Trp Ile Gly Ser Ile
        515                 520                525
Asn Pro Tyr Asn Asp Tyr Thr Lys Tyr Asn Glu Lys Phe Lys Gly Lys
        530                 535                540
Ala Thr Leu Thr Ser Asp Lys Ser Ser Ile Thr Ala Tyr Met Glu Phe
545                 550                 555                560
Ser Ser Leu Thr Ser Glu Asp Ser Ala Leu Tyr Tyr Cys Ala Arg Trp
                565                 570                575
Gly Asp Gly Asn Tyr Trp Gly Arg Gly Thr Thr Leu Thr Val Ser Ser
                580                 585                590
Gly Gly Gly Gly Ser Gly Gly Gly Gly Ser Gly Gly Gly Gly Ser Asp
        595                 600                605
Ile Glu Met Thr Gln Ser Pro Ala Ile Met Ser Ala Ser Leu Gly Glu
        610                 615                620
Arg Val Thr Met Thr Cys Thr Ala Ser Ser Ser Val Ser Ser Ser Tyr
625                 630                 635                640
Phe His Trp Tyr Gln Gln Lys Pro Gly Ser Ser Pro Lys Leu Cys Ile
                645                 650                655
Tyr Ser Thr Ser Asn Leu Ala Ser Gly Val Pro Pro Arg Phe Ser Gly
                660                 665                670
Ser Gly Ser Thr Ser Tyr Ser Leu Thr Ile Ser Ser Met Glu Ala Glu
        675                 680                685
Asp Ala Ala Thr Tyr Phe Cys His Gln Tyr His Arg Ser Pro Thr Phe
        690                 695                700
Gly Gly Gly Thr Lys Leu Glu Thr Lys Arg
705                 710
```

<210> SEQ ID NO 9
<211> LENGTH: 2088
<212> TYPE: DNA
<213> ORGANISM: Artificial Sequence
<220> FEATURE:
<223> OTHER INFORMATION: Description of Artificial Sequence: Synthetic
      polynucleotide

<400> SEQUENCE: 9

```
cagatcgtgc tgacccaaag ccccgccatc atgagcgcta gccccggtga gaaggtgacc      60
atgacatgct ccgcttccag ctccgtgtcc tacatgaact ggtatcagca gaaaagcgga     120
accagcccca aaggtggatc tacgacacc agcaagctgg cctccggagt gcccgctcat     180
ttccggggct ctggatccgg caccagctac tctttaacca tttccggcat ggaagctgaa     240
gacgctgcca cctactattg ccagcaatgg agcagcaacc ccttcacatt cggatctggc     300
accaagctcg aaatcaatcg tggaggaggt ggcagcggcg gcggtggatc cggcggagga     360
ggaagccaag ttcaactcca gcagagcggc gctgaactgg cccggccgg cgcctccgtc     420 aagatgagct gcaaggcttc cggctataca tttactcgtt acacaatgca ttgggtcaag     480
cagaggcccg gtcaaggttt agagtggatc ggatatatca cccttcccg gggctacacc     540 aactataacc aaaagttcaa ggataaagcc actttaacca ctgacaagag ctcctccacc     600
gcctacatgc agctgtcctc tttaaccagc gaggactccg ctgtttacta ctgcgctagg     660
tattacgacg accactactg tttagactat tggggacaag gtaccacttt aaccgtcagc     720
agctccggca ccaccaatac cgtggccgct ataaccctca catggaagag caccaacttc     780
aagacaattc tggaatggga acccaagccc gtcaatcaag tttacaccgt gcagatctcc     840
```

```
accaaatccg gagactggaa gagcaagtgc ttctacacaa cagacaccga gtgtgattta      900
accgacgaaa tcgtcaagga cgtcaagcaa acctatctgg ctcgggtctt ttcctacccc      960
gctggcaatg tcgagtccac cggctccgct ggcgagcctc tctacgagaa ttcccccgaa     1020
ttcaccccctt atttagagac caatttaggc cagcctacca tccagagctt cgagcaagtt     1080
ggcaccaagg tgaacgtcac cgtcgaggat gaaaggactt tagtgcggcg aataacaca      1140
tttttatccc tccgggatgt gttcggcaaa gacctcatct acacactgta ctattggaag     1200
tccagctcct ccggcaaaaa gaccgctaag accaacacca cgagttttt aattgacgtg      1260
gacaaaggcg agaactactg cttcagcgtg caagccgtga tcccttctcg taccgtcaac     1320
cggaagagca cagattcccc cgttgagtgc atgggccaag aaaagggcga gttccgggag     1380
gtccagctgc agcagagcgg acccgaactc gtgaaaccccg gtgcttccgt gaaaatgtct    1440
tgtaaggcca gcggatacac cttcacctcc tatgtgatcc agtgggtcaa acagaagccc     1500
ggacaaggtc tcgagtggat cggcagcatc aaccccttaca cgactatac caaatacaac     1560
gagaagttta agggaaaggc tactttaacc tccgacaaaa gctccatcac agcctacatg     1620
gagttcagct ctttaacatc cgaggacagc gctctgtact attgcgcccg gtgggcgac      1680
ggcaattact ggggacgggg cacaacactg accgtgagca gcggaggcgg aggctccggc     1740
ggaggcggat ctggcggtgg cggctccgac atcgagatga cccagtcccc cgctatcatg     1800
tccgcctctt taggcgagcg ggtcacaatg acttgtacag cctcctccag cgtctcctcc     1860
tcctacttcc attggtacca acagaaaccc ggaagctccc ctaaactgtg catctacagc     1920
accagcaatc tcgccagcgg cgtgccccct aggttttccg gaagcggaag caccagctac     1980
tcttaacca tctcctccat ggaggctgag gatgccgcca cctactttg tcaccagtac       2040
caccggtccc ccaccttcgg aggcggcacc aaactggaga caaagagg               2088

<210> SEQ ID NO 10
<211> LENGTH: 2142
<212> TYPE: DNA
<213> ORGANISM: Artificial Sequence
<220> FEATURE:
<223> OTHER INFORMATION: Description of Artificial Sequence: Synthetic
      polynucleotide

<400> SEQUENCE: 10
atgaagtggg tgaccttcat cagcttatta tttttattca gctccgccta ttcccagatc      60
gtgctgaccc aaagccccgc catcatgagc gctagcccg gtgagaaggt gaccatgaca      120
tgctccgctt ccagctccgt gtcctacatg aactggtatc agcagaaaag cggaaccagc     180
cccaaaaggt ggatctacga caccagcaag ctggcctccg gagtgcccgc tcatttccgg      240
ggctctggat ccggcaccag ctactcttta accatttccg gcatggaagc tgaagacgct     300
gccacctact attgccagca atggagcagc aacccccttca cattcggatc tggcaccaag     360
ctcgaaatca atcgtggagg aggtggcagc ggcggcggtg gatccggcgg aggaggaagc     420
caagttcaac tccagcagag cggcgctgaa ctggcccggc ccggcgcctc cgtcaagatg      480
agctgcaagg cttccggcta catttact cgttacacaa tgcattgggt caagcagagg       540
cccggtcaag gtttagagtg gatcggatat atcaacccctt cccggggcta caccaactat    600
aaccaaaagt tcaaggataa agccactta accactgaca agagctcctc caccgcctac     660
atgcagctgt cctcttta ac cagcgaggac tccgctgttt actactgcgc taggtattac    720
gacgaccact actgttaga ctattgggga caaggtacca ctttaaccgt cagcagctcc      780
```

```
ggcaccacca ataccgtggc cgcttataac ctcacatgga agagcaccaa cttcaagaca      840
attctggaat gggaacccaa gcccgtcaat caagtttaca ccgtgcagat ctccaccaaa      900
tccggagact ggaagagcaa gtgcttctac acaacagaca ccgagtgtga tttaaccgac      960
gaaatcgtca aggacgtcaa gcaaacctat ctggctcggg tcttttccta ccccgctggc     1020
aatgtcgagt ccaccggctc cgctggcgag cctctctacg agaattcccc cgaattcacc     1080
ccttatttag agaccaattt aggccagcct accatccaga gcttcgagca gttggcacc     1140 aaggtgaacg tcaccgtcga ggatgaaagg actttagtgc ggcggaataa cacattttta     1200
tccctccggg atgtgttcgg caaagacctc atctacacac tgtactattg gaagtccagc     1260
tcctccggca aaaagaccgc taagaccaac accaacgagt ttttaattga cgtggacaaa     1320
ggcgagaact actgcttcag cgtgcaagcc gtgatcccct tctcgtaccg tcaaccggaag    1380 agcacagatt ccccgttga gtgcatgggc caagaaaagg gcgagttccg ggaggtccag     1440
ctgcagcaga gcggacccga actcgtgaaa cccggtgctt ccgtgaaaat gtcttgtaag     1500
gccagcggat acaccttcac ctcctatgtg atccagtggg tcaaacagaa gcccggacaa     1560
ggtctcgagt ggatcggcag catcaaccct acaacgact ataccaaata caacgagaag     1620
tttaagggaa aggctacttt aacctccgac aaaagctcca tcacagccta catggagttc     1680
agctctttaa catccgagga cagcgctctg tactattgcg cccggtgggg cgacggcaat     1740
tactggggac ggggcacaac actgaccgtg agcagcggag gcggaggctc cggcggaggc     1800
ggatctggcg gtggcggctc cgacatcgag atgacccagt cccccgctat catgtccgcc     1860
tctttaggcg agcgggtcac aatgacttgt acagcctcct ccagcgtctc ctcctcctac     1920
ttccattggt accaacagaa acccggaagc tcccctaaac tgtgcatcta cagcaccagc     1980
aatctcgcca gcggcgtgcc ccctaggttt tccggaagcg gaagcaccag ctactcttta     2040
accatctcct ccatggaggc tgaggatgcc gccacctact tttgtcacca gtaccaccgg     2100 tccccccacct tcggaggcgg caccaaactg gagacaaaga gg                       2142
```

<210> SEQ ID NO 11
<211> LENGTH: 1455
<212> TYPE: DNA
<213> ORGANISM: Artificial Sequence
<220> FEATURE:
<223> OTHER INFORMATION: Description of Artificial Sequence: Synthetic
      polynucleotide

<400> SEQUENCE: 11

```
gcccccacct cctcctccac caagaagacc cagctgcagc tggagcattt actgctggat       60
ttacagatga ttttaaacgg catcaacaac tacaagaacc ccaagctgac tcgtatgctg      120
accttcaagt tctacatgcc caagaaggcc accgagctga agcatttaca gtgtttagag      180
gaggagctga agcccctcga ggaggtgctg aatttagccc agtccaagaa tttccatttta    240 aggccccggg atttaatcag caacatcaac gtgatcgttt tagagctgaa gggctccgag     300
accaccttca tgtgcgagta cgccgacgag accgccacca tcgtggagtt tttaaatcgt     360
tggatcacct tctgccagtc catcatctcc actttaacca gcggcacaac caacacagtc      420
gctgcctata acctcacttg aagagcacc aacttcaaaa ccatcctcga atgggaaccc      480
aaacccgtta accaagttta caccgtgcag atcagcacca agtccggcga ctggaagtcc     540
aaatgtttct ataccaccga caccgagtgc gatctcaccg atgagatcgt gaaagatgtg     600
aaacagacct acctcgcccg ggtgtttagc taccccgccg gcaatgtgga gagcactggt     660
```

```
tccgctggcg agcctttata cgagaacagc cccgaattta cccccttacct cgagaccaat    720
ttaggacagc ccaccatcca aagctttgag caagttggca caaaggtgaa tgtgacagtg    780
gaggacgagc ggactttagt gcggcggaac acaccttttc tcagcctccg ggatgtgttc    840
ggcaaagatt taatctacac actgtattac tggaagtcct cttcctccgg caagaagaca    900
gctaaaacca acacaaacga gttttttaatc gacgtggata aaggcgaaaa ctactgtttc    960
agcgtgcaag ctgtgatccc ctcccggacc gtgaatagga aaagcaccga tagcccgtt   1020
gagtgcatgg gccaagaaaa gggcgagttc cgggaggcac ctacttcaag ttctacaaag   1080
aaaacacagc tacaactgga gcatttactg ctggatttac agatgatttt gaatggaatt   1140
aataattaca agaatcccaa actcaccagg atgctcacat ttaagttttta catgcccaag   1200
aaggccacag aactgaaaca tcttcagtgt ctagaagaag aactcaaacc tctgaggaa   1260
gtgctaaatt tagctcaaag caaaaacttt cacttaagac ccagggactt aatcagcaat   1320
atcaacgtaa tagttctgga actaaaggga tctgaaacaa cattcatgtg tgaatatgct   1380
gatgagacag caaccattgt agaatttctg aacagatgga ttacctttttg tcaaagcatc   1440
atctcaacac taact                                                    1455

<210> SEQ ID NO 12
<211> LENGTH: 1509
<212> TYPE: DNA
<213> ORGANISM: Artificial Sequence
<220> FEATURE:
<223> OTHER INFORMATION: Description of Artificial Sequence: Synthetic
      polynucleotide

<400> SEQUENCE: 12
atgaagtggg tgaccttcat cagcctgctg ttcctgttct ccagcgccta ctccgccccc     60
acctcctcct ccaccaagaa gacccagctg cagctggagc atttactgct ggatttacag    120
atgattttaa acggcatcaa caactacaag aaccccaagc tgactcgtat gctgaccttc    180
aagttctaca tgcccaagaa ggccaccgag ctgaagcatt acagtgtttt agaggaggag    240
ctgaagcccc tcgaggaggt gctgaattta gcccagtcca agaatttcca tttaaggccc    300
cgggatttaa tcagcaacat caacgtgatc gttttagagc tgaagggctc cgagaccacc    360
ttcatgtgcg agtacgccga cgagaccgcc accatcgtgg agttttttaaa tcgttggatc    420
accttctgcc agtccatcat ctccacttta accagcggca caaccaacac agtcgctgcc    480
tataacctca cttggaagag caccaacttc aaaaccatcc tcgaatggga acccaaaccc    540
gttaaccaag tttacaccgt gcagatcagc accaagtccg gcgactggaa gtccaaatgt    600
ttctatacca ccgacaccga gtgcgatctc accgatgaga tcgtgaaaga tgtgaaacag    660
acctacctcg cccgggtgtt tagctacccc gccggcaatg tggagagcac tggttccgct    720
ggcgagcctt tatacgagaa cagccccgaa tttacccctt acctcgagac caatttagga    780
cagcccacca tccaaagctt tgagcaagtt ggcacaaagg tgaatgtgac agtggaggac    840
gagcggactt tagtgcggcg gaacaacacc tttctcagcc tccgggatgt gttcggcaaa    900
gatttaatct acacactgta ttactggaag tcctcttcct ccggcaagaa gacagctaaa    960
accaacacaa acgagttttt aatcgacgtg gataaaggcg aaaactactg tttcagcgtg   1020
caagctgtga tccctcccg gaccgtgaat aggaaaagca ccgatagccc cgttgagtgc   1080
atgggccaag aaaagggcga gttccgggag gcacctactt caagttctac aaagaaaaca   1140
cagctacaac tggagcattt actgctggat ttacagatga ttttgaatgg aattaataat   1200
```

```
tacaagaatc ccaaactcac caggatgctc acatttaagt tttacatgcc caagaaggcc   1260
acagaactga acatcttca gtgtctagaa gaagaactca aacctctgga ggaagtgcta   1320
aatttagctc aaagcaaaaa ctttcactta agacccaggg acttaatcag caatatcaac   1380
gtaatagttc tggaactaaa gggatctgaa acaacattca tgtgtgaata tgctgatgag   1440
acagcaacca ttgtagaatt tctgaacaga tggattacct tttgtcaaag catcatctca   1500
acactaact                                                           1509

<210> SEQ ID NO 13
<211> LENGTH: 657
<212> TYPE: DNA
<213> ORGANISM: Homo sapiens

<400> SEQUENCE: 13
agcggcacaa ccaacacagt cgctgcctat aacctcactt ggaagagcac caacttcaaa    60
accatcctcg aatgggaacc caaacccgtt aaccaagttt acaccgtgca gatcagcacc   120
aagtccggcg actggaagtc caaatgtttc tataccaccg acaccgagtg cgatctcacc   180
gatgagatcg tgaaagatgt gaaacagacc tacctcgccc gggtgtttag ctaccccgcc   240
ggcaatgtgg agagcactgg ttccgctggc gagcctttat acgagaacag ccccgaattt   300 acccccttacc tcgagaccaa tttaggacag cccaccatcc aaagctttga gcaagttggc   360
acaaaggtga atgtgacagt ggaggacgag cggactttag tgcggcggaa caacaccttt   420
ctcagcctcc gggatgtgtt cggcaaagat ttaatctaca cactgtatta ctggaagtcc   480
tcttcctccg gcaagaagac agctaaaacc aacacaaacg agtttttaat cgacgtggat   540
aaaggcgaaa actactgttt cagcgtgcaa gctgtgatcc cctcccggac cgtgaatagg   600
aaaagcaccg atagccccgt tgagtgcatg ggccaagaaa agggcgagtt ccgggag     657

<210> SEQ ID NO 14
<211> LENGTH: 223
<212> TYPE: PRT
<213> ORGANISM: Mus musculus

<400> SEQUENCE: 14

Ala Gly Ile Pro Glu Lys Ala Phe Asn Leu Thr Trp Ile Ser Thr Asp
1               5                   10                  15

Phe Lys Thr Ile Leu Glu Trp Gln Pro Lys Pro Thr Asn Tyr Thr Tyr
            20                  25                  30

Thr Val Gln Ile Ser Asp Arg Ser Arg Asn Trp Lys Asn Lys Cys Phe
        35                  40                  45

Ser Thr Thr Asp Thr Glu Cys Asp Leu Thr Asp Glu Ile Val Lys Asp
    50                  55                  60

Val Thr Trp Ala Tyr Glu Ala Lys Val Leu Ser Val Pro Arg Arg Asn
65                  70                  75                  80

Ser Val His Gly Asp Gly Asp Gln Leu Val Ile His Gly Glu Glu Pro
                85                  90                  95

Pro Phe Thr Asn Ala Pro Lys Phe Leu Pro Tyr Arg Asp Thr Asn Leu
            100                 105                 110

Gly Gln Pro Val Ile Gln Phe Glu Gln Asp Gly Arg Lys Leu Asn
        115                 120                 125

Val Val Val Lys Asp Ser Leu Thr Leu Val Arg Lys Asn Gly Thr Phe
    130                 135                 140

Leu Thr Leu Arg Gln Val Phe Gly Lys Asp Leu Gly Tyr Ile Ile Thr
```

```
145                 150                 155                 160
Tyr Arg Lys Gly Ser Ser Thr Gly Lys Thr Asn Ile Thr Asn Thr
                165                 170                 175

Asn Glu Phe Ser Ile Asp Val Glu Glu Gly Val Ser Tyr Cys Phe Phe
                180                 185                 190

Val Gln Ala Met Ile Phe Ser Arg Lys Thr Asn Gln Asn Ser Pro Gly
                195                 200                 205

Ser Ser Thr Val Cys Thr Glu Gln Trp Lys Ser Phe Leu Gly Glu
                210                 215                 220

<210> SEQ ID NO 15
<211> LENGTH: 224
<212> TYPE: PRT
<213> ORGANISM: Rattus rattus

<400> SEQUENCE: 15

Ala Gly Thr Pro Pro Gly Lys Ala Phe Asn Leu Thr Trp Ile Ser Thr
1               5                   10                  15

Asp Phe Lys Thr Ile Leu Glu Trp Gln Pro Lys Pro Thr Asn Tyr Thr
                20                  25                  30

Tyr Thr Val Gln Ile Ser Asp Arg Ser Arg Asn Trp Lys Tyr Lys Cys
                35                  40                  45

Thr Gly Thr Thr Asp Thr Glu Cys Asp Leu Thr Asp Glu Ile Val Lys
            50                  55                  60

Asp Val Asn Trp Thr Tyr Glu Ala Arg Val Leu Ser Val Pro Trp Arg
65              70                  75                  80

Asn Ser Thr His Gly Lys Glu Thr Leu Phe Gly Thr His Gly Glu Glu
                85                  90                  95

Pro Pro Phe Thr Asn Ala Arg Lys Phe Leu Pro Tyr Arg Asp Thr Lys
                100                 105                 110

Ile Gly Gln Pro Val Ile Gln Lys Tyr Glu Gln Gly Gly Thr Lys Leu
                115                 120                 125

Lys Val Thr Val Lys Asp Ser Phe Thr Leu Val Arg Lys Asn Gly Thr
            130                 135                 140

Phe Leu Thr Leu Arg Gln Val Phe Gly Asn Asp Leu Gly Tyr Ile Leu
145                 150                 155                 160

Thr Tyr Arg Lys Asp Ser Ser Thr Gly Arg Lys Thr Asn Thr Thr His
                165                 170                 175

Thr Asn Glu Phe Leu Ile Asp Val Glu Lys Gly Val Ser Tyr Cys Phe
                180                 185                 190

Phe Ala Gln Ala Val Ile Phe Ser Arg Lys Thr Asn His Lys Ser Pro
                195                 200                 205

Glu Ser Ile Thr Lys Cys Thr Glu Gln Trp Lys Ser Val Leu Gly Glu
                210                 215                 220

<210> SEQ ID NO 16
<211> LENGTH: 219
<212> TYPE: PRT
<213> ORGANISM: Artificial Sequence
<220> FEATURE:
<223> OTHER INFORMATION: Description of Artificial Sequence: Synthetic
      polypeptide

<400> SEQUENCE: 16

Ser Gly Thr Thr Asn Thr Val Ala Ala Tyr Asn Leu Thr Trp Lys Ser
1               5                   10                  15

Thr Asn Phe Ala Thr Ala Leu Glu Trp Glu Pro Lys Pro Val Asn Gln
```

```
                20                  25                  30
Val Tyr Thr Val Gln Ile Ser Thr Lys Ser Gly Asp Trp Lys Ser Lys
            35                  40                  45

Cys Phe Tyr Thr Thr Asp Thr Glu Cys Ala Leu Thr Asp Glu Ile Val
        50                  55                  60

Lys Asp Val Lys Gln Thr Tyr Leu Ala Arg Val Phe Ser Tyr Pro Ala
 65                 70                  75                  80

Gly Asn Val Glu Ser Thr Gly Ser Ala Gly Glu Pro Leu Tyr Glu Asn
                85                  90                  95

Ser Pro Glu Phe Thr Pro Tyr Leu Glu Thr Asn Leu Gly Gln Pro Thr
            100                 105                 110

Ile Gln Ser Phe Glu Gln Val Gly Thr Lys Val Asn Val Thr Val Glu
        115                 120                 125

Asp Glu Arg Thr Leu Val Ala Arg Asn Asn Thr Ala Leu Ser Leu Arg
    130                 135                 140

Asp Val Phe Gly Lys Asp Leu Ile Tyr Thr Leu Tyr Tyr Trp Lys Ser
145                 150                 155                 160

Ser Ser Ser Gly Lys Lys Thr Ala Lys Thr Asn Thr Asn Glu Phe Leu
                165                 170                 175

Ile Asp Val Asp Lys Gly Glu Asn Tyr Cys Phe Ser Val Gln Ala Val
            180                 185                 190

Ile Pro Ser Arg Thr Val Asn Arg Lys Ser Thr Asp Ser Pro Val Glu
        195                 200                 205

Cys Met Gly Gln Glu Lys Gly Glu Phe Arg Glu
    210                 215

<210> SEQ ID NO 17
<211> LENGTH: 219
<212> TYPE: PRT
<213> ORGANISM: Artificial Sequence
<220> FEATURE:
<223> OTHER INFORMATION: Description of Artificial Sequence: Synthetic
      polypeptide

<400> SEQUENCE: 17

Ser Gly Thr Thr Asn Thr Val Ala Ala Tyr Asn Leu Thr Trp Lys Ser
1               5                   10                  15

Thr Asn Phe Ala Thr Ala Leu Glu Trp Glu Pro Lys Pro Val Asn Gln
            20                  25                  30

Val Tyr Thr Val Gln Ile Ser Thr Lys Ser Gly Asp Ala Lys Ser Lys
            35                  40                  45

Cys Phe Tyr Thr Thr Asp Thr Glu Cys Ala Leu Thr Asp Glu Ile Val
        50                  55                  60

Lys Asp Val Lys Gln Thr Tyr Leu Ala Arg Val Phe Ser Tyr Pro Ala
 65                 70                  75                  80

Gly Asn Val Glu Ser Thr Gly Ser Ala Gly Glu Pro Leu Ala Glu Asn
                85                  90                  95

Ser Pro Glu Phe Thr Pro Tyr Leu Glu Thr Asn Leu Gly Gln Pro Thr
            100                 105                 110

Ile Gln Ser Phe Glu Gln Val Gly Thr Lys Val Asn Val Thr Val Glu
        115                 120                 125

Asp Glu Arg Thr Leu Val Ala Arg Asn Asn Thr Ala Leu Ser Leu Arg
    130                 135                 140

Asp Val Phe Gly Lys Asp Leu Ile Tyr Thr Leu Tyr Tyr Trp Lys Ser
145                 150                 155                 160
```

```
Ser Ser Ser Gly Lys Lys Thr Ala Lys Thr Asn Thr Asn Glu Phe Leu
            165                 170                 175

Ile Asp Val Asp Lys Gly Glu Asn Tyr Cys Phe Ser Val Gln Ala Val
        180                 185                 190

Ile Pro Ser Arg Thr Val Asn Arg Lys Ser Thr Asp Ser Pro Val Glu
    195                 200                 205

Cys Met Gly Gln Glu Lys Gly Glu Phe Arg Glu
210                 215
```

```
<210> SEQ ID NO 18
<211> LENGTH: 15
<212> TYPE: PRT
<213> ORGANISM: Artificial Sequence
<220> FEATURE:
<223> OTHER INFORMATION: Description of Artificial Sequence: Synthetic
      peptide

<400> SEQUENCE: 18

Gly Gly Gly Gly Ser Gly Gly Gly Gly Ser Gly Gly Gly Gly Ser
1               5                   10                  15

<210> SEQ ID NO 19
<211> LENGTH: 45
<212> TYPE: DNA
<213> ORGANISM: Artificial Sequence
<220> FEATURE:
<223> OTHER INFORMATION: Description of Artificial Sequence: Synthetic
      oligonucleotide

<400> SEQUENCE: 19
ggcggtggag gatccggagg aggtggctcc ggcggcggag gatct                45

<210> SEQ ID NO 20
<211> LENGTH: 8
<212> TYPE: PRT
<213> ORGANISM: Artificial Sequence
<220> FEATURE:
<223> OTHER INFORMATION: Description of Artificial Sequence: Synthetic
      peptide

<400> SEQUENCE: 20

Gly Gly Gly Ser Gly Gly Gly Ser
1               5

<210> SEQ ID NO 21
<211> LENGTH: 119
<212> TYPE: PRT
<213> ORGANISM: Artificial Sequence
<220> FEATURE:
<223> OTHER INFORMATION: Description of Artificial Sequence: Synthetic
      polypeptide

<400> SEQUENCE: 21

Gln Val Gln Leu Gln Gln Ser Gly Ala Glu Leu Ala Arg Pro Gly Ala
1               5                   10                  15

Ser Val Lys Met Ser Cys Lys Ala Ser Gly Tyr Thr Phe Thr Arg Tyr
            20                  25                  30

Thr Met His Trp Val Lys Gln Arg Pro Gly Gln Gly Leu Glu Trp Ile
        35                  40                  45

Gly Tyr Ile Asn Pro Ser Arg Gly Tyr Thr Asn Tyr Asn Gln Lys Phe
    50                  55                  60

Lys Asp Lys Ala Thr Leu Thr Thr Asp Lys Ser Ser Ser Thr Ala Tyr
65                  70                  75                  80
```

```
Met Gln Leu Ser Ser Leu Thr Ser Glu Asp Ser Ala Val Tyr Tyr Cys
            85                  90                  95

Ala Arg Tyr Tyr Asp Asp His Tyr Cys Leu Asp Tyr Trp Gly Gln Gly
        100                 105                 110

Thr Thr Leu Thr Val Ser Ser
        115

<210> SEQ ID NO 22
<211> LENGTH: 107
<212> TYPE: PRT
<213> ORGANISM: Artificial Sequence
<220> FEATURE:
<223> OTHER INFORMATION: Description of Artificial Sequence: Synthetic
      polypeptide

<400> SEQUENCE: 22

Gln Ile Val Leu Thr Gln Ser Pro Ala Ile Met Ser Ala Ser Pro Gly
1               5                   10                  15

Glu Lys Val Thr Met Thr Cys Ser Ala Ser Ser Val Ser Tyr Met
            20                  25                  30

Asn Trp Tyr Gln Gln Lys Ser Gly Thr Ser Pro Lys Arg Trp Ile Tyr
        35                  40                  45

Asp Thr Ser Lys Leu Ala Ser Gly Val Pro Ala His Phe Arg Gly Ser
    50                  55                  60

Gly Ser Gly Thr Ser Tyr Ser Leu Thr Ile Ser Gly Met Glu Ala Glu
65                  70                  75                  80

Asp Ala Ala Thr Tyr Tyr Cys Gln Gln Trp Ser Ser Asn Pro Phe Thr
                85                  90                  95

Phe Gly Ser Gly Thr Lys Leu Glu Ile Asn Arg
            100                 105

<210> SEQ ID NO 23
<211> LENGTH: 357
<212> TYPE: DNA
<213> ORGANISM: Artificial Sequence
<220> FEATURE:
<223> OTHER INFORMATION: Description of Artificial Sequence: Synthetic
      polynucleotide

<400> SEQUENCE: 23
caagttcagc tccagcaaag cggcgccgaa ctcgctcggc ccggcgcttc cgtgaagatg      60
tcttgtaagg cctccggcta taccttcacc cggtacacaa tgcactgggt caagcaacgg    120
cccggtcaag gtttagagtg gattggctat atcaacccct ccggggcta taccaactac     180 aaccagaagt tcaaggacaa agccacctc accaccgaca gtccagcag caccgcttac      240 atgcagctga gctctttaac atccgaggat tccgccgtgt actactgcgc tcggtactac    300
gacgatcatt actgcctcga ttactggggc caaggtacca ccttaacagt ctcctcc      357

<210> SEQ ID NO 24
<211> LENGTH: 321
<212> TYPE: DNA
<213> ORGANISM: Artificial Sequence
<220> FEATURE:
<223> OTHER INFORMATION: Description of Artificial Sequence: Synthetic
      polynucleotide

<400> SEQUENCE: 24
cagatcgtgc tgacccagtc ccccgctatt atgagcgcta gccccggtga aaaggtgact     60
atgacatgca gcgccagctc ttccgtgagc tacatgaact ggtatcagca gaagtccggc   120
```

```
accagcccta aaaggtggat ctacgacacc agcaagctgg ccagcggcgt ccccgctcac    180
tttcggggct ccggctccgg aacaagctac tctctgacca tcagcggcat ggaagccgag    240
gatgccgcta cctattactg tcagcagtgg agctccaacc ccttcacctt tggatccggc    300
accaagctcg agattaatcg t                                              321
```

<210> SEQ ID NO 25
<211> LENGTH: 723
<212> TYPE: DNA
<213> ORGANISM: Artificial Sequence
<220> FEATURE:
<223> OTHER INFORMATION: Description of Artificial Sequence: Synthetic polynucleotide

<400> SEQUENCE: 25

```
cagatcgtgc tgacccagtc ccccgctatt atgagcgcta gccccggtga aaaggtgact    60
atgacatgca gcgccagctc tttccgtgagc tacatgaact ggtatcagca gaagtccggc    120
accagcccta aaggtggat ctacgacacc agcaagctgg ccagcggcgt ccccgctcac     180
tttcggggct ccggctccgg aacaagctac tctctgacca tcagcggcat ggaagccgag    240
gatgccgcta cctattactg tcagcagtgg agctccaacc ccttcacctt tggatccggc    300
accaagctcg agattaatcg tggaggcgga ggtagcggag gaggcggatc cggcggtgga    360
ggtagccaag ttcagctcca gcaaagcggc gccgaactcg ctcggcccgg cgcttccgtg    420
aagatgtctt gtaaggcctc cggctatacc ttcacccggt acacaatgca ctgggtcaag    480
caacggcccg gtcaaggttt agagtggatt ggctatatca ccccctcccg ggctatacc    540 aactacaacc agaagttcaa ggacaaagcc accctcacca ccgacaagtc cagcagcacc    600
gcttacatgc agctgagctc tttaacatcc gaggattccg ccgtgtacta ctgcgctcgg    660
tactacgacg atcattactg cctcgattac tggggccaag gtaccacctt aacagtctcc    720
tcc                                                                  723
```

<210> SEQ ID NO 26
<211> LENGTH: 107
<212> TYPE: PRT
<213> ORGANISM: Artificial Sequence
<220> FEATURE:
<223> OTHER INFORMATION: Description of Artificial Sequence: Synthetic polypeptide

<400> SEQUENCE: 26

```
Asp Ile Glu Met Thr Gln Ser Pro Ala Ile Met Ser Ala Ser Leu Gly
1               5                   10                  15

Glu Arg Val Thr Met Thr Cys Thr Ala Ser Ser Val Ser Ser Ser
            20                  25                  30

Tyr Phe His Trp Tyr Gln Gln Lys Pro Gly Ser Ser Pro Lys Leu Cys
        35                  40                  45

Ile Tyr Ser Thr Ser Asn Leu Ala Ser Gly Val Pro Pro Arg Phe Ser
    50                  55                  60

Gly Ser Gly Ser Thr Ser Tyr Ser Leu Thr Ile Ser Ser Met Glu Ala
65                  70                  75                  80

Glu Asp Ala Ala Thr Tyr Phe Cys His Gln Tyr His Arg Ser Pro Thr
                85                  90                  95

Phe Gly Gly Gly Thr Lys Leu Glu Thr Lys Arg
            100                 105
```

<210> SEQ ID NO 27

```
<211> LENGTH: 114
<212> TYPE: PRT
<213> ORGANISM: Artificial Sequence
<220> FEATURE:
<223> OTHER INFORMATION: Description of Artificial Sequence: Synthetic
      polypeptide

<400> SEQUENCE: 27

Val Gln Leu Gln Gln Ser Gly Pro Glu Leu Val Lys Pro Gly Ala Ser
1               5                   10                  15

Val Lys Met Ser Cys Lys Ala Ser Gly Tyr Thr Phe Thr Ser Tyr Val
            20                  25                  30

Ile Gln Trp Val Lys Gln Lys Pro Gly Gln Gly Leu Glu Trp Ile Gly
        35                  40                  45

Ser Ile Asn Pro Tyr Asn Asp Tyr Thr Lys Tyr Asn Glu Lys Phe Lys
    50                  55                  60

Gly Lys Ala Thr Leu Thr Ser Asp Lys Ser Ser Ile Thr Ala Tyr Met
65                  70                  75                  80

Glu Phe Ser Ser Leu Thr Ser Glu Asp Ser Ala Leu Tyr Tyr Cys Ala
                85                  90                  95

Arg Trp Gly Asp Gly Asn Tyr Trp Gly Arg Gly Thr Thr Leu Thr Val
            100                 105                 110

Ser Ser

<210> SEQ ID NO 28
<211> LENGTH: 321
<212> TYPE: DNA
<213> ORGANISM: Artificial Sequence
<220> FEATURE:
<223> OTHER INFORMATION: Description of Artificial Sequence: Synthetic
      polynucleotide

<400> SEQUENCE: 28
gacatcgaga tgacacagtc ccccgctatc atgagcgcct ctttaggaga acgtgtgacc     60
atgacttgta cagcttcctc cagcgtgagc agctcctatt ccactggta ccagcagaaa    120 cccggctcct ccctaaaact gtgtatctac tccacaagca atttagctag cggcgtgcct    180
cctcgtttta gcggctccgg cagcacctct tactctttaa ccattagctc tatggaggcc    240
gaagatgccg ccacatactt ttgccatcag taccaccggt ccctacctt tggcggaggc     300 acaaagctgg agaccaagcg g                                              321

<210> SEQ ID NO 29
<211> LENGTH: 342
<212> TYPE: DNA
<213> ORGANISM: Artificial Sequence
<220> FEATURE:
<223> OTHER INFORMATION: Description of Artificial Sequence: Synthetic
      polynucleotide

<400> SEQUENCE: 29
gtgcagctgc agcagtccgg acccgaactg gtcaagcccg gtgcctccgt gaaaatgtct     60
tgtaaggctt ctggctacac ctttacctcc tacgtcatcc aatgggtgaa gcagaagccc    120
ggtcaaggtc tcgagtggat cggcagcatc aatccctaca cgattacac caagtataac    180 gaaaagttta agggcaaggc cactctgaca agcgacaaga gctccattac cgcctacatg    240
gagttttcct ctttaacttc tgaggactcc gctttatact attgcgctcg ttggggcgat    300
ggcaattatt ggggccgggg aactacttta acagtgagct cc                       342
```

```
<210> SEQ ID NO 30
<211> LENGTH: 708
<212> TYPE: DNA
<213> ORGANISM: Artificial Sequence
<220> FEATURE:
<223> OTHER INFORMATION: Description of Artificial Sequence: Synthetic
      polynucleotide

<400> SEQUENCE: 30
gtgcagctgc agcagtccgg acccgaactg gtcaagcccg gtgcctccgt gaaaatgtct      60
tgtaaggctt ctggctacac ctttacctcc tacgtcatcc aatgggtgaa gcagaagccc     120
ggtcaaggtc tcgagtggat cggcagcatc aatccctaca acgattacac caagtataac     180
gaaaagttta agggcaaggc cactctgaca agcgacaaga gctccattac cgcctacatg     240
gagttttcct ctttaacttc tgaggactcc gctttatact attgcgctcg ttggggcgat     300
ggcaattatt ggggccgggg aactacttta acagtgagct ccggcggcgg cggaagcgga     360
ggtggaggat ctggcggtgg aggcagcgac atcgagatga cacagtcccc cgctatcatg     420
agcgcctctt taggagaacg tgtgaccatg acttgtacag cttcctccag cgtgagcagc     480
tcctatttcc actggtacca gcagaaaccc ggctcctccc ctaaactgtg tatctactcc     540
acaagcaatt tagctagcgg cgtgcctcct cgttttagcg gctccggcag cacctcttac     600
tctttaacca ttagctctat ggaggccgaa gatgccgcca catacttttg ccatcagtac     660
caccggtccc ctacctttgg cggaggcaca aagctggaga ccaagcgg               708

<210> SEQ ID NO 31
<211> LENGTH: 399
<212> TYPE: DNA
<213> ORGANISM: Homo sapiens

<400> SEQUENCE: 31
gcacctactt caagttctac aaagaaaaca cagctacaac tggagcattt actgctggat      60
ttacagatga ttttgaatgg aattaataat tacaagaatc ccaaactcac caggatgctc     120
acatttaagt tttacatgcc caagaaggcc acagaactga acatcttca gtgtctagaa      180 gaagaactca aacctctgga ggaagtgcta aatttagctc aaagcaaaaa ctttcactta     240
agacccaggg acttaatcag caatatcaac gtaatagttc tggaactaaa gggatctgaa     300
acaacattca tgtgtgaata tgctgatgag acagcaacca ttgtagaatt tctgaacaga     360
tggattacct tttgtcaaag catcatctca acactaact                            399

<210> SEQ ID NO 32
<211> LENGTH: 399
<212> TYPE: DNA
<213> ORGANISM: Homo sapiens

<400> SEQUENCE: 32
gcccccacct cctcctccac caagaagacc cagctgcagc tggagcattt actgctggat      60
ttacagatga ttttaaacgg catcaacaac tacaagaacc ccaagctgac tcgtatgctg     120
accttcaagt tctacatgcc caagaaggcc accgagctga gcatttaca gtgtttagag      180 gaggagctga gcccctcga ggaggtgctg aatttagccc agtccaagaa tttccattta     240
aggccccggg atttaatcag caacatcaac gtgatcgttt tagagctgaa gggctccgag     300
accaccttca tgtgcgagta cgccgacgag accgccacca tcgtggagtt tttaaatcgt     360
tggatcacct tctgccagtc catcatctcc actttaacc                            399
```

```
<210> SEQ ID NO 33
<211> LENGTH: 18
<212> TYPE: PRT
<213> ORGANISM: Artificial Sequence
<220> FEATURE:
<223> OTHER INFORMATION: Description of Artificial Sequence: Synthetic
      peptide

<400> SEQUENCE: 33

Met Lys Trp Val Thr Phe Ile Ser Leu Leu Phe Leu Phe Ser Ser Ala
1               5                   10                  15

Tyr Ser

<210> SEQ ID NO 34
<211> LENGTH: 54
<212> TYPE: DNA
<213> ORGANISM: Artificial Sequence
<220> FEATURE:
<223> OTHER INFORMATION: Description of Artificial Sequence: Synthetic
      oligonucleotide

<400> SEQUENCE: 34
atgaaatggg tgacctttat ttctttactg ttcctcttta gcagcgccta ctcc            54

<210> SEQ ID NO 35
<211> LENGTH: 54
<212> TYPE: DNA
<213> ORGANISM: Artificial Sequence
<220> FEATURE:
<223> OTHER INFORMATION: Description of Artificial Sequence: Synthetic
      oligonucleotide

<400> SEQUENCE: 35
atgaagtggg tcacatttat ctctttactg ttcctcttct ccagcgccta cagc            54

<210> SEQ ID NO 36
<211> LENGTH: 54
<212> TYPE: DNA
<213> ORGANISM: Artificial Sequence
<220> FEATURE:
<223> OTHER INFORMATION: Description of Artificial Sequence: Synthetic
      oligonucleotide

<400> SEQUENCE: 36
atgaaatggg tgacctttat ttctttactg ttcctcttta gcagcgccta ctcc            54

<210> SEQ ID NO 37
<211> LENGTH: 16
<212> TYPE: PRT
<213> ORGANISM: Artificial Sequence
<220> FEATURE:
<223> OTHER INFORMATION: Description of Artificial Sequence: Synthetic
      peptide

<400> SEQUENCE: 37

Met Lys Cys Leu Leu Tyr Leu Ala Phe Leu Phe Leu Gly Val Asn Cys
1               5                   10                  15

<210> SEQ ID NO 38
<211> LENGTH: 58
<212> TYPE: PRT
<213> ORGANISM: Artificial Sequence
<220> FEATURE:
<223> OTHER INFORMATION: Description of Artificial Sequence: Synthetic
      polypeptide

<400> SEQUENCE: 38
```

```
Met Gly Gln Ile Val Thr Met Phe Glu Ala Leu Pro His Ile Ile Asp
1               5                   10                  15

Glu Val Ile Asn Ile Val Ile Val Leu Ile Ile Thr Ser Ile
            20                  25                  30

Lys Ala Val Tyr Asn Phe Ala Thr Cys Gly Ile Leu Ala Leu Val Ser
            35                  40                  45

Phe Leu Phe Leu Ala Gly Arg Ser Cys Gly
    50                  55

<210> SEQ ID NO 39
<211> LENGTH: 97
<212> TYPE: PRT
<213> ORGANISM: Artificial Sequence
<220> FEATURE:
<223> OTHER INFORMATION: Description of Artificial Sequence: Synthetic
      polypeptide

<400> SEQUENCE: 39

Met Pro Asn His Gln Ser Gly Ser Pro Thr Gly Ser Ser Asp Leu Leu
1               5                   10                  15

Leu Ser Gly Lys Lys Gln Arg Pro His Leu Ala Leu Arg Arg Lys Arg
            20                  25                  30

Arg Arg Glu Met Arg Lys Ile Asn Arg Lys Val Arg Met Asn Leu
            35                  40                  45

Ala Pro Ile Lys Glu Lys Thr Ala Trp Gln His Leu Gln Ala Leu Ile
    50                  55                  60

Ser Glu Ala Glu Val Leu Lys Thr Ser Gln Thr Pro Gln Asn Ser
65                  70                  75                  80

Leu Thr Leu Phe Leu Ala Leu Leu Ser Val Leu Gly Pro Pro Val Thr
                85                  90                  95

Gly

<210> SEQ ID NO 40
<211> LENGTH: 30
<212> TYPE: PRT
<213> ORGANISM: Artificial Sequence
<220> FEATURE:
<223> OTHER INFORMATION: Description of Artificial Sequence: Synthetic
      polypeptide

<400> SEQUENCE: 40

Met Asp Ser Lys Gly Ser Ser Gln Lys Gly Ser Arg Leu Leu Leu Leu
1               5                   10                  15

Leu Val Val Ser Asn Leu Leu Leu Cys Gln Gly Val Val Ser
            20                  25                  30

<210> SEQ ID NO 41
<211> LENGTH: 15
<212> TYPE: PRT
<213> ORGANISM: Artificial Sequence
<220> FEATURE:
<223> OTHER INFORMATION: Description of Artificial Sequence: Synthetic
      peptide

<400> SEQUENCE: 41

Gly Leu Asn Asp Ile Phe Glu Ala Gln Lys Ile Glu Trp His Glu
1               5                   10                  15

<210> SEQ ID NO 42
<211> LENGTH: 26
<212> TYPE: PRT
<213> ORGANISM: Artificial Sequence
```

```
<220> FEATURE:
<223> OTHER INFORMATION: Description of Artificial Sequence: Synthetic
      peptide

<400> SEQUENCE: 42

Lys Arg Arg Trp Lys Lys Asn Phe Ile Ala Val Ser Ala Ala Asn Arg
1               5                   10                  15

Phe Lys Lys Ile Ser Ser Ser Gly Ala Leu
            20                  25

<210> SEQ ID NO 43
<211> LENGTH: 6
<212> TYPE: PRT
<213> ORGANISM: Artificial Sequence
<220> FEATURE:
<223> OTHER INFORMATION: Description of Artificial Sequence: Synthetic
      peptide

<400> SEQUENCE: 43

Glu Glu Glu Glu Glu Glu
1               5

<210> SEQ ID NO 44
<211> LENGTH: 13
<212> TYPE: PRT
<213> ORGANISM: Artificial Sequence
<220> FEATURE:
<223> OTHER INFORMATION: Description of Artificial Sequence: Synthetic
      peptide

<400> SEQUENCE: 44

Gly Ala Pro Val Pro Tyr Pro Asp Pro Leu Glu Pro Arg
1               5                   10

<210> SEQ ID NO 45
<211> LENGTH: 8
<212> TYPE: PRT
<213> ORGANISM: Artificial Sequence
<220> FEATURE:
<223> OTHER INFORMATION: Description of Artificial Sequence: Synthetic
      peptide

<400> SEQUENCE: 45

Asp Tyr Lys Asp Asp Asp Asp Lys
1               5

<210> SEQ ID NO 46
<211> LENGTH: 9
<212> TYPE: PRT
<213> ORGANISM: Artificial Sequence
<220> FEATURE:
<223> OTHER INFORMATION: Description of Artificial Sequence: Synthetic
      peptide

<400> SEQUENCE: 46

Tyr Pro Tyr Asp Val Pro Asp Tyr Ala
1               5

<210> SEQ ID NO 47
<211> LENGTH: 5
<212> TYPE: PRT
<213> ORGANISM: Artificial Sequence
<220> FEATURE:
<223> OTHER INFORMATION: Description of Artificial Sequence: Synthetic
      peptide

<400> SEQUENCE: 47
```

His His His His His
1               5

<210> SEQ ID NO 48
<211> LENGTH: 6
<212> TYPE: PRT
<213> ORGANISM: Artificial Sequence
<220> FEATURE:
<223> OTHER INFORMATION: Description of Artificial Sequence: Synthetic
      peptide

<400> SEQUENCE: 48

His His His His His His
1               5

<210> SEQ ID NO 49
<211> LENGTH: 7
<212> TYPE: PRT
<213> ORGANISM: Artificial Sequence
<220> FEATURE:
<223> OTHER INFORMATION: Description of Artificial Sequence: Synthetic
      peptide

<400> SEQUENCE: 49

His His His His His His His
1               5

<210> SEQ ID NO 50
<211> LENGTH: 8
<212> TYPE: PRT
<213> ORGANISM: Artificial Sequence
<220> FEATURE:
<223> OTHER INFORMATION: Description of Artificial Sequence: Synthetic
      peptide

<400> SEQUENCE: 50

His His His His His His His His
1               5

<210> SEQ ID NO 51
<211> LENGTH: 9
<212> TYPE: PRT
<213> ORGANISM: Artificial Sequence
<220> FEATURE:
<223> OTHER INFORMATION: Description of Artificial Sequence: Synthetic
      peptide

<400> SEQUENCE: 51

His His His His His His His His His
1               5

<210> SEQ ID NO 52
<211> LENGTH: 10
<212> TYPE: PRT
<213> ORGANISM: Artificial Sequence
<220> FEATURE:
<223> OTHER INFORMATION: Description of Artificial Sequence: Synthetic
      peptide

<400> SEQUENCE: 52

His His His His His His His His His His
1               5                   10

<210> SEQ ID NO 53
<211> LENGTH: 10
<212> TYPE: PRT
<213> ORGANISM: Artificial Sequence
<220> FEATURE:

<223> OTHER INFORMATION: Description of Artificial Sequence: Synthetic
      peptide

<400> SEQUENCE: 53

Glu Gln Lys Leu Ile Ser Glu Glu Asp Leu
1               5                   10

<210> SEQ ID NO 54
<211> LENGTH: 18
<212> TYPE: PRT
<213> ORGANISM: Artificial Sequence
<220> FEATURE:
<223> OTHER INFORMATION: Description of Artificial Sequence: Synthetic
      peptide

<400> SEQUENCE: 54

Thr Lys Glu Asn Pro Arg Ser Asn Gln Glu Glu Ser Tyr Asp Asp Asn
1               5                   10                  15

Glu Ser

<210> SEQ ID NO 55
<211> LENGTH: 15
<212> TYPE: PRT
<213> ORGANISM: Artificial Sequence
<220> FEATURE:
<223> OTHER INFORMATION: Description of Artificial Sequence: Synthetic
      peptide

<400> SEQUENCE: 55

Lys Glu Thr Ala Ala Ala Lys Phe Glu Arg Gln His Met Asp Ser
1               5                   10                  15

<210> SEQ ID NO 56
<211> LENGTH: 38
<212> TYPE: PRT
<213> ORGANISM: Artificial Sequence
<220> FEATURE:
<223> OTHER INFORMATION: Description of Artificial Sequence: Synthetic
      polypeptide

<400> SEQUENCE: 56

Met Asp Glu Lys Thr Thr Gly Trp Arg Gly Gly His Val Val Glu Gly
1               5                   10                  15

Leu Ala Gly Glu Leu Glu Gln Leu Arg Ala Arg Leu Glu His His Pro
            20                  25                  30

Gln Gly Gln Arg Glu Pro
        35

<210> SEQ ID NO 57
<211> LENGTH: 13
<212> TYPE: PRT
<213> ORGANISM: Artificial Sequence
<220> FEATURE:
<223> OTHER INFORMATION: Description of Artificial Sequence: Synthetic
      peptide

<400> SEQUENCE: 57

Ser Leu Ala Glu Leu Leu Asn Ala Gly Leu Gly Gly Ser
1               5                   10

<210> SEQ ID NO 58
<211> LENGTH: 8
<212> TYPE: PRT
<213> ORGANISM: Artificial Sequence
<220> FEATURE:
<223> OTHER INFORMATION: Description of Artificial Sequence: Synthetic

```
                         peptide

<400> SEQUENCE: 58

Thr Gln Asp Pro Ser Arg Val Gly
1               5

<210> SEQ ID NO 59
<211> LENGTH: 12
<212> TYPE: PRT
<213> ORGANISM: Artificial Sequence
<220> FEATURE:
<223> OTHER INFORMATION: Description of Artificial Sequence: Synthetic
      peptide

<400> SEQUENCE: 59

Pro Asp Arg Val Arg Ala Val Ser His Trp Ser Ser
1               5                   10

<210> SEQ ID NO 60
<211> LENGTH: 8
<212> TYPE: PRT
<213> ORGANISM: Artificial Sequence
<220> FEATURE:
<223> OTHER INFORMATION: Description of Artificial Sequence: Synthetic
      peptide

<400> SEQUENCE: 60

Trp Ser His Pro Gln Phe Glu Lys
1               5

<210> SEQ ID NO 61
<211> LENGTH: 6
<212> TYPE: PRT
<213> ORGANISM: Artificial Sequence
<220> FEATURE:
<223> OTHER INFORMATION: Description of Artificial Sequence: Synthetic
      peptide

<400> SEQUENCE: 61

Cys Cys Pro Gly Cys Cys
1               5

<210> SEQ ID NO 62
<211> LENGTH: 10
<212> TYPE: PRT
<213> ORGANISM: Artificial Sequence
<220> FEATURE:
<223> OTHER INFORMATION: Description of Artificial Sequence: Synthetic
      peptide

<400> SEQUENCE: 62

Glu Val His Thr Asn Gln Asp Pro Leu Asp
1               5                   10

<210> SEQ ID NO 63
<211> LENGTH: 14
<212> TYPE: PRT
<213> ORGANISM: Artificial Sequence
<220> FEATURE:
<223> OTHER INFORMATION: Description of Artificial Sequence: Synthetic
      peptide

<400> SEQUENCE: 63

Gly Lys Pro Ile Pro Asn Pro Leu Leu Gly Leu Asp Ser Thr
1               5                   10

<210> SEQ ID NO 64
```

```
<211> LENGTH: 11
<212> TYPE: PRT
<213> ORGANISM: Artificial Sequence
<220> FEATURE:
<223> OTHER INFORMATION: Description of Artificial Sequence: Synthetic
      peptide

<400> SEQUENCE: 64

Tyr Thr Asp Ile Glu Met Asn Arg Leu Gly Lys
1               5                   10

<210> SEQ ID NO 65
<211> LENGTH: 8
<212> TYPE: PRT
<213> ORGANISM: Artificial Sequence
<220> FEATURE:
<223> OTHER INFORMATION: Description of Artificial Sequence: Synthetic
      peptide

<400> SEQUENCE: 65

Asp Leu Tyr Asp Asp Asp Asp Lys
1               5

<210> SEQ ID NO 66
<211> LENGTH: 5
<212> TYPE: PRT
<213> ORGANISM: Artificial Sequence
<220> FEATURE:
<223> OTHER INFORMATION: Description of Artificial Sequence: Synthetic
      peptide

<400> SEQUENCE: 66

Asp Tyr Asn Val Tyr
1               5

<210> SEQ ID NO 67
<211> LENGTH: 17
<212> TYPE: PRT
<213> ORGANISM: Artificial Sequence
<220> FEATURE:
<223> OTHER INFORMATION: Description of Artificial Sequence: Synthetic
      peptide

<400> SEQUENCE: 67

Tyr Ile Asp Pro Tyr Asn Gly Ile Thr Ile Tyr Asp Gln Asn Phe Lys
1               5                   10                  15

Gly

<210> SEQ ID NO 68
<211> LENGTH: 8
<212> TYPE: PRT
<213> ORGANISM: Artificial Sequence
<220> FEATURE:
<223> OTHER INFORMATION: Description of Artificial Sequence: Synthetic
      peptide

<400> SEQUENCE: 68

Asp Val Thr Thr Ala Leu Asp Phe
1               5

<210> SEQ ID NO 69
<211> LENGTH: 11
<212> TYPE: PRT
<213> ORGANISM: Artificial Sequence
<220> FEATURE:
<223> OTHER INFORMATION: Description of Artificial Sequence: Synthetic
      peptide
```

```
<400> SEQUENCE: 69

Leu Ala Ser Gln Thr Ile Asp Thr Trp Leu Ala
1               5                   10

<210> SEQ ID NO 70
<211> LENGTH: 7
<212> TYPE: PRT
<213> ORGANISM: Artificial Sequence
<220> FEATURE:
<223> OTHER INFORMATION: Description of Artificial Sequence: Synthetic
      peptide

<400> SEQUENCE: 70

Ala Ala Thr Asn Leu Ala Asp
1               5

<210> SEQ ID NO 71
<211> LENGTH: 9
<212> TYPE: PRT
<213> ORGANISM: Artificial Sequence
<220> FEATURE:
<223> OTHER INFORMATION: Description of Artificial Sequence: Synthetic
      peptide

<400> SEQUENCE: 71

Gln Gln Val Tyr Ser Ser Pro Phe Thr
1               5

<210> SEQ ID NO 72
<211> LENGTH: 117
<212> TYPE: PRT
<213> ORGANISM: Artificial Sequence
<220> FEATURE:
<223> OTHER INFORMATION: Description of Artificial Sequence: Synthetic
      polypeptide

<400> SEQUENCE: 72

Gln Ile Gln Leu Val Gln Ser Gly Gly Glu Val Lys Lys Pro Gly Ala
1               5                   10                  15

Ser Val Arg Val Ser Cys Lys Ala Ser Gly Tyr Ser Phe Thr Asp Tyr
                20                  25                  30

Asn Val Tyr Trp Val Arg Gln Ser Pro Gly Lys Gly Leu Glu Trp Ile
            35                  40                  45

Gly Tyr Ile Asp Pro Tyr Asn Gly Ile Thr Ile Tyr Asp Gln Asn Phe
        50                  55                  60

Lys Gly Lys Ala Thr Leu Thr Val Asp Lys Ser Thr Ser Thr Ala Tyr
65                  70                  75                  80

Met Glu Leu Ser Ser Leu Arg Ser Glu Asp Thr Ala Val Tyr Phe Cys
                85                  90                  95

Ala Arg Asp Val Thr Thr Ala Leu Asp Phe Trp Gly Gln Gly Thr Thr
            100                 105                 110

Val Thr Val Ser Ser
        115

<210> SEQ ID NO 73
<211> LENGTH: 107
<212> TYPE: PRT
<213> ORGANISM: Artificial Sequence
<220> FEATURE:
<223> OTHER INFORMATION: Description of Artificial Sequence: Synthetic
      polypeptide

<400> SEQUENCE: 73
```

```
Asp Ile Gln Met Thr Gln Ser Pro Ala Ser Leu Ser Ala Ser Val Gly
1               5                   10                  15

Asp Arg Val Thr Ile Thr Cys Leu Ala Ser Gln Thr Ile Asp Thr Trp
            20                  25                  30

Leu Ala Trp Tyr Leu Gln Lys Pro Gly Lys Ser Pro Gln Leu Leu Ile
            35                  40                  45

Tyr Ala Ala Thr Asn Leu Ala Asp Gly Val Pro Ser Arg Phe Ser Gly
50                  55                  60

Ser Gly Ser Gly Thr Asp Phe Ser Phe Thr Ile Ser Ser Leu Gln Pro
65                  70                  75                  80

Glu Asp Phe Ala Thr Tyr Tyr Cys Gln Gln Val Tyr Ser Ser Pro Phe
                85                  90                  95

Thr Phe Gly Gln Gly Thr Lys Leu Glu Ile Lys
            100                 105
```

<210> SEQ ID NO 74
<211> LENGTH: 17
<212> TYPE: PRT
<213> ORGANISM: Artificial Sequence
<220> FEATURE:
<223> OTHER INFORMATION: Description of Artificial Sequence: Synthetic
      peptide

<400> SEQUENCE: 74

```
Tyr Ile Asp Pro Tyr Asn Gly Ile Thr Ile Tyr Asp Gln Asn Leu Lys
1               5                   10                  15

Gly
```

<210> SEQ ID NO 75
<211> LENGTH: 133
<212> TYPE: PRT
<213> ORGANISM: Homo sapiens

<400> SEQUENCE: 75

```
Ala Pro Thr Ser Ser Ser Thr Lys Lys Thr Gln Leu Gln Leu Glu His
1               5                   10                  15

Leu Leu Leu Asp Leu Gln Met Ile Leu Asn Gly Ile Asn Asn Tyr Lys
            20                  25                  30

Asn Pro Lys Leu Thr Arg Met Leu Thr Phe Lys Phe Tyr Met Pro Lys
            35                  40                  45

Lys Ala Thr Glu Leu Lys His Leu Gln Cys Leu Glu Glu Leu Lys
50                  55                  60

Pro Leu Glu Glu Val Leu Asn Leu Ala Gln Ser Lys Asn Phe His Leu
65                  70                  75                  80

Arg Pro Arg Asp Leu Ile Ser Asn Ile Asn Val Ile Val Leu Glu Leu
                85                  90                  95

Lys Gly Ser Glu Thr Thr Phe Met Cys Glu Tyr Ala Asp Glu Thr Ala
            100                 105                 110

Thr Ile Val Glu Phe Leu Asn Arg Trp Ile Thr Phe Cys Gln Ser Ile
            115                 120                 125

Ile Ser Thr Leu Thr
            130
```

<210> SEQ ID NO 76
<211> LENGTH: 133
<212> TYPE: PRT
<213> ORGANISM: Homo sapiens

<400> SEQUENCE: 76

```
Ala Pro Met Thr Gln Thr Thr Pro Leu Lys Thr Ser Trp Val Asn Cys
1               5                   10                  15

Ser Asn Met Ile Asp Glu Ile Ile Thr His Leu Lys Gln Pro Pro Leu
            20                  25                  30

Pro Leu Leu Asp Phe Asn Asn Leu Asn Gly Glu Asp Gln Asp Ile Leu
        35                  40                  45

Met Glu Asn Asn Leu Arg Arg Pro Asn Leu Glu Ala Phe Asn Arg Ala
    50                  55                  60

Val Lys Ser Leu Gln Asn Ala Ser Ala Ile Glu Ser Ile Leu Lys Asn
65                  70                  75                  80

Leu Leu Pro Cys Leu Pro Leu Ala Thr Ala Ala Pro Thr Arg His Pro
                85                  90                  95

Ile His Ile Lys Asp Gly Asp Trp Asn Glu Phe Arg Arg Lys Leu Thr
            100                 105                 110

Phe Tyr Leu Lys Thr Leu Glu Asn Ala Gln Ala Gln Gln Thr Thr Leu
        115                 120                 125

Ser Leu Ala Ile Phe
    130
```

<210> SEQ ID NO 77
<211> LENGTH: 152
<212> TYPE: PRT
<213> ORGANISM: Homo sapiens

<400> SEQUENCE: 77

```
Asp Cys Asp Ile Glu Gly Lys Asp Gly Lys Gln Tyr Glu Ser Val Leu
1               5                   10                  15

Met Val Ser Ile Asp Gln Leu Leu Asp Ser Met Lys Glu Ile Gly Ser
            20                  25                  30

Asn Cys Leu Asn Asn Glu Phe Asn Phe Phe Lys Arg His Ile Cys Asp
        35                  40                  45

Ala Asn Lys Glu Gly Met Phe Leu Phe Arg Ala Ala Arg Lys Leu Arg
    50                  55                  60

Gln Phe Leu Lys Met Asn Ser Thr Gly Asp Phe Asp Leu His Leu Leu
65                  70                  75                  80

Lys Val Ser Glu Gly Thr Thr Ile Leu Leu Asn Cys Thr Gly Gln Val
                85                  90                  95

Lys Gly Arg Lys Pro Ala Ala Leu Gly Glu Ala Gln Pro Thr Lys Ser
            100                 105                 110

Leu Glu Glu Asn Lys Ser Leu Lys Glu Gln Lys Lys Leu Asn Asp Leu
        115                 120                 125

Cys Phe Leu Lys Arg Leu Leu Gln Glu Ile Lys Thr Cys Trp Asn Lys
    130                 135                 140

Ile Leu Met Gly Thr Lys Glu His
145                 150
```

<210> SEQ ID NO 78
<211> LENGTH: 79
<212> TYPE: PRT
<213> ORGANISM: Homo sapiens

<400> SEQUENCE: 78

```
Glu Gly Ala Val Leu Pro Arg Ser Ala Lys Glu Leu Arg Cys Gln Cys
1               5                   10                  15

Ile Lys Thr Tyr Ser Lys Pro Phe His Pro Lys Phe Ile Lys Glu Leu
            20                  25                  30
```

Arg Val Ile Glu Ser Gly Pro His Cys Ala Asn Thr Glu Ile Ile Val
          35                  40                  45

Lys Leu Ser Asp Gly Arg Glu Leu Cys Leu Asp Pro Lys Glu Asn Trp
 50                  55                  60

Val Gln Arg Val Val Glu Lys Phe Leu Lys Arg Ala Glu Asn Ser
 65                  70                  75

<210> SEQ ID NO 79
<211> LENGTH: 160
<212> TYPE: PRT
<213> ORGANISM: Homo sapiens

<400> SEQUENCE: 79

Ser Pro Gly Gln Gly Thr Gln Ser Glu Asn Ser Cys Thr His Phe Pro
 1               5                  10                  15

Gly Asn Leu Pro Asn Met Leu Arg Asp Leu Arg Asp Ala Phe Ser Arg
              20                  25                  30

Val Lys Thr Phe Phe Gln Met Lys Asp Gln Leu Asp Asn Leu Leu Leu
          35                  40                  45

Lys Glu Ser Leu Leu Glu Asp Phe Lys Gly Tyr Leu Gly Cys Gln Ala
 50                  55                  60

Leu Ser Glu Met Ile Gln Phe Tyr Leu Glu Glu Val Met Pro Gln Ala
 65                  70                  75                  80

Glu Asn Gln Asp Pro Asp Ile Lys Ala His Val Asn Ser Leu Gly Glu
              85                  90                  95

Asn Leu Lys Thr Leu Arg Leu Arg Leu Arg Arg Cys His Arg Phe Leu
          100                 105                 110

Pro Cys Glu Asn Lys Ser Lys Ala Val Glu Gln Val Lys Asn Ala Phe
      115                 120                 125

Asn Lys Leu Gln Glu Lys Gly Ile Tyr Lys Ala Met Ser Glu Phe Asp
 130                 135                 140

Ile Phe Ile Asn Tyr Ile Glu Ala Tyr Met Thr Met Lys Ile Arg Asn
 145                 150                 155                 160

<210> SEQ ID NO 80
<211> LENGTH: 114
<212> TYPE: PRT
<213> ORGANISM: Homo sapiens

<400> SEQUENCE: 80

Asn Trp Val Asn Val Ile Ser Asp Leu Lys Lys Ile Glu Asp Leu Ile
 1               5                  10                  15

Gln Ser Met His Ile Asp Ala Thr Leu Tyr Thr Glu Ser Asp Val His
              20                  25                  30

Pro Ser Cys Lys Val Thr Ala Met Lys Cys Phe Leu Leu Glu Leu Gln
          35                  40                  45

Val Ile Ser Leu Glu Ser Gly Asp Ala Ser Ile His Asp Thr Val Glu
 50                  55                  60

Asn Leu Ile Ile Leu Ala Asn Asn Ser Leu Ser Ser Asn Gly Asn Val
 65                  70                  75                  80

Thr Glu Ser Gly Cys Lys Glu Cys Glu Glu Leu Glu Glu Lys Asn Ile
              85                  90                  95

Lys Glu Phe Leu Gln Ser Phe Val His Ile Val Gln Met Phe Ile Asn
          100                 105                 110

Thr Ser

<210> SEQ ID NO 81
<211> LENGTH: 132
<212> TYPE: PRT
<213> ORGANISM: Homo sapiens

<400> SEQUENCE: 81

Gly Ile Thr Ile Pro Arg Asn Pro Gly Cys Pro Asn Ser Glu Asp Lys
1               5                   10                  15

Asn Phe Pro Arg Thr Val Met Val Asn Leu Asn Ile His Asn Arg Asn
            20                  25                  30

Thr Asn Thr Asn Pro Lys Arg Ser Ser Asp Tyr Tyr Asn Arg Ser Thr
        35                  40                  45

Ser Pro Trp Asn Leu His Arg Asn Glu Asp Pro Glu Arg Tyr Pro Ser
    50                  55                  60

Val Ile Trp Glu Ala Lys Cys Arg His Leu Gly Cys Ile Asn Ala Asp
65                  70                  75                  80

Gly Asn Val Asp Tyr His Met Asn Ser Val Pro Ile Gln Gln Glu Ile
                85                  90                  95

Leu Val Leu Arg Arg Glu Pro Pro His Cys Pro Asn Ser Phe Arg Leu
            100                 105                 110

Glu Lys Ile Leu Val Ser Val Gly Cys Thr Cys Val Thr Pro Ile Val
        115                 120                 125

His His Val Ala
    130

<210> SEQ ID NO 82
<211> LENGTH: 157
<212> TYPE: PRT
<213> ORGANISM: Homo sapiens

<400> SEQUENCE: 82

Tyr Phe Gly Lys Leu Glu Ser Lys Leu Ser Val Ile Arg Asn Leu Asn
1               5                   10                  15

Asp Gln Val Leu Phe Ile Asp Gln Gly Asn Arg Pro Leu Phe Glu Asp
            20                  25                  30

Met Thr Asp Ser Asp Cys Arg Asp Asn Ala Pro Arg Thr Ile Phe Ile
        35                  40                  45

Ile Ser Met Tyr Lys Asp Ser Gln Pro Arg Gly Met Ala Val Thr Ile
    50                  55                  60

Ser Val Lys Cys Glu Lys Ile Ser Thr Leu Ser Cys Glu Asn Lys Ile
65                  70                  75                  80

Ile Ser Phe Lys Glu Met Asn Pro Pro Asp Asn Ile Lys Asp Thr Lys
                85                  90                  95

Ser Asp Ile Ile Phe Phe Gln Arg Ser Val Pro Gly His Asp Asn Lys
            100                 105                 110

Met Gln Phe Glu Ser Ser Ser Tyr Glu Gly Tyr Phe Leu Ala Cys Glu
        115                 120                 125

Lys Glu Arg Asp Leu Phe Lys Leu Ile Leu Lys Lys Glu Asp Glu Leu
    130                 135                 140

Gly Asp Arg Ser Ile Met Phe Thr Val Gln Asn Glu Asp
145                 150                 155

<210> SEQ ID NO 83
<211> LENGTH: 352
<212> TYPE: PRT
<213> ORGANISM: Homo sapiens

<400> SEQUENCE: 83

| | | | | | | | | | | | | | | |
|---|---|---|---|---|---|---|---|---|---|---|---|---|---|---|
|Arg|Asp|Thr|Ser|Ala|Thr|Pro|Gln|Ser|Ala|Ser|Ile|Lys|Ala|Leu|Arg|
|1| | | |5| | | | |10| | | | |15|

Asn Ala Asn Leu Arg Arg Asp Glu Ser Asn His Leu Thr Asp Leu Tyr
            20                  25                  30

Arg Arg Asp Glu Thr Ile Gln Val Lys Gly Asn Gly Tyr Val Gln Ser
                35                  40                  45

Pro Arg Phe Pro Asn Ser Tyr Pro Arg Asn Leu Leu Leu Thr Trp Arg
            50                  55                  60

Leu His Ser Gln Glu Asn Thr Arg Ile Gln Leu Val Phe Asp Asn Gln
65                  70                  75                  80

Phe Gly Leu Glu Glu Ala Glu Asn Asp Ile Cys Arg Tyr Asp Phe Val
                85                  90                  95

Glu Val Glu Asp Ile Ser Glu Thr Ser Thr Ile Ile Arg Gly Arg Trp
                100                 105                 110

Cys Gly His Lys Glu Val Pro Pro Arg Ile Lys Ser Arg Thr Asn Gln
            115                 120                 125

Ile Lys Ile Thr Phe Lys Ser Asp Asp Tyr Phe Val Ala Lys Pro Gly
            130                 135                 140

Phe Lys Ile Tyr Tyr Ser Leu Leu Glu Asp Phe Gln Pro Ala Ala Ala
145                 150                 155                 160

Ser Glu Thr Asn Trp Glu Ser Val Thr Ser Ser Ile Ser Gly Val Ser
                165                 170                 175

Tyr Asn Ser Pro Ser Val Thr Asp Pro Thr Leu Ile Ala Asp Ala Leu
            180                 185                 190

Asp Lys Lys Ile Ala Glu Phe Asp Thr Val Glu Asp Leu Leu Lys Tyr
            195                 200                 205

Phe Asn Pro Glu Ser Trp Gln Glu Asp Leu Glu Asn Met Tyr Leu Asp
            210                 215                 220

Thr Pro Arg Tyr Arg Gly Arg Ser Tyr His Asp Arg Lys Ser Lys Val
225                 230                 235                 240

Asp Leu Asp Arg Leu Asn Asp Asp Ala Lys Arg Tyr Ser Cys Thr Pro
            245                 250                 255

Arg Asn Tyr Ser Val Asn Ile Arg Glu Glu Leu Lys Leu Ala Asn Val
            260                 265                 270

Val Phe Phe Pro Arg Cys Leu Leu Val Gln Arg Cys Gly Gly Asn Cys
            275                 280                 285

Gly Cys Gly Thr Val Asn Trp Arg Ser Cys Thr Cys Asn Ser Gly Lys
            290                 295                 300

Thr Val Lys Lys Tyr His Glu Val Leu Gln Phe Glu Pro Gly His Ile
305                 310                 315                 320

Lys Arg Arg Gly Arg Ala Lys Thr Met Ala Leu Val Asp Ile Gln Leu
                325                 330                 335

Asp His His Glu Arg Cys Asp Cys Ile Cys Ser Ser Arg Pro Pro Arg
            340                 345                 350

<210> SEQ ID NO 84
<211> LENGTH: 248
<212> TYPE: PRT
<213> ORGANISM: Homo sapiens

<400> SEQUENCE: 84

Glu Gly Ile Cys Arg Asn Arg Val Thr Asn Asn Val Lys Asp Val Thr
1               5                   10                  15

```
Lys Leu Val Ala Asn Leu Pro Lys Asp Tyr Met Ile Thr Leu Lys Tyr
                20                  25                  30

Val Pro Gly Met Asp Val Leu Pro Ser His Cys Trp Ile Ser Glu Met
        35                  40                  45

Val Val Gln Leu Ser Asp Ser Leu Thr Asp Leu Leu Asp Lys Phe Ser
 50                  55                  60

Asn Ile Ser Glu Gly Leu Ser Asn Tyr Ser Ile Ile Asp Lys Leu Val
 65                  70                  75                  80

Asn Ile Val Asp Asp Leu Val Glu Cys Val Lys Glu Asn Ser Ser Lys
                85                  90                  95

Asp Leu Lys Lys Ser Phe Lys Ser Pro Glu Pro Arg Leu Phe Thr Pro
                100                 105                 110

Glu Glu Phe Phe Arg Ile Phe Asn Arg Ser Ile Asp Ala Phe Lys Asp
                115                 120                 125

Phe Val Val Ala Ser Glu Thr Ser Asp Cys Val Val Ser Ser Thr Leu
130                 135                 140

Ser Pro Glu Lys Asp Ser Arg Val Ser Val Thr Lys Pro Phe Met Leu
145                 150                 155                 160

Pro Pro Val Ala Ala Ser Ser Leu Arg Asn Asp Ser Ser Ser Ser Asn
                165                 170                 175

Arg Lys Ala Lys Asn Pro Pro Gly Asp Ser Ser Leu His Trp Ala Ala
                180                 185                 190

Met Ala Leu Pro Ala Leu Phe Ser Leu Ile Ile Gly Phe Ala Phe Gly
                195                 200                 205

Ala Leu Tyr Trp Lys Lys Arg Gln Pro Ser Leu Thr Arg Ala Val Glu
        210                 215                 220

Asn Ile Gln Ile Asn Glu Glu Asp Asn Glu Ile Ser Met Leu Gln Glu
225                 230                 235                 240

Lys Glu Arg Glu Phe Gln Glu Val
                245

<210> SEQ ID NO 85
<211> LENGTH: 209
<212> TYPE: PRT
<213> ORGANISM: Homo sapiens

<400> SEQUENCE: 85

Thr Gln Asp Cys Ser Phe Gln His Ser Pro Ile Ser Ser Asp Phe Ala
1               5                   10                  15

Val Lys Ile Arg Glu Leu Ser Asp Tyr Leu Leu Gln Asp Tyr Pro Val
                20                  25                  30

Thr Val Ala Ser Asn Leu Gln Asp Glu Glu Leu Cys Gly Gly Leu Trp
        35                  40                  45

Arg Leu Val Leu Ala Gln Arg Trp Met Glu Arg Leu Lys Thr Val Ala
 50                  55                  60

Gly Ser Lys Met Gln Gly Leu Leu Glu Arg Val Asn Thr Glu Ile His
 65                  70                  75                  80

Phe Val Thr Lys Cys Ala Phe Gln Pro Pro Pro Ser Cys Leu Arg Phe
                85                  90                  95

Val Gln Thr Asn Ile Ser Arg Leu Leu Gln Glu Thr Ser Glu Gln Leu
                100                 105                 110

Val Ala Leu Lys Pro Trp Ile Thr Arg Gln Asn Phe Ser Arg Cys Leu
                115                 120                 125

Glu Leu Gln Cys Gln Pro Asp Ser Ser Thr Leu Pro Pro Pro Trp Ser
130                 135                 140
```

```
Pro Arg Pro Leu Glu Ala Thr Ala Pro Thr Ala Pro Gln Pro Pro Leu
145                 150                 155                 160

Leu Leu Leu Leu Leu Leu Pro Val Gly Leu Leu Leu Ala Ala Ala
            165                 170                 175

Trp Cys Leu His Trp Gln Arg Thr Arg Arg Arg Thr Pro Arg Pro Gly
            180                 185                 190

Glu Gln Val Pro Pro Val Pro Ser Pro Gln Asp Leu Leu Leu Val Glu
        195                 200                 205

His

<210> SEQ ID NO 86
<211> LENGTH: 360
<212> TYPE: PRT
<213> ORGANISM: Homo sapiens

<400> SEQUENCE: 86

Glu Pro His Ser Leu Arg Tyr Asn Leu Thr Val Leu Ser Trp Asp Gly
1               5                   10                  15

Ser Val Gln Ser Gly Phe Leu Thr Glu Val His Leu Asp Gly Gln Pro
            20                  25                  30

Phe Leu Arg Cys Asp Arg Gln Lys Cys Arg Ala Lys Pro Gln Gly Gln
        35                  40                  45

Trp Ala Glu Asp Val Leu Gly Asn Lys Thr Trp Asp Arg Glu Thr Arg
    50                  55                  60

Asp Leu Thr Gly Asn Gly Lys Asp Leu Arg Met Thr Leu Ala His Ile
65                  70                  75                  80

Lys Asp Gln Lys Glu Gly Leu His Ser Leu Gln Glu Ile Arg Val Cys
                85                  90                  95

Glu Ile His Glu Asp Asn Ser Thr Arg Ser Ser Gln His Phe Tyr Tyr
            100                 105                 110

Asp Gly Glu Leu Phe Leu Ser Gln Asn Leu Glu Thr Lys Glu Trp Thr
        115                 120                 125

Met Pro Gln Ser Ser Arg Ala Gln Thr Leu Ala Met Asn Val Arg Asn
    130                 135                 140

Phe Leu Lys Glu Asp Ala Met Lys Thr Lys Thr His Tyr His Ala Met
145                 150                 155                 160

His Ala Asp Cys Leu Gln Glu Leu Arg Arg Tyr Leu Lys Ser Gly Val
                165                 170                 175

Val Leu Arg Arg Thr Val Pro Pro Met Val Asn Val Thr Arg Ser Glu
            180                 185                 190

Ala Ser Glu Gly Asn Ile Thr Val Thr Cys Arg Ala Ser Gly Phe Tyr
        195                 200                 205

Pro Trp Asn Ile Thr Leu Ser Trp Arg Gln Asp Gly Val Ser Leu Ser
    210                 215                 220

His Asp Thr Gln Gln Trp Gly Asp Val Leu Pro Asp Gly Asn Gly Thr
225                 230                 235                 240

Tyr Gln Thr Trp Val Ala Thr Arg Ile Cys Gln Gly Glu Glu Gln Arg
                245                 250                 255

Phe Thr Cys Tyr Met Glu His Ser Gly Asn His Ser Thr His Pro Val
            260                 265                 270

Pro Ser Gly Lys Val Leu Val Leu Gln Ser His Trp Gln Thr Phe His
        275                 280                 285

Val Ser Ala Val Ala Ala Ala Ile Phe Val Ile Ile Ile Phe Tyr
    290                 295                 300
```

Val Arg Cys Cys Lys Lys Thr Ser Ala Ala Glu Gly Pro Glu Leu
305                 310                 315                 320

Val Ser Leu Gln Val Leu Asp Gln His Pro Val Gly Thr Ser Asp His
            325                 330                 335

Arg Asp Ala Thr Gln Leu Gly Phe Gln Pro Leu Met Ser Asp Leu Gly
        340                 345                 350

Ser Thr Gly Ser Thr Glu Gly Ala
        355             360

<210> SEQ ID NO 87
<211> LENGTH: 361
<212> TYPE: PRT
<213> ORGANISM: Homo sapiens

<400> SEQUENCE: 87

Ala Glu Pro His Ser Leu Arg Tyr Asn Leu Met Val Leu Ser Gln Asp
1               5                   10                  15

Glu Ser Val Gln Ser Gly Phe Leu Ala Glu Gly His Leu Asp Gly Gln
            20                  25                  30

Pro Phe Leu Arg Tyr Asp Arg Gln Lys Arg Arg Ala Lys Pro Gln Gly
        35                  40                  45

Gln Trp Ala Glu Asp Val Leu Gly Ala Lys Thr Trp Asp Thr Glu Thr
50                  55                  60

Glu Asp Leu Thr Glu Asn Gly Gln Asp Leu Arg Arg Thr Leu Thr His
65                  70                  75                  80

Ile Lys Asp Gln Lys Gly Gly Leu His Ser Leu Gln Glu Ile Arg Val
                85                  90                  95

Cys Glu Ile His Glu Asp Ser Ser Thr Arg Gly Ser Arg His Phe Tyr
            100                 105                 110

Tyr Asp Gly Glu Leu Phe Leu Ser Gln Asn Leu Glu Thr Gln Glu Ser
        115                 120                 125

Thr Val Pro Gln Ser Ser Arg Ala Gln Thr Leu Ala Met Asn Val Thr
130                 135                 140

Asn Phe Trp Lys Glu Asp Ala Met Lys Thr Lys Thr His Tyr Arg Ala
145                 150                 155                 160

Met Gln Ala Asp Cys Leu Gln Lys Leu Gln Arg Tyr Leu Lys Ser Gly
                165                 170                 175

Val Ala Ile Arg Arg Thr Val Pro Pro Met Val Asn Val Thr Cys Ser
            180                 185                 190

Glu Val Ser Glu Gly Asn Ile Thr Val Thr Cys Arg Ala Ser Ser Phe
        195                 200                 205

Tyr Pro Arg Asn Ile Thr Leu Thr Trp Arg Gln Asp Gly Val Ser Leu
210                 215                 220

Ser His Asn Thr Gln Gln Trp Gly Asp Val Leu Pro Asp Gly Asn Gly
225                 230                 235                 240

Thr Tyr Gln Thr Trp Val Ala Thr Arg Ile Arg Gln Gly Glu Glu Gln
                245                 250                 255

Arg Phe Thr Cys Tyr Met Glu His Ser Gly Asn His Gly Thr His Pro
            260                 265                 270

Val Pro Ser Gly Lys Val Leu Val Leu Gln Ser Gln Arg Thr Asp Phe
        275                 280                 285

Pro Tyr Val Ser Ala Ala Met Pro Cys Phe Val Ile Ile Ile Ile Leu
290                 295                 300

Cys Val Pro Cys Cys Lys Lys Lys Thr Ser Ala Ala Glu Gly Pro Glu

```
                305                 310                 315                 320
Leu Val Ser Leu Gln Val Leu Asp Gln His Pro Val Gly Thr Gly Asp
                    325                 330                 335

His Arg Asp Ala Ala Gln Leu Gly Phe Gln Pro Leu Met Ser Ala Thr
                340                 345                 350

Gly Ser Thr Gly Ser Thr Glu Gly Ala
                355                 360

<210> SEQ ID NO 88
<211> LENGTH: 190
<212> TYPE: PRT
<213> ORGANISM: Homo sapiens

<400> SEQUENCE: 88

Trp Val Asp Thr His Cys Leu Cys Tyr Asp Phe Ile Ile Thr Pro Lys
1               5                   10                  15

Ser Arg Pro Glu Pro Gln Trp Cys Glu Val Gln Gly Leu Val Asp Glu
                20                  25                  30

Arg Pro Phe Leu His Tyr Asp Cys Val Asn His Lys Ala Lys Ala Phe
            35                  40                  45

Ala Ser Leu Gly Lys Lys Val Asn Val Thr Lys Thr Trp Glu Glu Gln
        50                  55                  60

Thr Glu Thr Leu Arg Asp Val Val Asp Phe Leu Lys Gly Gln Leu Leu
65                  70                  75                  80

Asp Ile Gln Val Glu Asn Leu Ile Pro Ile Glu Pro Leu Thr Leu Gln
                85                  90                  95

Ala Arg Met Ser Cys Glu His Glu Ala His Gly His Gly Arg Gly Ser
            100                 105                 110

Trp Gln Phe Leu Phe Asn Gly Gln Lys Phe Leu Leu Phe Asp Ser Asn
        115                 120                 125

Asn Arg Lys Trp Thr Ala Leu His Pro Gly Ala Lys Lys Met Thr Glu
    130                 135                 140

Lys Trp Glu Lys Asn Arg Asp Val Thr Met Phe Phe Gln Lys Ile Ser
145                 150                 155                 160

Leu Gly Asp Cys Lys Met Trp Leu Glu Glu Phe Leu Met Tyr Trp Glu
                165                 170                 175

Gln Met Leu Asp Pro Thr Lys Pro Pro Ser Leu Ala Pro Gly
            180                 185                 190

<210> SEQ ID NO 89
<211> LENGTH: 191
<212> TYPE: PRT
<213> ORGANISM: Homo sapiens

<400> SEQUENCE: 89

Gly Arg Ala Asp Pro His Ser Leu Cys Tyr Asp Ile Thr Val Ile Pro
1               5                   10                  15

Lys Phe Arg Pro Gly Pro Arg Trp Cys Ala Val Gln Gly Gln Val Asp
                20                  25                  30

Glu Lys Thr Phe Leu His Tyr Asp Cys Gly Asn Lys Thr Val Thr Pro
            35                  40                  45

Val Ser Pro Leu Gly Lys Lys Leu Asn Val Thr Thr Ala Trp Lys Ala
        50                  55                  60

Gln Asn Pro Val Leu Arg Glu Val Val Asp Ile Leu Thr Glu Gln Leu
65                  70                  75                  80

Arg Asp Ile Gln Leu Glu Asn Tyr Thr Pro Lys Glu Pro Leu Thr Leu
```

```
                85                  90                  95
Gln Ala Arg Met Ser Cys Glu Gln Lys Ala Glu Gly His Ser Ser Gly
            100                 105                 110

Ser Trp Gln Phe Ser Phe Asp Gly Gln Ile Phe Leu Leu Phe Asp Ser
            115                 120                 125

Glu Lys Arg Met Trp Thr Thr Val His Pro Gly Ala Arg Lys Met Lys
            130                 135                 140

Glu Lys Trp Glu Asn Asp Lys Val Val Ala Met Ser Phe His Tyr Phe
145                 150                 155                 160

Ser Met Gly Asp Cys Ile Gly Trp Leu Glu Asp Phe Leu Met Gly Met
                165                 170                 175

Asp Ser Thr Leu Glu Pro Ser Ala Gly Ala Pro Leu Ala Met Ser
                180                 185                 190

<210> SEQ ID NO 90
<211> LENGTH: 188
<212> TYPE: PRT
<213> ORGANISM: Homo sapiens

<400> SEQUENCE: 90

Asp Ala His Ser Leu Trp Tyr Asn Phe Thr Ile Ile His Leu Pro Arg
1               5                   10                  15

His Gly Gln Gln Trp Cys Glu Val Gln Ser Gln Val Asp Gln Lys Asn
            20                  25                  30

Phe Leu Ser Tyr Asp Cys Gly Ser Asp Lys Val Leu Ser Met Gly His
        35                  40                  45

Leu Glu Glu Gln Leu Tyr Ala Thr Asp Ala Trp Gly Lys Gln Leu Glu
    50                  55                  60

Met Leu Arg Glu Val Gly Gln Arg Leu Arg Leu Glu Leu Ala Asp Thr
65                  70                  75                  80

Glu Leu Glu Asp Phe Thr Pro Ser Gly Pro Leu Thr Leu Gln Val Arg
                85                  90                  95

Met Ser Cys Glu Cys Glu Ala Asp Gly Tyr Ile Arg Gly Ser Trp Gln
            100                 105                 110

Phe Ser Phe Asp Gly Arg Lys Phe Leu Leu Phe Asp Ser Asn Asn Arg
            115                 120                 125

Lys Trp Thr Val Val His Ala Gly Ala Arg Arg Met Lys Glu Lys Trp
            130                 135                 140

Glu Lys Asp Ser Gly Leu Thr Thr Phe Phe Lys Met Val Ser Met Arg
145                 150                 155                 160

Asp Cys Lys Ser Trp Leu Arg Asp Phe Leu Met His Arg Lys Lys Arg
                165                 170                 175

Leu Glu Pro Thr Ala Pro Pro Thr Met Ala Pro Gly
            180                 185

<210> SEQ ID NO 91
<211> LENGTH: 233
<212> TYPE: PRT
<213> ORGANISM: Homo sapiens

<400> SEQUENCE: 91

His Ser Leu Cys Phe Asn Phe Thr Ile Lys Ser Leu Ser Arg Pro Gly
1               5                   10                  15

Gln Pro Trp Cys Glu Ala Gln Val Phe Leu Asn Lys Asn Leu Phe Leu
            20                  25                  30

Gln Tyr Asn Ser Asp Asn Asn Met Val Lys Pro Leu Gly Leu Leu Gly
```

```
            35                  40                  45
Lys Lys Val Tyr Ala Thr Ser Thr Trp Gly Glu Leu Thr Gln Thr Leu
 50                  55                  60

Gly Glu Val Gly Arg Asp Leu Arg Met Leu Leu Cys Asp Ile Lys Pro
 65                  70                  75                  80

Gln Ile Lys Thr Ser Asp Pro Ser Thr Leu Gln Val Glu Met Phe Cys
                 85                  90                  95

Gln Arg Glu Ala Glu Arg Cys Thr Gly Ala Ser Trp Gln Phe Ala Thr
                100                 105                 110

Asn Gly Glu Lys Ser Leu Leu Phe Asp Ala Met Asn Met Thr Trp Thr
                115                 120                 125

Val Ile Asn His Glu Ala Ser Lys Ile Lys Glu Thr Trp Lys Lys Asp
            130                 135                 140

Arg Gly Leu Glu Lys Tyr Phe Arg Lys Leu Ser Lys Gly Asp Cys Asp
145                 150                 155                 160

His Trp Leu Arg Glu Phe Leu Gly His Trp Glu Ala Met Pro Glu Pro
                    165                 170                 175

Thr Val Ser Pro Val Asn Ala Ser Asp Ile His Trp Ser Ser Ser Ser
                180                 185                 190

Leu Pro Asp Arg Trp Ile Ile Leu Gly Ala Phe Ile Leu Leu Val Leu
                195                 200                 205

Met Gly Ile Val Leu Ile Cys Val Trp Trp Gln Asn Gly Glu Trp Gln
210                 215                 220

Ala Gly Leu Trp Pro Leu Arg Thr Ser
225                 230

<210> SEQ ID NO 92
<211> LENGTH: 193
<212> TYPE: PRT
<213> ORGANISM: Homo sapiens

<400> SEQUENCE: 92

Gly Leu Ala Asp Pro His Ser Leu Cys Tyr Asp Ile Thr Val Ile Pro
 1               5                  10                  15

Lys Phe Arg Pro Gly Pro Arg Trp Cys Ala Val Gln Gly Gln Val Asp
                20                  25                  30

Glu Lys Thr Phe Leu His Tyr Asp Cys Gly Ser Lys Thr Val Thr Pro
                35                  40                  45

Val Ser Pro Leu Gly Lys Lys Leu Asn Val Thr Thr Ala Trp Lys Ala
 50                  55                  60

Gln Asn Pro Val Leu Arg Glu Val Val Asp Ile Leu Thr Glu Gln Leu
 65                  70                  75                  80

Leu Asp Ile Gln Leu Glu Asn Tyr Ile Pro Lys Glu Pro Leu Thr Leu
                85                  90                  95

Gln Ala Arg Met Ser Cys Glu Gln Lys Ala Glu Gly His Gly Ser Gly
                100                 105                 110

Ser Trp Gln Leu Ser Phe Asp Gly Gln Ile Phe Leu Leu Phe Asp Ser
                115                 120                 125

Glu Asn Arg Met Trp Thr Thr Val His Pro Gly Ala Arg Lys Met Lys
130                 135                 140

Glu Lys Trp Glu Asn Asp Lys Asp Met Thr Met Ser Phe His Tyr Ile
145                 150                 155                 160

Ser Met Gly Asp Cys Thr Gly Trp Leu Glu Asp Phe Leu Met Gly Met
                165                 170                 175
```

```
Asp Ser Thr Leu Glu Pro Ser Ala Gly Ala Pro Pro Thr Met Ser Ser
            180                 185                 190

Gly

<210> SEQ ID NO 93
<211> LENGTH: 193
<212> TYPE: PRT
<213> ORGANISM: Homo sapiens

<400> SEQUENCE: 93

Arg Arg Asp Asp Pro His Ser Leu Cys Tyr Asp Ile Thr Val Ile Pro
1               5                   10                  15

Lys Phe Arg Pro Gly Pro Arg Trp Cys Ala Val Gln Gly Gln Val Asp
            20                  25                  30

Glu Lys Thr Phe Leu His Tyr Asp Cys Gly Asn Lys Thr Val Thr Pro
        35                  40                  45

Val Ser Pro Leu Gly Lys Lys Leu Asn Val Thr Met Ala Trp Lys Ala
    50                  55                  60

Gln Asn Pro Val Leu Arg Glu Val Val Asp Ile Leu Thr Glu Gln Leu
65                  70                  75                  80

Leu Asp Ile Gln Leu Glu Asn Tyr Thr Pro Lys Glu Pro Leu Thr Leu
                85                  90                  95

Gln Ala Arg Met Ser Cys Glu Gln Lys Ala Glu Gly His Ser Ser Gly
            100                 105                 110

Ser Trp Gln Phe Ser Ile Asp Gly Gln Thr Phe Leu Leu Phe Asp Ser
        115                 120                 125

Glu Lys Arg Met Trp Thr Thr Val His Pro Gly Ala Arg Lys Met Lys
    130                 135                 140

Glu Lys Trp Glu Asn Asp Lys Asp Val Ala Met Ser Phe His Tyr Ile
145                 150                 155                 160

Ser Met Gly Asp Cys Ile Gly Trp Leu Glu Asp Phe Leu Met Gly Met
                165                 170                 175

Asp Ser Thr Leu Glu Pro Ser Ala Gly Ala Pro Leu Ala Met Ser Ser
            180                 185                 190

Gly

<210> SEQ ID NO 94
<211> LENGTH: 65
<212> TYPE: PRT
<213> ORGANISM: Artificial Sequence
<220> FEATURE:
<223> OTHER INFORMATION: Description of Artificial Sequence: Synthetic
      polypeptide

<400> SEQUENCE: 94

Ile Thr Cys Pro Pro Pro Met Ser Val Glu His Ala Asp Ile Trp Val
1               5                   10                  15

Lys Ser Tyr Ser Leu Tyr Ser Arg Glu Arg Tyr Ile Cys Asn Ser Gly
            20                  25                  30

Phe Lys Arg Lys Ala Gly Thr Ser Ser Leu Thr Glu Cys Val Leu Asn
        35                  40                  45

Lys Ala Thr Asn Val Ala His Trp Thr Thr Pro Ser Leu Lys Cys Ile
    50                  55                  60

Arg
65

<210> SEQ ID NO 95
```

<211> LENGTH: 195
<212> TYPE: DNA
<213> ORGANISM: Artificial Sequence
<220> FEATURE:
<223> OTHER INFORMATION: Description of Artificial Sequence: Synthetic
      polynucleotide

<400> SEQUENCE: 95
attacatgcc ccctcccat gagcgtggag cacgccgaca tctgggtgaa gagctatagc      60
ctctacagcc gggagaggta tatctgtaac agcggcttca agaggaaggc cggcaccagc    120
agcctcaccg agtgcgtgct gaataaggct accaacgtgg ctcactggac aacaccctct    180
ttaaagtgca tccgg                                                     195

<210> SEQ ID NO 96
<211> LENGTH: 114
<212> TYPE: PRT
<213> ORGANISM: Artificial Sequence
<220> FEATURE:
<223> OTHER INFORMATION: Description of Artificial Sequence: Synthetic
      polypeptide

<400> SEQUENCE: 96

Asn Trp Val Asn Val Ile Ser Asp Leu Lys Lys Ile Glu Asp Leu Ile
1               5                   10                  15

Gln Ser Met His Ile Asp Ala Thr Leu Tyr Thr Glu Ser Asp Val His
            20                  25                  30

Pro Ser Cys Lys Val Thr Ala Met Lys Cys Phe Leu Leu Glu Leu Gln
        35                  40                  45

Val Ile Ser Leu Glu Ser Gly Asp Ala Ser Ile His Asp Thr Val Glu
    50                  55                  60

Asn Leu Ile Ile Leu Ala Asn Asn Ser Leu Ser Ser Asn Gly Asn Val
65                  70                  75                  80

Thr Glu Ser Gly Cys Lys Glu Cys Glu Glu Leu Glu Glu Lys Asn Ile
                85                  90                  95

Lys Glu Phe Leu Gln Ser Phe Val His Ile Val Gln Met Phe Ile Asn
            100                 105                 110

Thr Ser

<210> SEQ ID NO 97
<211> LENGTH: 342
<212> TYPE: DNA
<213> ORGANISM: Artificial Sequence
<220> FEATURE:
<223> OTHER INFORMATION: Description of Artificial Sequence: Synthetic
      polynucleotide

<400> SEQUENCE: 97
aactgggtga acgtcatcag cgatttaaag aagatcgaag atttaattca gtccatgcat     60
atcgacgcca ctttatacac agaatccgac gtgcacccct cttgtaaggt gaccgccatg    120
aaatgttttt tactggagct gcaagttatc tctttagaga gcggagacgc tagcatccac    180
gacaccgtgg agaatttaat catttagcc aataactctt tatccagcaa cggcaacgtg     240
acagagtccg gctgcaagga gtgcgaagag ctggaggaga gaacatcaa ggagtttctg     300 caatcctttg tgcacattgt ccagatgttc atcaataacct cc                      342

<210> SEQ ID NO 98
<211> LENGTH: 220
<212> TYPE: PRT
<213> ORGANISM: Homo sapiens

<400> SEQUENCE: 98

Pro Cys Pro Ala Pro Glu Leu Leu Gly Gly Pro Ser Val Phe Leu Phe
1               5                   10                  15

Pro Pro Lys Pro Lys Asp Thr Leu Met Ile Ser Arg Thr Pro Glu Val
                20                  25                  30

Thr Cys Val Val Val Asp Val Ser His Glu Asp Pro Glu Val Lys Phe
            35                  40                  45

Asn Trp Tyr Val Asp Gly Val Glu Val His Asn Ala Lys Thr Lys Pro
        50                  55                  60

Arg Glu Glu Gln Tyr Asn Ser Thr Tyr Arg Val Val Ser Val Leu Thr
65                  70                  75                  80

Val Leu His Gln Asp Trp Leu Asn Gly Lys Glu Tyr Lys Cys Lys Val
                85                  90                  95

Ser Asn Lys Ala Leu Pro Ala Pro Ile Glu Lys Thr Ile Ser Lys Ala
            100                 105                 110

Lys Gly Gln Pro Arg Glu Pro Gln Val Tyr Thr Leu Pro Pro Ser Arg
        115                 120                 125

Asp Glu Leu Thr Lys Asn Gln Val Ser Leu Thr Cys Leu Val Lys Gly
130                 135                 140

Phe Tyr Pro Ser Asp Ile Ala Val Glu Trp Glu Ser Asn Gly Gln Pro
145                 150                 155                 160

Glu Asn Asn Tyr Lys Thr Thr Pro Pro Val Leu Asp Ser Asp Gly Ser
                165                 170                 175

Phe Phe Leu Tyr Ser Lys Leu Thr Val Asp Lys Ser Arg Trp Gln Gln
            180                 185                 190

Gly Asn Val Phe Ser Cys Ser Val Met His Glu Ala Leu His Asn His
        195                 200                 205

Tyr Thr Gln Lys Ser Leu Ser Leu Ser Pro Gly Lys
        210                 215                 220

<210> SEQ ID NO 99
<211> LENGTH: 114
<212> TYPE: PRT
<213> ORGANISM: Artificial Sequence
<220> FEATURE:
<223> OTHER INFORMATION: Description of Artificial Sequence: Synthetic
      polypeptide

<400> SEQUENCE: 99

Asn Trp Val Asn Val Ile Ser Asn Leu Lys Lys Ile Glu Asp Leu Ile
1               5                   10                  15

Gln Ser Met His Ile Asp Ala Thr Leu Tyr Thr Glu Ser Asp Val His
                20                  25                  30

Pro Ser Cys Lys Val Thr Ala Met Lys Cys Phe Leu Leu Glu Leu Gln
            35                  40                  45

Val Ile Ser Leu Glu Ser Gly Asp Ala Ser Ile His Asp Thr Val Glu
        50                  55                  60

Asn Leu Ile Ile Leu Ala Asn Asn Ser Leu Ser Ser Asn Gly Asn Val
65                  70                  75                  80

Thr Glu Ser Gly Cys Lys Glu Cys Glu Glu Leu Glu Glu Lys Asn Ile
                85                  90                  95

Lys Glu Phe Leu Gln Ser Phe Val His Ile Val Gln Met Phe Ile Asn
            100                 105                 110

Thr Ser

<210> SEQ ID NO 100
<211> LENGTH: 342
<212> TYPE: DNA
<213> ORGANISM: Artificial Sequence
<220> FEATURE:
<223> OTHER INFORMATION: Description of Artificial Sequence: Synthetic
      polynucleotide

<400> SEQUENCE: 100
aactgggtga acgtcatcag caatttaaag aagatcgaag atttaattca gtccatgcat     60
atcgacgcca ctttatacac agaatccgac gtgcacccct cttgtaaggt gaccgccatg    120
aaatgttttt tactggagct gcaagttatc tctttagaga gcggagacgc tagcatccac    180
gacaccgtgg agaatttaat cattttagcc aataactctt tatccagcaa cggcaacgtg    240
acagagtccg gctgcaagga gtgcgaagag ctggaggaga gaacatcaa ggagtttctg     300 caatcctttg tgcacattgt ccagatgttc atcaatacct cc                       342

<210> SEQ ID NO 101
<211> LENGTH: 54
<212> TYPE: DNA
<213> ORGANISM: Artificial Sequence
<220> FEATURE:
<223> OTHER INFORMATION: Description of Artificial Sequence: Synthetic
      oligonucleotide

<400> SEQUENCE: 101
atgaaatggg tcaccttcat ctctttactg tttttattta gcagcgccta cagc           54

<210> SEQ ID NO 102
<211> LENGTH: 574
<212> TYPE: PRT
<213> ORGANISM: Artificial Sequence
<220> FEATURE:
<223> OTHER INFORMATION: Description of Artificial Sequence: Synthetic
      polypeptide

<400> SEQUENCE: 102

Gln Ile Val Leu Thr Gln Ser Pro Ala Ile Met Ser Ala Ser Pro Gly
1               5                   10                  15

Glu Lys Val Thr Met Thr Cys Ser Ala Ser Ser Ser Val Ser Tyr Met
                20                  25                  30

Asn Trp Tyr Gln Gln Lys Ser Gly Thr Ser Pro Lys Arg Trp Ile Tyr
            35                  40                  45

Asp Thr Ser Lys Leu Ala Ser Gly Val Pro Ala His Phe Arg Gly Ser
        50                  55                  60

Gly Ser Gly Thr Ser Tyr Ser Leu Thr Ile Ser Gly Met Glu Ala Glu
65                  70                  75                  80

Asp Ala Ala Thr Tyr Tyr Cys Gln Gln Trp Ser Ser Asn Pro Phe Thr
                85                  90                  95

Phe Gly Ser Gly Thr Lys Leu Glu Ile Asn Arg Gly Gly Gly Gly Ser
            100                 105                 110

Gly Gly Gly Gly Ser Gly Gly Gly Ser Gln Val Gln Leu Gln Gln
        115                 120                 125

Ser Gly Ala Glu Leu Ala Arg Pro Gly Ala Ser Val Lys Met Ser Cys
        130                 135                 140

Lys Ala Ser Gly Tyr Thr Phe Thr Arg Tyr Thr Met His Trp Val Lys
145                 150                 155                 160

Gln Arg Pro Gly Gln Gly Leu Glu Trp Ile Gly Tyr Ile Asn Pro Ser
                165                 170                 175

Arg Gly Tyr Thr Asn Tyr Asn Gln Lys Phe Lys Asp Lys Ala Thr Leu
                180                 185                 190

Thr Thr Asp Lys Ser Ser Thr Ala Tyr Met Gln Leu Ser Ser Leu
            195                 200                 205

Thr Ser Glu Asp Ser Ala Val Tyr Tyr Cys Ala Arg Tyr Tyr Asp Asp
210                 215                 220

His Tyr Cys Leu Asp Tyr Trp Gly Gln Gly Thr Thr Leu Thr Val Ser
225                 230                 235                 240

Ser Ser Gly Thr Thr Asn Thr Val Ala Ala Tyr Asn Leu Thr Trp Lys
                245                 250                 255

Ser Thr Asn Phe Lys Thr Ile Leu Glu Trp Glu Pro Lys Pro Val Asn
            260                 265                 270

Gln Val Tyr Thr Val Gln Ile Ser Thr Lys Ser Gly Asp Trp Lys Ser
            275                 280                 285

Lys Cys Phe Tyr Thr Thr Asp Thr Glu Cys Asp Leu Thr Asp Glu Ile
            290                 295                 300

Val Lys Asp Val Lys Gln Thr Tyr Leu Ala Arg Val Phe Ser Tyr Pro
305                 310                 315                 320

Ala Gly Asn Val Glu Ser Thr Gly Ser Ala Gly Glu Pro Leu Tyr Glu
                325                 330                 335

Asn Ser Pro Glu Phe Thr Pro Tyr Leu Glu Thr Asn Leu Gly Gln Pro
            340                 345                 350

Thr Ile Gln Ser Phe Glu Gln Val Gly Thr Lys Val Asn Val Thr Val
            355                 360                 365

Glu Asp Glu Arg Thr Leu Val Arg Arg Asn Asn Thr Phe Leu Ser Leu
370                 375                 380

Arg Asp Val Phe Gly Lys Asp Leu Ile Tyr Thr Leu Tyr Tyr Trp Lys
385                 390                 395                 400

Ser Ser Ser Ser Gly Lys Lys Thr Ala Lys Thr Asn Thr Asn Glu Phe
                405                 410                 415

Leu Ile Asp Val Asp Lys Gly Glu Asn Tyr Cys Phe Ser Val Gln Ala
            420                 425                 430

Val Ile Pro Ser Arg Thr Val Asn Arg Lys Ser Thr Asp Ser Pro Val
            435                 440                 445

Glu Cys Met Gly Gln Glu Lys Gly Glu Phe Arg Glu Asn Trp Val Asn
450                 455                 460

Val Ile Ser Asn Leu Lys Lys Ile Glu Asp Leu Ile Gln Ser Met His
465                 470                 475                 480

Ile Asp Ala Thr Leu Tyr Thr Glu Ser Asp Val His Pro Ser Cys Lys
                485                 490                 495

Val Thr Ala Met Lys Cys Phe Leu Leu Glu Leu Gln Val Ile Ser Leu
            500                 505                 510

Glu Ser Gly Asp Ala Ser Ile His Asp Thr Val Glu Asn Leu Ile Ile
            515                 520                 525

Leu Ala Asn Asn Ser Leu Ser Ser Asn Gly Asn Val Thr Glu Ser Gly
            530                 535                 540

Cys Lys Glu Cys Glu Glu Leu Glu Glu Lys Asn Ile Lys Glu Phe Leu
545                 550                 555                 560

Gln Ser Phe Val His Ile Val Gln Met Phe Ile Asn Thr Ser
                565                 570

<210> SEQ ID NO 103
<211> LENGTH: 1722

<212> TYPE: DNA
<213> ORGANISM: Artificial Sequence
<220> FEATURE:
<223> OTHER INFORMATION: Description of Artificial Sequence: Synthetic
      polynucleotide

<400> SEQUENCE: 103

```
cagatcgtgc tgacccaaag ccccgccatc atgagcgcta gccccggtga aaggtgacc      60
atgacatgct ccgcttccag ctccgtgtcc tacatgaact ggtatcagca gaaaagcgga     120
accagcccca aaggtggat ctacgacacc agcaagctgg cctccggagt gcccgctcat     180
ttccggggct ctggatccgg caccagctac tctttaacca tttccggcat ggaagctgaa     240
gacgctgcca cctactattg ccagcaatgg agcagcaacc ccttcacatt cggatctggc     300
accaagctcg aaatcaatcg tggaggaggt ggcagcggcg gcgtggatc cggcggagga     360
ggaagccaag ttcaactcca gcagagcggc gctgaactgg cccggcccgg cgcctccgtc     420
aagatgagct gcaaggcttc cggctataca tttactcgtt acacaatgca ttgggtcaag     480
cagaggcccg gtcaaggttt agagtggatc ggatatatca ccccttcccg gggctacacc     540
aactataacc aaaagttcaa ggataaagcc acttttaacca ctgacaagag ctcctccacc     600
gcctacatgc agctgtcctc tttaaccagc gaggactccg ctgtttacta ctgcgctagg     660
tattacgacg accactactg tttagactat tggggacaag gtaccacttt aaccgtcagc     720
agctccggca ccaccaatac cgtggccgct tataacctca catggaagag caccaacttc     780
aagacaattc tggaatggga acccaagccc gtcaatcaag tttacaccgt gcagatctcc     840
accaaatccg gagactggaa gagcaagtgc ttctacacaa cagacaccga gtgtgattta     900
accgacgaaa tcgtcaagga cgtcaagcaa acctatctgg ctcgggtctt tcctacccc      960
gctggcaatg tcgagtccac cggctccgct ggcgagcctc tctacgagaa ttcccccgaa    1020
ttcaccccctt atttagagac caatttaggc cagcctacca tccagagctt cgagcaagtt    1080
ggcaccaagg tgaacgtcac cgtcgaggat gaaaggactt tagtgcggcg aataacaca     1140
ttttttatccc tccgggatgt gttcggcaaa gacctcatct acacactgta ctattggaag    1200
tccagctcct ccggcaaaaa gaccgctaag accaacacca cgagttttt aattgacgtg     1260
gacaaaggcg agaactactg cttcagcgtg caagccgtga tcccttctcg taccgtcaac    1320
cggaagagca cagattcccc cgttgagtgc atgggccaag aaaagggcga gttccgggag    1380
aactgggtga acgtcatcag caatttaaag aagatcgaag atttaattca gtccatgcat    1440
atcgacgcca ctttatacac agaatccgac gtgcaccccct cttgtaaggt gaccgccatg    1500
aaatgttttt tactggagct gcaagttatc tctttagaga gcggagacgc tagcatccac    1560
gacaccgtgg agaatttaat cattttagcc aataactctt tatccagcaa cggcaacgtg    1620
acagagtccg gctgcaagga gtgcgaagag ctggaggaga agaacatcaa ggagtttctg    1680
caatcctttg tgcacattgt ccagatgttc atcaatacct cc                       1722
```

<210> SEQ ID NO 104
<211> LENGTH: 592
<212> TYPE: PRT
<213> ORGANISM: Artificial Sequence
<220> FEATURE:
<223> OTHER INFORMATION: Description of Artificial Sequence: Synthetic
      polypeptide

<400> SEQUENCE: 104

```
Met Lys Trp Val Thr Phe Ile Ser Leu Leu Phe Leu Phe Ser Ser Ala
1               5                   10                  15
```

```
Tyr Ser Gln Ile Val Leu Thr Gln Ser Pro Ala Ile Met Ser Ala Ser
            20                  25                  30

Pro Gly Glu Lys Val Thr Met Thr Cys Ser Ala Ser Ser Ser Val Ser
            35                  40                  45

Tyr Met Asn Trp Tyr Gln Gln Lys Ser Gly Thr Ser Pro Lys Arg Trp
 50                  55                  60

Ile Tyr Asp Thr Ser Lys Leu Ala Ser Gly Val Pro Ala His Phe Arg
 65                  70                  75                  80

Gly Ser Gly Ser Gly Thr Ser Tyr Ser Leu Thr Ile Ser Gly Met Glu
                 85                  90                  95

Ala Glu Asp Ala Ala Thr Tyr Tyr Cys Gln Gln Trp Ser Ser Asn Pro
            100                 105                 110

Phe Thr Phe Gly Ser Gly Thr Lys Leu Glu Ile Asn Arg Gly Gly Gly
            115                 120                 125

Gly Ser Gly Gly Gly Ser Gly Gly Gly Ser Gln Val Gln Leu
    130                 135                 140

Gln Gln Ser Gly Ala Glu Leu Ala Arg Pro Gly Ala Ser Val Lys Met
145                 150                 155                 160

Ser Cys Lys Ala Ser Gly Tyr Thr Phe Thr Arg Tyr Thr Met His Trp
                165                 170                 175

Val Lys Gln Arg Pro Gly Gln Gly Leu Glu Trp Ile Gly Tyr Ile Asn
            180                 185                 190

Pro Ser Arg Gly Tyr Thr Asn Tyr Asn Gln Lys Phe Lys Asp Lys Ala
            195                 200                 205

Thr Leu Thr Thr Asp Lys Ser Ser Thr Ala Tyr Met Gln Leu Ser
    210                 215                 220

Ser Leu Thr Ser Glu Asp Ser Ala Val Tyr Tyr Cys Ala Arg Tyr Tyr
225                 230                 235                 240

Asp Asp His Tyr Cys Leu Asp Tyr Trp Gly Gln Gly Thr Thr Leu Thr
            245                 250                 255

Val Ser Ser Ser Gly Thr Thr Asn Thr Val Ala Ala Tyr Asn Leu Thr
            260                 265                 270

Trp Lys Ser Thr Asn Phe Lys Thr Ile Leu Glu Trp Glu Pro Lys Pro
            275                 280                 285

Val Asn Gln Val Tyr Thr Val Gln Ile Ser Thr Lys Ser Gly Asp Trp
            290                 295                 300

Lys Ser Lys Cys Phe Tyr Thr Thr Asp Thr Glu Cys Asp Leu Thr Asp
305                 310                 315                 320

Glu Ile Val Lys Asp Val Lys Gln Thr Tyr Leu Ala Arg Val Phe Ser
                325                 330                 335

Tyr Pro Ala Gly Asn Val Glu Ser Thr Gly Ser Ala Gly Glu Pro Leu
            340                 345                 350

Tyr Glu Asn Ser Pro Glu Phe Thr Pro Tyr Leu Glu Thr Asn Leu Gly
            355                 360                 365

Gln Pro Thr Ile Gln Ser Phe Glu Gln Val Gly Thr Lys Val Asn Val
            370                 375                 380

Thr Val Glu Asp Glu Arg Thr Leu Val Arg Arg Asn Asn Thr Phe Leu
385                 390                 395                 400

Ser Leu Arg Asp Val Phe Gly Lys Asp Leu Ile Tyr Thr Leu Tyr Tyr
                405                 410                 415

Trp Lys Ser Ser Ser Ser Gly Lys Lys Thr Ala Lys Thr Asn Thr Asn
            420                 425                 430
```

```
Glu Phe Leu Ile Asp Val Asp Lys Gly Glu Asn Tyr Cys Phe Ser Val
            435                 440                 445
Gln Ala Val Ile Pro Ser Arg Thr Val Asn Arg Lys Ser Thr Asp Ser
        450                 455                 460
Pro Val Glu Cys Met Gly Gln Glu Lys Gly Glu Phe Arg Glu Asn Trp
465                 470                 475                 480
Val Asn Val Ile Ser Asn Leu Lys Lys Ile Glu Asp Leu Ile Gln Ser
                485                 490                 495
Met His Ile Asp Ala Thr Leu Tyr Thr Glu Ser Asp Val His Pro Ser
            500                 505                 510
Cys Lys Val Thr Ala Met Lys Cys Phe Leu Leu Glu Leu Gln Val Ile
        515                 520                 525
Ser Leu Glu Ser Gly Asp Ala Ser Ile His Asp Thr Val Glu Asn Leu
    530                 535                 540
Ile Ile Leu Ala Asn Asn Ser Leu Ser Ser Asn Gly Asn Val Thr Glu
545                 550                 555                 560
Ser Gly Cys Lys Glu Cys Glu Glu Leu Glu Glu Lys Asn Ile Lys Glu
                565                 570                 575
Phe Leu Gln Ser Phe Val His Ile Val Gln Met Phe Ile Asn Thr Ser
            580                 585                 590

<210> SEQ ID NO 105
<211> LENGTH: 1776
<212> TYPE: DNA
<213> ORGANISM: Artificial Sequence
<220> FEATURE:
<223> OTHER INFORMATION: Description of Artificial Sequence: Synthetic
      polynucleotide

<400> SEQUENCE: 105
atgaagtggg tgaccttcat cagcttatta tttttattca gctccgccta ttcccagatc      60
gtgctgaccc aaagccccgc catcatgagc gctagccccg gtgagaaggt gaccatgaca     120
tgctccgctt ccagctccgt gtcctacatg aactggtatc agcagaaaag cggaaccagc     180
cccaaaaggt ggatctacga caccagcaag ctggcctccg gagtgcccgc tcatttccgg     240
ggctctggat ccggcaccag ctactcttta accatttccg gcatggaagc tgaagacgct     300
gccacctact attgccagca atggagcagc aacccctcca cattcggatc tggcaccaag     360
ctcgaaatca tcgtggagg aggtggcagc ggcggcggtg gatccggcgg aggaggaagc     420
caagttcaac tccagcagag cggcgctgaa ctggcccggc ccggcgcctc cgtcaagatg     480
agctgcaagg cttccggcta cattact cgttacacaa tgcattgggt caagcagagg     540
cccggtcaag gtttagagtg gatcggatat atcaacccctt cccggggcta caccaactat     600
aaccaaaagt tcaaggataa agccactta accactgaca gagctcctc caccgcctac     660 atgcagctgt cctctttaac cagcgaggac tccgctgttt actactgcgc taggtattac     720
gacgaccact actgtttaga ctattgggga caaggtacca cttaaccgt cagcagctcc     780 ggcaccacca taccgtggc cgcttataac ctcacatgga agagcaccaa cttcaagaca     840
attctggaat gggaacccaa gcccgtcaat caagtttaca ccgtgcagat ctccaccaaa     900
tccggagact ggaagagcaa gtgcttctac acaacagaca ccgagtgtga ttaaccgac     960 gaaatcgtca aggacgtcaa gcaaaccac ctggctcggg tcttttccta ccccgctggc    1020
aatgtcgagt ccaccggctc cgctggcgag cctctctacg agaattcccc cgaattcacc    1080
ccttatttag agaccaattt aggccagcct accatccaga gcttcgagca agttggcacc    1140
```

```
aaggtgaacg tcaccgtcga ggatgaaagg actttagtgc ggcggaataa cacattttta   1200
tccctccggg atgtgttcgg caaagacctc atctacacac tgtactattg gaagtccagc   1260
tcctccggca aaagaccgc taagaccaac accaacgagt ttttaattga cgtggacaaa    1320
ggcgagaact actgcttcag cgtgcaagcc gtgatcccctt ctcgtaccgt caaccggaag   1380
agcacagatt cccccgttga gtgcatgggc caagaaaagg gcgagttccg ggagaactgg    1440
gtgaacgtca tcagcaattt aaagaagatc gaagatttaa ttcagtccat gcatatcgac    1500
gccactttat acacagaatc cgacgtgcac ccctcttgta aggtgaccgc catgaaatgt    1560
tttttactgg agctgcaagt tatctcttta gagagcggag acgctagcat ccacgacacc    1620
gtggagaatt taatcatttt agccaataac tctttatcca gcaacggcaa cgtgacagag    1680
tccggctgca aggagtgcga agagctggag gagaagaaca tcaaggagtt tctgcaatcc    1740
tttgtgcaca ttgtccagat gttcatcaat acctcc                               1776
```

<210> SEQ ID NO 106
<211> LENGTH: 301
<212> TYPE: PRT
<213> ORGANISM: Artificial Sequence
<220> FEATURE:
<223> OTHER INFORMATION: Description of Artificial Sequence: Synthetic
      polypeptide

<400> SEQUENCE: 106

```
Val Gln Leu Gln Gln Ser Gly Pro Glu Leu Val Lys Pro Gly Ala Ser
1               5                   10                  15

Val Lys Met Ser Cys Lys Ala Ser Gly Tyr Thr Phe Thr Ser Tyr Val
            20                  25                  30

Ile Gln Trp Val Lys Gln Lys Pro Gly Gln Gly Leu Glu Trp Ile Gly
        35                  40                  45

Ser Ile Asn Pro Tyr Asn Asp Tyr Thr Lys Tyr Asn Glu Lys Phe Lys
    50                  55                  60

Gly Lys Ala Thr Leu Thr Ser Asp Lys Ser Ser Ile Thr Ala Tyr Met
65                  70                  75                  80

Glu Phe Ser Ser Leu Thr Ser Glu Asp Ser Ala Leu Tyr Tyr Cys Ala
                85                  90                  95

Arg Trp Gly Asp Gly Asn Tyr Trp Gly Arg Gly Thr Thr Leu Thr Val
            100                 105                 110

Ser Ser Gly Gly Gly Ser Gly Gly Gly Ser Gly Gly Gly Gly
        115                 120                 125

Ser Asp Ile Glu Met Thr Gln Ser Pro Ala Ile Met Ser Ala Ser Leu
    130                 135                 140

Gly Glu Arg Val Thr Met Thr Cys Thr Ala Ser Ser Ser Val Ser Ser
145                 150                 155                 160

Ser Tyr Phe His Trp Tyr Gln Gln Lys Pro Gly Ser Ser Pro Lys Leu
                165                 170                 175

Cys Ile Tyr Ser Thr Ser Asn Leu Ala Ser Gly Val Pro Pro Arg Phe
            180                 185                 190

Ser Gly Ser Gly Ser Thr Ser Tyr Ser Leu Thr Ile Ser Ser Met Glu
        195                 200                 205

Ala Glu Asp Ala Ala Thr Tyr Phe Cys His Gln Tyr His Arg Ser Pro
    210                 215                 220

Thr Phe Gly Gly Gly Thr Lys Leu Glu Thr Lys Arg Ile Thr Cys Pro
225                 230                 235                 240

Pro Pro Met Ser Val Glu His Ala Asp Ile Trp Val Lys Ser Tyr Ser
```

```
                    245                 250                 255
Leu Tyr Ser Arg Glu Arg Tyr Ile Cys Asn Ser Gly Phe Lys Arg Lys
        260                 265                 270

Ala Gly Thr Ser Ser Leu Thr Glu Cys Val Leu Asn Lys Ala Thr Asn
        275                 280                 285

Val Ala His Trp Thr Thr Pro Ser Leu Lys Cys Ile Arg
        290                 295                 300

<210> SEQ ID NO 107
<211> LENGTH: 903
<212> TYPE: DNA
<213> ORGANISM: Artificial Sequence
<220> FEATURE:
<223> OTHER INFORMATION: Description of Artificial Sequence: Synthetic
      polynucleotide

<400> SEQUENCE: 107
gtgcagctgc agcagtccgg acccgaactg gtcaagcccg gtgcctccgt gaaaatgtct      60
tgtaaggctt ctggctacac ctttacctcc tacgtcatcc aatgggtgaa gcagaagccc     120
ggtcaaggtc tcgagtggat cggcagcatc aatccctaca cgattacac caagtataac     180 gaaaagttta agggcaaggc cactctgaca agcgacaaga gctccattac cgcctacatg     240
gagttttcct ctttaacttc tgaggactcc gctttatact attgcgctcg ttggggcgat     300
ggcaattatt ggggccgggg aactacttta acagtgagct ccggcggcgg cggaagcgga     360
ggtggaggat ctggcggtgg aggcagcgac atcgagatga cacagtcccc cgctatcatg     420
agcgcctctt taggagaacg tgtgaccatg acttgtacag cttcctccag cgtgagcagc     480
tcctatttcc actggtacca gcagaaaccc ggctcctccc ctaaactgtg tatctactcc     540
acaagcaatt tagctagcgg cgtgcctcct cgttttagcg gctccggcag cacctcttac     600
tctttaacca ttagctctat ggaggccgaa gatgccgcca catactttg ccatcagtac     660 caccggtccc ctacctttgg cggaggcaca aagctggaga ccaagcggat tacatgcccc     720
cctcccatga gcgtggagca cgccgacatc tgggtgaaga gctatagcct ctacagccgg     780
gagaggtata tctgtaacag cggcttcaag aggaaggccg gcaccagcag cctcaccgag     840
tgcgtgctga ataaggctac caacgtggct cactggacaa caccctcttt aaagtgcatc     900
cgg                                                                   903

<210> SEQ ID NO 108
<211> LENGTH: 319
<212> TYPE: PRT
<213> ORGANISM: Artificial Sequence
<220> FEATURE:
<223> OTHER INFORMATION: Description of Artificial Sequence: Synthetic
      polypeptide

<400> SEQUENCE: 108

Met Lys Trp Val Thr Phe Ile Ser Leu Leu Phe Leu Phe Ser Ser Ala
1               5                   10                  15

Tyr Ser Val Gln Leu Gln Gln Ser Gly Pro Glu Leu Val Lys Pro Gly
            20                  25                  30

Ala Ser Val Lys Met Ser Cys Lys Ala Ser Gly Tyr Thr Phe Thr Ser
        35                  40                  45

Tyr Val Ile Gln Trp Val Lys Gln Lys Pro Gly Gln Gly Leu Glu Trp
    50                  55                  60

Ile Gly Ser Ile Asn Pro Tyr Asn Asp Tyr Thr Lys Tyr Asn Glu Lys
65                  70                  75                  80
```

```
Phe Lys Gly Lys Ala Thr Leu Thr Ser Asp Lys Ser Ser Ile Thr Ala
                85                  90                  95

Tyr Met Glu Phe Ser Ser Leu Thr Ser Glu Asp Ser Ala Leu Tyr Tyr
            100                 105                 110

Cys Ala Arg Trp Gly Asp Gly Asn Tyr Trp Gly Arg Gly Thr Thr Leu
        115                 120                 125

Thr Val Ser Ser Gly Gly Gly Ser Gly Gly Gly Ser Gly Gly
    130                 135                 140

Gly Gly Ser Asp Ile Glu Met Thr Gln Ser Pro Ala Ile Met Ser Ala
145                 150                 155                 160

Ser Leu Gly Glu Arg Val Thr Met Thr Cys Thr Ala Ser Ser Ser Val
                165                 170                 175

Ser Ser Ser Tyr Phe His Trp Tyr Gln Gln Lys Pro Gly Ser Ser Pro
            180                 185                 190

Lys Leu Cys Ile Tyr Ser Thr Ser Asn Leu Ala Ser Gly Val Pro Pro
        195                 200                 205

Arg Phe Ser Gly Ser Gly Ser Thr Ser Tyr Ser Leu Thr Ile Ser Ser
    210                 215                 220

Met Glu Ala Glu Asp Ala Ala Thr Tyr Phe Cys His Gln Tyr His Arg
225                 230                 235                 240

Ser Pro Thr Phe Gly Gly Gly Thr Lys Leu Glu Thr Lys Arg Ile Thr
                245                 250                 255

Cys Pro Pro Pro Met Ser Val Glu His Ala Asp Ile Trp Val Lys Ser
            260                 265                 270

Tyr Ser Leu Tyr Ser Arg Glu Arg Tyr Ile Cys Asn Ser Gly Phe Lys
        275                 280                 285

Arg Lys Ala Gly Thr Ser Ser Leu Thr Glu Cys Val Leu Asn Lys Ala
    290                 295                 300

Thr Asn Val Ala His Trp Thr Thr Pro Ser Leu Lys Cys Ile Arg
305                 310                 315

<210> SEQ ID NO 109
<211> LENGTH: 957
<212> TYPE: DNA
<213> ORGANISM: Artificial Sequence
<220> FEATURE:
<223> OTHER INFORMATION: Description of Artificial Sequence: Synthetic
      polynucleotide

<400> SEQUENCE: 109
atgaaatggg tcaccttcat ctctttactg ttttattta  gcagcgccta cagcgtgcag       60
ctgcagcagt ccggacccga actggtcaag cccggtgcct ccgtgaaaat gtcttgtaag      120
gcttctggct acacctttac ctcctacgtc atccaatggg tgaagcagaa gcccggtcaa      180
ggtctcgagt ggatcggcag catcaatccc tacaacgatt acaccaagta taacgaaaag      240
tttaagggca aggccactct gacaagcgac aagagctcca ttaccgccta catggagttt      300
tcctctttaa cttctgagga ctccgcttta tactattgcg ctcgttgggg cgatggcaat      360
tattggggcc ggggaactac tttaacagtg agctccggcg gcggcggaag cggaggtgga      420
ggatctggcg gtgaggcag  cgacatcgag atgacacagt cccccgctat catgagcgcc      480
tctttaggag aacgtgtgac catgacttgt acagcttcct ccagcgtgag cagctcctat      540
ttccactggt accagcagaa acccggctcc tccctaaaac tgtgtatcta ctccacaagc      600
aatttagcta gcggcgtgcc tcctcgtttt agcggctccg gcagcacctc ttactcttta      660
```

-continued

```
accattagct ctatggaggc cgaagatgcc gccacatact tttgccatca gtaccaccgg    720
tcccctacct ttggcggagg cacaaagctg gagaccaagc ggattacatg ccccctccc    780 atgagcgtgg agcacgccga catctgggtg aagagctata gcctctacag ccgggagagg    840
tatatctgta acagcggctt caagaggaag gccggcacca gcagcctcac cgagtgcgtg    900
ctgaataagg ctaccaacgt ggctcactgg acaacaccct ctttaaagtg catccgg      957

<210> SEQ ID NO 110
<211> LENGTH: 5
<212> TYPE: PRT
<213> ORGANISM: Artificial Sequence
<220> FEATURE:
<223> OTHER INFORMATION: Linker

<400> SEQUENCE: 110

Gly Gly Gly Gly Ser
1               5

<210> SEQ ID NO 111
<211> LENGTH: 4
<212> TYPE: PRT
<213> ORGANISM: Artificial Sequence
<220> FEATURE:
<223> OTHER INFORMATION: Linker

<400> SEQUENCE: 111

Gly Gly Gly Ser
1

<210> SEQ ID NO 112
<211> LENGTH: 4
<212> TYPE: PRT
<213> ORGANISM: Artificial Sequence
<220> FEATURE:
<223> OTHER INFORMATION: Linker

<400> SEQUENCE: 112

Gly Gly Ser Gly
1
```